(12) United States Patent
Celanire et al.

(10) Patent No.: US 7,790,720 B2
(45) Date of Patent: Sep. 7, 2010

(54) COMPOUNDS COMPRISING AN OXAZOLE OR THIAZOLE MOIETY, PROCESSES FOR MAKING THEM, AND THEIR USES

(75) Inventors: Sylvain Celanire, Feigeres (FR); Frederic Denonne, Brussels (BE)

(73) Assignee: UCB Pharma, S.A., Brussels (BE)

( * ) Notice: Subject to any disclaimer, the term of this patent is extended or adjusted under 35 U.S.C. 154(b) by 0 days.

(21) Appl. No.: 11/910,191

(22) PCT Filed: Mar. 28, 2006

(86) PCT No.: PCT/EP2006/002806

§ 371 (c)(1),
(2), (4) Date: Apr. 24, 2008

(87) PCT Pub. No.: WO2006/103045

PCT Pub. Date: Oct. 5, 2006

(65) Prior Publication Data

US 2008/0275046 A1    Nov. 6, 2008

(30) Foreign Application Priority Data

Mar. 31, 2005   (EP) ................................. 05006971

(51) Int. Cl.
*A61K 31/5377* (2006.01)
*A61K 31/4545* (2006.01)
*A61K 31/454* (2006.01)
*C07D 417/14* (2006.01)
*C07D 413/14* (2006.01)
*C07D 401/14* (2006.01)

(52) U.S. Cl. ..................... 514/236.8; 514/316; 514/326; 544/133; 544/137; 546/187; 546/209

(58) Field of Classification Search ............. 514/236.8, 514/326, 316, 278, 365, 374, 343, 217.1; 546/209, 187, 16, 271.4; 544/137, 133; 548/235, 236, 202, 204; 540/603, 609
See application file for complete search history.

(56) References Cited

U.S. PATENT DOCUMENTS

| | | | |
|---|---|---|---|
| 1,970,656 A | | 8/1934 | Johnson |
| 4,559,354 A | | 12/1985 | Fuhrere et al. |
| 4,735,961 A | | 4/1988 | Baldwin et al. |
| 4,843,087 A | | 6/1989 | Diana |
| 5,614,520 A | * | 3/1997 | Kondo et al. ............. 514/236.8 |
| 6,436,939 B2 | | 8/2002 | Carruthers et al. |

FOREIGN PATENT DOCUMENTS

| | | |
|---|---|---|
| DE | 21 30 709 | 12/1971 |
| EP | 0 207 454 | 1/1987 |
| EP | 0 435 381 | 7/1991 |
| EP | 0 513 379 | 11/1992 |
| GB | 1 180 268 | 2/1970 |
| WO | WO 98/27061 | 6/1998 |
| WO | WO 01/74763 | 10/2001 |
| WO | WO 02/12214 | 2/2002 |
| WO | WO/02/32897 | 4/2002 |
| WO | WO 03/097047 | 11/2003 |
| WO | WO 2004/058174 | 7/2004 |
| WO | WO 2004/098498 | 11/2004 |
| WO | WO 2006/019833 | 2/2006 |
| WO | WO 2006/044707 | 4/2006 |

OTHER PUBLICATIONS

Robert B. Layzer, Section Five- Degenerative Diseases of the Nervous System, Cecil Textbook of Medicine, 20th edition (1996), vol. 2, pp. 2050-2057.*

Antonio R. Damasio, Alzheimer's Disease and Related Dementias, Cecil Textbook of Medicine, 20th edition (1996), vol. 2, pp. 1992-1996.*

"FDA mulls drug to slow late-stage Alzheimer's," [retrieved on Sep. 23, 2003]. Retrieved online via Internet, URL: http://www.cnn.com/2003/HEALTH/conditions/09/24/alzheimers.drug.ap/index.html.*

"Autism," [retrieved on May 14, 2008]. Retrieved online via Internet, URL: http://www.nlm.nih.gov/medlineplus/autism.html.*

(Continued)

*Primary Examiner*—Kamal A Saeed
*Assistant Examiner*—Kristin Bianchi
(74) *Attorney, Agent, or Firm*—McDonnell Boehnen Hulbert & Berghoff LLP

(57) ABSTRACT

The present invention relates to compounds comprising an oxazole or thiazole moiety of formula (I), processes for preparing them, pharmaceutical compositions comprising said compounds and their uses as $H_3$-receptor ligands, Formula (I), wherein, $A^1$ is CH, C(alkyl), C-halogen or N; $R^1$ is hydrogen, halogen, $C_{1-6}$ alkyl or alkoxy; $R^2$ is, Formula (II'), $A^3$ is O or S; $R^3$ is hydrogen, halogen, $C_{1-6}$ alkyl or alkoxy; $R^4$ is hydrogen, halogen, $C_{1-6}$ alkyl, alkoxy or —O-L; $R^5$ is hydrogen or —O-L, wherein L is an aminoalkyl group and at least one of $R^4$ and $R^5$ should be —O-L.

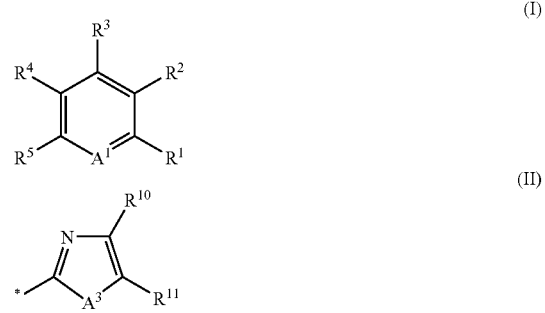

31 Claims, No Drawings

OTHER PUBLICATIONS

"Anxiety," [retrieved on May 14, 2008]. Retrieved online via Internet, URL: http://www.nlm.nih.gov/medlineplus/anxiety.html#cat3.*

Ram, Bhagat, et al., (1988) "*Synthesis & Biological Activity of Some New 1-Amino-3-(4-oxazolyl)phenoxy-2propanols*" Indian Journal of Chemistry, vol. 2, pp. 242-244, XP008066390.

Li et al., (2006) "*Synthesis and structure-activity relationship of 3,4'-bispyridinylethylenes: Discovery of a potent 3-isoquinolinylpyridine inhibitor of protein kinase B (PKB/Akt) for the treatment of cancer*" Bioorganic & Medicinal Chemistry Letters, vol. 16, No. 7, pp. 2000-2007, XP005330434.

Istanbullu, Ismail, et al., (1986) Chemical Abstracts Services, vol. 6, No. 1, pp. 7-10, XP002352587.

Yamane, Taihei, et al., (2004) "*A New Approach to the Synthesis of 2-Aryl-4halomethyl-2-methyl-1-1,3-oxazoles by Highly Regioselective Direct Halogenation with NBS or NCS/meCN*" Synthesis, No. 17, pp. 2825-2832, XP002389683.

Rix, M.J. et al., (1971) "*The Electron Impact-Induced Fragmentation of 2-Arylthiazoles*" Organic Mass Spectrometry, vol. 5m pp. 311-315, XP008066389.

Csavassy, et al., (1974) "*Synthese and Umsetzung von 2-Aryl-5-Diazoacetyl-4-methylthiazolen*" Liebigs Ann. Chemical, pp. 1195-1205, XP001026825.

Database Registry ACS; Feb. 6, 2001, XP002389717.

Database Registry ACS; May 24, 2001, XP002389718.

Database Registry ACS; Jan. 3, 2003, XP002389719.

Divya Vohora: "Histamine-selective H3 receptor ligands and cognitive functions: An Overview," IDrugs (2004) 7 (7):667-663.

J.M. Witkin et al.: "Selective histamine H3 receptor antagonists for treatment of cognitive deficiencies and other disorders of the central nervous system," Pharmacology & Therapeutics 103 (2004) pp. 1-20.

Rob Leurs et al.: "The Histamine H3 receptor: From Gene Cloning to H3 Receptor Drugs," Nature Reviews, vol. 4, Feb. 2005, pp. 107-120.

Maria Beatrice Passani et al.: "The histamine H3 receptor as a novel therapeutic target for cognitive and sleep disorders," Trends in Pharmacological Sciences, vol. 25, No. 12, Dec. 2004, pp. 618-625.

* cited by examiner

COMPOUNDS COMPRISING AN OXAZOLE OR THIAZOLE MOIETY, PROCESSES FOR MAKING THEM, AND THEIR USES

CROSS-REFERENCE TO RELATED APPLICATIONS

This application is a U.S. National Stage of International Application No. PCT/EP2006/002806, filed Mar. 28, 2006.

The present invention relates to compounds comprising an oxazole or thiazole moiety, processes for preparing them, pharmaceutical compositions comprising said compounds and their uses as pharmaceuticals.

The histamine $H_3$ receptor has been known for several years and identified pharmacologically in 1983 by Arrang, J. M. et al. (Nature 1983, 302, 832). Since the cloning of the human histamine H3 receptor in 1999, histamine $H_3$ receptors have been successively cloned by sequence homology from a variety of species, including rat, guinea pig, mouse and monkey.

Histamine $H_3$-receptor agonists, antagonists and inverse agonists have shown potential therapeutic applications as described in the literature, for example by Stark, H. (Exp. Opin. Ther. Patents 2003, 13, 851).

The histamine $H_3$ receptor is predominantly expressed in the mammalian central nervous system but can also be found in the autonomic nervous system. Evidence has been shown that the histamine $H_3$ receptor displays high constitutive activity, which activity occurs in the absence of endogenous histamine or of a $H_3$-receptor agonist. Thus, a histamine $H_3$-receptor antagonist and/or inverse agonist could inhibit this activity.

The general pharmacology of histamine $H_3$-receptor, including $H_3$-receptor subtypes, has been reviewed by Hancock, A. A (Life Sci. 2003, 73, 3043). The histamine $H_3$-receptor is not only considered as a presynaptic autoreceptor on histaminergic neurons, but also as a heteroreceptor on non-histaminergic neurons (Barnes, W. et al., Eur. J. Pharmacol. 2001, 431, 215). Indeed, the histamine $H_3$-receptor has been shown to regulate the release of histamine but also of other important neurotransmitters, including acetylcholine, dopamine, serotonin, norepinephrin and γ-aminobutyric acid (GABA).

Thus, the histamine $H_3$ receptor is of current interest for the development of new therapeutics and the literature suggests that novel histamine $H_3$-receptor antagonists or inverse agonists may be useful for the treatment and prevention of diseases or pathological conditions of the central nervous system including as Mild Cognitive Impairment (MCI), Alzheimer's disease, learning and memory disorders, cognitive disorders, attention deficit disorder (ADD), attention-deficit hyperactivity disorder (ADHD), Parkinson's disease, schizophrenia, dementia, depression, epilepsy, seizures or convulsions, sleep/wake disorders, narcolepsy, and/or obesity.

$H_3$-receptor ligands alone or in combination with an acetylcholinesterase inhibitor may also be useful in the treatment of cholinergic-deficit disorders, Mild Cognitive Impairment and Alzheimer's disease as reported by Morisset, S. et al. in Eur. J. Pharmacol. 1996, 315, R1-R2.

$H_3$-receptor ligands, alone or in combination with a histamine $H_1$-receptor antagonist may be useful for the treatment of upper airway allergic disorders, as reported by McLeod, R. et al. in J. Pharmacol. Exp. Ther. 2003, 305, 1037.

As described in international patent application WO02/072093, $H_3$-receptor ligands alone or in combination with a muscarinic receptor ligands and particularly with a muscarinic $M_2$-receptor antagonist, may be useful for the treatment of cognitive disorders, Alzheimer's disease, attention-deficit hyperactivity disorder.

$H_3$-receptor ligands may also be useful in the treatment of sleep/wake and arousal/vigilance disorders such as hypersomnia, and narcolepsy according to Passani, M. B. et al. in Trends Pharmacol. Sci. 2004, 25(12), 618-25.

In general, $H_3$-receptor ligands, and particularly $H_3$-receptor antagonists or inverse agonists may be useful in the treatment of all type of cognitive-related disorders as reviewed by Hancock, A. A and Fox, G. B. in Expert Opin. Ivest. Drugs 2004, 13, 1237

In particular, histamine $H_3$-receptor antagonists or inverse agonists may be useful in the treatment of cognitive dysfunctions in diseases such as mild cognitive impairment, dementia, Alzheimer's disease, Parkinson's disease, Down's syndrome as well as in the treatment of attention-deficit hyperactivity disorder (ADHD) as non-psychostimulant agents (see for example Witkin, J. M. et al., Pharmacol. Ther. 2004, 103(1), 1-20.

$H_3$-receptor antagonists or inverse agonists may also be useful in the treatment of psychotic disorders such as schizophrenia, migraine, eating disorders such as obesity, inflammation, pain, anxiety, stress, depression and cardiovascular disorders, in particular acute myocardial infarction.

There is therefore a need to manufacture new compounds which can potentially act as $H_3$-receptor ligands.

Early literature reports (e.g. Ali, S. M. et al. in J. Med. Chem. 1999, 42, 903 and Drugs Fut. 1996, 21, 507) describe that an imidazole function is essential for high affinity histamine $H_3$-receptor ligands; this is confirmed, for example, by United States patents U.S. Pat. No. 6,506,756B2, U.S. Pat. No. 6,518,287B2, U.S. Pat. No. 6,528,522B2 and U.S. Pat. No. 6,762,186B2 which relate to substituted imidazole compounds that have $H_3$ receptor antagonist or dual histamine-$H_1$-receptor and $H_3$-receptor antagonist activity.

International patent application WO 02/12214 describes non-imidazole aryloxyalkylamines useful for the treatment of conditions and disorders mediated by the histamine receptor.

United States patent U.S. Pat. No. 6,436,939B2 relates to $H_3$-receptor antagonists comprising benzoxazole or benzothiazole moieties.

International patent application WO 03/097047 relates to compounds comprising an oxazole moiety for use as melanin concentrating antagonist in the treatment of obesity and diabetes.

International patent application WO 98/27061 describes compounds comprising an oxazole moiety which may be used, for example, for the treatment of hypertension, angina pectoris and diabetic complications.

It has now surprisingly been found that certain compounds comprising an oxazole or thiazole moiety may act as $H_3$-receptor ligands and therefore may demonstrate therapeutic properties for one or more pathologies that we have described above.

Thus, the present invention relates to compounds of formula (I), geometrical isomers, enantiomers, diastereoisomers, pharmaceutically acceptable salts and all possible mixtures thereof, (I)

[Structure: benzene-like ring with substituents $R^3$, $R^4$, $R^2$, $R^5$, $R^1$, and $A^1$]

wherein
$A^1$ is CH, C(alkyl), C-halogen or N;
$R^1$ is hydrogen, halogen, $C_{1-6}$ alkyl or alkoxy;
$R^2$ is (II')

[Structure: five-membered heterocycle with $R^{10}$, $R^{11}$, $A^3$, N, and * attachment point]

$A^3$ is O or S;
$R^3$ is hydrogen, halogen, $C_{1-6}$ alkyl or alkoxy;
$R^4$ is hydrogen, halogen, $C_{1-6}$ alkyl, alkoxy or —O-L;
$R^5$ is hydrogen or —O-L;
L is $C_{1-6}$-alkyl amino;
$R^{10}$ is hydrogen, sulfonyl, amino, $C_{1-6}$ alkyl, $C_{2-6}$-alkenyl, $C_{2-6}$-alkynyl, aryl, heteroaryl, $C_{3-8}$ cycloalkyl, 3-8 membered heterocycloalkyl, acyl, $C_{1-6}$-alkyl aryl, $C_{1-6}$-alkyl heteroaryl, $C_{2-6}$-alkenyl aryl, $C_{2-6}$-alkenyl heteroaryl, $C_{2-6}$ alkynyl aryl, $C_{2-6}$ alkynyl heteroaryl, $C_{1-6}$-alkyl cycloalkyl, $C_{1-6}$-alkyl heterocycloalkyl, $C_{2-6}$-alkenyl cycloalkyl, $C_{2-6}$-alkenyl heterocycloalkyl, $C_{2-6}$-alkynyl cycloalkyl, $C_{2-6}$-alkynyl heterocycloalkyl, alkoxycarbonyl, aminocarbonyl, $C_{1-6}$-alkyl carboxy, $C_{1-6}$-alkyl acyl, $C_{3-8}$-cycloalkyl acyl, aryl acyl, heteroaryl acyl, $C_{3-8}$-heterocycloalkyl acyl, $C_{1-6}$-alkyl acyloxy, $C_{1-6}$-alkyl alkoxy, $C_{1-6}$-alkyl alkoxycarbonyl, $C_{1-6}$-alkyl aminocarbonyl, $C_{1-6}$-alkyl acylamino, acylamino, $C_{1-6}$-alkyl ureido, $C_{1-6}$-alkyl carbamate, $C_{1-6}$-alkyl amino, $C_{3-8}$-cycloalkyl amino, $C_{1-6}$-alkyl sulfonyl, $C_{1-6}$-alkyl sulfinyl, $C_{1-6}$-alkyl sulfanyl, $C_{1-6}$-alkyl sulfonylamino, $C_{1-6}$-alkyl aminosulfonyl, hydroxy, halogen or cyano;
$R^{11}$ is hydrogen, sulfonyl, amino, $C_{1-6}$ alkyl, $C_{2-6}$-alkenyl, $C_{2-6}$-alkynyl, aryl, heteroaryl, $C_{3-8}$ cycloalkyl, 3-8 membered heterocycloalkyl, acyl, $C_{1-6}$-alkyl aryl, $C_{1-6}$-alkyl heteroaryl, $C_{2-6}$-alkenyl aryl, $C_{2-6}$-alkenyl heteroaryl, $C_{2-6}$ alkynyl aryl, $C_{2-6}$ alkynyl heteroaryl, $C_{1-6}$-alkyl cycloalkyl, $C_{1-6}$-alkyl heterocycloalkyl, $C_{2-6}$-alkenyl cycloalkyl, $C_{2-6}$-alkenyl heterocycloalkyl, $C_{2-6}$-alkynyl cycloalkyl, $C_{2-6}$-alkynyl heterocycloalkyl, alkoxycarbonyl, aminocarbonyl, $C_{1-6}$-alkyl carboxy, $C_{1-6}$-alkyl acyl, $C_{3-8}$-cycloalkyl acyl, aryl acyl, heteroaryl acyl, $C_{3-8}$-heterocycloalkyl acyl, $C_{1-6}$-alkyl acyloxy, $C_{1-6}$-alkyl alkoxy, $C_{1-6}$-alkyl alkoxycarbonyl, $C_{1-6}$-alkyl aminocarbonyl, $C_{1-6}$-alkyl acylamino, acylamino, $C_{1-6}$-alkyl ureido, $C_{1-6}$-alkyl carbamate, $C_{1-6}$-alkyl amino, $C_{3-8}$-cycloalkyl amino, $C_{1-6}$-alkyl sulfonyl, $C_{1-6}$-alkyl sulfinyl, $C_{1-6}$-alkyl sulfanyl, $C_{1-6}$-alkyl sulfonylamino, $C_{1-6}$-alkyl aminosulfonyl, hydroxy, halogen or cyano; and
with the proviso that when $R^{11}$ is an alkoxycarbonyl, $R^4$ is hydrogen, halogen, $C_{1-6}$ alkyl or alkoxy; and
with the proviso that $R^4$ is —O-L, when $R^5$ is hydrogen and that $R^5$ is —O-L, when $R^4$ is hydrogen, halogen, $C_{1-6}$ alkyl or alkoxy.

The term "alkyl", as used herein, is a group which represents saturated, monovalent hydrocarbon radicals having straight (unbranched), branched or cyclic moieties, or combinations thereof and containing 1-10 carbon atoms, preferably 1-8 carbon atoms; more preferably alkyl groups have 1-6 carbon atoms, most preferably alkyl groups have 1-4 carbon atoms. Preferred alkyl groups, are methyl, ethyl, trifluoromethyl, n-propyl, isopropyl, n-butyl, sec-butyl, isobutyl, tert-butyl, 1,3-dimethylbutyl, 3-methylbutyl, n-hexyl, 2-methoxy-1-methylethyl and 1-(hydroxymethyl)-3-methylbutyl.

The term "$C_{1-6}$ alkyl" refers to alkyl groups as defined here above having 1 to 6 carbon atoms. This term is exemplified by groups such as methyl, ethyl, n-propyl, isopropyl, n-butyl, isobutyl, sec-butyl, tert-butyl, n-pentyl, n-hexyl, 1,3-dimethylbutyl, 3-methylbutyl and the like.

The term "$C_{2-6}$ alkenyl" refers to alkenyl groups preferably having from 2 to 6 carbon atoms and having at least 1 or 2 sites of alkenyl unsaturation. Preferred alkenyl groups include ethenyl (vinyl, —CH=CH$_2$), n-2-propenyl (allyl, —CH$_2$—CH=CH$_2$) and the like.

The term "$C_{2-6}$-alkynyl" refers to alkynyl groups preferably having from 2 to 6 carbon atoms and having at least 1 to 2 sites of alkynyl unsaturation. Preferred alkynyl groups include ethynyl (—C≡CH), propargyl (—CH$_2$C≡CH), and the like.

The term "$C_{3-8}$ cycloalkyl", as used herein, is a monovalent group of 3 to 8 carbon atoms usually 3 to 6 carbon atoms derived from an unsaturated or saturated monocyclic or bicyclic hydrocarbon. Preferred cycloalkyl are cyclopropyl, cyclopentyl, 3,4-dimethylcyclopentyl and cyclohexyl.

The term "$C_{1-6}$-alkyl cycloalkyl", as used herein, refers to a $C_{1-6}$ alkyl having a cycloalkyl substituent. Examples include cyclopropylmethyl and the like.

The term "$C_{2-6}$-alkenyl cycloalkyl", as used herein, refers to a $C_{2-6}$ alkenyl having a cycloalkyl substituent.

The term "$C_{2-6}$-alkynyl cycloalkyl", as used herein, refers to a $C_{2-6}$ alkynyl having a cycloalkyl substituent.

The term "heteroatom" as used herein represents a nitrogen, oxygen or sulfur atom.

The term "halogen", as used herein, represents an atom of fluorine, chlorine, bromine, or iodine.

The term "hydroxy", as used herein, represents a group of formula —OH.

The term "heterocycloalkyl" refers to a $C_{3-8}$ cycloalkyl group according to the definition here above, in which 1 to 3 carbon atoms are replaced by heteroatoms chosen from the group consisting of O, S, N.

Each carbon of the heterocycloalkyl may be unsubstituted or substituted by one or more $C_{1-4}$ alkyl, $C_{3-8}$-cycloalkyl, $C_{1-6}$-alkyl aryl or halogen as defined herein. Examples of such heterocycloalkyls are pyrrolidine, piperidine, piperazine, morpholine, 2-methylpyrrolidine, (2S)-2-methylpyrrolidine, (2R)-2-methylpyrrolidine, 4-methylpyridine, 2-methylpiperidine, 2,6-dimethylpiperidine, 4-methylpiperidine, 4-benzylpiperidine, 4-isopropylpiperazine, 3,5-dimethylpiperidine, 2-isobutylpyrrolidine, 4,4-difluoropiperidine, 2-ethylpyrrolidine, 4-cyclopentylpiperazine, 4-(2-pyrrolidin-1-yl-ethyl)piperazine, azepane, 2-azaspiro[5.5]undecane and 7,8-dimethyl-1-azaspiro[4.4]nonane. The heterocycloalkyl may also be fused with a $C_{3-8}$ cycloalkyl to form a bicyclic heterocycloalkyl. Examples include (4aR,8aS)-decahydroisoquinoline and the like.

One carbon of the heterocycloalkyl may be replaced by a carbonyl and/or substituted by an amino group or a heterocycloalkyl or $C_{1-6}$ alkyl heterocycloalkyl as defined herein. Examples of such heterocycloalkyl are 2-oxopyrrolidine, 2-oxopiperidine, (5S)-2-oxo-5-(pyrrolidin-1-ylmethyl)pyrrolidine, 3-(dimethylamino)pyrrolidine, (2S)-2-(pyrrolidin- 1-ylmethyl)pyrrolidine, 2-(pyrrolidin-1-ylmethyl)pyrrolidine and (2S)-2-(4morpholin-1-ylmethyl)pyrrolidine.

The term "$C_{1-6}$-alkyl heterocycloalkyl", as used herein, refers to a $C_{1-6}$ alkyl having a heterocycloalkyl as defined hereabove as substitutent.

The term "$C_{2-6}$-alkenyl heterocycloalkyl", as used herein, refers to a $C_{2-6}$ alkenyl having a heterocycloalkyl as defined here above as substitutent.

The term "$C_{2-6}$-alkynyl heterocycloalkyl", as used herein, refers to a $C_{2-6}$ alkynyl having a heterocycloalkyl as defined here above as substitutent.

The term "amino group", as used herein, represents a group of formula —$NR^bR^c$ wherein $R^b$ and $R^c$ are independently hydrogen, "$C_{1-6}$ alkyl", "$C_{2-6}$ alkenyl", "$C_{2-6}$ alkynyl", "$C_{3-8}$ cycloalkyl", "heterocycloalkyl", "aryl", "heteroaryl", "$C_{1-6}$-alkyl aryl", "$C_{1-6}$-alkyl heteroaryl", "$C_{2-6}$-alkenyl aryl", "$C_{2-6}$-alkenyl heteroaryl", "$C_{2-6}$-alkynyl aryl", "$C_{2-6}$-alkynylheteroaryl", "$C_{1-6}$-alkyl cycloalkyl" or "$C_{1-6}$-alkyl heterocycloalkyl" groups; or $R^b$ and $R^c$ are linked together with N to form a 3 to 8 membered heterocycloalkyl ring.

Preferred "amino groups" are hexyl(methyl)amino, benzyl(methyl)amino, (2-methoxy-1-methylethyl)amino, [1-(hydroxymethyl)-3-methylbutyl]amino, cyclopentylamino, (1,3-dimethylbutyl)amino, (cyclopropylmethyl)(propyl)amino, (2-furylmethyl)(methyl)amino, sec-butyl(propyl)amino, benzylamino, (4aR,8aS)-octahydroisoquinolin-2-(1H)-yl, (4-chlorobenzyl)amino, (3-methoxyphenyl)amino, (2S)-2-(morpholin-4-ylmethyl)pyrrolidin-1-yl, (2-methyl-2H-tetrazol-5-yl)amino, anilino, (pyridin-3-yl)amino, (4-fluorobenzyl)amino, (4-fluorophenyl)amino, 1-pyrrolidinyl, 1-piperidinyl, 1-piperazinyl, 4-morpholinyl, 1-azepanyl, 2-methylpyrrolidin-1-yl, (2S)-2-methylpyrrolidin-1-yl, (2R)-2-methylpyrrolidin-1-yl, 2-methylpiperidin-1-yl, 2,6-dimethylpiperidin-1-yl, 4-methylpiperidin-1-yl, 4-benzylpiperidin-1-yl, 4-isopropylpiperazin-1-yl, 3,5-dimethylpiperidin-1-yl, 2-isobutylpyrrolidin-1-yl, 4,4-difluoropiperidin-1-yl, 2-ethylpyrrolidin-1-yl, 2-oxopyrrolidin-1-yl, 2-oxopiperidin-1-yl, (5S)-2-oxo-5-(pyrrolidin-1-ylmethyl)pyrrolidin-1-yl), 3-(dimethylamino)pyrrolidin-1-yl, (2S)-2-(pyrrolidin-1-ylmethyl)pyrrolidin-1-yl, 2-(pyrrolidin-1-ylmethyl)pyrrolidin-1-yl, 2-azaspiro[5.5]undec-2-yl, 7,8-dimethyl-1 azaspiro[4.4]non-1-yl, 4-cyclopentylpiperazin-1-yl (4aR,8aS)-octahydroisoquinolin-2(1H)-yl and 4-(2-pyrrolidin-1-ylethyl)piperazin-1-yl.

The term "aminocarbonyl" as used herein refers to a group of formula —C(O)N $R^bR^c$ wherein $R^b$ and $R^c$ are as defined here above for the amino group. Preferably $R^b$ and $R^c$ together do not form a guanidine group. Preferred aminocarbonyl groups include [(cyclopropylmethyl)(propyl)amino]carbonyl, (cyclopentylamino)carbonyl, (benzylamino)carbonyl, [(4-fluoro)benzylaminocarbonyl, [(4-fluoro)phenyl)amino]carbonyl, pyrrolidin-1-ylcarbonyl, piperidin-1-ylcarbonyl, 4,4-difluoropiperidin-1-ylcarbonyl, (2S)-2-(pyrrolidin-1-ylmethyl)pyrrolidin-1-ylcarbonyl, azepan-1-ylcarbonyl are morpholin-4-ylcarbonyl and (4-cyclopentylpiperazin-1-yl)carbonyl.

The term "$C_{1-6}$ alkyl aminocarbonyl" as used herein, refers to a $C_{1-6}$ alkyl substituted by an aminocarbonyl as defined hereabove.

The term "a $C_{1-6}$ alkyl amino", as used herein, represents a $C_{1-6}$ alkyl group substituted by an amino group as defined above. Preferred $C_{1-6}$ alkyl amino groups include 2-pyrrolidin-1-ylethyl, pyrrolidin-1 ylmethyl, piperidin-1-ylmethyl, azepan-1-ylmethyl, (2-methylpyrrolidin-1-yl)methyl, (2-methylpiperidin-1-yl)methyl, (2,6-dimethylpiperidin-1-ylmethyl), (4-methylpiperidin-1-yl)methyl, 4-benzylpiperidin-1-ylmethyl, 4-isopropylpiperazin-1-ylmethyl, 3,5-dimethylpiperidin-1-ylmethyl, 2-isobutylpyrrolidin-1-ylmethyl, (4-cyclopentylpiperazin-1-yl)methyl, (4,4-difluoro)piperidin-1-yl methyl, 2-ethylpyrrolidin-1-ylmethyl, (2-azaspiro[5.5]undec-2-yl)methyl, (7,8-dimethyl-1-azaspiro[4.4]non-1-yl)methyl, 2-oxopyrrolidin-1-ylmethyl, 2-oxopiperidin-1-ylmethyl, [(5S)-2-oxo-5-(pyrrolidin-1-ylmethyl)pyrrolidin-1-yl]methyl, (4aR,8aS)-octahydroisoquinolin-2(1H)-ylmethyl, morpholin-4-ylmethyl, [(2S)-2-(morpholin-4-ylmethyl)pyrrolidin-1-yl] methyl, 3-piperidin-1-ylpropyl, 3-(2-methylpiperidin-1-yl)propyl, 3-(4-methylpiperidin-1-yl)propyl, 3-pyrrolidin-1-ylpropyl, 3-(2-methylpyrrolidin-1-yl)propyl, 3-((2R)-2-methylpyrrolidin-1-yl)propyl, 3-((2S)-2-methylpyrrolidin-1-yl)propyl, 3-(4-isopropylpiperazin-1-yl)propyl, 3-[2-(pyrrolidin-1-ylmethyl)pyrrolidin-1-yl]propyl, 3-[(2S)-2-(pyrrolidin-1-ylmethyl)pyrrolidin-1-yl]propyl, 3-(2-isobutylpyrrolidin-1-yl)propyl, 3-(2-ethylpyrrolidin-1-yl)propyl, 3-[(4aR,8aS)-octahydroisoquinolin-2(1H)-yl]propyl, 3-(4-cyclopentylpiperazin-1-yl)propyl, 3-azepan-1-ylpropyl, 2-piperidin-1-ylethyl, 2-(2-methylpiperidin-1-yl)ethyl, 2-azepan-1-ylethyl, 2-[4-(2-pyrrolidin-1-ylethyl)piperazin-1-yl]ethyl, 4-(2-methylpiperidin-1-yl)butyl, 4-[3-(dimethylamino)pyrrolidin-1-yl]butyl, 4-azepan-1-ylbutyl, [hexyl(methyl)amino]methyl, [benzyl(methyl)amino]methyl, [(2-methoxy-1-methylethyl)amino]methyl, anilinomethyl, {[1-(hydroxymethyl)-3-methylbutyl]amino}methyl, (cyclopentylamino)methyl, [(1,3-dimethylbutyl)amino]methyl, [(2-methyl-2H-tetrazol-5-yl)amino]methyl, [(cyclopropylmethyl)(propyl)amino]methyl, [(2-furylmethyl)(methyl)amino]methyl, [sec-butyl(propyl)amino]methyl, (benzylamino)methyl, [(4-chlorobenzyl)amino]methyl, [(3-methoxyphenyl)amino]methyl, [(4-fluorophenyl)amino]methyl, (pyridin-3-ylamino)methyl, 3-(2,6-dimethyl-piperidin-1-yl)propyl and 2-(2-methylpyrrolidin-1-yl)ethyl.

The term "$C_{3-8}$-cycloalkyl amino", as used herein, represents a $C_{3-8}$ cycloalkyl group substituted by an amino group as defined above.

The term "acylamino", as used herein refers to a group of formula —$NR^bC(O)R^c$ wherein $R^b$ and $R^c$ are as defined hereabove for the amino group.

The term "$C_{1-6}$-alkyl acylamino", as used herein refers to a $C_{1-6}$ alkyl substituted by an acylamino as defined hereabove.

The term "alkylene", as used herein, represents a group of formula —$(CH_2)_x$— in which x is comprised between 1 and 10, preferably comprised between 2 and 8, more preferably comprised between 2 and 6.

The term "methylene" as used herein represents a group of formula —$CH_2$—.

The term "aryl" as used herein, refers to an unsaturated aromatic carbocyclic group of from 6 to 14 carbon atoms having a single ring (e.g., phenyl) or multiple condensed rings (e.g., naphthyl). Preferred aryl include phenyl, 4-fluorophenyl, 4-chlorophenyl, 3-methoxyphenyl, naphthyl, phenantrenyl and the like.

The term "$C_{1-6}$-alkyl aryl", as used herein, refers to a group of formula —$R^d$-aryl in which $R^d$ is a $C_{1-6}$ alkyl. Preferred "$C_{1-6}$-alkyl aryl" are benzyl, 4-fluorobenzyl and 4-chlorobenzyl.

The term "$C_{2-6}$-alkenyl aryl", as used herein, refers to a $C_{2-6}$ alkenyl having an aryl substitutent.

The term "$C_{2-6}$-alkynyl aryl", as used herein, refers to a $C_{2-6}$ alkynyl having an aryl substitutent.

The term "heteroaryl" as used herein represents an aryl group as defined here above wherein one or more of the carbon atoms have been replaced by a heteroatom as defined herein. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo [1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl. Preferred heteroaryls are 2H-tetrazolyl, furyl and pyridinyl.

The term "$C_{1-6}$-alkyl heteroaryl" refers to a $C_{1-6}$ alkyl having a heteroaryl substituent as defined hereabove. Examples include 2-furylmethyl, (2-methyl-1H-imidazol-1yl)methyl and (1H-1,2,4-triazol-1-yl)methyl.

The term "$C_{2-6}$-alkenyl heteroaryl", as used herein, refers to a $C_{2-6}$ alkenyl having a heteroaryl substitutent.

The term "$C_{2-6}$-alkynyl heteroaryl", as used herein, refers to a $C_{2-6}$ alkynyl having a heteroaryl substitutent.

The term "alkoxy", as used herein, represents a group of formula —$OR^a$ wherein $R^a$ is "$C_{1-6}$ alkyl", "$C_{2-6}$ alkenyl", "$C_{2-6}$ alkynyl", "$C_{3-8}$ cycloalkyl", "heterocycloalkyl", "aryl", "heteroaryl", "$C_{1-6}$-alkyl aryl" or "$C_{1-6}$-alkyl heteroaryl", "$C_{2-6}$-alkenyl aryl", "$C_{2-6}$-alkenyl heteroaryl", "$C_{2-6}$-alkynyl aryl", "$C_{2-6}$-alkynyl heteroaryl", "$C_{1-6}$-alkyl cycloalkyl" or "$C_{1-6}$-alkyl heterocycloalkyl". Preferred alkoxy group is methoxy.

The term "$C_{1-6}$-alkyl alkoxy" as used herein refers to a $C_{1-6}$-alkyl substituted by an alkoxy as defined here above.

The term "carbonyl", as used herein represents a group of formula C=O.

The term "$C_{1-6}$-alkyl carboxy", as used herein refers to a $C_{1-6}$-alkyl substituted by a carboxy group including 2-carboxyethyl and the like.

The term "acyl" as used herein, refers to the group —C(O) $R^e$ wherein $R^e$ includes H, "$C_{1-6}$ alkyl", "$C_{2-6}$ alkenyl", "$C_{2-6}$ alkynyl", "$C_{3-8}$ cycloalkyl", "heterocycloalkyl", "aryl", "heteroaryl", "$C_{1-6}$-alkyl aryl" or "$C_{1-6}$-alkyl heteroaryl", "$C_{2-6}$-alkenyl aryl", "$C_{2-6}$-alkenyl heteroaryl", "$C_{2-6}$-alkynyl aryl", "$C_{2-6}$-alkynylheteroaryl", "$C_{1-6}$-alkyl cycloalkyl" and "$C_{1-6}$-alkyl heterocycloalkyl".

The term "$C_{1-6}$-alkyl acyl" as used herein refers to a $C_{1-6}$ alkyl having an acyl substituent as defined here above, including 2-acetylethyl and the like.

The term "$C_{3-8}$-cycloalkyl acyl" as used herein refers to a $C_{3-8}$ alkyl having an acyl substituent as defined here above.

The term "aryl acyl" refers to an aryl group having an acyl substituent as defined here above.

The term "heteroaryl acyl" refers to a heteroaryl group having an acyl substituent as defined here above.

The term "heterocycloalkyl acyl" refers to a heterocycloalkyl group having an acyl substituent as defined here above.

The term "acyloxy" refers to the group —OC(O)$R^f$ wherein $R^f$ includes H, "$C_{1-6}$ alkyl", "$C_{2-6}$ alkenyl", "$C_{2-6}$ alkynyl", "$C_{3-8}$ cycloalkyl", "heterocycloalkyl", "heteroaryl", "$C_{1-6}$-alkyl aryl", "$C_{1-6}$-alkyl heteroaryl", "$C_{2-6}$-alkenyl aryl", "$C_{2-6}$-alkenyl heteroaryl", "$C_{2-6}$-alkynyl aryl", "$C_{2-6}$-alkynyl heteroaryl", "$C_{2-6}$-alkyl cycloalkyl" or "$C_{1-6}$-alkyl heterocycloalkyl".

The term "$C_{1-6}$-alkyl acyloxy" refers to a $C_{1-6}$ alkyl having an acyloxy as defined here above as substituent.

The term "alkoxycarbonyl" refers to the group —C(O)$OR^g$ wherein $R^g$ includes H, "$C_{1-6}$ alkyl", "$C_{2-6}$ alkenyl", "$C_{2-6}$ alkynyl", "$C_{3-8}$ cycloalkyl", "heterocycloalkyl", "aryl", "heteroaryl", "$C_{1-6}$-alkyl aryl" or "$C_{1-6}$-alkyl heteroaryl", "$C_{2-6}$-alkenyl aryl", "$C_{2-6}$-alkenyl heteroaryl", "$C_{2-6}$-alkynyl aryl", "$C_{2-6}$-alkynylheteroaryl", "$C_{2-6}$-alkyl cycloalkyl", "$C_{1-6}$-alkyl heterocycloalkyl". Preferred alkoxycarbonyl are methoxycarbonyl, ethoxycarbonyl and hydroxycarbonyl.

The term "$C_{1-6}$-alkyl alkoxycarbonyl" refers to a refers to a $C_{1-6}$ alkyl having a alkoxycarbonyl as defined here above as substituent.

The term "ureido" as used herein refers to a group of formula —$NR^iC(O)NR^bR^c$ wherein $R^i$ is as defined hereabove for $R^b$ or $R^c$, and $R^b$ and $R^c$ are as defined here above for the amino group.

The term "$C_{1-6}$-alkyl ureido" as used herein refers to a $C_{1-6}$ alkyl substituted by a ureido as defined here above.

The term "carbamate", as used herein, refers to a group of formula —$NR^bC(O)OR^c$ wherein $R^b$ and $R^c$ are as defined here above for the amino group.

The term "$C_{1-6}$-alkyl carbamate" as used herein refers to a $C_{1-6}$-alkyl substituted by a carbamate as defined here above.

The term "sulfonyl" refers to group of formula "—$SO_2$—$R^h$" wherein $R^h$ is selected from H, "aryl", "heteroaryl", "$C_{1-6}$ alkyl", "$C_{1-6}$ alkyl" substituted with halogens, e.g., an —$SO_2$—$CF_3$ group, "$C_{2-6}$ alkenyl", "$C_{2-6}$ alkynyl", "$C_{3-8}$ cycloalkyl", "heterocycloalkyl", "aryl", "heteroaryl", "$C_{1-6}$-alkyl aryl" or "$C_{1-6}$-alkyl heteroaryl", "$C_{2-6}$-alkenyl aryl", "$C_{2-6}$-alkenyl heteroaryl", "$C_{2-6}$-alkynyl aryl", "$C_{2-6}$ alkynyl heteroaryl", "$C_{1-6}$-alkyl cycloalkyl", "$C_{1-6}$-alkyl heterocycloalkyl".

The term "sulfinyl" refers to group of formula "—$S(O)$—$R^j$" wherein $R^j$ is selected from H, "aryl", "heteroaryl", "$C_{1-6}$ alkyl", "$C_{1-6}$ alkyl" substituted with halogens, e.g., an —$SO$—$CF_3$ group, "$C_{2-6}$ alkenyl", "$C_{2-6}$ alkynyl", "$C_{3-8}$ cycloalkyl", "heterocycloalkyl", "aryl", "heteroaryl", "$C_{1-6}$-alkyl aryl" or "$C_{1-6}$-alkyl heteroaryl", "$C_{2-6}$-alkenyl aryl", "$C_{2-6}$-alkenyl heteroaryl", "$C_{2-6}$-alkynyl aryl", "$C_{2-6}$-alkynyl heteroaryl", "$C_{1-6}$-alkyl cycloalkyl", "$C_{1-6}$-alkyl heterocycloalkyl".

The term "sulfanyl" refers to group of formula "—S—$R^k$" wherein $R^k$ is selected from H, "aryl", "heteroaryl", "$C_{1-6}$ alkyl", "$C_{1-6}$ alkyl" substituted with halogens, e.g., an —S—$CF_3$ group, "$C_{2-6}$ alkenyl", "$C_{2-6}$ alkynyl", "$C_{3-8}$ cycloalkyl", "heterocycloalkyl", "aryl", "heteroaryl", "$C_{1-6}$-alkyl aryl" or "$C_{1-6}$-alkyl heteroaryl", "$C_{2-6}$-alkenyl aryl", "$C_{2-6}$-alkenyl heteroaryl", "$C_{2-6}$-alkynyl aryl", "$C_{2-6}$-alkynyl heteroaryl", "$C_{1-6}$-alkyl cycloalkyl", "$C_{1-6}$-alkyl heterocycloalkyl".

The term "$C_{1-6}$-alkyl sulfonyl" refers to $C_{1-6}$-alkyl groups having a sulfonyl substituent, including 2-(methylsulfonyl)ethyl and the like.

The term "$C_{1-6}$-alkyl sulfinyl" refers to $C_{1-6}$-alkyl groups having a sulfinyl as defined here above as substituent, including 2-(methylsulfinyl)ethyl and the like.

The term "$C_{1-6}$-alkyl sulfanyl" refers to $C_{1-6}$-alkyl groups having a sulfanyl as defined here above substituent.

The term "sulfonylamino" as used herein refers to a group of formula —$NR^bSO_2$—$R^c$ wherein $R^b$ and $R^c$ are as defined here above for the amino group.

The term "$C_{1-6}$-alkyl sulfonylamino" refers to $C_{1-6}$-alkyl groups having a sulfonylamino as defined here above as substituent.

The term "aminosulfonyl" as used herein refers to a group of formula —$SO_2$—$NR^bR^c$ wherein $R^b$ and $R^c$ are as defined here above for the amino group.

The term "$C_{1-6}$-alkyl aminosulfonyl" refers to $C_{1-6}$-alkyl groups having an aminosulfonyl as defined here above as substituent.

The term "ester", as used herein represents a group of formula —COOR$^e$, in which R$^e$ is a C$_{1-4}$ alkyl.

The term "carboxylic acid" as used herein represents a group of formula —COOH.

Unless otherwise constrained by the definition of the individual substituent, the above set out groups including "alkyl", "alkenyl", "alkynyl", "aryl" and "heteroaryl" and the like can optionally be substituted with from 1 to 5 substituents selected from the group consisting of "C$_{1-6}$ alkyl", "C$_{2-6}$ alkenyl", "C$_{2-6}$ alkynyl", "C$_{3-8}$ cycloalkyl", "heterocycloalkyl", "C$_{1-6}$-alkyl aryl", "C$_{1-6}$-alkyl heteroaryl", "C$_{1-6}$-alkyl cycloalkyl", "C$_{1-6}$-alkyl heterocycloalkyl", "amino", "acyl", "acyloxy", "acylamino", "aminocarbonyl", "alkoxycarbonyl", "ureido", "carbamate", "aryl", "heteroaryl", "sulfinyl", "sulfonyl", "alkoxy", "sulfanyl", "halogen", "carboxylic acid", trihalomethyl, cyano, hydroxy, mercapto, nitro, alkylene and the like.

In a particular embodiment, the C$_{1-6}$ alkyl of L is not substituted by a hydroxy group.

In a further particular embodiment when R$^{11}$ is a C$_{1-6}$ alkyl, said alkyl is unsubstituted.

In a particular embodiment of compounds of formula (I), R$^4$ is hydrogen and R$^5$ is —O-L.

Generally, the present invention relates to compounds of formula (I), geometrical isomers, enantiomers, diastereoisomers, pharmaceutically acceptable salts and all possible mixtures thereof,

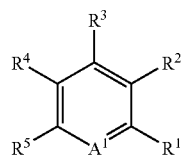

(I)

wherein
A$^1$ is CH, C(CH$_3$), C-halogen or N;
R$^1$ is hydrogen or halogen;
R$^2$ is

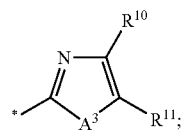

(II')

A$^3$ is O or S;
R$^3$ is hydrogen, halogen, C$_{1-4}$ alkyl or C$_{1-4}$ alkoxy;
R$^4$ is hydrogen, halogen, C$_{1-4}$ alkyl, C$_{1-4}$ alkoxy or —O—(CH$_2$)$_n$—NR$^{12a}$R$^{12b}$;
R$^5$ is hydrogen or —O—(CH$_2$)$_m$—NR$^{13a}$R$^{13b}$;
R$^{10}$ is hydrogen, C$_{1-8}$ alkyl or —(CH$_2$)$_w$—(C=O)$_t$—NR$^{15}$R$^{16}$;
R$^{11}$ is hydrogen, C$_{1-8}$ alkyl, ester, carboxylic acid, halogen, or —(CH$_2$)$_r$—(C=O)$_z$—NR$^{17}$R$^{18}$;
R$^{12a}$ and R$^{12b}$ are linked together to form a C$_{3-6}$ alkylene, each methylene of the alkylene being optionally substituted by one or two C$_{1-4}$ alkyl;
R$^{13a}$ and R$^{13b}$ are linked together to form a C$_{3-6}$ alkylene, each methylene of the alkylene being optionally substituted by one or two C$_{1-4}$ alkyl, an amino group or a C$_{1-6}$ alkyl amino, one methylene being optionally replaced by a nitrogen atom, said nitrogen atom being optionally substituted by a C$_{1-8}$ alkyl, C$_{3-6}$ cycloalkyl or C$_{1-6}$ alkyl amino; or one methylene of the alkylene being linked with a second methylene of the alkylene to form a C$_{3-6}$ alkylene;
R$^{15}$ is hydrogen or a C$_{1-8}$ alkyl;
R$^{16}$ is aryl, heteroaryl, C$_{1-8}$ alkyl, C$_{1-6}$ alkyl cycloalkyl, C$_{3-6}$ cycloalkyl, C$_{1-6}$ alkyl aryl or CH$_2$-heteroaryl;
or R$^{15}$ and R$^{16}$ are linked together to form a C$_{3-6}$ alkylene, each methylene of the alkylene being optionally substituted by one or two C$_{1-4}$ alkyl or by one or two halogen; or one methylene of the alkylene being optionally substituted by an alkylamine or by an C$_{1-6}$ alkyl aryl; one methylene of the alkylene being optionally replaced by a nitrogen atom or an oxygen atom, said nitrogen atom being optionally substituted by a C$_{1-8}$ alkyl or a C$_{3-6}$ cycloalkyl; or one methylene of the alkylene being optionally replaced by a C$_{3-8}$ cycloalkyl or a carbonyl and another methylene being optionally substituted by an alkylamine; or one methylene of the alkylene being linked with a second methylene of the alkylene to form a C$_{3-6}$ alkylene; or R$^{15}$ and R$^{16}$ are linked together to form with N an unsaturated 5- or 6-membered heteroaryl optionally substituted by a C$_{1-4}$ alkyl;
R$^{17}$ is hydrogen or a C$_{1-8}$ alkyl;
R$^{18}$ is C$_{1-8}$ alkyl, C$_{1-6}$ alkyl aryl or C$_{1-6}$ alkyl cycloalkyl;
or R$^{17}$ and R$^{18}$ are linked together to form a C$_{3-6}$ alkylene, each methylene of the alkylene being optionally substituted by one or two C$_{1-4}$ alkyl or by one or two halogen, one methylene of the alkylene being optionally replaced by a carbonyl, a nitrogen atom or an oxygen atom, said nitrogen atom being optionally substituted by a C$_{1-8}$ alkyl or C$_{3-6}$ cycloalkyl;
n and m are independently an integer comprised between 2 and 8;
w and r are independently an integer comprised between 0 and 4;
t and z are independently an integer equal to 0 or 1;
with the proviso that R$^4$ is —O—(CH$_2$)$_n$—NR$^{12a}$R$^{12b}$, when R$^5$ is hydrogen and that R$^5$ is —O—(CH$_2$)$_m$—NR$^{13a}$R$^{13b}$, when R$^4$ is hydrogen, halogen, C$_{1-4}$ alkyl or C$_{1-4}$ alkoxy;
with the proviso that when R$^{11}$ is an ester or a carboxylic acid, R$^4$ is hydrogen, halogen, C$_{1-4}$ alkyl or C$_{1-4}$ alkoxy;
with the proviso that at least one of w and t is different from 0; and
with the proviso that at least one of r and z is different from 0.

Usually each CH$_2$ in —O—(CH$_2$)$_n$—NR$^{12a}$R$^{12b}$ or —O—(CH$_2$)$_m$—NR$^{13a}$R$^{13b}$ may be unsubstituted or substituted by one or more C$_{1-4}$ alkyl.

Usually, A$^1$ is CH, C(CH$_3$), C—F or N.

More preferably A$^1$ is CH, C—F or N. Most preferably, A$^1$ is CH or C—F. In a particular embodiment A$^1$ is CH.

Usually, A$^3$ is O or S. In a particular embodiment A$^3$ is O. In another particular embodiment A$^3$ is S.

Usually in an embodiment, R$^1$ is hydrogen or fluorine.

Preferably, R$^1$ is hydrogen.

Usually in one embodiment, R$^3$ is hydrogen, halogen or C$_{1-4}$ alkyl. Usually, in another embodiment, R$^3$ is hydrogen, fluorine, methyl or methoxy.

Preferably, R$^3$ is hydrogen or fluorine or methyl. Most preferably, R$^3$ is hydrogen or methyl.

Usually, in one embodiment, R$^4$ is hydrogen, halogen, C$_{1-4}$ alkyl, C$_{1-4}$ alkoxy, or —O—(CH$_2$)$_n$—NR$^{12a}$R$^{12b}$. Usually, in another embodiment, R$^4$ is hydrogen, bromine, fluorine, chlorine, methyl, methoxy, trifluoromethyl or —O—(CH$_2$)$_n$—NR$^{12a}$R$^{12b}$ each CH$_2$ in —O—(CH$_2$)$_n$—NR$^{12a}$R$^{12b}$ being optionally substituted by one or two methyl.

Preferably, R$^4$ is hydrogen, chlorine, bromine, fluorine, methyl, methoxy or —O—(CH$_2$)$_n$—NR$^{12a}$R$^{12b}$. More preferably, R$^4$ is hydrogen, chlorine, bromine, fluorine or methoxy. Most preferably, R$^4$ is hydrogen or fluorine.

Preferably, —NR$^{12a}$R$^{12b}$ is 1-pyrrolidinyl.

Usually, n is comprised between 2 and 4. Preferably, n is equal to 3.

Usually in one embodiment, R$^5$ is hydrogen or —O—(CH$_2$)$_m$—NR$^{13a}$R$^{13b}$. Usually in another embodiment, R$^5$ is hydrogen or —O—(CH$_2$)$_m$—NR$^{13a}$R$^{13b}$, each CH$_2$ in —O—(CH$_2$)$_m$—NR$^{13a}$R$^{13b}$ being optionally substituted by one or two methyl.

Preferably, R$^5$ is hydrogen or —O—(CH$_2$)$_m$—NR$^{13a}$R$^{13b}$. More preferably, R$^5$ is —O—(CH$_2$)$_m$—NR$^{13a}$R$^{13b}$.

Preferably, —NR$^{13a}$R$^{13b}$ is selected from the group consisting of 1-piperidinyl, 1-pyrrolidinyl, 2-methylpyrrolidin-1-yl, (2S)-2-methylpyrrolidin-1-yl, (2R)-2-methylpyrrolidin-1-yl, 4-isopropylpiperazin-1-yl, 4-methylpiperidin-1-yl, 2-methylpiperidin-1-yl, 2-(pyrrolidin-1-ylmethyl)pyrrolidin-1-yl, 4-cyclopentylpiperazin-1-yl, 3-(dimethylamino)pyrrolidin-1-yl, 4-(2-pyrrolidin-1-ylethyl)piperazin-1-yl, 1-azepanyl, 2,6-dimethylpiperidin-1-yl, (2S)-2-(pyrrolidin-1-ylmethyl)pyrrolidin-1-yl, 2-isobutylpyrrolidin-1-yl, 2-ethylpyrrolidinyl or (4aR,8aS)-octahydroisoquinolin-2-(1H)-yl.

Most preferably, —NR$^{13a}$R$^{13b}$ is selected from the group consisting of 1-piperidinyl, 2-methylpyrrolidin-1-yl, (2S)-2-methylpyrrolidin-1-yl, (2R)-2-methylpyrrolidin-1-yl, 4-methylpiperidin-1-yl, 2-methylpiperidin-1-yl, 2-(pyrrolidin-1-ylmethyl)pyrrolidin-1-yl, (2S)-2-(pyrrolidin-1-ylmethyl)pyrrolidin-1-yl, 2-isobutylpyrrolidin-1-yl, 2-ethylpyrrolidin-1-yl, (4aR,8aS)-octahydroisoquinolin-2-(1H)-yl, 1-azepanyl, and 2,6-dimethylpiperidin-1-yl.

In a particular embodiment, —NR$^{13a}$R$^{13b}$ is 2-methylpyrrolidin-1-yl, (2S)-2-methylpyrrolidin-1-yl or (2R)-2-methylpyrrolidin-1-yl.

Usually, m is comprised between 2 and 5. Preferably, m is comprised between 2 and 4. Most preferably, m is equal to 3 or 4. In a particular embodiment, m is equal to 3.

Preferably, R$^{10}$ is hydrogen, methyl or —(CH$_2$)$_w$—(C═O)$_t$—NR$^{15}$R$^{16}$.

Most preferably, R$^{10}$ is methyl or —(CH$_2$)$_w$—(C═O)$_t$—NR$^{15}$R$^{16}$. In a particular embodiment, R$^{10}$ is methyl.

Preferably —NR$^{15}$R$^{16}$ is selected from the group consisting of 1-piperidinyl, 2-methylpyrrolidin-1-yl, 1-pyrrolidinyl, 1-azepanyl, 4-methylpiperidin-1-yl, 2-methylpiperidin-1-yl, (3,5-dimethyl)piperidin-1-yl, hexyl(methyl)amino, benzyl(methyl)amino, (2-methoxy-1-methylethyl)amino, 2-azaspiro[5.5]undec-2-yl, 7,8-dimethyl-1 azaspiro[4.4]non-1-yl, 2-oxopyrrolidin-1-yl, anilino, 2-methyl-1H-imidazol-1-yl, 1H-1,2,4-triazol-1-yl, [1-(hydroxymethyl)-3-methylbutyl]amino, cyclopentylamino, (1,3-dimethylbutyl)amino, (cyclopropylmethyl)(propyl)amino, 2,6-dimethylpiperidin-1-yl, (2-furylmethyl)(methyl)amino, sec-butyl(propyl)amino, 4-benzylpiperidine-1-yl, 4-cyclopentylpiperazin-1-yl, 4-morpholin-1-yl, (4-fluorobenzyl)amino, (4-chlorobenzyl)amino, 2-oxo-piperidin-1-yl, (5S)-2-oxo-(5-pyrrolidin-1-yl-methyl)pyrrolidin-1-yl, (4-fluorophenyll)amino, (4aR,8aS)octahydroisoquinoline-2-(1H)-yl, (2S)-2-(pyrrolidin-1-ylmethyl)pyrrolidin-1-yl, (2-methyl-2H-tetrazol-5-yl)amino, (3-methoxyphenyl)amino, (pyridin-3-yl)amino, (2S)-2-(morpholin-4-ylmethyl)pyrrolidin-1-yl, (2S)-2-(morpholin-4-ylmethyl)-5-oxopyrrolidin-1-yl, benzylamino and 4,4-difluoropiperidin-1-yl.

More preferably —NR$^{15}$R$^{16}$ is selected from the group consisting of 1-piperidinyl, 2-methylpyrrolidin-1-yl, 1-pyrrolidinyl, 1-azepanyl, 2-methylpiperidin-1-yl, (3,5-dimethyl) piperidin-1-yl, hexyl(methyl)amino, benzyl(methyl)amino, 2-azaspiro[5.5]undec-2-yl, 7,8-dimethyl-1azaspiro[4.4]non-1-yl, 2-oxopyrrolidin-1-yl, anilino, 2-methyl-1H-imidazol-1-yl, 1H-1,2,4-triazol-1-yl, [1-(hydroxymethyl)-3-methylbutyl]amino, cyclopentylamino, (1,3-dimethylbutyl)amino, (cyclopropylmethyl)(propyl)amino, 2,6-dimethylpiperidin-1-yl, (2-furylmethyl)(methyl)amino, sec-butyl(propyl)amino, 4-benzylpiperidin-1-yl, 4-cyclopentylpiperazin-1-yl, 4-morpholinyl, (4-fluorobenzyl)amino, (4-chlorobenzyl)amino, 2-oxo-piperidin-1-yl, (5S)-2-oxo-5-pyrrolidin-1-yl, (4-fluorophenyl)amino, (4aR,8aS)-octahydroisoquinolin-2 (1H)-yl, (2S)-2-(pyrrolidin-1-ylmethyl)pyrrolidin-1-yl, (3-methoxyphenyl)amino, (pyridin-3-yl)amino, benzylamino and 4,4-difluoropiperidin-1-yl;

Most preferably, —NR$^{15}$R$^{16}$ is selected from the group consisting of 1-piperidinyl, 1-pyrrolidinyl, 2-methylpyrrolidin-1-yl, 7,8-dimethyl-1azaspiro[4.4]non-1-yl, 1H-1,2,4-triazol-1-yl, [1-(hydroxymethyl)-3-methylbutyl]amino, 2,6-dimethylpiperidin-1-yl, benzylamino, sec-butyl(propyl)amino, (4aR,8aS)-octahydroisoquinolin-2(1H)-yl and (2S)-2-(pyrrolidin-1-ylmethyl)pyrrolidin-1-yl. In a particular embodiment according to the present invention, —NR$^{15}$R$^{16}$ is 1-piperidinyl.

Preferably, w is an integer equal to 0, 1 or 2. In a particular embodiment w is equal to 1.

In a particular embodiment, t is an integer equal to 0. In another particular embodiment, t is an integer equal to 1.

Preferably, R$^{11}$ is hydrogen, methyl, COOCH$_3$, COOH, bromine or —(CH$_2$)$_r$—(C═O)$_z$—NR$^{17}$R$^{18}$. More preferably, R$^{11}$ is hydrogen, methyl, COOCH$_3$, bromine or —(CH$_2$)$_r$—(C═O)$_z$—NR$^{17}$R$^{18}$. Most preferably, R$^{11}$ is hydrogen, COOCH$_3$, bromine or —(CH$_2$)$_r$—(C═O)$_z$—NR$^{17}$R$^{18}$. In a particular embodiment according to the present invention, R$^{11}$ is H or —(CH$_2$)$_r$—(C═O)$_z$—NR$^{17}$R$^{18}$.

Preferably, —NR$^{17}$R$^{18}$ is 1-piperidinyl, 2-oxopyrrolidin-1-yl, (cyclopropylmethyl)(propyl)amino, cyclopentylamino, benzylamino, (4-cyclopentyl)piperazin-1-yl, 4-morpholinyl or 4,4-difluoropiperidin-1-yl.

In a particular embodiment according to the present invention, —NR$^{17}$R$^{18}$ is 4-morpholinyl or 4,4-difluoropiperidin-1-yl.

Preferably, z is equal to 0 or 1. In a particular embodiment z is equal to 0. In another particular embodiment z is equal to 1.

Preferably, r is an integer equal to 0, 1 or 2. In a particular embodiment r is an integer equal to 0.

Preferably, when R$^{10}$ is —(CH$_2$)$_w$—(C═O)$_t$—NR$^{15}$R$^{16}$, R$^{11}$ is hydrogen, methyl, COOCH$_3$, COOH or bromine. In a particular embodiment according to the present invention when R$^{10}$ is —(CH$_2$)$_w$—(C═O)$_t$—NR$^{15}$R$^{16}$, R$^{11}$ is hydrogen.

Combinations of one or more of these preferred groups are especially preferred.

Usually in one embodiment, the present invention relates to compounds of formula (I), geometrical isomers, enantiomers, diastereoisomers, pharmaceutically acceptable salts and all possible mixtures thereof,

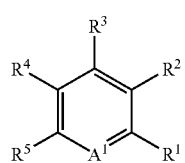

(I)

wherein
A$^1$ is CH, C(CH$_3$), C-halogen or N;

$R^1$ is hydrogen;
$R^2$ is

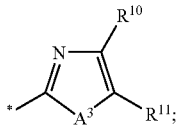

(II')

$A^3$ is O or S;
$R^3$ is hydrogen, halogen or $C_{1-4}$ alkyl;
$R^4$ is hydrogen, halogen, $C_{1-4}$ alkyl, $C_{1-4}$ alkoxy or —O—$(CH_2)_n$—$NR^{12a}R^{12b}$
$R^5$ is hydrogen or —O—$(CH_2)_m$—$NR^{13a}R^{13b}$;
$R^{10}$ is hydrogen, $C_{1-8}$ alkyl or —$(CH_2)_w$—(C=O)$_t$—$NR^{15}R^{16}$;
$R^{11}$ is hydrogen, $C_{1-8}$ alkyl, ester, carboxylic acid, halogen, or —$(CH_2)_r$—(C=O)$_z$—$NR^{17}R^{18}$;
$R^{12a}$ and $R^{12b}$ are linked together to form a $C_{3-6}$ alkylene, each methylene of the alkylene being optionally substituted by one or two $C_{1-4}$ alkyl;
$R^{13a}$ and $R^{13b}$ are linked together to form a $C_{3-6}$ alkylene, each methylene of the alkylene being optionally substituted by one or two $C_{1-4}$ alkyl, an amino group or an $C_{1-6}$ alkyl amino, one methylene being optionally replaced by a nitrogen atom, said nitrogen atom being optionally substituted by a $C_{1-8}$ alkyl, $C_{3-6}$ cycloalkyl or $C_{1-6}$ alkyl amino; or one methylene of the alkylene being linked with a second methylene of the alkylene to form a $C_{3-6}$ alkylene;
$R^{15}$ is hydrogen or a $C_{1-8}$ alkyl;
$R^{16}$ is aryl, heteroaryl, $C_{1-8}$ alkyl, $C_{3-6}$ cycloalkyl, $C_{1-6}$ alkyl cycloalkyl, $C_{1-6}$ alkyl aryl or a $CH_2$-heteroaryl;
or $R^{15}$ and $R^{16}$ are linked together to form a $C_{3-6}$ alkylene, each methylene of the alkylene being optionally substituted by one or two $C_{1-4}$ alkyl or by one or two halogen; or one methylene of the alkylene being optionally substituted by an alkylamine or by an $C_{1-6}$ alkyl aryl; one methylene of the alkylene being optionally replaced by a nitrogen atom or an oxygen atom, said nitrogen atom being optionally substituted by a $C_{1-8}$ alkyl or $C_{3-6}$ cycloalkyl; or one methylene of the alkylene being optionally replaced by a $C_{3-8}$ cycloalkyl or a carbonyl and another methylene being optionally substituted by an alkylamine; or one methylene of the alkylene being linked with a second methylene of the alkylene to form a $C_{3-6}$ alkylene; or $R^{15}$ and $R^{16}$ are linked together to form with N an unsaturated 5- or 6-membered heteroaryl optionally substituted by a $C_{1-4}$ alkyl;
$R^{17}$ is hydrogen or a $C_{1-8}$ alkyl;
$R^{18}$ is $C_{1-8}$ alkyl, $C_{1-6}$ alkyl cycloalkyl or a $C_{1-6}$ alkyl aryl;
or $R^{17}$ and $R^{18}$ are linked together to form a $C_{3-6}$ alkylene, each methylene of the alkylene being optionally substituted by one or two $C_{1-4}$ alkyl or by one or two halogen, one methylene of the alkylene being optionally replaced by a carbonyl, a nitrogen atom or an oxygen atom, said nitrogen atom being optionally substituted by a $C_{1-8}$ alkyl or $C_{3-6}$ cycloalkyl;
n and m are independently an integer comprised between 2 and 8;
w and r are independently an integer comprised between 0 and 4;
t and z are independently an integer equal to 0 or 1;
with the proviso that $R^4$ is —O—$(CH_2)_n$—$NR^{12a}R^{12b}$, when $R^5$ is hydrogen and that $R^5$ is —O—$(CH_2)_m$—$NR^{13a}R^{13b}$, when $R^4$ is hydrogen, halogen, trifluoromethyl, $C_{1-4}$ alkyl or $C_{1-4}$ alkoxy;

with the proviso that when $R^{11}$ is an ester or a carboxylic acid, $R^4$ is hydrogen, halogen, $C_{1-4}$ alkyl or $C_{1-4}$ alkoxy.

with the proviso that at least one of w and t is different from 0; and with the proviso that at least one of r and z is different from 0.

Usually in another embodiment, the invention relates to compounds of formula (I), geometrical isomers, enantiomers, diastereoisomers, pharmaceutically acceptable salts and all possible mixtures thereof,

(I)

wherein
$A^1$ is CH, C(CH$_3$), C-halogen or N;
$R^1$ is hydrogen or fluorine;
$R^2$ is

(II')

$A^3$ is O or S;
$R^3$ is hydrogen, fluorine, methyl or methoxy;
$R^4$ is hydrogen, bromine, fluorine, chlorine, methyl, methoxy, trifluoromethyl or —O—$(CH_2)_n$—$NR^{12a}R^{12b}$, each $CH_2$ in —O—$(CH_2)_n$—$NR^{12a}R^{12b}$ being optionally substituted by one or two methyl;
$R^5$ is hydrogen or —O—$(CH_2)_m$—$NR^{13a}R^{13b}$, each $CH_2$ in —O—$(CH_2)_m$—$NR^{13a}R^{13b}$ being optionally substituted by one or two methyl;
$R^{10}$ is hydrogen, $C_{1-8}$ alkyl or —$(CH_2)_w$—(C=O)$_t$—$NR^{15}R^{16}$;
$R^{11}$ is hydrogen, $C_{1-8}$ alkyl, ester, carboxylic acid, halogen, or —$(CH_2)_r$—(C=O)$_z$—$NR^{17}R^{18}$;
$R^{12a}$ and $R^{12b}$ are linked together to form a $C_{3-6}$ alkylene, each methylene of the alkylene being optionally substituted by one or two $C_{1-4}$ alkyl;
$R^{13a}$ and $R^{13b}$ are linked together to form a $C_{3-6}$ alkylene, each methylene of the alkylene being optionally substituted by one or two $C_{1-4}$ alkyl, an amino group or $C_{1-6}$ alkyl amino, one methylene being optionally replaced by a nitrogen atom, said nitrogen atom being optionally substituted by a $C_{1-8}$ alkyl, a $C_{3-6}$ cycloalkyl or $C_{1-6}$ alkyl amino; or one methylene of the alkylene being linked with a second methylene of the alkylene to form a $C_{3-6}$ alkylene;
$R^{15}$ is hydrogen or a $C_{1-8}$ alkyl;
$R^{16}$ is aryl, heteroaryl, $C_{1-8}$ alkyl, $C_{3-6}$ cycloalkyl, $C_{1-6}$ alkyl cycloalkyl, $C_{1-6}$ alkyl aryl or a $CH_2$-heteroaryl;
or $R^{15}$ and $R^{16}$ are linked together to form a $C_{3-6}$ alkylene, each methylene of the alkylene being optionally substituted by one or two $C_{1-4}$ alkyl or by one or two halogen; or one methylene of the alkylene being optionally substituted by an alkylamine or by $C_{1-6}$ alkyl aryl; one methylene of the alkylene being optionally replaced by a nitrogen atom or an oxygen atom, said nitrogen atom being optionally substituted by a $C_{1-8}$ alkyl or $C_{3-6}$ cycloalkyl; or one methylene of the alkylene being optionally replaced by a $C_{3-8}$ cycloalkyl or a carbonyl and another methylene being optionally substituted by an alkylamine; or one methylene of the alkylene being linked with a second methylene of the alkylene to form a $C_{3-6}$ alkylene; or $R^{15}$ and $R^{16}$ are linked together to form with N an unsaturated 5- or 6-membered heteroaryl optionally substituted by a $C_{1-4}$ alkyl;

$R^{17}$ is hydrogen or a $C_{1-8}$ alkyl;

$R^{18}$ is $C_{1-8}$ alkyl, $C_{1-6}$ alkyl cycloalkyl or $C_{1-6}$ alkyl aryl;

or $R^{17}$ and $R^{18}$ are linked together to form a $C_{3-6}$ alkylene, each methylene of the alkylene being optionally substituted by one or two $C_{1-4}$ alkyl or by one or two halogen, one methylene of the alkylene being optionally replaced by a carbonyl, a nitrogen atom or an oxygen atom, said nitrogen atom being optionally substituted by a $C_{1-8}$ alkyl or $C_{3-6}$ cycloalkyl;

n and m are independently an integer comprised between 2 and 8;

w and r are independently an integer comprised between 0 and 4;

t and z are independently an integer equal to 0 or 1;

with the proviso that $R^4$ is $-O-(CH_2)_n-NR^{12a}R^{12b}$, when $R^5$ is hydrogen and that $R^5$ is $-O-(CH_2)_m-NR^{13a}R^{13b}$, when $R^4$ is hydrogen, bromine, fluorine, chlorine, methyl, methoxy, trifluoromethyl;

with the proviso that when $R^{11}$ is an ester or a carboxylic acid, $R^4$ is hydrogen, halogen, $C_{1-4}$ alkyl or $C_{1-4}$ alkoxy;

with the proviso that at least one of w and t is different from 0; and with the proviso that at least one of r and z is different from 0.

Preferably, the invention relates to compounds of formula (I), geometrical isomers, enantiomers, diastereoisomers, pharmaceutically acceptable salts and all possible mixtures thereof,

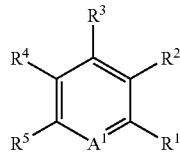

(I)

wherein
$A^1$ is CH, C(CH$_3$), C—F or N;
$R^1$ is hydrogen;
$R^2$ is

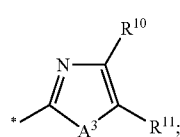

(II')

$A^3$ is O or S;
$R^3$ is hydrogen, fluorine or methyl;
$R^4$ is hydrogen, chlorine, bromine, fluorine, methyl, methoxy or $-O-(CH_2)_n-NR^{12a}R^{12b}$;
$R^5$ is hydrogen or $-O-(CH_2)_m-NR^{13a}R^{13b}$;
$R^{10}$ is hydrogen, methyl or $-(CH_2)_w-(C=O)_t-NR^{15}R^{16}$;

$R^{11}$ is hydrogen, methyl, COOCH$_3$, COOH, bromine or $-(CH_2)_r-(C=O)_z-NR^{17}R^{18}$;

$-NR^{12a}R^{12b}$ is 1-pyrrolidinyl.

$-NR^{13a}R^{13b}$ is selected from the group consisting of 1-piperidinyl, 1-pyrrolidinyl, 2-methylpyrrolidin-1-yl, (2S)-2-methylpyrrolidin-1-yl, (2R)-2-methylpyrrolidin-1-yl, 4-isopropylpiperazin-1-yl, 4-methylpiperidin-1-yl, 2-methylpiperidin-1-yl, 2-(pyrrolidin-1-ylmethyl)pyrrolidin-1-yl, 4-cyclopentylpiperazin-1-yl, 3-(dimethylamino)pyrrolidin-1-yl, 4-(2-pyrrolidin-1-ylethyl)piperazin-1-yl, 1-azepanyl, 2,6-dimethylpiperidin-1-yl, (2S)-2-(pyrrolidin-1-ylmethyl)pyrrolidin-1-yl, 2-isobutylpyrrolidin-1-yl, 2-ethylpyrrolidinyl and (4aR,8aS)-octahydroisoquinolin-2-(1H)-yl.

$-NR^{15}R^{16}$ is selected from the group consisting of 1-piperidinyl, 2-methylpyrrolidin-1-yl, 1-pyrrolidinyl, 1-azepanyl, 4-methylpiperidin-1-yl, 2-methylpiperidin-1-yl, (3,5-dimethyl)piperidin-1-yl, hexyl(methyl)amino, benzyl(methyl)amino, (2-methoxy-1-methylethyl)amino, 2-azaspiro[5.5]undec-2-yl, 7,8-dimethyl-1azaspiro[4.4]non-1-yl, 2-oxopyrrolidin-1-yl, anilino, 2-methyl-1H-imidazol-1-yl, 1H-1,2,4-triazol-1-yl, [1-(hydroxymethyl)-3-methylbutyl]amino, cyclopentylamino, (1,3-dimethylbutyl)amino, (cyclopropylmethyl)(propyl)amino, 2,6-dimethylpiperidin-1-yl, (2-furylmethyl)(methyl)amino, sec-butyl(propyl)amino, 4-benzylpiperidin-1-yl, 4-cyclopentylpiperazin-1-yl, 4-morpholinyl, (4-fluorobenzyl)amino, (4-chlorobenzyl)amino, 2-oxo-piperidin-1-yl, (5S)-2-oxo-(5-pyrrolidin-1-ylmethyl)pyrrolidin-1-yl, (4-fluorophenyl)amino, (4aR,8aS)-octahydroisoquinoline-2(1H)-yl, (2S)-2-(pyrrolidin-1-ylmethyl)pyrrolidin-1-yl, (2-methyl-2H-tetrazol-5-yl)amino, (3-methoxyphenyl)amino, (pyridin-3-yl)amino, (2S)-2-(morpholin-4-ylmethyl)pyrrolidin-1-yl, (2S)-2-(morpholin-4-ylmethyl)-5-oxopyrrolidin-1-yl, benzylamino and 4,4-difluoropiperidin-1-yl.

$-NR^{17}R^{18}$ is 1-piperidinyl, 2-oxopyrrolidin-1-yl, (cyclopropylmethyl)(propyl)amino, cyclopentylamino, benzylamino, (4-cyclopentyl)piperazin-1-yl, 4-morpholinyl or 4,4-difluoropiperidin-1-yl.

n is equal to 3;
m is an integer comprised between 2 and 4;
w is an integer equal to 0, 1 or 2;
z is an integer equal to 0 or 1;
r is an integer equal to 0, 1 or 2;
t is an integer equal to 0 or 1;
with the proviso that $R^4$ is $-O-(CH_2)_n-NR^{12a}R^{12b}$ when $R^5$ is hydrogen and that $R^5$ is $-O-(CH_2)_m-NR^{13a}R^{13b}$ when $R^4$ is hydrogen, chlorine, bromine, fluorine, methyl, or methoxy;

with the proviso that when $R^{11}$ is COOCH$_3$ or COOH, $R^4$ is hydrogen, chlorine, bromine, fluorine, methyl, or methoxy; and with the proviso that when $R^{10}$ is $-(CH_2)_w-(C=O)_t-NR^{15}R^{16}$, $R^{11}$ is hydrogen, methyl, COOCH$_3$, COOH or bromine; and with the proviso that at least one of w and t is different from 0; and with the proviso that at least one of r and z is different from 0.

More preferably, the invention relates to compounds of formula (I), geometrical isomers, enantiomers, diastereoisomers, pharmaceutically acceptable salts and all possible mixtures thereof,

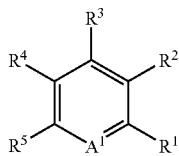

wherein
$A^1$ is CH, C—F or N;
$R^1$ is hydrogen;
$R^2$ is

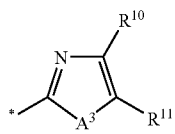

$A^3$ is O or S;
$R^3$ is hydrogen, fluorine or methyl;
$R^4$ is hydrogen, chlorine, bromine, fluorine or methoxy;
$R^5$ is —O—$(CH_2)_m$—$NR^{13a}R^{13b}$;
$R^{10}$ is hydrogen, methyl or —$(CH_2)_w$—$(C=O)_t$—$NR^{15}R^{16}$;
$R^{11}$ is hydrogen, methyl, COOCH$_3$, bromine or —$(CH_2)_r$—$(C=O)_z$—$NR^{17}R^{18}$.
—$NR^{13a}R^{13b}$ is selected from the group consisting of 1-piperidinyl, 1-pyrrolidinyl, 2-methylpyrrolidin-1-yl, (2S)-2-methylpyrrolidin-1-yl, (2R)-2-methylpyrrolidin-1-yl, 4-isopropylpiperazin-1-yl, 4-methylpiperidin-1-yl, 2-methylpiperidin-1-yl, 2-(pyrrolidin-1-ylmethyl)pyrrolidin-1-yl, 4-cyclopentylpiperazin-1-yl, 3-(dimethylamino)pyrrolidin-1-yl, 4-(2-pyrrolidin-1-ylethyl)piperazin-1-yl, 1-azepanyl, 2,6-dimethylpiperidin-1-yl, (2S)-2-(pyrrolidin-1-ylmethyl)pyrrolidin-1-yl, 2-isobutylpyrrolidin-1-yl, 2-ethylpyrrolidinyl and (4aR,8aS)-octahydroisoquinolin-2(1H)-yl.
—$NR^{15}R^{16}$ is selected from the group consisting of 1-piperidinyl, 2-methylpyrrolidin-1-yl, 1-pyrrolidinyl, 1-azepanyl, 2-methylpiperidin-1-yl, (3,5-dimethyl)piperidin-1-yl, hexyl(methyl)amino, benzyl(methyl)amino, 2-azaspiro[5.5]undec-2-yl, 7,8-dimethyl-1 azaspiro[4.4]non-1-yl, 2-oxopyrrolidin-1-yl, anilino, 2-methyl-1H-imidazol-1-yl, 1H-1,2,4-triazol-1-yl, [1-(hydroxymethyl)-3-methylbutyl]amino, cyclopentylamino, (1,3-dimethylbutyl)amino, (cyclopropylmethyl)(propyl)amino, 2,6-dimethylpiperidin-1-yl, (2-furylmethyl)(methyl)amino, sec-butyl(propyl)amino, 4-benzylpiperidine-1-yl, 4-cyclopentylpiperazin-1-yl, 4-morpholinyl, (4-fluorobenzyl)amino, (4-chlorobenzyl)amino, 2-oxo-piperidin-1-yl, (5S)-2-oxo-5-pyrrolidin-1-yl, (4-fluorophenyl)amino, (4aR,8aS)-octahydroisoquinolin-2(1H)-yl, (2S)-2-(pyrrolidin-1-ylmethyl)pyrrolidin-1-yl, (3-methoxyphenyl)amino, (pyridin-3-yl)amino, benzylamino and 4,4-difluoropiperidin-1-yl;
—$NR^{17}R^{18}$ is 1-piperidinyl, 2-oxopyrrolidin-1-yl, (cyclopropylmethyl)(propyl)amino, cyclopentylamino, benzylamino, (4-cyclopentyl)piperazinyl, 4-morpholinyl or 4,4-difluoropiperidin-1-yl;
m is an integer comprised between 2 and 4;
w is an integer equal to 0, 1 or 2;
z is an integer equal to 0 or 1;
r is an integer equal to 0, 1 or 2;
t is an integer equal to 0 or 1;
and
with the proviso that when $R^{10}$ is —$(CH_2)_w$—$(C=O)_t$—$NR^{15}R^{16}$, $R^{11}$ is hydrogen, methyl, COOCH$_3$ or bromine;
with the proviso that at least one of w and t is different from 0; and
with the proviso that at least one of r and z is different from 0.

Most preferably, the invention relates to compounds of formula (I), geometrical isomers, enantiomers, diastereoisomers, pharmaceutically acceptable salts and all possible mixtures thereof,

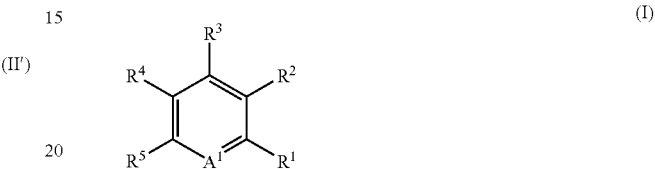

wherein
$A^1$ is CH or C—F;
$R^1$ is hydrogen;
$R^2$ is

$A^3$ is O or S;
$R^3$ is hydrogen or methyl;
$R^4$ is hydrogen or fluorine;
$R^5$ is —O—$(CH_2)_m$—$NR^{13a}R^{13b}$;
$R^{10}$ is methyl or —$(CH_2)_w$—$(C=O)_t$—$NR^{15}R^{16}$;
$R^{11}$ is hydrogen, bromine, COOCH$_3$ or —$(CH_2)_r$—$(C=O)_z$—$NR^{17}R^{18}$;
—$NR^{13a}R^{13b}$ is selected from the group consisting of 1-piperidinyl, 2-methylpyrrolidin-1-yl, (2S)-2-methylpyrrolidin-1-yl, (2R)-2-methylpyrrolidin-1-yl, 4-methylpiperidin-1-yl, 2-methylpiperidin-1-yl, 2-(pyrrolidin-1-ylmethyl)pyrrolidin-1-yl, (2S)-2-(pyrrolidin-1-ylmethyl)pyrrolidin-1-yl, 2-isobutylpyrrolidin-1-yl, 2-ethylpyrrolidin-1-yl, (4aR,8aS)-octahydroisoquinolin-2(1H)-yl, 1-azepanyl and 2,6-dimethylpiperidin-1-yl;
—$NR^{15}R^{16}$ is 1-piperidinyl, 1-pyrrolidinyl, 2-methylpyrrolidin-1-yl, 7,8-dimethyl-1azaspiro[4.4]non-1-yl, 1H-1,2,4-triazol-1-yl, [1-(hydroxymethyl)-3-methylbutyl]amino, 2,6-dimethylpiperidin-1-yl, benzylamino, sec-butyl(propyl)amino, (4aR,8aS)-octahydroisoquinolin-2(1H)-yl and (2S)-2-(pyrrolidin-1-ylmethyl)pyrrolidin-1-yl.
—$NR^{17}R^{18}$ is selected from the group consisting of 1-piperidinyl, 2-oxopyrrolidin-1-yl, (cyclopropylmethyl)(propyl)amino, cyclopentylamino, benzylamino, (4-cyclopentyl)piperazin-1-yl, 4-morpholinyl and 4,4-difluoropiperidin-1-yl.
m is an integer equal to 3 and 4;
w is an integer equal to 0, 1 or 2;
z is an integer equal to 0 or 1;
r is an integer equal to 0, 1 or 2;
t is an integer equal to 0 or 1;
and with the proviso that when $R^{10}$ is —$(CH_2)_w$—$(C=O)_t$—$NR^{15}R^{16}$, $R^{11}$ is hydrogen, $COOCH_3$ or bromine;

with the proviso that at least one of w and t is different from 0; and with the proviso that at least one of r and z is different from 0.

In a particular embodiment, the present invention relates to compounds of formula (Ih) geometrical isomers, enantiomers, diastereoisomers, pharmaceutically acceptable salts and all possible mixtures thereof,

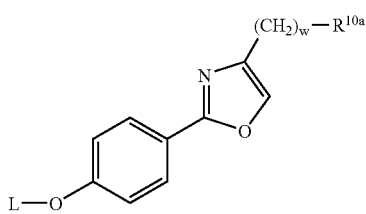
(Ih)

wherein L and w are as defined hereabove in the specification; and $R^{10a}$ is an amino group.

Preferably, $R^{10a}$ is $NR^{15}R^{16}$, $R^{15}$ and $R^{16}$ being as defined here above in the specification.

Preferably, w is equal to 1.

Preferably, L is —$(CH_2)_m$—$NR^{13a}R^{13b}$, m, $R^{13a}$ and $R^{13b}$ being as defined here above in the specification.

Preferably, m is equal to 3.

In another particular embodiment, the present invention relates to compounds of formula (Ii) geometrical isomers, enantiomers, diastereoisomers, pharmaceutically acceptable salts and all possible mixtures thereof,

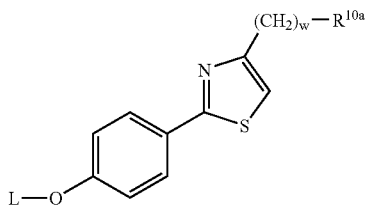
(Ii)

wherein L is as defined hereabove in the specification;

w is an integer comprised between 1 and 4; and $R^{10a}$ is an amino group.

Preferably, $R^{10a}$ is $NR^{15}R^{16}$, $R^{15}$ and $R^{16}$ being as defined here above in the specification.

Preferably w is equal to 1.

Preferably, L is —$(CH_2)_m$—$NR^{13a}R^{13b}$, m, $R^{13a}$ and $R^{13b}$ being as defined here above in the specification.

Preferably m is equal to 3.

In another particular embodiment, the present invention relates to compounds of formula (Ij) geometrical isomers, enantiomers, diastereoisomers, pharmaceutically acceptable salts and all possible mixtures thereof,

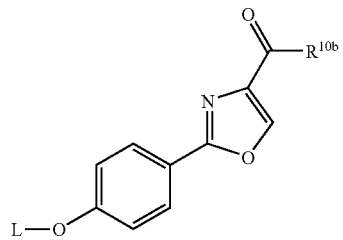
(Ij)

wherein L is as defined hereabove in the specification; and $R^{10b}$ is an amino group.

Preferably, $R^{10b}$ is $NR^{15}R^{16}$, $R^{15}$ and $R^{16}$ being as defined here above in the specification.

Preferably, L is —$(CH_2)_m$—$NR^{13a}R^{13b}$, m, $R^{13a}$ and $R^{13b}$ being as defined here above in the specification.

Preferably m is equal to 3.

In another particular embodiment, the present invention relates to compounds of formula (Ik) geometrical isomers, enantiomers, diastereoisomers, pharmaceutically acceptable salts and all possible mixtures thereof,

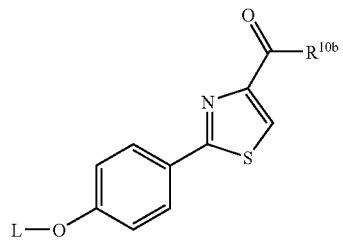
(Ik)

wherein L is as defined hereabove in the specification and $R^{10b}$ is an amino group.

Preferably, $R^{10b}$ is $NR^{15}R^{16}$, $R^{15}$ and $R^{16}$ being as defined here above in the specification.

Preferably, L is —$(CH_2)_m$—$NR^{13a}R^{13b}$, m, $R^{13a}$ and $R^{13b}$ being as defined here above in the specification.

Preferably m is equal to 3.

In another particular embodiment, the present invention relates to compounds of formula (Il) geometrical isomers, enantiomers, diastereoisomers, pharmaceutically acceptable salts and all possible mixtures thereof,

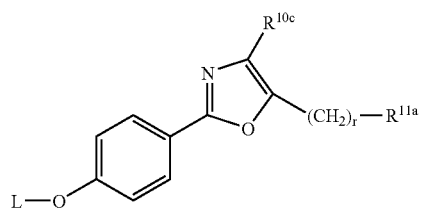
(Il)

wherein L is as defined hereabove in the specification;

r is an integer comprised between 1 and 4;

$R^{10c}$ is a $C_{1-6}$ alkyl;

$R^{11a}$ is an amino group.

Preferably, $R^{11a}$ is $NR^{17}R^{18}$, $R^{17}$ and $R^{18}$ being as defined here above in the specification.

Preferably, r is equal to 1 or 2.

Preferably, L is —(CH$_2$)$_m$—NR$^{13a}$R$^{13b}$, m, R$^{13a}$ and R$^{13b}$ being as defined here above in the specification.

Preferably m is equal to 3.

In another particular embodiment, the present invention relates to compounds of formula (Im), geometrical isomers, enantiomers, diastereoisomers, pharmaceutically acceptable salts and all possible mixtures thereof,

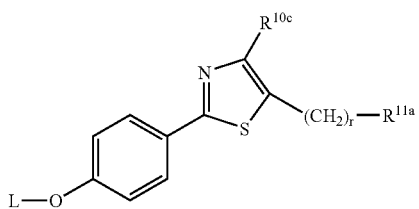

(Im)

wherein L is as defined hereabove in the specification;
r is an integer comprised between 1 and 4;
R$^{10c}$ is a C$_{1-6}$ alkyl;
R$^{11a}$ is an amino group.
Preferably, R$^{11a}$ is NR$^{17}$R$^{18}$, R$^{17}$ and R$^{18}$ being as defined here above in the specification.
Preferably, r is equal to 1 or 2.
Preferably, L is —(CH$_2$)$_m$—NR$^{13a}$R$^{13b}$, m, R$^{13a}$ and R$^{13b}$ being as defined here above in the specification.
Preferably m is equal to 3.

In another particular embodiment, the present invention relates to compounds of formula (In) geometrical isomers, enantiomers, diastereoisomers, pharmaceutically acceptable salts and all possible mixtures thereof,

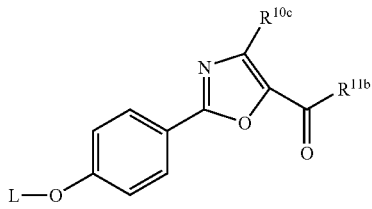

(In)

wherein L is as defined hereabove in the specification;
R$^{10c}$ is a C$_{1-6}$ alkyl;
R$^{11b}$ is an amino group.
Preferably, R$^{11b}$ is NR$^{17}$R$^{18}$, R$^{17}$ and R$^{18}$ being as defined here above in the specification.
Preferably, r is equal to 1 or 2.
Preferably, L is —(CH$_2$)$_m$—NR$^{13a}$R$^{13b}$, m, R$^{13a}$ and R$^{13b}$ being as defined here above in the specification.
Preferably m is equal to 3.

In another particular embodiment, the present invention relates to compounds of formula (Io), geometrical isomers, enantiomers, diastereoisomers, pharmaceutically acceptable salts and all possible mixtures thereof,

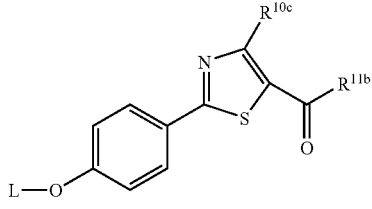

(Io)

wherein L is as defined hereabove in the specification;
R$^{10c}$ is a C$_{1-6}$ alkyl;
R$^{11b}$ is an amino group.
Preferably, R$^{11b}$ is NR$^{17}$R$^{18}$, R$^{17}$ and R$^{18}$ being as defined here above in the specification.
Preferably, r is equal to 1 or 2.
Preferably, L is —(CH$_2$)$_m$—NR$^{13a}$R$^{13b}$, m, R$^{13a}$ and R$^{13b}$ being as defined here above in the specification.
Preferably m is equal to 3

Preferred compounds of formula (I) according to the invention are:
1-(3-{4-[4-(piperidin-1-ylmethyl)-1,3-oxazol-2-yl]phenoxy}propyl)piperidine;
1-[3-(4-{4-[(2-methylpyrrolidin-1-yl)methyl]-1,3-oxazol-2-yl}phenoxy)propyl]piperidine;
1-(3-{4-[4-(pyrrolidin-1-ylmethyl)-1,3-oxazol-2-yl]phenoxy}propyl)piperidine;
1-({2-[4-(3-piperidin-1-ylpropoxy)phenyl]-1,3-oxazol-4-yl}methyl)azepane;
4-methyl-1-({2-[4-(3-piperidin-1-ylpropoxy)phenyl]-1,3-oxazol-4-yl}methyl)piperidine;
2-methyl-1-({2-[4-(3-piperidin-1-ylpropoxy)phenyl]-1,3-oxazol-4-yl}methyl)piperidine;
3,5-dimethyl-1-({2-[4-(3-piperidin-1-ylpropoxy)phenyl]-1,3-oxazol-4-yl}methyl)piperidine;
N-hexyl-N-methyl-N-({2-[4-(3-piperidin-1-ylpropoxy)phenyl]-1,3-oxazol-4-yl}methyl)amine;
N-benzyl-N-methyl-N-({2-[4-(3-piperidin-1-ylpropoxy)phenyl]-1,3-oxazol-4-yl}methyl)amine;
4-(pyrrolidin-1-ylmethyl)-2-[4-(3-pyrrolidin-1-ylpropoxy)phenyl]-1,3-oxazole;
N-[(2-{4-[3-(4-isopropylpiperazin-1-yl)propoxy]phenyl}-1,3-oxazol-4-yl)methyl]-N-methylhexan-1-amine;
N-(2-methoxy-1-methylethyl)-N-({2-[4-(3-piperidin-1-ylpropoxy)phenyl]-1,3-oxazol-4-yl}methyl)amine;
2-[(2-{4-[3-(2-methylpyrrolidin-1-yl)propoxy]phenyl}-1,3-oxazol-4-yl)methyl]-2-azaspiro[5.5]undecane;
7,8-dimethyl-1-({2-[4-(3-piperidin-1-ylpropoxy)phenyl]-1,3-oxazol-4-yl}methyl)-1-azaspiro[4.4]nonane;
4-[(2-methylpyrrolidin-1-yl)methyl]-2-{4-[3-(2-methylpyrrolidin-1-yl)propoxy]phenyl}-1,3-oxazole;
1-isopropyl-4-(3-{4-[4-(pyrrolidin-1-ylmethyl)-1,3-oxazol-2-yl]phenoxy}propyl)piperazine;
1-isopropyl-4-[3-(4-{4-[(2-methylpiperidin-1-yl)methyl]-1,3-oxazol-2-yl}phenoxy)propyl]piperazine;
4-methyl-1-[3-(4-{4-[(2-methylpyrrolidin-1-yl)methyl]-1,3-oxazol-2-yl}phenoxy)propyl]piperidine;
2-methyl-1-[3-(4-{4-[(2-methylpyrrolidin-1-yl)methyl]-1,3-oxazol-2-yl}phenoxy)propyl]piperidine;
4-[(2-methylpyrrolidin-1-yl)methyl]-2-(4-{3-[2-(pyrrolidin-1-ylmethyl)pyrrolidin-1-yl]propoxy}phenyl)-1,3-oxazole;
1-cyclopentyl-4-[3-(4-{4-[(2-methylpyrrolidin-1-yl)methyl]-1,3-oxazol-2-yl}phenoxy)propyl]piperazine;
N,N-dimethyl-1-[4-(4-{4-[(2-methylpyrrolidin-1-yl)methyl]-1,3-oxazol-2-yl}phenoxy)butyl]pyrrolidin-3-amine;
1-[2-(4-{4-[(2-methylpyrrolidin-1-yl)methyl]-1,3-oxazol-2-yl}phenoxy)ethyl]-4-(2-pyrrolidin-1-ylethyl)piperazine;
2-{4-[3-(2-methylpyrrolidin-1-yl)propoxy]phenyl}-4-(2-oxo-2-pyrrolidin-1-ylethyl)-1,3-oxazole;
1-[(2-{4-[3-(2-methylpyrrolidin-1-yl)propoxy]phenyl}-1,3-oxazol-4-yl)methyl]pyrrolidin-2-one;
N-[(2-{4-[3-(2-methylpyrrolidin-1-yl)propoxy]phenyl}-1,3-oxazol-4-yl)methyl]-N-phenylamine;
2-{4-[3-(2-methylpyrrolidin-1-yl)propoxy]phenyl}-4-(2-pyrrolidin-1-ylethyl)-1,3-oxazole;
4-[(2-methyl-1H-imidazol-1-yl)methyl]-2-{4-[3-(2-methylpyrrolidin-1-yl)propoxy]phenyl}-1,3-oxazole;
1-[(2-{4-[3-(2-methylpyrrolidin-1-yl)propoxy]phenyl}-1,3-oxazol-4-yl)methyl]-1H-1,2,4-triazole;

4-(pyrrolidin-1-ylmethyl)-2-[3-(3-pyrrolidin-1-ylpropoxy) phenyl]-1,3-oxazole;

1-[(2-{4-[3-(2-methylpyrrolidin-1-yl)propoxy]phenyl}-1,3-oxazol-4-yl)methyl]piperidine;

1-[3-(4-{4-[(2-methylpyrrolidin-1-yl)methyl]-1,3-oxazol-2-yl}phenoxy)propyl]azepane;

1-(3-{4-[4-methyl-5-(piperidin-1-ylmethyl)-1,3-oxazol-2-yl]phenoxy}propyl)piperidine;

(2R)-4-methyl-2-{[(2-{4-[3-(2-methylpyrrolidin-1-yl)propoxy]phenyl}-1,3-oxazol-4-yl)methyl]amino}pentan-1-ol;

N-[(2-{4-[3-(2-methylpyrrolidin-1-yl)propoxy]phenyl}-1,3-oxazol-4-yl)methyl]cyclopentanamine;

1-[4-(4-{4-[(2-methylpyrrolidin-1-yl)methyl]-1,3-oxazol-2-yl}phenoxy)butyl]azepane;

1-[2-(4-{4-[(2-methylpyrrolidin-1-yl)methyl]-1,3-oxazol-2-yl}phenoxy)ethyl]azepane;

N-(1,3-dimethylbutyl)-N-[(2-{4-[3-(2-methylpyrrolidin-1-yl)propoxy]phenyl}-1,3-oxazol-4-yl)methyl]amine;

N-(cyclopropylmethyl)-N-[(2-{4-[3-(2-methylpyrrolidin-1-yl)propoxy]phenyl}-1,3-oxazol-4-yl)methyl]-N-propylamine;

1-[3-(4-{4-[(2,6-dimethylpiperidin-1-yl)methyl]-1,3-oxazol-2-yl}phenoxy)propyl]-2,6-dimethylpiperidine;

1-({2-[4-(2-piperidin-1-ylethoxy)phenyl]-1,3-oxazol-4-yl}methyl)piperidine;

1-[(2-{4-[2-(2-methylpyrrolidin-1-yl)ethoxy]phenyl}-1,3-oxazol-4-yl)methyl]piperidine;

2-methyl-1-[4-(4-{4-[(2-methylpyrrolidin-1-yl)methyl]-1,3-oxazol-2-yl}phenoxy)butyl]piperidine;

1-(3-{4-[4-(piperidin-1-ylmethyl)-1,3-thiazol-2-yl]phenoxy}propyl)piperidine;

4-(pyrrolidin-1-ylmethyl)-2-[4-(3-pyrrolidin-1-ylpropoxy) phenyl]-1,3-thiazole;

7,8-dimethyl-1-[(2-{4-[3-(2-methylpyrrolidin-1-yl)propoxy]phenyl}-1,3-thiazol-4-yl)methyl]-1-azaspiro[4.4] nonane;

N-(2-furylmethyl)-N-methyl-N-[(2-{4-[3-(2-methylpyrrolidin-1-yl)propoxy]phenyl}-1,3-thiazol-4-yl)methyl] amine;

N-(sec-butyl)-N-[(2-{4-[3-(2-methylpyrrolidin-1-yl)propoxy]phenyl}-1,3-thiazol-4-yl)methyl]-N-propylamine;

1-(3-{4-[4-(pyrrolidin-1-ylmethyl)-1,3-thiazol-2-yl] phenoxy}propyl)piperidine;

1-({2-[4-(3-piperidin-1-ylpropoxy)phenyl]-1,3-thiazol-4-yl}methyl)azepane;

1-[(2-{4-[3-(2-methylpyrrolidin-1-yl)propoxy]phenyl}-1,3-thiazol-4-yl)methyl]piperidine;

1-[(2-{4-[3-(2-methylpyrrolidin-1-yl)propoxy]phenyl}-1,3-oxazol-4-yl)acetyl]piperidine;

1-(3-{4-[4-(2-oxo-2-piperidin-1-ylethyl)-1,3-oxazol-2-yl] phenoxy}propyl)piperidine;

1-[2-(2-{4-[3-(2-methylpyrrolidin-1-yl)propoxy]phenyl}-1,3-oxazol-4-yl)ethyl]piperidine;

2-{4-[3-(2-methylpyrrolidin-1-yl)propoxy]phenyl}-1,3-thiazole;

4-benzyl-1-[(2-{4-[3-(2-methylpyrrolidin-1-yl)propoxy] phenyl}-1,3-oxazol-4-yl)methyl]piperidine;

1-cyclopentyl-4-[(2-{4-[3-(2-methylpyrrolidin-1-yl)propoxy]phenyl}-1,3-oxazol-4-yl)methyl]piperazine;

1-{[2-(4-{3-[(2S)-2-(pyrrolidin-1-ylmethyl)pyrrolidin-1-yl] propoxy}phenyl)-1,3-oxazol-4-yl]methyl}piperidine;

1-(3-{4-[5-methyl-4-(piperidin-1-ylmethyl)-1,3-oxazol-2-yl]phenoxy}propyl)piperidine;

1-(3-{2-fluoro-4-(piperidin-1-ylmethyl)-1,3-oxazol-2-yl] phenoxy}propyl)piperidine;

1-(3-{2,6-dimethyl-4-[4-(piperidin-1-ylmethyl)-1,3-oxazol-2-yl]phenoxy}propyl)piperidine;

4-[(2-{4-[3-(2-methylpyrrolidin-1-yl)propoxy]phenyl}-1,3-oxazol-4-yl)carbonyl]morpholine;

1-cyclopentyl-4-({2-[4-(3-piperidin-1-ylpropoxy)phenyl]-1,3-oxazol-4-yl}carbonyl)piperazine;

1-[(2-{4-[3-(2-methylpyrrolidin-1-yl)propoxy]phenyl}-1,3-oxazol-4-yl)carbonyl]piperidine;

1-cyclopentyl-4-[(2-{4-[3-(2-methylpyrrolidin-1-yl)propoxy]phenyl}-1,3-oxazol-4-yl)carbonyl]piperazine;

4-[(2-methylpyrrolidin-1-yl)methyl]-2-(4-{3-[(2S)-2-(pyrrolidin-1-ylmethyl)pyrrolidin-1-yl]propoxy}phenyl)-1,3-oxazole;

1-[(2-{3-fluoro-4-[3-(2-methylpyrrolidin-1-yl)propoxy] phenyl}-1,3-oxazol-4-yl)methyl]piperidine;

1-[(4-methyl-2-{4-[3-(2-methylpyrrolidin-1-yl)propoxy] phenyl}-1,3-oxazol-5-yl)carbonyl]piperidine;

N-(cyclopropylmethyl)-4-methyl-2-{4-[3-(2-methylpyrrolidin-1-yl)propoxy]phenyl}-N-propyl-1,3-oxazole-5-carboxamide;

N-cyclopentyl-4-methyl-2-{4-[3-(2-methylpyrrolidin-1-yl) propoxy]phenyl}-1,3-oxazole-5-carboxamide;

methyl 4-[(benzylamino)methyl]-2-{4-[3-(2-methylpyrrolidin-1-yl)propoxy]phenyl}-1,3-oxazole-5-carboxylate;

methyl 4-methyl-2-{4-[3-(2-methylpyrrolidin-1-yl)propoxy]phenyl}-1,3-thiazole-5-carboxylate;

2-{4-[3-(2-methylpyrrolidin-1-yl)propoxy]phenyl}-4-(piperidin-1-ylmethyl)-1,3-oxazole-5-carboxylic acid;

N-(cyclopropylmethyl)-2-{4-[3-(2-methylpyrrolidin-1-yl) propoxy]phenyl}-N-propyl-1,3-oxazole-4-carboxamide;

N-cyclopentyl-2-{4-[3-(2-methylpyrrolidin-1-yl)propoxy] phenyl}-1,3-oxazole-4-carboxamide;

N-(4-fluorobenzyl)-2-{4-[3-(2-methylpyrrolidin-1-yl)propoxy]phenyl}-1,3-oxazole-4-carboxamide;

N-benzyl-4-methyl-2-{4-[3-(2-methylpyrrolidin-1-yl)propoxy]phenyl}-1,3-oxazole-5-carboxamide;

1-cyclopentyl-4-[(4-methyl-2-{4-[3-(2-methylpyrrolidin-1-yl)propoxy]phenyl}-1,3-oxazol-5-yl)carbonyl]piperazine;

2-{4-[3-(2-methylpyrrolidin-1-yl)propoxy]phenyl}-4-(pyrrolidin-1-ylcarbonyl)-1,3-oxazole;

4-[(4-methyl-2-{4-[3-(2-methylpyrrolidin-1-yl)propoxy] phenyl}-1,3-oxazol-5-yl)carbonyl]morpholine;

4-{[4-methyl-2-(4-{3-[(2R)-2-methylpyrrolidin-1-yl] propoxy}phenyl)-1,3-oxazol-5-yl]carbonyl}morpholine;

4-{[4-methyl-2-(4-{3-[(2S)-2-methylpyrrolidin-1-yl] propoxy}phenyl)-1,3-oxazol-5-yl]carbonyl}morpholine;

1-cyclopentyl-4-[(4-methyl-2-{4-[3-(2-methylpyrrolidin-1-yl)propoxy]phenyl}-1,3-oxazol-5-yl)methyl]piperazine;

N-(cyclopropylmethyl)-N-[(4-methyl-2-{4-[3-(2-methylpyrrolidin-1-yl)propoxy]phenyl}-1,3-oxazol-5-yl)methyl]-N-propylamine;

N-benzyl-N-[(4-methyl-2-{4-[3-(2-methylpyrrolidin-1-yl) propoxy]phenyl}-1,3-oxazol-5-yl)methyl]amine;

1-[(2-{3-methoxy-4-[3-(2-methylpyrrolidin-1-yl)propoxy] phenyl}-1,3-oxazol-4-yl)methyl]piperidine;

N-(4-chlorobenzyl)-N-[(2-{4-[3-(2-methylpyrrolidin-1-yl) propoxy]phenyl}-1,3-oxazol-4-yl)methyl]amine;

N-[(4-methyl-2-{4-[3-(2-methylpyrrolidin-1-yl)propoxy] phenyl}-1,3-oxazol-5-yl)methyl]cyclopentanamine;

1-[(5-bromo-2-{4-[3-(2-methylpyrrolidin-1-yl)propoxy] phenyl}-1,3-oxazol-4-yl)methyl]piperidine;

1-{[2-(4-{3-[(2R)-2-methylpyrrolidin-1-yl] propoxy}phenyl)-1,3-oxazol-4-yl]methyl}piperidine;

1-{[2-(4-{3-[(2S)-2-methylpyrrolidin-1-yl] propoxy}phenyl)-1,3-oxazol-4-yl]methyl}piperidine;

4-[(2-{4-[3-(2-methylpyrrolidin-1-yl)propoxy]phenyl}-1,3-oxazol-4-yl)methyl]morpholine;
1-[2-(2-{4-[2-(2-methylpyrrolidin-1-yl)ethoxy]phenyl}-1,3-oxazol-4-yl)ethyl]piperidine;
1-[(2-{4-[3-(2-methylpyrrolidin-1-yl)propoxy]phenyl}-1,3-oxazol-4-yl)methyl]piperidin-2-one;
(5S)-1-[(2-{4-[3-(2-methylpyrrolidin-1-yl)propoxy]phenyl}-1,3-oxazol-4-yl)methyl]-5-(pyrrolidin-1-ylmethyl)pyrrolidin-2-one;
1-[(2-{3-chloro-4-[3-(2-methylpyrrolidin-1-yl)propoxy]phenyl}-1,3-oxazol-4-yl)methyl]piperidine;
1-[(2-{4-[3-(2-isobutylpyrrolidin-1-yl)propoxy]phenyl}-1,3-oxazol-4-yl)methyl]piperidine;
methyl 2-{3-bromo-4-[3-(2-methylpyrrolidin-1-yl)propoxy]phenyl}-4-methyl-1,3-thiazole-5-carboxylate;
1-(3-{4-[4-methyl-5-(2-oxo-2-piperidin-1-ylethyl)-1,3-thiazol-2-yl]phenoxy}propyl)piperidine;
N-(4-fluorophenyl)-2-(2-{4-[3-(2-methylpyrrolidin-1-yl)propoxy]phenyl}-1,3-oxazol-4-yl)acetamide;
1-[(2-{4-[3-(2-ethylpyrrolidin-1-yl)propoxy]phenyl}-1,3-oxazol-4-yl)methyl]piperidine;
(4aR,8aS)-2-[(2-{4-[3-(2-methylpyrrolidin-1-yl)propoxy]phenyl}-1,3-oxazol-4-yl)methyl]decahydroisoquinoline;
2-{4-[3-(2-methylpyrrolidin-1-yl)propoxy]phenyl}-4-{[(2S)-2-(pyrrolidin-1-ylmethyl)pyrrolidin-1-yl]carbonyl}-1,3-oxazole;
4-[(2-{4-[3-(2-methylpyrrolidin-1-yl)propoxy]phenyl}-1,3-oxazol-4-yl)acetyl]morpholine;
N-cyclopentyl-2-(2-{4-[3-(2-methylpyrrolidin-1-yl)propoxy]phenyl}-1,3-oxazol-4-yl)acetamide;
N-(cyclopropylmethyl)-2-(2-{4-[3-(2-methylpyrrolidin-1-yl)propoxy]phenyl}-1,3-oxazol-4-yl)-N-propylacetamide;
1-[(2-{4-[3-(2-methylpyrrolidin-1-yl)propoxy]phenyl}-1,3-oxazol-4-yl)acetyl]azepane;
1-(3-{4-[4-methyl-5-(2-piperidin-1-ylethyl)-1,3-thiazol-2-yl]phenoxy}propyl)piperidine;
(5S)-1-[(2-{4-[3-(2-methylpyrrolidin-1-yl)propoxy]phenyl}-1,3-oxazol-4-yl)methyl]-5-(morpholin-4-ylmethyl)pyrrolidin-2-one;
(4aS,8aR)-2-(3-{4-[4-(piperidin-1-ylmethyl)-1,3-oxazol-2-yl]phenoxy}propyl)decahydroisoquinoline;
2-methyl-N-[(2-{4-[3-(2-methylpyrrolidin-1-yl)propoxy]phenyl}-1,3-oxazol-4-yl)methyl]-2H-tetraazol-5-amine;
N-(3-methoxyphenyl)-N-[(2-{4-[3-(2-methylpyrrolidin-1-yl)propoxy]phenyl}-1,3-oxazol-4-yl)methyl]amine;
N-(4-fluorophenyl)-N-[(2-{4-[3-(2-methylpyrrolidin-1-yl)propoxy]phenyl}-1,3-oxazol-4-yl)methyl]amine;
N-[(2-{4-[3-(2-methylpyrrolidin-1-yl)propoxy]phenyl}-1,3-oxazol-4-yl)methyl]pyridin-3-amine;
4-[(4-methyl-2-{4-[3-(2-methylpyrrolidin-1-yl)propoxy]phenyl}-1,3-oxazol-5-yl)methyl]morpholine;
4-({(2S)-1-[(2-{4-[3-(2-methylpyrrolidin-1-yl)propoxy]phenyl}-1,3-oxazol-4-yl)methyl]pyrrolidin-2-yl}methyl)morpholine;
1-[(2-{2-fluoro-4-[3-(2-methylpyrrolidin-1-yl)propoxy]phenyl}-1,3-oxazol-4-yl)methyl]piperidine;
4,4-difluoro-1-[(2-{4-[3-(2-methylpyrrolidin-1-yl)propoxy]phenyl}-1,3-oxazol-4-yl)methyl]piperidine;
4-[(4-methyl-2-{6-[3-(2-methylpyrrolidin-1-yl)propoxy]pyridin-3-yl}-1,3-thiazol-5-yl)carbonyl]morpholine;
1-[(2-{3,5-difluoro-4-[3-(2-methylpyrrolidin-1-yl)propoxy]phenyl}-1,3-oxazol-4-yl)methyl]piperidine;
4,4-difluoro-1-[(4-methyl-2-{4-[3-(2-methylpyrrolidin-1-yl)propoxy]phenyl}-1,3-thiazol-5-yl)carbonyl]piperidine;
4,4-difluoro-1-{[4-methyl-2-(4-{3-[(2R)-2-methylpyrrolidin-1-yl]propoxy}phenyl)-1,3-thiazol-5-yl]carbonyl}piperidine;
4,4-difluoro-1-{[4-methyl-2-(4-{3-[(2S)-2-methylpyrrolidin-1-yl]propoxy}phenyl)-1,3-thiazol-5-yl]carbonyl}piperidine;
4-[(4-methyl-2-{4-[3-(2-methylpyrrolidin-1-yl)propoxy]phenyl}-1,3-thiazol-5-yl)carbonyl]morpholine;
4-{[4-methyl-2-(4-{3-[(2R)-2-methylpyrrolidin-1-yl]propoxy}phenyl)-1,3-thiazol-5-yl]carbonyl}morpholine;
4-{[4-methyl-2-(4-{3-[(2S)-2-methylpyrrolidin-1-yl]propoxy}phenyl)-1,3-thiazol-5-yl]carbonyl}morpholine;
1-[(2-{2-methyl-4-[3-(2-methylpyrrolidin-1-yl)propoxy]phenyl}-1,3-oxazol-4-yl)methyl]piperidine; and
1-[(4-methyl-2-{4-[3-(2-methylpyrrolidin-1-yl)propoxy]phenyl}-1,3-thiazol-5-yl)methyl]pyrrolidin-2-one.

More preferred compounds of formula (I) according to the invention are 1-(3-{4-[4-(piperidin-1-ylmethyl)-1,3-oxazol-2-yl]phenoxy}propyl)piperidine;
1-[3-(4-{4-[(2-methylpyrrolidin-1-yl)methyl]-1,3-oxazol-2-yl}phenoxy)propyl]piperidine;
1-(3-{4-[4-(pyrrolidin-1-ylmethyl)-1,3-oxazol-2-yl]phenoxy}propyl)piperidine;
1-({2-[4-(3-piperidin-1-ylpropoxy)phenyl]-1,3-oxazol-4-yl}methyl)azepane;
2-methyl-1-({2-[4-(3-piperidin-1-ylpropoxy)phenyl]-1,3-oxazol-4-yl}methyl)piperidine;
3,5-dimethyl-1-({2-[4-(3-piperidin-1-ylpropoxy)phenyl]-1,3-oxazol-4-yl}methyl)piperidine;
N-hexyl-N-methyl-N-({2-[4-(3-piperidin-1-ylpropoxy)phenyl]-1,3-oxazol-4-yl}methyl)amine;
N-benzyl-N-methyl-N-({2-[4-(3-piperidin-1-ylpropoxy)phenyl]-1,3-oxazol-4-yl}methyl)amine;
4-(pyrrolidin-1-ylmethyl)-2-[4-(3-pyrrolidin-1-ylpropoxy)phenyl]-1,3-oxazole;
2-[(2-{4-[3-(2-methylpyrrolidin-1-yl)propoxy]phenyl}-1,3-oxazol-4-yl)methyl]-2-azaspiro[5.5]undecane;
7,8-dimethyl-1-({2-[4-(3-piperidin-1-ylpropoxy)phenyl]-1,3-oxazol-4-yl}methyl)-1-azaspiro[4.4]nonane;
4-[(2-methylpyrrolidin-1-yl)methyl]-2-{4-[3-(2-methylpyrrolidin-1-yl)propoxy]phenyl}-1,3-oxazole;
1-isopropyl-4-(3-{4-[4-(pyrrolidin-1-ylmethyl)-1,3-oxazol-2-yl]phenoxy}propyl)piperazine;
1-isopropyl-4-(3-(4-{4-[(2-methylpiperidin-1-yl)methyl]-1,3-oxazol-2-yl}phenoxy)propyl)piperazine;
4-methyl-1-[3-(4-{4-[(2-methylpyrrolidin-1-yl)methyl]-1,3-oxazol-2-yl}phenoxy)propyl]piperidine;
2-methyl-1-[3-(4-{4-[(2-methylpyrrolidin-1-yl)methyl]-1,3-oxazol-2-yl}phenoxy)propyl]piperidine;
4-[(2-methylpyrrolidin-1-yl)methyl]-2-(4-{3-[2-(pyrrolidin-1-ylmethyl)pyrrolidin-1-yl]propoxy}phenyl)-1,3-oxazole;
1-cyclopentyl-4-[3-(4-{4-[(2-methylpyrrolidin-1-yl)methyl]-1,3-oxazol-2-yl}phenoxy)propyl]piperazine;
N,N-dimethyl-1-[4-(4-{4-[(2-methylpyrrolidin-1-yl)methyl]-1,3-oxazol-2-yl}phenoxy)butyl]pyrrolidin-3-amine;
1-[2-(4-{4-[(2-methylpyrrolidin-1-yl)methyl]-1,3-oxazol-2-yl}phenoxy)ethyl]-4-(2-pyrrolidin-1-ylethyl)piperazine;
2-{4-[3-(2-methylpyrrolidin-1-yl)propoxy]phenyl}-4-(2-oxo-2-pyrrolidin-1-ylethyl)-1,3-oxazole;
1-[(2-{4-[3-(2-methylpyrrolidin-1-yl)propoxy]phenyl}-1,3-oxazol-4-yl)methyl]pyrrolidin-2-one;
N-[(2-{4-[3-(2-methylpyrrolidin-1-yl)propoxy]phenyl}-1,3-oxazol-4-yl)methyl]-N-phenylamine;
2-{4-[3-(2-methylpyrrolidin-1-yl)propoxy]phenyl}-4-(2-pyrrolidin-1-ylethyl)-1,3-oxazole.

4-[(2-methyl-1H-imidazol-1-yl)methyl]-2-{4-[3-(2-methylpyrrolidin-1-yl)propoxy]phenyl}-1,3-oxazole;
1-[(2-{4-[3-(2-methylpyrrolidin-1-yl)propoxy]phenyl}-1,3-oxazol-4-yl)methyl]-1H-1,2,4-triazole;
1-[(2-{4-[3-(2-methylpyrrolidin-1-yl)propoxy]phenyl}-1,3-oxazol-4-yl)methyl]piperidine;
1-[3-(4-{[2-methylpyrrolidin-1-yl)methyl]-1,3-oxazol-2-yl}phenoxy)propyl]azepane;
1-(3-{4-[4-methyl-5-(piperidin-1-ylmethyl)-1,3-oxazol-2-yl]phenoxy}propyl)piperidine;
(2R)-4-methyl-2-{[(2-{4-[3-(2-methylpyrrolidin-1-yl)propoxy]phenyl}-1,3-oxazol-4-yl)methyl]amino}pentan-1-ol;
N-[(2-{4-[3-(2-methylpyrrolidin-1-yl)propoxy]phenyl}-1,3-oxazol-4-yl)methyl]cyclopentanamine;
1-[4-(4-{4-[(2-methylpyrrolidin-1-yl)methyl]-1,3-oxazol-2-yl}phenoxy)butyl]azepane;
1-[2-(4-{4-[(2-methylpyrrolidin-1-yl)methyl]-1,3-oxazol-2-yl}phenoxy)ethyl]azepane;
N-(1,3-dimethylbutyl)-N-[(2-{4-[3-(2-methylpyrrolidin-1-yl)propoxy]phenyl}-1,3-oxazol-4-yl)methyl]amine;
N-(cyclopropylmethyl)-N-[(2-{4-[3-(2-methylpyrrolidin-1-yl)propoxy]phenyl}-1,3-oxazol-4-yl)methyl]-N-propylamine;
1-[3-(4-{4-[(2,6-dimethylpiperidin-1-yl)methyl]-1,3-oxazol-2-yl}phenoxy)propyl]-2,6-dimethylpiperidine;
1-[(2-{4-[2-(2-methylpyrrolidin-1-yl)ethoxy]phenyl}-1,3-oxazol-4-yl)methyl]piperidine;
2-methyl-1-[4-(4-{4-[(2-methylpyrrolidin-1-yl)methyl]-1,3-oxazol-2-yl}phenoxy)butyl]piperidine;
1-(3-{4-[4-(piperidin-1-ylmethyl)-1,3-thiazol-2-yl]phenoxy}propyl)piperidine;
4-(pyrrolidin-1-ylmethyl)-2-[4-(3-pyrrolidin-1-ylpropoxy)phenyl]-1,3-thiazole;
7,8-dimethyl-1-[(2-{4-[3-(2-methylpyrrolidin-1-yl)propoxy]phenyl}-1,3-thiazol-4-yl)methyl]-1-azaspiro[4.4]nonane;
N-(2-furylmethyl)-N-methyl-N-[(2-{4-[3-(2-methylpyrrolidin-1-yl)propoxy]phenyl}-1,3-thiazol-4-yl)methyl]amine;
N-(sec-butyl)-N-[(2-{4-[3-(2-methylpyrrolidin-1-yl)propoxy]phenyl}-1,3-thiazol-4-yl)methyl]-N-propylamine;
1-(3-{4-[4-(pyrrolidin-1-ylmethyl)-1,3-thiazol-2-yl]phenoxy}propyl)piperidine;
1-({2-[4-(3-piperidin-1-ylpropoxy)phenyl]-1,3-thiazol-4-yl}methyl)azepane;
1-[(2-{4-[3-(2-methylpyrrolidin-1-yl)propoxy]phenyl}-1,3-thiazol-4-yl)methyl]piperidine;
1-[(2-{4-[3-(2-methylpyrrolidin-1-yl)propoxy]phenyl}-1,3-oxazol-4-yl)acetyl]piperidine;
1-[2-(2-{4-[3-(2-methylpyrrolidin-1-yl)propoxy]phenyl}-1,3-oxazol-4-yl)ethyl]piperidine;
2-{4-[3-(2-methylpyrrolidin-1-yl)propoxy]phenyl}-1,3-thiazole;
4-benzyl-1-[(2-{4-[3-(2-methylpyrrolidin-1-yl)propoxy]phenyl}-1,3-oxazol-4-yl)methyl]piperidine;
1-cyclopentyl-4-[(2-{4-[3-(2-methylpyrrolidin-1-yl)propoxy]phenyl}-1,3-oxazol-4-yl)methyl]piperazine;
1-{[2-(4-{3-[(2S)-2-(pyrrolidin-1-ylmethyl)pyrrolidin-1-yl]propoxy}phenyl)-1,3-oxazol-4-yl]methyl}piperidine;
1-(3-{4-[5-methyl-4-(piperidin-1-ylmethyl)-1,3-oxazol-2-yl]phenoxy}propyl)piperidine;
1-(3-{2-fluoro-4-[4-(piperidin-1-ylmethyl)-1,3-oxazol-2-yl]phenoxy}propyl)piperidine;
4-[(2-{4-[3-(2-methylpyrrolidin-1-yl)propoxy]phenyl}-1,3-oxazol-4-yl)carbonyl]morpholine;

1-[(2-{4-[3-(2-methylpyrrolidin-1-yl)propoxy]phenyl}-1,3-oxazol-4-yl)carbonyl]piperidine;
1-cyclopentyl-4-[(2-{4-[3-(2-methylpyrrolidin-1-yl)propoxy]phenyl}-1,3-oxazol-4-yl)carbonyl]piperazine;
4-[(2-methylpyrrolidin-1-yl)methyl]-2-(4-{3-[(2S)-2-(pyrrolidin-1-ylmethyl)pyrrolidin-1-yl]propoxy}phenyl)-1,3-oxazole;
1-[(2-{3-fluoro-4-[3-(2-methylpyrrolidin-1-yl)propoxy]phenyl}-1,3-oxazol-4-yl)methyl]piperidine;
1-[(4-methyl-2-{4-[3-(2-methylpyrrolidin-1-yl)propoxy]phenyl}-1,3-oxazol-5-yl)carbonyl]piperidine;
N-(cyclopropylmethyl)-4-methyl-2-{4-[3-(2-methylpyrrolidin-1-yl)propoxy]phenyl}-N-propyl-1,3-oxazole-5-carboxamide;
N-cyclopentyl-4-methyl-2-{4-[3-(2-methylpyrrolidin-1-yl)propoxy]phenyl}-1,3-oxazole-5-carboxamide;
methyl 4-[(benzylamino)methyl]-2-{4-[3-(2-methylpyrrolidin-1-yl)propoxy]phenyl}-1,3-oxazole-5-carboxylate;
methyl 4-methyl-2-{4-[3-(2-methylpyrrolidin-1-yl)propoxy]phenyl}-1,3-thiazole-5-carboxylate;
N-(cyclopropylmethyl)-2-{4-[3-(2-methylpyrrolidin-1-yl)propoxy]phenyl}-N-propyl-1,3-oxazole-4-carboxamide;
N-cyclopentyl-2-{4-[3-(2-methylpyrrolidin-1-yl)propoxy]phenyl}-1,3-oxazole-4-carboxamide;
N-(4-fluorobenzyl)-2-{4-[3-(2-methylpyrrolidin-1-yl)propoxy]phenyl}-1,3-oxazole-4-carboxamide;
N-benzyl-4-methyl-2-{4-[3-(2-methylpyrrolidin-1-yl)propoxy]phenyl}-1,3-oxazole-5-carboxamide;
1-cyclopentyl-4-[(4-methyl-2-{4-[3-(2-methylpyrrolidin-1-yl)propoxy]phenyl}-1,3-oxazol-5-yl)carbonyl]piperazine;
2-{4-[3-(2-methylpyrrolidin-1-yl)propoxy]phenyl}-4-(pyrrolidin-1-ylcarbonyl)-1,3-oxazole;
4-[(4-methyl-2-{4-[3-(2-methylpyrrolidin-1-yl)propoxy]phenyl}-1,3-oxazol-5-yl)carbonyl]morpholine;
4-{[4-methyl-2-(4-{3-[(2R)-2-methylpyrrolidin-1-yl]propoxy}phenyl)-1,3-oxazol-5-yl]carbonyl}morpholine;
4-{[4-methyl-2-(4-{3-[(2S)-2-methylpyrrolidin-1-yl]propoxy}phenyl)-1,3-oxazol-5-yl]carbonyl}morpholine;
1-cyclopentyl-4-[(4-methyl-2-{4-[3-(2-methylpyrrolidin-1-yl)propoxy]phenyl}-1,3-oxazol-5-yl)methyl]piperazine;
N-(cyclopropylmethyl)-N-[(4-methyl-2-{4-[3-(2-methylpyrrolidin-1-yl)propoxy]phenyl}-1,3-oxazol-5-yl)methyl]-N-propylamine;
N-benzyl-N-[(4-methyl-2-{4-[3-(2-methylpyrrolidin-1-yl)propoxy]phenyl}-1,3-oxazol-5-yl)methyl]amine;
1-[(2-{3-methoxy-4-[3-(2-methylpyrrolidin-1-yl)propoxy]phenyl}-1,3-oxazol-4-yl)methyl]piperidine;
N-(4-chlorobenzyl)-N-[(2-{4-[3-(2-methylpyrrolidin-1-yl)propoxy]phenyl}-1,3-oxazol-4-yl)methyl]amine;
N-[(4-methyl-2-{4-[3-(2-methylpyrrolidin-1-yl)propoxy]phenyl}-1,3-oxazol-5-yl)methyl]cyclopentanamine;
1-[(5-bromo-2-{4-[3-(2-methylpyrrolidin-1-yl)propoxy]phenyl}-1,3-oxazol-4-yl)methyl]piperidine;
1-{[2-(4-{3-[(2R)-2-methylpyrrolidin-1-yl]propoxy}phenyl)-1,3-oxazol-4-yl]methyl}piperidine;
1-{[2-(4-{3-[(2S)-2-methylpyrrolidin-1-yl]propoxy}phenyl)-1,3-oxazol-4-yl]methyl}piperidine;
4-[(2-{4-[3-(2-methylpyrrolidin-1-yl)propoxy]phenyl}-1,3-oxazol-4-yl)methyl]morpholine;
1-[2-(2-{4-[2-(2-methylpyrrolidin-1-yl)ethoxy]phenyl}-1,3-oxazol-4-yl)ethyl]piperidine;
1-[(2-{4-[3-(2-methylpyrrolidin-1-yl)propoxy]phenyl}-1,3-oxazol-4-yl)methyl]piperidin-2-one;
(5S)-1-[(2-{4-[3-(2-methylpyrrolidin-1-yl)propoxy]phenyl}-1,3-oxazol-4-yl)methyl]-5-(pyrrolidin-1-ylmethyl)pyrrolidin-2-one;

1-[(2-{3-chloro-4-[3-(2-methylpyrrolidin-1-yl)propoxy]phenyl}-1,3-oxazol-4-yl)methyl]piperidine;
1-[(2-{4-[3-(2-isobutylpyrrolidin-1-yl)propoxy]phenyl}-1,3-oxazol-4-yl)methyl]piperidine;
methyl 2-{3 bromo-4-[3-(2-methylpyrrolidin-1-yl)propoxy]phenyl}-4-methyl-1,3-thiazole-5-carboxylate;
N-(4-fluorophenyl)-2-(2-{4-[3-(2-methylpyrrolidin-1-yl)propoxy]phenyl}-1,3-oxazol-4-yl)acetamide;
1-[(2-{4-[3-(2-ethylpyrrolidin-1-yl)propoxy]phenyl}-1,3-oxazol-4-yl)methyl]piperidine;
(4aR,8aS)-2-[(2-{4-[3-(2-methylpyrrolidin-1-yl)propoxy]phenyl}-1,3-oxazol-4-yl)methyl]decahydroisoquinoline;
2-{4-[3-(2-methylpyrrolidin-1-yl)propoxy]phenyl}-4-{[(2S)-2-(pyrrolidin-1-ylmethyl)pyrrolidin-1-yl]carbonyl}-1,3-oxazole;
4-[(2-{4-[3-(2-methylpyrrolidin-1-yl)propoxy]phenyl}-1,3-oxazol-4-yl)acetyl]morpholine;
N-cyclopentyl-2-(2-{4-[3-(2-methylpyrrolidin-1-yl)propoxy]phenyl}-1,3-oxazol-4-yl)acetamide;
N-(cyclopropylmethyl)-2-(2-{4-[3-(2-methylpyrrolidin-1-yl)propoxy]phenyl}-1,3-oxazol-4-yl)-N-propylacetamide;
1-[(2-{4-[3-(2-methylpyrrolidin-1-yl)propoxy]phenyl}-1,3-oxazol-4-yl)acetyl]azepane;
1-(3-{4-[4-methyl-5-(2-piperidin-1-ylethyl)-1,3-thiazol-2-yl]phenoxy}propyl)piperidine;
(4aS,8aR)-2-(3-{4-[4-(piperidin-1-ylmethyl)-1,3-oxazol-2-yl]phenoxy}propyl)decahydroisoquinoline;
N-(3-methoxyphenyl)-N-[(2-{4-[3-(2-methylpyrrolidin-1-yl)propoxy]phenyl}-1,3-oxazol-4-yl)methyl]amine;
N-(4-fluorophenyl)-N-[(2-{4-[3-(2-methylpyrrolidin-1-yl)propoxy]phenyl}-1,3-oxazol-4-yl)methyl]amine;
N-[(2-{4-[3-(2-methylpyrrolidin-1-yl)propoxy]phenyl}-1,3-oxazol-4-yl)methyl]pyridin-3-amine;
1-[(2-{2-fluoro-4-[3-(2-methylpyrrolidin-1-yl)propoxy]phenyl}-1,3-oxazol-4-yl)methyl]piperidine;
4,4-difluoro-1-[(2-{4-[3-(2-methylpyrrolidin-1-yl)propoxy]phenyl}-1,3-oxazol-4-yl)methyl]piperidine;
4-[(4-methyl-2-{6-[3-(2-methylpyrrolidin-1-yl)propoxy]pyridin-3-yl}-1,3-thiazol-5-yl)carbonyl]morpholine;
1-[(2-{3,5-difluoro-4-[3-(2-methylpyrrolidin-1-yl)propoxy]phenyl}-1,3-oxazol-4-yl)methyl]piperidine;
4,4-difluoro-1-[(4-methyl-2-{4-[3-(2-methylpyrrolidin-1-yl)propoxy]phenyl}-1,3-thiazol-5-yl)carbonyl]piperidine;
4,4-difluoro-1-{[4-methyl-2-(4-{3-[(2R)-2-methylpyrrolidin-1-yl]propoxy}phenyl)-1,3-thiazol-5-yl]carbonyl}piperidine;
4,4-difluoro-1-{[4-methyl-2-(4-{3-[(2S)-2-methylpyrrolidin-1-yl]propoxy}phenyl)-1,3-thiazol-5-yl]carbonyl}piperidine;
4-[(4-methyl-2-{4-[3-(2-methylpyrrolidin-1-yl)propoxy]phenyl}-1,3-thiazol-5-yl)carbonyl]morpholine;
4-{[4-methyl-2-(4-{3-[(2R)-2-methylpyrrolidin-1-yl]propoxy}phenyl)-1,3-thiazol-5-yl]carbonyl}morpholine;
4-{[4-methyl-2-(4-{3-[(2S)-2-methylpyrrolidin-1-yl]propoxy}phenyl)-1,3-thiazol-5-yl]carbonyl}morpholine;
1-[(2-{2-methyl-4-[3-(2-methylpyrrolidin-1-yl)propoxy]phenyl}-1,3-oxazol-4-yl)methyl]piperidine; and
1-[(4-methyl-2-{4-[3-(2-methylpyrrolidin-1-yl)propoxy]phenyl}-1,3-thiazol-5-yl)methyl]pyrrolidin-2-one.

Most preferred compounds of formula (I) according to the invention are 1-(3-{4-[4-(piperidin-1-ylmethyl)-1,3-oxazol-2-yl]phenoxy}propyl)piperidine;
1-[3-(4-{4-[(2-methylpyrrolidin-1-yl)methyl]-1,3-oxazol-2-yl}phenoxy)propyl]piperidine;
4-[(2-methylpyrrolidin-1-yl)methyl]-2-{4-[3-(2-methylpyrrolidin-1-yl)propoxy]phenyl}-1,3-oxazole;
4-methyl-1-[3-(4-{4-[(2-methylpyrrolidin-1-yl)methyl]-1,3-oxazol-2-yl}phenoxy)propyl]piperidine;
2-methyl-1-[3-(4-{4-[(2-methylpyrrolidin-1-yl)methyl]-1,3-oxazol-2-yl}phenoxy)propyl]piperidine;
4-[(2-methylpyrrolidin-1-yl)methyl]-2-(4-{3-[2-(pyrrolidin-1-ylmethyl)pyrrolidin-1-yl]propoxy}phenyl)-1,3-oxazole;
2-{4-[3-(2-methylpyrrolidin-1-yl)propoxy]phenyl}-4-(2-pyrrolidin-1-ylethyl)-1,3-oxazole;
1-[(2-{4-[3-(2-methylpyrrolidin-1-yl)propoxy]phenyl}-1,3-oxazol-4-yl)methyl]-1H-1,2,4-triazole;
1-[(2-{4-[3-(2-methylpyrrolidin-1-yl)propoxy]phenyl}-1,3-oxazol-4-yl)methyl]piperidine;
1-[3-(4-{[(2-methylpyrrolidin-1-yl)methyl]-1,3-oxazol-2-yl}phenoxy)propyl]azepane;
(2R)-4-methyl-2-{[(2-{4-[3-(2-methylpyrrolidin-1-yl)propoxy]phenyl}-1,3-oxazol-4-yl)methyl]amino}pentan-1-ol;
1-[4-(4-{[(2-methylpyrrolidin-1-yl)methyl]-1,3-oxazol-2-yl}phenoxy)butyl]azepane;
1-[3-(4-{[(2,6-dimethylpiperidin-1-yl)methyl]-1,3-oxazol-2-yl}phenoxy)propyl]-2,6-dimethylpiperidine;
2-methyl-1-[4-(4-{[(2-methylpyrrolidin-1-yl)methyl]-1,3-oxazol-2-yl}phenoxy)butyl]piperidine;
7,8-dimethyl-1-[(2-{4-[3-(2-methylpyrrolidin-1-yl)propoxy]phenyl}-1,3-thiazol-4-yl)methyl]-1-azaspiro[4.4]nonane;
N-(sec-butyl)-N-[(2-{4-[3-(2-methylpyrrolidin-1-yl)propoxy]phenyl}-1,3-thiazol-4-yl)methyl]-N-propylamine;
1-[(2-{4-[3-(2-methylpyrrolidin-1-yl)propoxy]phenyl}-1,3-thiazol-4-yl)methyl]piperidine;
1-{[2-(4-{3-[(2S)-2-(pyrrolidin-1-ylmethyl)pyrrolidin-1-yl]propoxy}phenyl)-1,3-oxazol-4-yl]methyl}piperidine;
4-[(2-methylpyrrolidin-1-yl)methyl]-2-(4-{3-[(2S)-2-(pyrrolidin-1-ylmethyl)pyrrolidin-1-yl]propoxy}phenyl)-1,3-oxazole;
methyl 4-[(benzylamino)methyl]-2-{4-[3-(2-methylpyrrolidin-1-yl)propoxy]phenyl}-1,3-oxazole-5-carboxylate;
4-[(4-methyl-2-{4-[3-(2-methylpyrrolidin-1-yl)propoxy]phenyl}-1,3-oxazol-5-yl)carbonyl]morpholine;
4-{[4-methyl-2-(4-{3-[(2R)-2-methylpyrrolidin-1-yl]propoxy}phenyl)-1,3-oxazol-5-yl]carbonyl}morpholine;
4-{[4-methyl-2-(4-{3-[(2S)-2-methylpyrrolidin-1-yl]propoxy}phenyl)-1,3-oxazol-5-yl]carbonyl}morpholine;
1-cyclopentyl-4-[(4-methyl-2-{4-[3-(2-methylpyrrolidin-1-yl)propoxy]phenyl}-1,3-oxazol-5-yl)methyl]piperazine;
N-(cyclopropylmethyl)-N-[(4-methyl-2-{4-[3-(2-methylpyrrolidin-1-yl)propoxy]phenyl}-1,3-oxazol-5-yl)methyl]-N-propylamine;
N-benzyl-N-[(4-methyl-2-{4-[3-(2-methylpyrrolidin-1-yl)propoxy]phenyl}-1,3-oxazol-5-yl)methyl]amine;
N-[(4-methyl-2-{4-[3-(2-methylpyrrolidin-1-yl)propoxy]phenyl}-1,3-oxazol-5-yl)methyl]cyclopentanamine;
1-[(5-bromo-2-{4-[3-(2-methylpyrrolidin-1-yl)propoxy]phenyl}-1,3-oxazol-4-yl)methyl]piperidine;
1-{[2-(4-{3-[(2R)-2-methylpyrrolidin-1-yl]propoxy}phenyl)-1,3-oxazol-4-yl]methyl}piperidine;
1-[(2-{4-[3-(2-isobutylpyrrolidin-1-yl)propoxy]phenyl}-1,3-oxazol-4-yl)methyl]piperidine;
1-[(2-{4-[3-(2-ethylpyrrolidin-1-yl)propoxy]phenyl}-1,3-oxazol-4-yl)methyl]piperidine;
(4aR,8aS)-2-[(2-{4-[3-(2-methylpyrrolidin-1-yl)propoxy]phenyl}-1,3-oxazol-4-yl)methyl]decahydroisoquinoline;

2-{4-[3-(2-methylpyrrolidin-1-yl)propoxy]phenyl}-4-{[(2S)-2-(pyrrolidin-1-ylmethyl)pyrrolidin-1-yl]carbonyl}-1,3-oxazole;
1-(3-{4-[4-methyl-5-(2-piperidin-1-ylethyl)-1,3-thiazol-2-yl]phenoxy}propyl)piperidine;
(4aS,8aR)-2-(3-{4-[4-(piperidin-1-ylmethyl)-1,3-oxazol-2-yl]phenoxy}propyl)decahydroisoquinoline;
1-[(2-{3,5-difluoro-4-[3-(2-methylpyrrolidin-1-yl)propoxy]phenyl}-1,3-oxazol-4-yl)methyl]piperidine;
4,4-difluoro-1-[(4-methyl-2-{4-[3-(2-methylpyrrolidin-1-yl)propoxy]phenyl}-1,3-thiazol-5-yl)carbonyl]piperidine;
4,4-difluoro-1-{[4-methyl-2-(4-{3-[(2R)-2-methylpyrrolidin-1-yl]propoxy}phenyl)-1,3-thiazol-5-yl]carbonyl}piperidine;
4-[(4-methyl-2-{4-[3-(2-methylpyrrolidin-1-yl)propoxy]phenyl}-1,3-thiazol-5-yl)carbonyl]morpholine;
4-{[4-methyl-2-(4-{3-[(2R)-2-methylpyrrolidin-1-yl]propoxy}phenyl)-1,3-thiazol-5-yl]carbonyl}morpholine;
1-[(2-{2-methyl-4-[3-(2-methylpyrrolidin-1-yl)propoxy]phenyl}-1,3-oxazol-4-yl)methyl]piperidine;
1-[(4-ethyl-2-{4-[3-(2-methylpyrrolidin-1-yl)propoxy]phenyl}-1,3-thiazol-5-yl)methyl]pyrrolidin-2-one.

The "pharmaceutically acceptable salts" according to the invention include therapeutically active, non-toxic acid salt forms which the compounds of formula (I) are able to form.

The acid addition salt form of a compound of formula (I) that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic, and the like.

Conversely said salt forms can be converted into the free forms by treatment with an appropriate base.

Preferred salt forms are maleate, tartrate, fumarate, chlorhydrate, and trifluoroacetate.

Compounds of the formula (I) and their salts can be in the form of a solvate, which is included within the scope of the present invention. Such solvates include for example hydrates, alcoholates and the like.

Many of the compounds of formula (I) and some of their intermediates have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereoisomeric forms of the compounds of formula (I) or mixtures thereof (including all possible mixtures of stereoisomers).

With respect to the present invention reference to a compound or compounds is intended to encompass that compound in each of its possible isomeric forms and mixtures thereof, unless the particular isomeric form is referred to specifically.

Compounds according to the present invention may exist in different polymorphic forms. Although not explicitly indicated in the above formula, such forms are included within the scope of the present invention.

The invention also includes within its scope prodrug forms of the compounds of formula (I) and its various sub-scopes and sub-groups.

The term "prodrug" as used herein includes compound forms which are rapidly transformed in vivo to the parent compound according to the invention, for example, by hydrolysis in blood. Prodrugs are compounds bearing groups which are removed by biotransformation prior to exhibiting their pharmacological action. Such groups include moieties which are readily cleaved in vivo from the compound bearing it, which compound after cleavage remain or becomes pharmacologically active. Metabolically cleavable groups form a class of groups well known to practitioners of the art. They include, but are not limited to such groups as alkanoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialklysilyl (such as trimethyl- and triethylsilyl), monoesters formed with dicarboxylic acids (such as succinyl), phosphate, sulfate, sulfonate, sulfonyl, sulfinyl and the like. The compounds bearing the metabolically cleavable groups have the advantage that they may exhibit improved bioavailability as a result of enhanced solubility and/or rate of absorption conferred upon the parent compound by virtue of the presence of the metabolically cleavable group. T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987.

A. According to one embodiment of the present invention, compounds of general formula (I) wherein $R^2$ is (II'), $A^3$ is an oxygen atom or a sulfur atom, hereafter referred to as compounds of formula (Id), may be obtained after several reaction steps starting from compounds (XI) and (XII), via intermediates (XIII), as shown in Scheme 9.

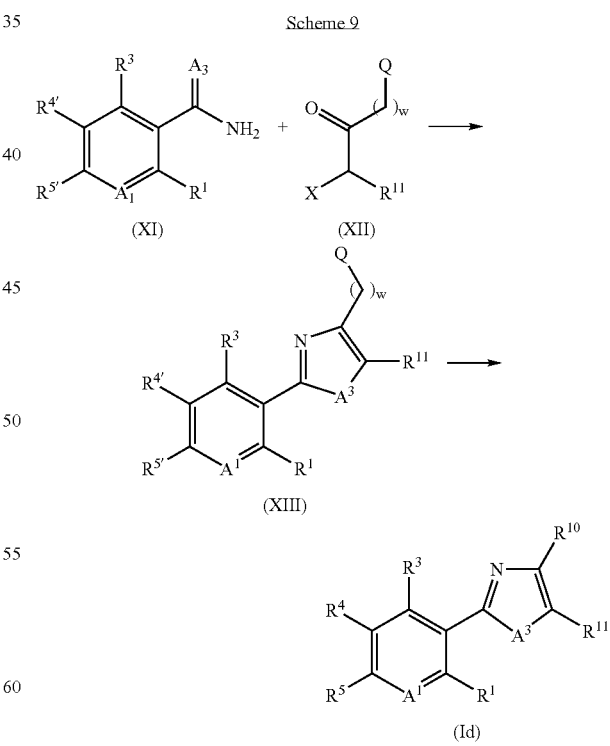

Alternatively, compounds of general formula (Id) may be obtained from compounds (XI) and (XIIbis), via intermediates (XIIIbis), as shown in Scheme 9bis.

Scheme 9bis

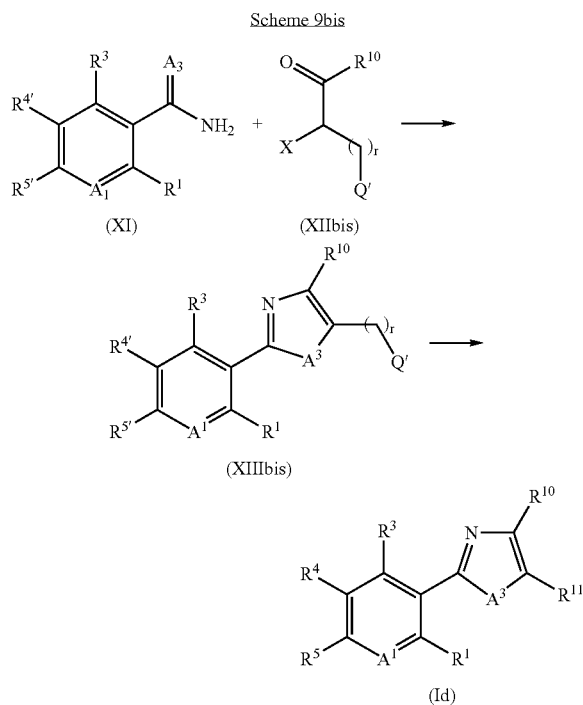

Unless specified otherwise in Schemes 9 to 13,
groups $R^1$, $R^3$, $R^4$, $R^5$, $R^{12a}$, $R^{12b}$, $R^{13a}$, $R^{13b}$, $R^{15}$ and $R^{16}$,
$A^1$ and $A^3$, w, r, z and t, and provisos are as defined for compounds of general formula (I);

$R^{10}$ is $C_{1-4}$ alkyl, preferably methyl, or —$(CH_2)_w$—$(C=O)_t$—$NR^{15}R^{16}$;

$R^{11}$ is H, a $C_{1-4}$ alkyl, preferably a methyl or —$(CH_2)_r$—$(C=O)_z$—$NR^{17}R^{18}$ $R^{4'}$ is $R^4$ as defined above in the specification for compounds of formula (I); or is —O—$(CH_2)_n$—Cl or hydroxy or O—$CH_2$-phenyl; when $R^{4'}$ is $C_{1-4}$ alkoxy, it is preferably a methoxy.

$R^{5'}$ is $R^5$ as defined above in the specification for compounds of formula (I); or —O—$(CH_2)_m$—Cl or hydroxy or $C_{1-4}$ alkoxy or O—$CH_2$-phenyl or a chlorine atom; when $R^{5'}$ is $C_{1-4}$ alkoxy, it is preferably a methoxy.

Q is hydrogen, COOR', CO—$NR^{15}R^{16}$ or a halogen atom, said halogen atom being preferably a chlorine or a bromine atom;

Q' is hydrogen, COOR', halogen or —$(C=O)_z$—$NR^{17}R^{18}$

R' is hydrogen or a $C_{1-4}$ alkyl, preferably a methyl or an ethyl.

X is a halogen atom, preferably chlorine or bromine atom;

In a particular embodiment, when $A^3$ is a sulfur atom, compounds (XI) may be obtained by reacting compounds of formula (XI), in which $A^3$ is an oxygen atom, with a sulfur-releasing reagent according to any conventional method known to the man skilled in the art.

Preferably, the reaction represented in Scheme 9 and Scheme 9 bis is applied to compounds of formula (XI) wherein $A^1$ is CH.

Compounds (XI), wherein $A^3$ is an oxygen or a sulfur atom and $R^{4'}$ is —O—$(CH_2)_n$—Cl or $R^{5'}$ is —O—$(CH_2)_m$—Cl, may be obtained from the corresponding hydroxy-amides, i.e. (XI) wherein $R^{4'}$ or $R^{5'}$ is hydroxy, according to the same procedure described in step (iiib) of Scheme 15, or according to conventional methods known to the man skilled in the art.

Hydroxy-amides of formula (XI) wherein $R^{4'}$ or $R^{5'}$ is hydroxy are commercially available or obtained according to conventional methods known to the man skilled in the art.

Compounds (XII) and (XIIbis) are commercially available or may be synthetized according to conventional methods known to the man skilled in the art. Preferably, bromination of the corresponding methyl-ketone according to Ebike, H. et al. Tetrahedron: Asymmetry 1992, 3, 1153 will be used.

Compounds (XIII), wherein $A^3$ is an oxygen or a sulfur atom, Q is halogen, preferably chlorine or bromine, w is equal to 1, t is equal to 0; $R^{4'}$ is —O—$(CH_2)_n$—Cl or $R^{5'}$ is —O—$(CH_2)_m$—Cl, may be obtained from the reaction of compounds (XI) and compounds (XII), wherein Q is as defined for compounds (XIII), according to methods described by Prager et al. in J. Chem. Soc., Perkin Trans. I, 1997, 17, 2665.

Compounds (XIIIbis), wherein $A^3$ is an oxygen or a sulfur atom, Q' is a halogen atom, preferably a chlorine or a bromine atom, w is equal to 1, t is equal to 0; $R^{4'}$ is —O—$(CH_2)_n$—Cl or $R^{5'}$ is —O—$(CH_2)_m$—Cl, may be obtained from the reaction of compounds (XI) and compounds (XIIbis), wherein Q' is as defined for compounds (XIIIbis), according to methods described by Prager et al. in J. Chem. Soc., Perkin Trans. I, 1997, 17, 2665.

Alternatively, compounds (XIII) and (XIIbis) wherein Q or Q' is a halogen, wherein $A^3$ is an oxygen or a sulfur atom, may be obtained from compounds (XIII) and (XIIIbis), wherein Q or Q'=H by the reaction with N-bromosuccinimide or N-chlorosuccinimide in a solvent such as carbon tetrachloride, or according to conventional methods known to the man skilled in the art.

Alternatively, compounds (Id), may be obtained via intermediates (XIII) or (XIIIbis), according to methods represented in Scheme 10 and Scheme 10bis.

Scheme 10

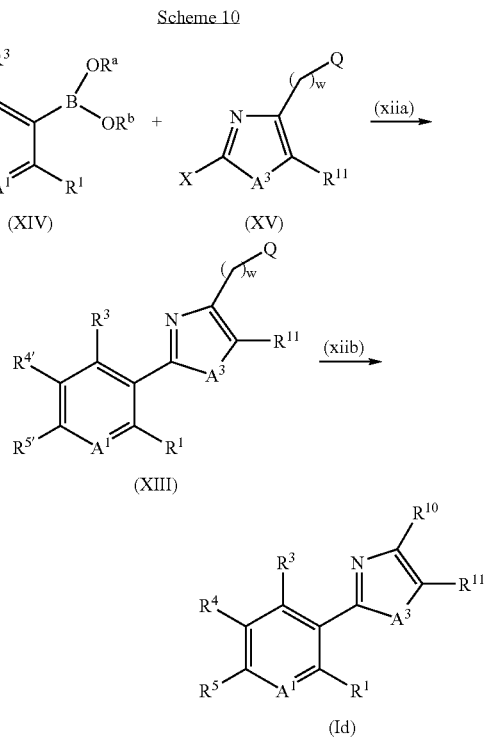

-continued
Scheme 10 bis

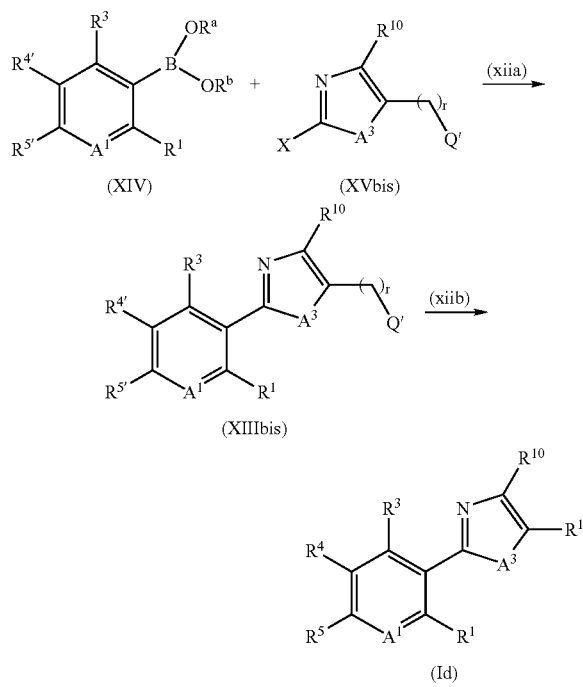

Usually, reactions according to Schemes 10 and 10bis are applied to compounds of formula (XIII), (XIIIbis) and (Id), wherein $R^a$ and $R^b$ are H, $C_{1-4}$ alkyl, or $R^a$ and $R^b$ are linked together to form a $C_{2-3}$ alkylene; and $A^1$ is CH or C(CH$_3$); $R^1$ is hydrogen or halogen, preferably a fluorine atom; $R^3$ is hydrogen, halogen, $C_{1-4}$ alkyl or $C_{1-4}$ alkoxy; $R^{4'}$ is hydrogen, halogen, $C_{1-4}$ alkyl, $C_{1-4}$ alkoxy or trifluoromethyl; $R^{5'}$ is respectively $R^5$ as defined in general formula (I), or $R^{5'}$ is hydroxy, O—CH$_2$-Phenyl or $C_{1-4}$ alkoxy, O—(CH$_2$)$_n$—Cl or O—(CH$_2$)$_n$—NR$^{13a}$R$^{13b}$, or chlorine; $R^4$ and $R^5$ are as defined above in the specification for compounds of formula (I); $R^{10}$ is —(CH$_2$)$_w$—(C=O)$_t$—NR$^{15}$R$^{16}$ wherein t is equal to 0 and w is equal to 1 or wherein t is equal to 1 and w is equal to 0 or 1; $R^{11}$ is —(CH$_2$)$_r$—(C=O)$_z$—NR$^{17}$R$^{18}$ wherein z is equal to 0 and w is equal to 1 or wherein z is equal to 1 and r is equal to 0 or 1; or $A^1$ is a nitrogen atom, $R^1$, $R^3$ and $R^{4'}$ is $R^4$ as defined in general formula (I), or hydrogen; $R^{5'}$ is respectively $R^5$ as defined in general formula (I), or $R^{5'}$ is O—(CH$_2$)$_n$—Cl or O—(CH$_2$)$_n$—NR$^{13a}$R$^{13b}$, or an halogen atom, preferably a chlorine atom; $R^{11}$, $R^4$ and $R^5$ are as defined above in the specification for compounds of formula (I); $R^{11}$, $R^4$ and $R^5$ are as defined above in the specification for compounds of formula (I); $R^{10}$ is —(CH$_2$)$_w$—(C=O)$_t$—NR$^{15}$R$^{16}$ wherein t is equal to 0 and w is equal to 1 or wherein t is equal to 1 and w is equal to 0 or 1.

Hereafter, reference is made to steps (xiia) of Scheme 10 and Scheme 10bis. Intermediates (XV), wherein X is a halogen, preferably a chlorine or a bromine, are reacted with intermediates (XIV) to provide compounds of formula (XIII), preferably in the presence of a palladium-based catalyst such as described by Hodgetts and Kershaw in Org. Lett. 2002, 4, 2905, or according to conventional methods known to the man skilled in the art. Alternatively, intermediates (XI) are reacted with intermediates (XVbis), wherein X is a halogen, preferably a chlorine or a bromine atom, to provide compounds of formula (XIIIbis).

Depending on the nature of the Q group, and $R^{4'}$ or $R^{5'}$ in intermediate (XIII), the reaction conditions to afford compound (Id) may vary. For example, when $R^{4'}$ or $R^{5'}$ is O—CH$_2$-Phenyl or O—CH$_3$, intermediates (XIII) may be treated with a deprotecting agent, for example boron tribromide or H$_2$—Pd/C system according to conventional methods known to the man skilled in the art to afford the same intermediates (XIII) wherein $R^{4'}$ or $R^{5'}$ is hydroxy. Said intermediates may be converted to compound (Id) according to methods that we have already described for step (iii) of Scheme 15.

In a similar manner, the above described reactions could be applied to compound (XIIIbis).

Hereafter, reference is made to steps (xiib) of Scheme 10 and Scheme 10 bis.

Compounds of formula (XIII) in Scheme 10, wherein w=0; Q is halogen (except fluorine) or trifluoromethanesulfonate; $R^{11}$ is as defined for (Id), but not halogen, may be transformed into compounds (Id) by metal-mediated coupling reactions with $R^{10}$-M, wherein the man skilled in the art will appropriately choose $R^{10}$-M amongst boron, tin, magnesium or zinc derivatives. These reactions may be carried out in the presence of a transition metal catalyst complex that the man skilled in the art will deem appropriate, and according to conventional methods known to him. $R^{10}$ in $R^{10}$-M is amino, $C_{1-6}$ alkyl, $C_{2-6}$ alkenyl, $C_{2-6}$ alkynyl, aryl, heteroaryl, $C_{3-8}$ cycloalkyl, 3-8-membered heterocycloalkyl, $C_{1-6}$-alkyl aryl, $C_{1-6}$-alkyl heteroaryl, $C_{2-6}$-alkenyl aryl, $C_{2-6}$-alkenyl heteroaryl, $C_{2-6}$-alkynyl aryl, $C_{2-6}$-alkynyl heteroaryl, $C_{1-6}$-alkyl cycloalkyl, $C_{1-6}$-alkyl heterocycloalkyl, $C_{2-6}$-alkenyl cycloalkyl, $C_{2-6}$-alkenyl heterocycloalkyl, $C_{2-6}$-alkynyl cycloalkyl, $C_{2-6}$ alkynyl, heterocycloalkyl, $C_{1-6}$-alkyl carboxy, $C_{1-6}$-alkyl acyl, $C_{3-8}$-cycloalkyl acyl, aryl acyl, heteroaryl acyl, $C_{3-8}$-heterocycloalkyl acyl, $C_{1-6}$-alkyl acyloxy, $C_{1-6}$-alkyl alkoxy, $C_{1-6}$-alkyl alkoxycarbonyl, $C_{1-6}$-alkyl aminocarbonyl, $C_{1-6}$-alkyl acylamino, acylamino, $C_{3-8}$-cycloalkyl acylamino.

Similarly, compounds of formula (XIIIbis) in Scheme 10 bis, wherein r=0; Q' is halogen or trifluoromethanesulfonate; $R^{10}$ is as defined for (Id), but not halogen, may be transformed into compounds (Id) by metal-mediated coupling reactions with $R^{11}$-M, wherein the man skilled in the art will appropriately choose amongst boron, tin, magnesium or zinc derivatives. These reactions maybe carried out in the presence of a transition metal catalyst complex that the man skilled in the art will deem appropriate, and according to conventional methods known to him. $R^{11}$ in $R^{11}$-M is amino, $C_{1-6}$ alkyl, $C_{2-6}$ alkenyl, $C_{2-6}$ alkynyl, aryl, heteroaryl, $C_{3-8}$ cycloalkyl, 3-8-membered heterocycloalkyl, $C_{1-6}$-alkyl aryl, $C_{1-6}$-alkyl heteroaryl, $C_{2-6}$-alkenyl aryl, $C_{2-6}$-alkenyl heteroaryl, $C_{2-6}$-alkynyl aryl, $C_{2-6}$-alkynyl heteroaryl, $C_{1-6}$-alkyl cycloalkyl, $C_{1-6}$-alkyl heterocycloalkyl, $C_{2-6}$-alkenyl cycloalkyl, $C_{2-6}$-alkenyl heterocycloalkyl, $C_{2-6}$-alkynyl cycloalkyl, $C_{2-6}$ alkynyl and heterocycloalkyl, $C_{1-6}$-alkyl carboxy, $C_{1-6}$-alkyl acyl, $C_{3-8}$-cycloalkyl acyl, aryl acyl, heteroaryl acyl, $C_{3-8}$-heterocycloalkyl acyl, $C_{1-6}$-alkyl acyloxy, $C_{1-6}$-alkyl alkoxy, $C_{1-6}$-alkyl alkoxycarbonyl, $C_{1-6}$-alkyl aminocarbonyl, $C_{1-6}$-alkyl acylamino, acylamino, $C_{3-8}$-cycloalkyl acylamino.

Compounds of formula (XIIIbis) in Scheme 10bis, wherein r=0; Q' is halogen (except fluorine) or hydrogen, $R^{10}$ is as defined for (Id), but not halogen, hydrogen or any acidic functional group, may be transformed into compounds (Id) wherein $R^{11}$ is $C_{1-6}$ alkyl aminosulfonyl, or $C_{1-6}$ aryl aminosulfonyl by sequential treatment with an alkyllithium reagent at low temperature, sulfur dioxide and an alkyl or arylamino group as described in Mader, M. M. et al. in Bioorg. Med. Chem. Let. 2005, 15, 617-620 or Rooney, C. S. et al in J. Org. Chem. 1984, 49, 2212-2217 or any conventional methods known to the man skilled in the art.

Compounds of general formula (XV) or (XVbis) may be prepared according to methods described by Hodgett and Kershaw in Org. Lett. 2002, 4, 2905, or Young at al. in Tetrahedron Lett. 2004, 45, 3797, or according to conventional methods known to the man skilled in the art.

Compounds (XV) and (XVbis) wherein w=0 and Q is trifluoromethanesulfonate or r=0 and Q' is trifluoromethanesulfonate may be obtained according to the procedure described in Arcadi, A. et al. Eur. J. Org. Chem. 1999, 3117-3126, or Liu, X. et al. in Org. Lett. 2003, 5, 1915-1918, or according to any conventional methods known to the man skilled in the art.

Compounds (XIV) are commercially available or may be synthetized as shown in Scheme 11, from intermediates (XIVa), according to conventional methods known to the man skilled in the art.

In intermediates (XIV) and (XIVa):
X is a halogen atom, preferably a halogen atom different from fluorine;
$A^1$, $R^1$ and $R^3$ as defined in general formula (I);
$R^{4'}$ is $R^4$ as defined above in the specification for compounds of formula (I); or is —O—$(CH_2)_n$—Cl or hydroxy or O—$CH_2$-Phenyl. When $R^{4'}$ is $C_{1-4}$ alkoxy, it is preferably a methoxy;
$R^{5'}$ is $R^5$ as defined above in the specification for compounds of formula (I); or —O—$(CH_2)_m$—Cl or hydroxy or $C_{1-4}$ alkoxy or O—$CH_2$-Phenyl or a chlorine atom. When $R^{5'}$ is $C_{1-4}$ alkoxy, it is preferably a methoxy;

Scheme 11

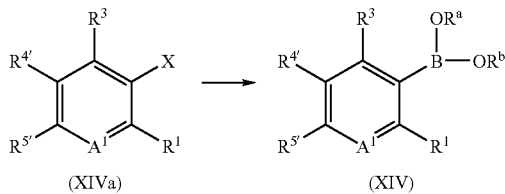

(XIVa)     (XIV)

Preferably, compounds (XIVa) react with a boron reagent, such as bis(pinacolato)diboron in the presence of a palladium-based catalyst to provide intermediates (XIV) according to method described by Ishiyama, T. et al. in J. Org. Chem. 1995, 60, 7508.

Compounds (Id) wherein $A^3$ is an oxygen or a sulfur atom, $R^{10}$ is —$(CH_2)_w$—(C=O)$_t$—$NR^{15}R^{16}$, w is equal to 1, and t is equal to 0 may be obtained from intermediates (XIII), Q is a halogen atom, preferably Cl or Br and $R^{4'}$ is OH or —O—$(CH_2)_n$—Cl, or $R^{5'}$ is —OH or —O—$(CH_2)_n$—Cl according to Scheme 12.

Scheme 12

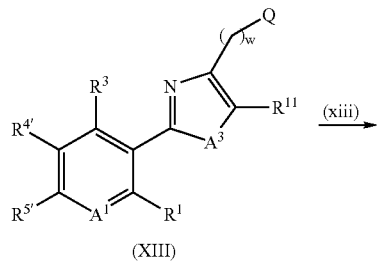

(XIII)

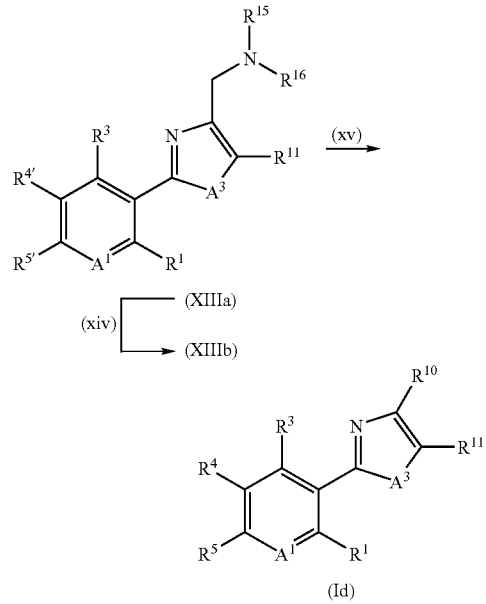

Hereafter, reference is made respectively to steps (xiii), (xiv) and (xv) of Scheme 12:

Step (xiii): intermediates (XIII) are reacted with $HNR^{15}R^{16}$ in the presence of a base, such as triethylamine, to afford intermediates (XIIIa), wherein $R^{4'}$ or $R^{5'}$ is —OH. Alternatively, intermediates (XIII) may react with $HNR^{15}R^{16}$ wherein $R^{15}$ and $R^{16}$ are linked together to form a $C_{3-6}$ alkylene, one methylene of the alkylene being optionally replaced by a carbonyl, such as pyrrolidone in the presence of a base such as sodium hydride in a solvent such as dimethylformamide to afford intermediate (XIIIa).

Step (xiv): intermediates (XIIIa) are converted to intermediates (XIIIb) wherein $R^{4'}$ is —O—$(CH_2)_n$—Cl or $R^{5'}$ is —O—$(CH_2)_m$—Cl according to conventional methods known to the man skilled in the art or according to conditions described for step (iiib) of Scheme 15.

Step (xv): intermediates (XIIIb) are reacted with $HNR^{12a}R^{12b}$ or $HNR^{13a}R^{13b}$ according to reaction conditions described for step (iiic) of Scheme 15.

Additionally, compound of formula (XIII) wherein Q=H, et w=1 and $R^{11}$=$CO_2R$, may be treated with a halogen-releasing agent such as N-bromosuccinimide or N-chlorosuccinimide to afford compounds of formula (XIII) wherein Q=Cl or Br and w=1.

Compounds of formula (XIII) in Scheme 12, wherein w=1; Q is halogen (except fluorine); or compounds of formula (XIIIbis) in Scheme 12bis, wherein w=1; Q' is halogen (except fluorine), all other groups of (Id) as defined in the general formula, may also be transformed into compounds (Id), wherein $R^{10}$ is $C_{1-6}$ alkyl sulfanyl, according to methods described in WO 03/097047.

Alternatively, compounds (Id) wherein $A^3$ is an oxygen or a sulfur atom, $R^{11}$ is —$(CH_2)_r$—(C=O)$_z$—$NR^{17}R^{18}$, r is equal to 1, and z is equal to 0 may be obtained from intermediates (XIIIbis) wherein Q' is a halogen atom, preferably Cl or Br, and $R^{4'}$ is OH or —O—$(CH_2)_n$—Cl, or $R^{5'}$ is —OH or —O—$(CH_2)_n$—Cl, according to Scheme 12bis. Reference made for step (xiii), (xiv and (xv) in Scheme 12 here above may be applied accordingly to Scheme 12bis.

Scheme 12bis

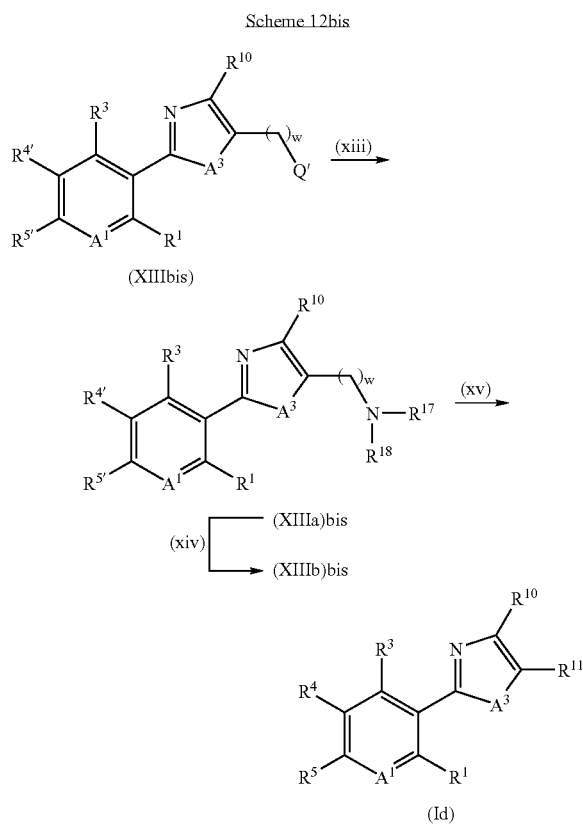

Alternatively, compounds (Id) wherein $A^3$ is oxygen or sulfur, $R^{10}$ is —$(CH_2)_w$—$(C=O)_t$—$NR^{15}R^{16}$, w is equal to 1 or 2 and t is equal to 0 may be obtained from intermediates (XIII) wherein Q=COOR$^1$ and $R^{4'}$ is —O—$(CH_2)_n$—Cl or $R^{5'}$ is —O—$(CH_2)_m$—Cl according to Scheme 13.

Scheme 13

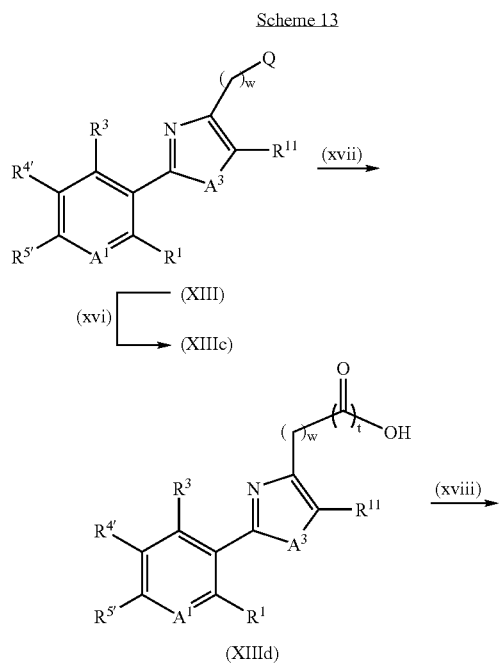

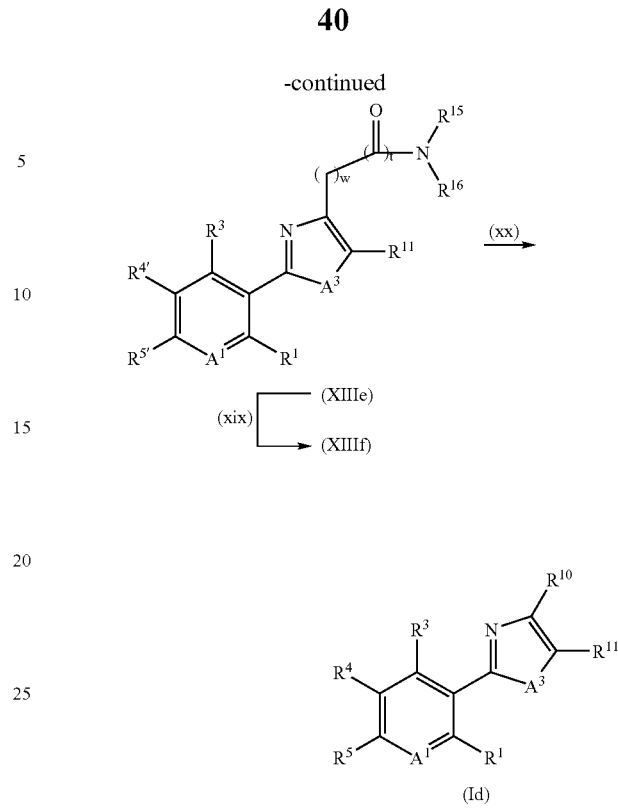

Hereafter, reference is made respectively to steps (xvi), (xvii), (xviii), (xix) and (xx) of Scheme 13.

Step (xvi): intermediates (XIII) are reacted with HNR$^{12a}$R$^{12b}$ or HNR$^{13a}$R$^{13b}$ to afford intermediates (XIIIc) wherein $R^{4'}$ or $R^{5'}$ is respectively $R^4$ or $R^5$ as defined in general formula (I).

Step (xvii): intermediates (XIIIc) are hydrolysed to provide the corresponding acid intermediates (XIIId), according to conventional methods known to the man skilled in the art.

Step (xviii): intermediates (XIIId) are reacted with HNR$^{15}$R$^{16}$ in the presence of a coupling agent, such as 1-(3-dimethylaminopropyl)-3-ethylcarbodiimide hydrochloride and an activating agent, such as 1-hydroxy-benzotriazole, according to conventional methods known to the man skilled in the art, to afford compounds (XIIIe) in which preferably w is equal to 0 or 1, and t is equal to 1.

Step (xix): compounds (XIIIe) are converted to intermediates (XIIIf) using reaction conditions described in step (iii) of Scheme 15, depending on the nature of $R^{4'}$ and $R^{5'}$.

Step (xx): intermediates (XIIIf) are reacted with a reducing agent according to conventional methods known to the man skilled in the art to afford compounds (Id).

Alternatively, compounds (Id) wherein $A^3$ is oxygen or sulfur, $R^{11}$ is —$(CH_2)_r$—$(C=O)_z$—$NR^{17}R^{18}$, r is equal to 1 or 2 and z is equal to 1 may be obtained from intermediates (XIIIbis) wherein Q'=COOR$^1$ and $R^{4'}$ is —O—$(CH_2)_n$—Cl or $R^{5'}$ is —O—$(CH_2)_m$—Cl according to Scheme 13bis. Reference made respectively to steps (xvi), (xvii), (xviii), (xix) and (xx) of Scheme 13 may be applied to Scheme 13bis.

Schema 13bis

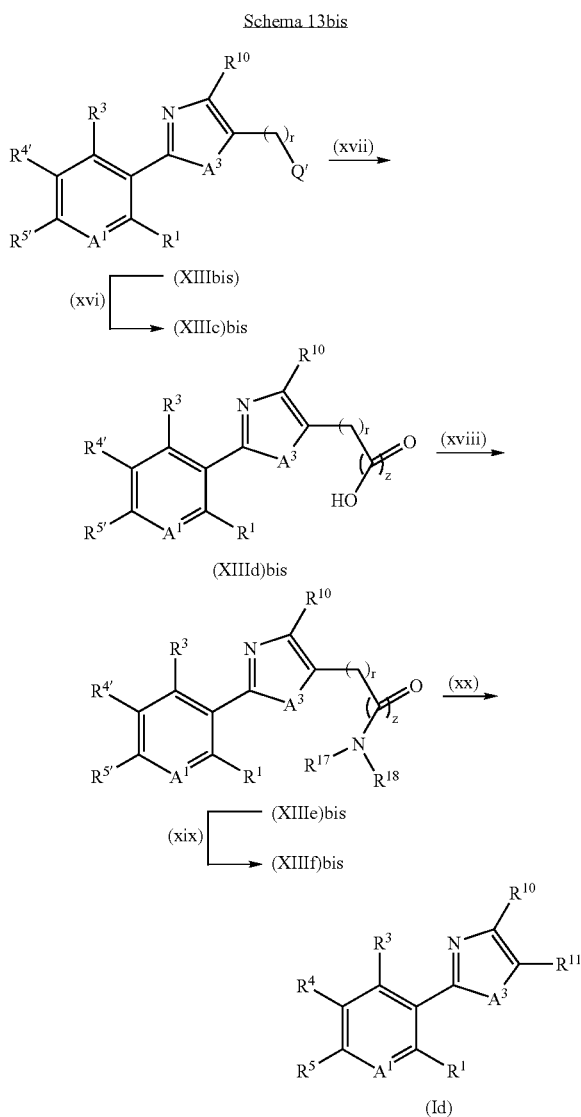

(Id)

In some cases, depending on the nature of the $R^{4'}$ and $R^{5'}$ groups, intermediates (XIIIe) may correspond to compounds (Id), wherein in $R^{10}$, w is equal to 0 or 1 and t is equal to 1.

In a similar manner, intermediates (XIIIebis) may correspond to compounds (Id), wherein in $R^{11}$, r is equal to 0 or 1 and z is equal to 1.

Compounds of formula (Id), wherein $R^{11}$ is $C_{1-6}$ alkyl sulfonyl, $C_{1-6}$ alkyl sulfinyl, may be obtained by reacting compounds (Id), wherein $R^{11}$ is $C_{1-6}$ alkyl sulfanyl, using an oxidizing agent in stoechiometric or excess amount, such as m-chloroperbenzoic acid, according to Brown, T. J. et al. in J. Med. Chem. 1992, 35, 3613-3624 or any methods known to the man skilled in the art.

Compounds of formula (Id), wherein $R^{11}$ is $C_{1-6}$ alkyl aminosulfonyl or $C_{1-6}$ aryl aminosulfonyl may be obtained by the reaction of compound (Id) wherein $R^{11}$ is an amino group with a $C_{1-6}$ alkyl sulfonyl chloride or $C_{1-6}$ aryl sulfonyl chloride according to conventional methods known to the man skilled in the art. Compounds (Id) wherein $R^{10}$ is $C_{1-6}$ alkyl aminosulfonyl or $C_{1-6}$ aryl aminosulfonyl may be obtained in a similar manner, according to Hulin, B. et al. in J. Med. Chem. 1992, 35, 1853-1864.

F. According yet to another embodiment of the present invention, compounds of general formula (I), hereafter referred to as compounds (Ie) and unless otherwise specified:
$R^1$, $R^3$, $R^{12a}$, $R^{12b}$, $R^{13a}$, $R^{13b}$, $A^1$ and $A^3$, r and z, and provisos are as defined for compounds of general formula (I);
$R^{4'}$ is —O—$(CH_2)_n$—Cl or $R^{5'}$ is —O—$(CH_2)_m$—Cl or a chlorine atom;
$R^{10}$ is $C_{1-4}$ alkyl. Preferably, $R^{10}$ is a methyl;
$R^{11}$ is —$CH_2$—$NR^{17}R^{18}$;
may be obtained after several reaction steps starting from compounds (XIIIbis) wherein Q'=COOR', r is equal to 0 and z is equal to 1, $R^{4'}$ is —O—$(CH_2)_n$—Cl or $R^{5'}$ is —O—$(CH_2)_m$—Cl, as shown in Scheme 14.

In Scheme 14, R' is $C_{1-4}$ alkyl, preferably a methyl and X is a halogen atom, preferably a chlorine or bromine atom.

Scheme 14

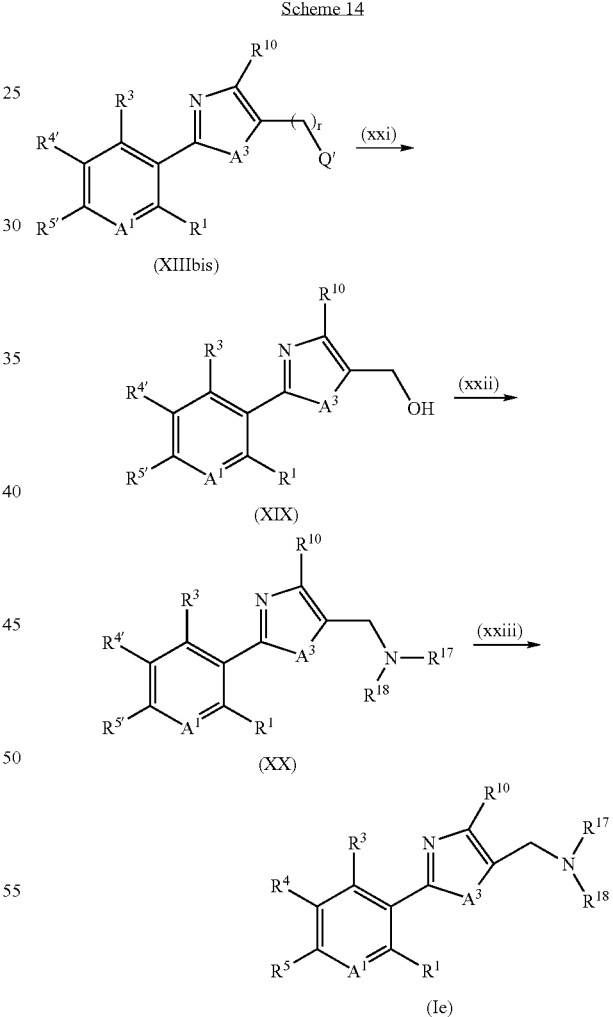

Hereafter, reference is made respectively to steps (xxi), (xxii) and (xxiii) of Scheme 14.

Step (xxi): intermediates (XIIIbis) are reacted with a reducing agent, such as lithium borohydride, according to conventional methods known to the man skilled in the art, to afford intermediate (XIX).

Step (xxii): alcohols of formula (XIX) are reacted with methanesulfonyl chloride in the presence of a base, and then reacted with $HNR^{17}R^{18}$ according to conventional methods known to the man skilled in the art to afford intermediate (XX).

Alternatively, alcohols of formula (XIX) are reacted with amide of formula $HNR^{17}R^{18}$, wherein $R^{17}$ and $R^{18}$ are linked together to form a $C_{3-6}$ alkylene, one methylene of the alkylene adjacent to the nitrogen being replaced by a carbonyl, such as in pyrrolidone in the presence of para-toluene sulfonic acid in a solvent such as toluene to afford intermediate (XX).

Step (xiii): intermediates (XX) are subsequently reacted with $HNR^{12a}R^{12b}$ or $HNR^{13a}R^{13b}$ to afford compounds (Ie), according to conditions described for step (xvi) above in the specification.

Preferably, reactions represented in Scheme 14 are applied to compounds of formula (XI) wherein $A^1$ is CH.

According yet to another embodiment of the present invention, compounds of general formula (Id) could be obtained from compounds (XIII) as described in Scheme 15.

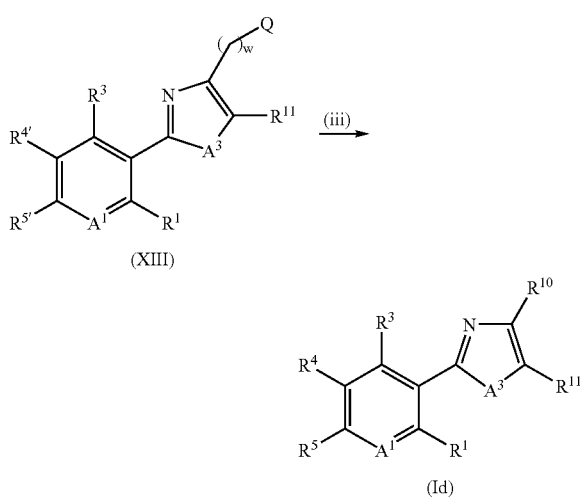

Conversion of compounds of formula (XIII) into compounds of formula (Id), may occur in one or more steps, under a variety of reaction conditions depending on the nature of $R^{4'}$, $R^{5'}$, $A^1$ and Q groups, according to conditions described hereafter in steps (iiia), (iiib), (iiic), (iiid) and (iiie):

Step (iiia): intermediates of formula (XIII) wherein $A^1$ is CH and $R^{4'}$ or $R^{5'}$ is —O—$CH_2$-phenyl may be converted to intermediates of same general formula as intermediates (XIII) wherein $R^{4'}$ or $R^{5'}$ is —OH, using a catalyst, for example palladium on charcoal (Pd/C or Pd(OH)$_2$/C), in the presence of a solvent such as methanol or ethanol under a hydrogen atmosphere.

Step (iiib): intermediates (XIII) wherein $A^1$ is CH and $R^{4'}$ or $R^{5'}$ is OH may be converted into intermediates (XIII), wherein $A^1$ is CH and $R^{4'}$ is —O—$(CH_2)_n$—Cl or $R^{5'}$ is —O—$(CH_2)_m$—Cl by reacting with a di-haloalkane respectively of general formula —Y—$(CH_2)_n$—Cl or Y—$(CH_2)_m$—Cl, wherein Y is a halogen except a fluorine, in the presence of a base. Preferably, Y is a bromine atom. This reaction may occur according to methods described by Walsh et al. in J. Med. Chem. 1989, 32, 105.

Step (iiic): intermediates (XIII) wherein AI is CH and $R^{4'}$ is —O—$(CH_2)_n$—Cl or $R^{5'}$ is —O—$(CH_2)_m$—Cl may react respectively with $HNR^{12a}R^{12b}$ or with $HNR^{13a}R^{13b}$ in the presence of a base such as triethylamine or potassium carbonate in acetonitrile or acetone as solvent, to afford compounds of formula (Id). The reaction may be performed according to conventional methods known to the man skilled in the art.

Step (iiid): intermediates (XIII), wherein $A^1$ is a nitrogen atom, and $R^{4'}$ or $R^{5'}$ is a halogen atom, preferably a chlorine or a bromine atom, are reacted respectively with amino alcohols of formula HO-L, L being as defined here above in the specification, preferably with amino alcohols of formula HO—$(CH_2)_n$—$NR^{12a}R^{12b}$ or HO—$(CH_2)_m$—$NR^{13a}R^{13b}$, to afford compound (Id) according to conventional methods known to the man skilled in the art. Alternatively a base, such as potassium tert-butylate, cesium carbonate or sodium hydride, with a solvent, such as dimethylformamide or tetrahydrofuran, in the presence of a palladium- or a copper-based catalyst, may be added, according to methods described by Penning et al. in J. Med. Chem. 2000, 43, 721.

Step (iiie): intermediates (XIII), wherein $A^1$ is CH, and $R^{4'}$ or $R^{5'}$ is a hydroxy group, are reacted respectively with amino alcohols of formula HO-L, L being as defined here above in the specification, preferably with amino alcohols of formula HO—$(CH_2)_n$—$NR^{12a}R^{12b}$ or HO—$(CH_2)_m$—$NR^{13a}R^{13b}$, to afford compound (Id) according to conventional methods known to the man skilled in the art.

Alternatively, diethylazodicarboxylate in the presence of triphenylphosphine in a solvent such as dichloromethane may be used.

Alternatively, compounds of general formula (Id) may be obtained from compound (XIIIbis) following steps (iiia), (iiib), (iiic), (iiid) and (iiie) described in Scheme 15.

G. According yet to another embodiment of the present invention, compounds of general formula (I), hereafter referred to as compounds (Id) and unless otherwise specified:

$R^1$, $R^3$, $R^{12a}$, $R^{12b}$, $R^{13a}$, $R^{13b}$, $A^1$ and $A^3$, r and z, and provisos are as defined for compounds of general formula (I);

$R^{4'}$ is —O—$(CH_2)_n$—Cl or $R^{5'}$ is —O—$(CH_2)_m$—Cl or a chlorine atom;

$R^{10}$ is —$CH_2$—$NR^{15}R^{16}$;

$R^{11}$ is H or $C_{1-4}$ alkyl. Preferably, $R^{11}$ is a methyl;

may be obtained after several reaction steps starting from compounds (XIII) wherein Q is a hydroxy group or chlorine atom, w is equal to 0, $R^{4'}$ is —O—$(CH_2)_n$—Cl or $R^{5'}$ is —O—$(CH_2)_m$—Cl, as shown in Scheme 16.

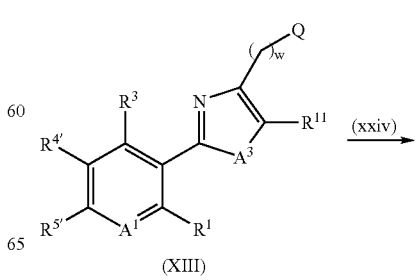

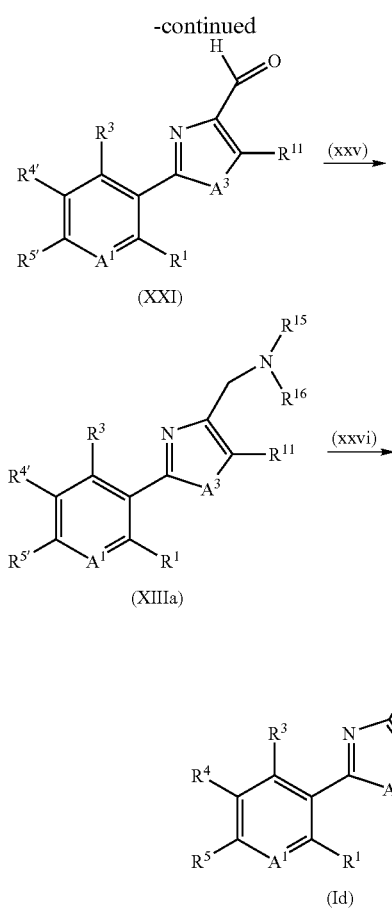

(XXI)

(XIIIa)

(Id)

Hereafter, reference is made respectively to steps, (xxiv), (xxv) and (xxvi) of Scheme 16:

Step (xxiv): intermediated (XIII), wherein Q is a hydroxy group are reacted with an oxidizing agent, according to conventional methods known to the man skilled in the art, to afford intermediates of formula (XXI). Alternatively, intermediates of formula (XIII), wherein Q is a chlorine atom, may react with anhydrous trimethylamine N-oxide in a mixture of solvent such as dichloromethane and dimethylsulfoxide, to afford intermediates or formula (XXI).

Step (xxv): compounds of formula (XXI) are reacted with $HNR^{15}R^{16}$ in the presence of a reducing agent, such as sodium cyanoborohydride in a solvent such as tetrahydrofuran, according to conventional methods known to the man skilled in the art to afford intermediate (XIIIa).

Step (xxvi): intermediates (XIIIa) are subsequently reacted with $HNR^{12a}R^{12b}$ or $HNR^{13a}R^{13b}$ to afford compounds (Id), according to conditions described for step (iii) above in Scheme 15.

Unless otherwise specified, preferred groups, more preferred and most preferred $R^1$, $R^2$, $R^3$, $R^4$, $R^5$, $R^{10}$, $R^{11}$, $R^{12a}$, $R^{12b}$, $R^{13a}$, $R^{13b}$, $R^{15}$, $R^{16}$, $R^{17}$, $R^{18}$ groups of compounds represented in Schemes 9 to 16 are as defined above in the specification for compounds of general formula (I).

H. According to another embodiment, some compounds of general formula (I) may be prepared by functional group transformation.

Compounds of general formula (If) may be obtained from intermediates (XIII), wherein $A^1$, $A^3$, $R^1$, $R^2$, $R^3$, $R^4$, $R^5$, w and t are defined above in the specification for compounds of formula (I), Q is Cl, $R^{11}$ is a hydrogen, according to step (xxvii) in Scheme 17.

Scheme 17

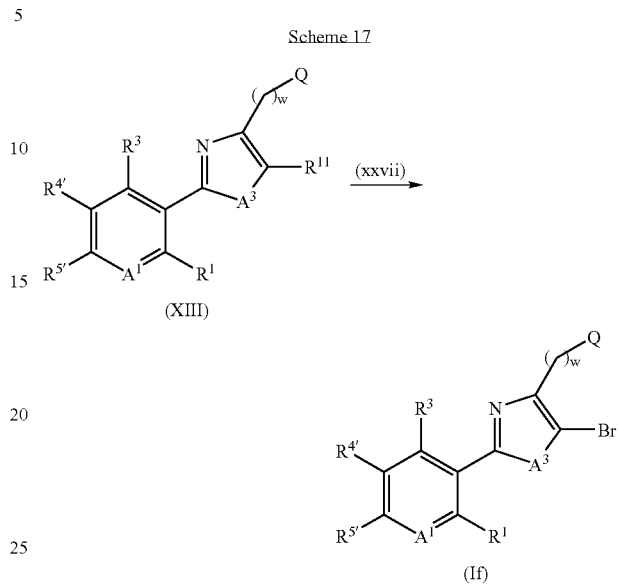

(XIII)

(If)

Hereafter, reference is made to step (xxvii) of Scheme 17;
Step (xxvii): compounds of formula (XIII) are reacted with a halide-releasing agent, such as N-bromosuccinimide in a solvent, such as acetonitrile, to afford compounds of formula (If).

In a particular embodiment, the present invention relates to a compound of formula (VII), geometrical isomers, enantiomers, diastereoisomers, pharmaceutically acceptable salts and all possible mixtures thereof,

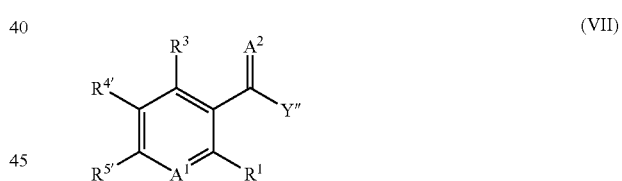

(VII)

wherein
$A^1$ is CH, C(CH$_3$) or N;
$A^2$ is O or S;
Y" is halogen, hydroxy or $C_{1-4}$ alkoxy;
$R^1$ is hydrogen or halogen;
$R^3$ is hydrogen, halogen, $C_{1-4}$ alkyl or $C_{1-4}$ alkoxy;
$R^{4'}$ is hydrogen, halogen, $C_{1-4}$ alkyl, $C_{1-4}$ alkoxy, O—CH$_2$-Phenyl; or —O—(CH$_2$)$_n$—Cl or —O—(CH$_2$)$_n$—NR$^{12a}$R$^{12b}$;
$R^{5'}$ is hydrogen, halogen, —O—CH$_2$-Phenyl, —O—(CH$_2$)$_m$—Cl or —O—(CH$_2$)$_m$—NR$^{13a}$R$^{13b}$, each CH$_2$ in —O—(CH$_2$)$_m$—NR$^{13a}$R$^{13b}$ being optionally substituted by one or two $C_{1-4}$ alkyl;
$R^{12a}$ and $R^{12b}$ are linked together to form a $C_{3-6}$ alkylene, each methylene of the alkylene being optionally substituted by a $C_{1-4}$ alkyl;
$R^{13a}$ and $R^{13b}$ are linked together to form a $C_{3-6}$ alkylene, each methylene of the alkylene being optionally substituted by a $C_{1-4}$ alkyl, an amino group or $C_{1-6}$ alkyl amino, one methylene of the alkylene being optionally replaced by a nitrogen atom, said nitrogen atom being optionally substituted by a $C_{1-8}$ alkyl or $C_{1-6}$ alkyl amino;

n and m are independently an integer comprised between 2 and 8;

with the proviso that $R^{4'}$ is —O—$(CH_2)_n$—$NR^{12a}R^{12b}$, —O—$(CH_2)_n$—Cl, or —O—$CH_2$-Phenyl when $R^{5'}$ is hydrogen and that $R^{5'}$ is —O—$(CH_2)_m$—$NR^{13a}R^{13b}$, —O—$(CH_2)_m$—Cl, or —O—$CH_2$-Phenyl when $R^{4'}$ is hydrogen, halogen, $C_{1-4}$ alkyl or $C_{1-4}$ alkoxy; and with the proviso that said compound of formula (VII) is different from methyl 4-(3-chloropropoxy)benzoate, 4-(3-chloropropoxy)benzoic acid, 4-(3-chloropropoxy)benzoylchloride, methyl 3-(3-chloropropoxy)benzoate, methyl 4-(3-piperidin-1-ylpropoxy)benzoate, methyl 3-(3-piperidin-1-ylpropoxy)benzoate, methyl 4-(3-pyrrolidin-1-ylpropoxy) benzoate), 4-(3-piperidin-1-ylpropoxy)benzoic acid and 4-(3-pyrrolidin-1-ylpropoxy)benzoic acid.

Preferably, $A^1$ is CH or $C(CH_3)$. More preferably, $A^1$ is CH. Preferably, $A^2$ is O.

Y'' is preferably a hydroxy, a chlorine atom or a methoxy.

In a further particular embodiment, the present invention relates to a compound of formula (XI), geometrical isomers, enantiomers, diastereoisomers, pharmaceutically acceptable salts and all possible mixtures thereof,

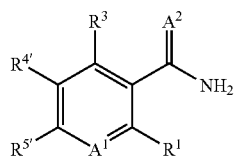

(XI)

$A^1$ is CH, $C(CH_3)$ or N;
$A^3$ is O or S;
$R^1$ is hydrogen or halogen;
$R^3$ is hydrogen, halogen, $C_{1-4}$ alkyl or $C_{1-4}$ alkoxy;
$R^{4'}$ is hydrogen, halogen, $C_{1-4}$ alkyl, $C_{1-4}$ alkoxy, hydroxy, —O—$CH_2$-Phenyl; —O—$(CH_2)_n$—Cl or —O—$(CH_2)_n$—$NR^{12a}R^{12b}$;
$R^{5'}$ is hydrogen, halogen, $C_{1-4}$ alkoxy, hydroxy, —O—$CH_2$-Phenyl, —O—$(CH_2)_m$—Cl or —O—$(CH_2)_m$—$NR^{13a}R^{13b}$, each $CH_2$ in —O—$(CH_2)_m$—$NR^{13a}R^{13b}$ being optionally substituted by one or two $C_{1-4}$ alkyl;
$R^{12a}$ and $R^{12b}$ are linked together to form a $C_{3-6}$ alkylene, each methylene of the alkylene being optionally substituted by a $C_{1-4}$ alkyl;
$R^{13a}$ and $R^{13b}$ are linked together to form a $C_{3-6}$ alkylene, each methylene of the alkylene being optionally substituted by a $C_{1-4}$ alkyl, an amino group or $C_{1-6}$ alkyl amino, one methylene of the alkylene being optionally replaced by a nitrogen atom, said nitrogen atom being optionally substituted by a $C_{1-8}$ alkyl or $C_{1-6}$ alkyl amino;

n and m are independently an integer comprised between 2 and 8;

with the proviso that $R^{4'}$ is —O—$(CH_2)_n$—$NR^{12a}R^{12b}$, —O—$(CH_2)_n$—Cl, or —O—$CH_2$-Phenyl when $R^{5'}$ is hydrogen and that $R^{5'}$ is —O—$(CH_2)_n$—$NR^{13a}R^{13b}$, —O—$(CH_2)_m$—Cl, or —O—$CH_2$-Phenyl when $R^{4'}$ is hydrogen, halogen, $C_{1-4}$ alkyl or $C_{1-4}$ alkoxy; and with the proviso that said compound of formula (XI) is different from 4-(3-chloropropoxy)benzamide and 4-(2-chloroethoxy)benzamide.

Preferably, $A^1$ is CH or $C(CH_3)$. More preferably, $A^1$ is CH. Preferably, $A^3$ is O.

When $R^{5'}$ is halogen, it is preferably a chlorine atom.

When $R^{4'}$ is a $C_{1-4}$ alkoxy, it is preferably a methoxy.

In a particular embodiment, the present invention relates to a synthetic intermediate of formula (XIII) geometrical isomers, enantiomers, diastereoisomers, pharmaceutically acceptable salts and all possible mixtures thereof,

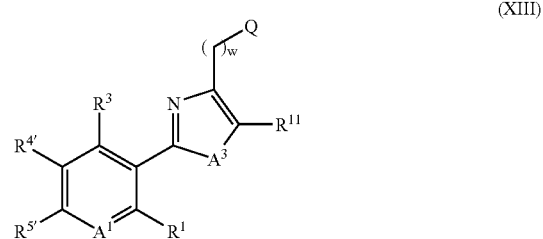

(XIII)

wherein
$A^1$ is CH, $C(CH_3)$ or C-halogen;
$A^3$ is O or S;
Q is hydrogen, COOR', —(C=O)$_t$—$NR^{15}R^{16}$ or halogen;
R' is hydrogen or $C_{1-4}$ alkyl;
$R^1$ is hydrogen, halogen or $C_{1-4}$ alkyl;
$R^3$ is hydrogen;
$R^{4'}$ is hydrogen, halogen, $C_{1-4}$ alkyl, $C_{1-4}$ alkoxy or —O—$(CH_2)_n$—Cl.
$R^{5'}$ is hydrogen, hydroxy, —O—$(CH_2)_m$-halogen, —O—$CH_2$-Phenyl, or —O—$(CH_2)_m$—$NR^{13a}R^{13b}$;
$R^{11}$ is hydrogen, $C_{1-4}$ alkyl, halogen or —$(CH_2)_r$—$(C=O)_z$—$NR^{17}R^{18}$;
$R^{13a}$ and $R^{13b}$ are linked together to form a $C_{3-6}$ alkylene, each methylene of the alkylene being optionally substituted by one or two $C_{1-4}$ alkyl, an amino group or $C_{1-6}$ alkyl amino, one methylene being optionally replaced by a nitrogen atom, said nitrogen atom being optionally substituted by a $C_{1-8}$ alkyl, $C_{3-6}$ cycloalkyl or $C_{1-6}$ alkyl amino; or one methylene of the alkylene being linked with a second methylene of the alkylene to form a $C_{3-6}$ alkylene.

$R^{15}$ is hydrogen or a $C_{1-8}$ alkyl;
$R^{16}$ is aryl, heteroaryl, $C_{1-8}$ alkyl, $C_{1-6}$ alkyl cycloalkyl, $C_{3-6}$ cycloalkyl, $C_{1-6}$ alkyl aryl or a $CH_2$— heteroaryl;
or $R^{15}$ and $R^{16}$ are linked together to form a $C_{3-6}$ alkylene, each methylene of the alkylene being optionally substituted by one or two $C_{1-4}$ alkyl or by one or two halogen; or one methylene of the alkylene being optionally substituted by an alkylamine or by $C_{1-6}$ alkyl aryl; one methylene of the alkylene being optionally replaced by a nitrogen atom or an oxygen atom, said nitrogen atom being optionally substituted by a $C_{1-8}$ alkyl or $C_{3-6}$ cycloalkyl; or one methylene of the alkylene being optionally replaced by a $C_{3-8}$ cycloalkyl or a carbonyl and another methylene being optionally substituted by an alkylamine; or one methylene of the alkylene being linked with a second methylene of the alkylene to form a $C_{3-6}$ alkylene; or $R^{15}$ and $R^{16}$ are linked together to form with N an unsaturated 5- or 6-membered heteroaryl optionally substituted by a $C_{1-4}$ alkyl;

$R^{17}$ is hydrogen or a $C_{1-8}$ alkyl;
$R^{18}$ is $C_{1-8}$ alkyl, $C_{1-6}$ alkyl cycloalkyl or $C_{1-6}$ alkyl aryl;
or $R^{17}$ and $R^{18}$ are linked together to form a $C_{3-6}$ alkylene, each methylene of the alkylene being optionally substituted by one or two $C_{1-4}$ alkyl or by one or two halogen, one methylene of the alkylene being optionally replaced by a carbonyl, a nitrogen atom or an oxygen atom, said nitrogen atom being optionally substituted by a $C_{1-8}$ alkyl or $C_{3-6}$ cycloalkyl;

w is an integer equal to 0 or 1;

t is an integer equal to 0 or 1;
z is an integer equal to 0 or 1; and
m is an integer equal to 2, 3 or 4;
and provided that
when $R^{5'}$ is O—CH$_2$-Phenyl, $R^{4'}$ is halogen and that compound (XIII) is different from 4-(2-oxazolylphenol), 4-(4-chloromethyl-oxazol-2-yl)phenol; 4-(4-chloromethyl-thiazol-2-yl)phenol, ethyl 2-(4-hydroxyphenyl)oxazole-4-carboxylate, 2-(4-hydroxy-phenyl)-4-[2-(methoxycarbonyl)ethyl]-1,3-thiazole; 4-(5-ethyl-2-thiazolyl)phenol and 4-(4-methyl-oxazol-2-yl)phenol.

In a another particular embodiment the present invention relates to a synthetic intermediates of formula (XIIIbis), geometrical isomers, enantiomers, diastereoisomers, pharmaceutically acceptable salts and all possible mixtures thereof,

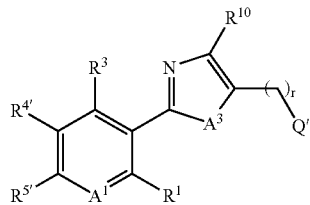

(XIIIbis)

wherein
$A^1$ is CH or N;
$A^3$ is O or S;
Q' is hydrogen, COOR', halogen or —(C=O)$_z$—NR$^{17}$R$^{18}$;
R' is hydrogen or $C_{1-4}$ alkyl;
$R^1$ is hydrogen;
$R^3$ is hydrogen;
$R^{4'}$ is hydrogen;
$R^{5'}$ is hydrogen, halogen, —O—(CH$_2$)$_m$-halogen or —O—(CH$_2$)$_m$—NR$^{13a}$R$^{13b}$;
$R^{10}$ is $C_{1-4}$ alkyl or —(C=O)$_t$—NR$^{15}$R$^{16}$;
$R^{13a}$ and $R^{13b}$ are linked together to form a $C_{3-6}$ alkylene, each methylene of the alkylene being optionally substituted by one or two $C_{1-4}$ alkyl, an amino group or $C_{1-6}$ alkyl amino, one methylene being optionally replaced by a nitrogen atom, said nitrogen atom being optionally substituted by a $C_{1-8}$ alkyl, $C_{3-6}$ cycloalkyl or $C_{1-6}$ alkyl amino; or one methylene of the alkylene being linked with a second methylene of the alkylene to form a $C_{3-6}$ alkylene.
$R^{15}$ is hydrogen or a $C_{1-8}$ alkyl;
$R^{16}$ is aryl, a heteroaryl, $C_{1-8}$ alkyl, $C_{3-6}$ cycloalkyl, $C_{1-6}$ alkyl cycloalkyl, $C_{1-6}$ alkyl aryl or a CH$_2$—heteroaryl;
or $R^{15}$ and $R^{16}$ are linked together to form a $C_{3-6}$ alkylene, each methylene of the alkylene being optionally substituted by one or two $C_{1-4}$ alkyl or by one or two halogen; or one methylene of the alkylene being optionally substituted by an alkylamine or by $C_{1-6}$ alkyl aryl; one methylene of the alkylene being optionally replaced by a nitrogen atom or an oxygen atom, said nitrogen atom being optionally substituted by a $C_{1-8}$ alkyl or $C_{3-6}$ cycloalkyl; or one methylene of the alkylene being optionally replaced by a $C_{3-8}$ cycloalkyl or a carbonyl and another methylene being optionally substituted by an alkylamine; or one methylene of the alkylene being linked with a second methylene of the alkylene to form a $C_{3-6}$ alkylene; or $R^{15}$ and $R^{16}$ are linked together to form with N an unsaturated 5- or 6-membered heteroaryl optionally substituted by a $C_{1-4}$ alkyl;
$R^{17}$ is hydrogen or a $C_{1-8}$ alkyl;
$R^{18}$ is $C_{1-8}$ alkyl, $C_{1-6}$ alkyl cycloalkyl or $C_{1-6}$ alkyl aryl;
or $R^{17}$ and $R^{18}$ are linked together to form a $C_{3-6}$ alkylene, each methylene of the alkylene being optionally substituted by one or two $C_{1-4}$ alkyl or by one or two halogen, one methylene of the alkylene being optionally replaced by a carbonyl, a nitrogen atom or an oxygen atom, said nitrogen atom being optionally substituted by a $C_{1-8}$ alkyl or $C_{3-6}$ cycloalkyl;
t is an integer equal to 0 or 1;
m is an integer equal to 2, 3 or 4;
z is an integer equal to 0 or 1; and
r is an integer equal to 0 or 1.

In a further particular aspect, the present invention relates to compounds of formula (Id),

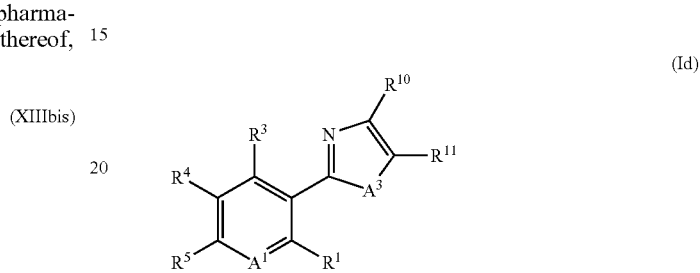

(Id)

wherein, $A^1$, $A^3$, $R^1$, $R^3$, $R^4$, $R^5$, $R^{10}$, $R^{11}$ and provisos are as defined above in the specification for compounds of formula (I).

In yet another further particular aspect, the present invention relates to compounds of formula (Ie),

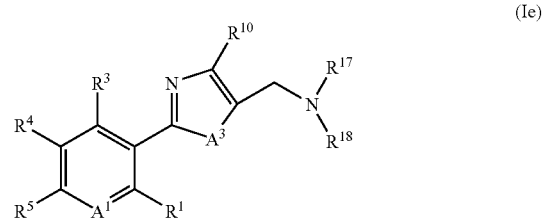

(Ie)

wherein, $A^1$, $A^3$, $R^1$, $R^3$, $R^4$, $R^5$, $R^{10}$, $R^{17}$, $R^{18}$ and provisos are as defined above in the specification for compounds of formula (I).

In a further embodiment, the invention relates to a synthetic intermediate selected from the group consisting of
4-(4-chlorobutoxy)benzamide;
3-(3-chloropropoxy)benzamide;
4-(3-chloropropoxy)benzenecarbothioamide;
4-(chloromethyl)-2-[4-(3-chloropropoxy)phenyl]-1,3-oxazole;
2-[4-(2-chloroethoxy)phenyl]-4-(chloromethyl)-1,3-oxazole;
2-[4-(4-chlorobutoxy)phenyl]-4-(chloromethyl)-1,3-oxazole;
methyl {2-[4-(3-chloropropoxy)phenyl]-1,3-oxazol-4-yl}acetate;
{2-[4-(3-chloropropoxy)phenyl]-1,3-oxazol-4-yl}acetic acid;
2-[4-(3-chloropropoxy)phenyl]-4-(2-oxo-2-pyrrolidin-1-ylethyl)-1,3-oxazole;
4-{4-[(2-methylpyrrolidin-1-yl)methyl]-1,3-oxazol-2-yl}phenol;
2-[4-(3-chloropropoxy)phenyl]-4-[(2-methylpyrrolidin-1-yl)methyl]-1,3-oxazole;

2-[4-(2-chloroethoxy)phenyl]-4-[(2-methylpyrrolidin-1-yl)methyl]-1,3-oxazole;
2-[4-(4-chlorobutoxy)phenyl]-4-[(2-methylpyrrolidin-1-yl)methyl]-1,3-oxazole;
4-(chloromethyl)-2-[3-(3-chloropropoxy)phenyl]-1,3-oxazole;
4-(chloromethyl)-2-[4-(3-chloropropoxy)phenyl]-1,3-thiazole;
{2-[4-(3-chloropropoxy)phenyl]-4-methyl-1,3-oxazol-5-yl}methanol;
methyl 2-[4-(3-chloropropoxy)phenyl]-4-methyl-1,3-oxazole-5-carboxylate;
1-({2-[4-(3-chloropropoxy)phenyl]-1,3-oxazol-4-yl}acetyl)piperidine;
2-{2-[4-(3-chloropropoxy)phenyl]-1,3-oxazol-4-yl}-N-(4-fluorophenyl)acetamide;
4-({2-[4-(3-chloropropoxy)phenyl]-1,3-oxazol-4-yl}acetyl)morpholine;
2-{2-[4-(3-chloropropoxy)phenyl]-1,3-oxazol-4-yl}-N-cyclopentylacetamide;
2-{2-[4-(3-chloropropoxy)phenyl]-1,3-oxazol-4-yl}-N-(cyclopropylmethyl)-N-propylacetamide;
1-({2-[4-(3-chloropropoxy)phenyl]-1,3-oxazol-4-yl}acetyl)azepane;
2-[4-(3-chloropropoxy)phenyl]-4,5-dimethyl-1,3-oxazole;
4-(bromomethyl)-2-[4-(3-chloropropoxy)phenyl]-5-methyl-1,3-oxazole;
4-(bromomethyl)-2-[4-(3-bromopropoxy)phenyl]-5-methyl-1,3-oxazole;
ethyl 2-[4-(3-chloropropoxy)phenyl]-1,3-oxazole-4-carboxylate;
2-[4-(3-chloropropoxy)phenyl]-1,3-oxazole-4-carboxylic acid;
4-({2-[4-(3-chloropropoxy)phenyl]-1,3-oxazol-4-yl}carbonyl)morpholine;
1-({2-[4-(3-chloropropoxy)phenyl]-1,3-oxazol-4-yl}carbonyl)piperidine;
1-({2-[4-(3-chloropropoxy)phenyl]-1,3-oxazol-4-yl}carbonyl)-4-cyclopentylpiperazine;
2-[4-(3-chloropropoxy)phenyl]-N-(cyclopropylmethyl)-N-propyl-1,3-oxazole-4-carboxamide;
2-[4-(3-chloropropoxy)phenyl]-N-cyclopentyl-1,3-oxazole-4-carboxamide;
2-[4-(3-chloropropoxy)phenyl]-N-(4-fluorobenzyl)-1,3-oxazole-4-carboxamide;
2-[4-(3-chloropropoxy)phenyl]-4-(pyrrolidin-1-ylcarbonyl)-1,3-oxazole;
2-[4-(3-chloropropoxy)phenyl]-4-{[(2S)-2-(pyrrolidin-1-ylmethyl)pyrrolidin-1-yl]carbonyl}-1,3-oxazole;
2-[4-(3-chloropropoxy)phenyl]-4-methyl-1,3-oxazole-5-carboxylic acid;
2-[4-(3-chloropropoxy)phenyl]-N-(cyclopropylmethyl)-4-methyl-N-propyl-1,3-oxazole-5-carboxamide;
1-({2-[4-(3-chloropropoxy)phenyl]-4-methyl-1,3-oxazol-5-yl}carbonyl)piperidine;
1-({2-[4-(3-chloropropoxy)phenyl]-4-methyl-1,3-oxazol-5-yl}carbonyl)-4-cyclopentylpiperazine;
N-benzyl-2-[4-(3-chloropropoxy)phenyl]-4-methyl-1,3-oxazole-5-carboxamide;
4-({2-[4-(3-chloropropoxy)phenyl]-4-methyl-1,3-oxazol-5-yl}carbonyl)morpholine;
2-[4-(3-chloropropoxy)phenyl]-N-cyclopentyl-4-methyl-1,3-oxazole-5-carboxamide;
methyl[2-(4-hydroxyphenyl)-1,3-oxazol-4-yl]acetate;
methyl {2-[4-(2-chloroethoxy)phenyl]-1,3-oxazol-4-yl}acetate;
methyl (2-{4-[2-(2-methylpyrrolidin-1-yl)ethoxy]phenyl}-1,3-oxazol-4-yl)acetate;
(2-{4-[2-(2-methylpyrrolidin-1-yl)ethoxy]phenyl}-1,3-oxazol-4-yl)acetic acid;
1-[(2-{4-[2-(2-methylpyrrolidin-1-yl)ethoxy]phenyl}-1,3-oxazol-4-yl)acetyl]piperidine;
1-({2-[4-(3-chloropropoxy)phenyl]-1,3-oxazol-4-yl}methyl)piperidin-2-one;
(5S)-1-({2-[4-(3-chloropropoxy)phenyl]-1,3-oxazol-4-yl}methyl)-5-(pyrrolidin-1-ylmethyl)pyrrolidin-2-one;
(5S)-1-({2-[4-(3-chloropropoxy)phenyl]-1,3-oxazol-4-yl}methyl)-5-(morpholin-4-ylmethyl)pyrrolidin-2-one;
1-({2-[4-(3-chloropropoxy)phenyl]-1,3-oxazol-4-yl}methyl)pyrrolidin-2-one;
(2-chloro-1,3-oxazol-4-yl)methyl methanesulfonate;
1-[(2-chloro-1,3-oxazol-4-yl)methyl]piperidine;
1-({2-[4-(benzyloxy)-3-chlorophenyl]-1,3-oxazol-4-yl}methyl)piperidine;
1-({2-[4-(benzyloxy)-3-fluorophenyl]-1,3-oxazol-4-yl}methyl)piperidine;
2,6-dimethyl-4-[4-(piperidin-1-ylmethyl)-1,3-oxazol-2-yl]phenol;
2-methoxy-4-[4-(piperidin-1-ylmethyl)-1,3-oxazol-2-yl]phenol;
2-chloro-4-[4-(piperidin-1-ylmethyl)-1,3-oxazol-2-yl]phenol;
2-fluoro-4-[4-(piperidin-1-ylmethyl)-1,3-oxazol-2-yl]phenol;
1-({2-[3-chloro-4-(3-chloropropoxy)phenyl]-1,3-oxazol-4-yl}methyl)piperidine;
1-({2-[4-(3-chloropropoxy)-3,5-dimethylphenyl]-1,3-oxazol-4-yl}methyl)piperidine;
1-({2-[4-(3-chloropropoxy)-3-fluorophenyl]-1,3-oxazol-4-yl}methyl)piperidine;
1-({2-[4-(3-chloropropoxy)-3-methoxyphenyl]-1,3-oxazol-4-yl}methyl)piperidine;
3-chloropropyl 4-(3-chloropropoxy)-2-fluorobenzoate;
3-chloropropyl 4-(3-chloropropoxy)-2-methylbenzoate;
3-chloropropyl 4-(3-chloropropoxy)-3,5-difluorobenzoate;
4-(3-chloropropoxy)-2-fluorobenzoic acid;
4-(3-chloropropoxy)-2-methylbenzoic acid;
4-(3-chloropropoxy)-3,5-difluorobenzoic acid;
4-(3-chloropropoxy)-2-fluorobenzoyl chloride;
4-(3-chloropropoxy)-2-methylbenzoyl chloride;
4-(3-chloropropoxy)-3,5-difluorobenzoyl chloride;
4-(3-chloropropoxy)-2-fluorobenzamide;
4-(3-chloropropoxy)-2-methylbenzamide;
4-(3-chloropropoxy)-3,5-difluorobenzamide;
4-(chloromethyl)-2-[4-(3-chloropropoxy)-2-fluorophenyl]-1,3-oxazole;
4-(chloromethyl)-2-[4-(3-chloropropoxy)-2-methylphenyl]-1,3-oxazole;
4-(chloromethyl)-2-[4-(3-chloropropoxy)-3,5-difluorophenyl]-1,3-oxazole;
1-({2-[4-(3-chloropropoxy)-2-fluorophenyl]-1,3-oxazol-4-yl}methyl)piperidine;
1-({2-[4-(3-chloropropoxy)-2-methylphenyl]-1,3-oxazol-4-yl}methyl)piperidine;
1-({2-[4-(3-chloropropoxy)-3,5-difluorophenyl]-1,3-oxazol-4-yl}methyl)piperidine;
2-[4-(3-chloropropoxy)phenyl]-1,3-thiazole;
5-bromo-4-(chloromethyl)-2-[4-(3-chloropropoxy)phenyl]-1,3-oxazole;
1-({5-bromo-2-[4-(3-chloropropoxy)phenyl]-1,3-oxazol-4-yl}methyl)piperidine;
methyl 2-[3-bromo-4-(3-chloropropoxy)phenyl]-4-methyl-1,3-thiazole-5-carboxylate;

methyl 4-(bromomethyl)-2-[4-(3-chloropropoxy)phenyl]-1,3-oxazole-5-carboxylate;
ethyl 4-(bromomethyl)-2-[4-(3-chloropropoxy)phenyl]-1,3-oxazole-5-carboxylate;
methyl 4-[(benzylamino)methyl]-2-[4-(3-chloropropoxy)phenyl]-1,3-oxazole-5-carboxylate;
ethyl 2-[4-(3-chloropropoxy)phenyl]-4-(piperidin-1-ylmethyl)-1,3-oxazole-5-carboxylate;
ethyl 2-{4-[3-(2-methylpyrrolidin-1-yl)propoxy]phenyl}-4-(piperidin-1-ylmethyl)-1,3-oxazole-5-carboxylate;
ethyl 2-(6-chloropyridin-3-yl)-4-methyl-1,3-thiazole-5-carboxylate;
2-(6-chloropyridin-3-yl)-4-methyl-1,3-thiazole-5-carboxylic acid;
4-{[2-(6-chloropyridin-3-yl)-4-methyl-1,3-thiazol-5-yl]carbonyl}morpholine;
2-[4-(3-chloropropoxy)phenyl]-1,3-oxazole-4-carbaldehyde;
N-({2-[4-(3-chloropropoxy)phenyl]-1,3-oxazol-4-yl}methyl)-2-methyl-2H-tetrazol-5-amine;
ethyl {2-[4-(3-chloropropoxy)phenyl]-4-methyl-1,3-thiazol-5-yl}acetate;
{2-[4-(3-chloropropoxy)phenyl]-4-methyl-1,3-thiazol-5-yl}acetic acid;
1-({2-[4-(3-chloropropoxy)phenyl]-4-methyl-1,3-thiazol-5-yl}acetyl)piperidine;
methyl 2-[4-(3-chloropropoxy)phenyl]-4-methyl-1,3-thiazole-5-carboxylate;
2-[4-(3-chloropropoxy)phenyl]-4-methyl-1,3-thiazole-5-carboxylic acid;
4-({2-[4-(3-chloropropoxy)phenyl]-4-methyl-1,3-thiazol-5-yl}carbonyl)morpholine;
1-({2-[4-(3-chloropropoxy)phenyl]-4-methyl-1,3-thiazol-5-yl}carbonyl)-4,4-difluoropiperidine;
{2-[4-(3-chloropropoxy)phenyl]-4-methyl-1,3-thiazol-5-yl}methanol; and
1-({2-[4-(3-chloropropoxy)phenyl]-4-methyl-1,3-thiazol-5-yl}methyl)pyrrolidin-2-one.

In a particular embodiment, the present invention relates to the use of a synthetic intermediate of formula (XIII) or (XIIIbis) for the preparation of compound of formula (I).

It has now been found that compounds of formula (I) according to the present invention and their pharmaceutically acceptable salts are useful in a variety of medical disorders.

For example, the compounds according to the invention are useful for the treatment and prevention of diseases or pathological conditions of the central nervous system including mild-cognitive impairment, Alzheimer's disease, learning and memory disorders, cognitive disorders, attention deficit disorder, attention-deficit hyperactivity disorder, Parkinson's disease, schizophrenia, dementia, depression, epilepsy, seizures, convulsions, sleep/wake disorders, narcolepsy, and/or obesity.

Furthermore, compounds according to the invention alone or in combination with an antiepileptic drug (AED) may be useful in the treatment of epilepsy, seizure or convulsions. It is known from literature that the combination of $H_3$-receptor ligands with an AED may produce additive synergistic effects on efficacy with reduced side-effects such as decreased vigilance, sedation or cognitive problems.

Furthermore, compounds of general formula (I) alone or in combination with a histamine $H_1$-receptor antagonist may also be used for the treatment of upper airway allergic disorders.

In a particular embodiment of the present invention, compounds of general formula (I), alone or in combination with muscarinic receptor ligands and particularly with a muscarinic $M_2$-receptor antagonist, may be useful for the treatment of cognitive disorders, Alzheimer's disease, and attention-deficit hyperactivity disorder.

Particularly, compounds of general formula (I) displaying NO-donor properties, alone or in combination with a nitric oxide (NO) releasing agent may be useful in the treatment of cognitive dysfunctions.

Compounds of general formula (I) may also be used in the treatment of sleep/wake and arousal/vigilance disorders such as hypersomnia, and narcolepsy.

Usually, compounds of general formula (I) may be used in the treatment of all types of cognitive-related disorders.

Preferably, compounds of general formula (I) may be used for the treatment of cognitive dysfunctions in diseases such as mild cognitive impairment, dementia, Alzheimer's disease, Parkinson's disease, Down's syndrome as well as for the treatment of attention-deficit hyperactivity disorder.

In another preferred embodiment, compounds of general formula (I) may also be used for the treatment of psychotic disorders, such as schizophrenia; or for the treatment of eating disorders, such as obesity; or for the treatment of inflammation and pain; or for the treatment of anxiety, stress and depression; or for the treatment of cardiovascular disorders, for example, myocardial infarction.

In a further aspect, compounds of formula (I) according to the present invention may be used as a medicament.

In a particular embodiment, the present invention concerns the use of a compound of formula (I) or a pharmaceutically acceptable salt thereof or of a pharmaceutical composition comprising an effective amount of said compound for the manufacture of a medicament for the treatment and prevention of mild-cognitive impairment, Alzheimer's disease, learning and memory disorders, attention-deficit hyperactivity disorder, Parkinson's disease, schizophrenia, dementia, depression, epilepsy, seizures, convulsions, sleep/wake disorders, cognitive dysfunctions, narcolepsy, hypersomnia, obesity, upper airway allergic disorders, Down's syndrome, anxiety, stress, cardiovascular disorders, inflammation and pain.

Preferably, the present invention concerns the use of a compound of formula (I) or a pharmaceutically acceptable salt thereof or a pharmaceutical composition comprising an effective amount of said compound for the manufacture of a medicament for the treatment of cognitive dysfunctions in diseases such as mild cognitive impairment, dementia, Alzheimer's disease, Parkinson's disease, Down's syndrome as well as for the treatment of attention-deficit hyperactivity disorder.

The methods of the invention comprise administration to a mammal (preferably human) suffering from above mentioned conditions or disorders, of a compound according to the invention in an amount sufficient to alleviate or prevent the disorder or condition.

The compound is conveniently administered in any suitable unit dosage form, including but not limited to one containing 3 to 3000 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The expression "cognitive disorders" as used herein refers to disturbances of cognition, which encompasses perception, learning and reasoning or in other terms the physiological (mental/neuronal) process of selectively acquiring, storing, and recalling information.

The expression "attention-deficit hyperactivity disorder" (ADHD) as used herein refers to a problem with inattentiveness, over-activity, impulsivity, or a combination of these. For these problems to be diagnosed as ADHD, they must be out of the normal range for the child's age and development. The term "attention-deficit disorder" (ADD) is also commonly used for the same disorder.

The expression "Alzheimer's disease" (AD) as used herein refers to a progressive, neurodegenerative disease characterized in the brain by abnormal clumps (amyloid plaques) and tangled bundles of fibers (neurofibrillary tangles) composed of misplaced proteins. Age is the most important risk factor for AD; the number of people with the disease doubles every 5 years beyond age 65. Three genes have been discovered that cause early onset (familial) AD. Other genetic mutations that cause excessive accumulation of amyloid protein are associated with age-related (sporadic) AD. Symptoms of AD include memory loss, language deterioration, impaired ability to mentally manipulate visual information, poor judgment, confusion, restlessness, and mood swings. Eventually AD destroys cognition, personality, and the ability to function. The early symptoms of AD, which include forgetfulness and loss of concentration, are often missed because they resemble natural signs of aging.

The expression "Parkinson's disease" (PD) as used herein refers to a group of conditions called motor system disorders, which are the result of the loss of dopamine-producing brain cells. The four primary symptoms of PD are tremor, or trembling in hands, arms, legs, jaw, and face; rigidity, or stiffness of the limbs and trunk; bradykinesia, or slowness of movement; and postural instability, or impaired balance and coordination. As these symptoms become more pronounced, patients may have difficulty walking, talking, or completing other simple tasks. PD usually affects people over the age of 50. Early symptoms of PD are subtle and occur gradually. In some people the disease progresses more quickly than in others. As the disease progresses, the shaking, or tremor, which affects the majority of PD patients may begin to interfere with daily activities. Other symptoms may include depression and other emotional changes; difficulty in swallowing, chewing, and speaking; urinary problems or constipation; skin problems; and sleep disruptions.

The expression "Down's syndrome" as used herein refers to a chromosome abnormality, usually due to an extra copy of the 21st chromosome. This syndrome, usually but not always, results in mental retardation and other conditions. The term "mental retardation" refers to a below-average general intellectual function with associated deficits in adaptive behavior that occurs before age 18.

The term "mild-cognitive impairment" as used herein refers to a transitional stage of cognitive impairment between normal aging and early Alzheimer's disease. It refers particularly to a clinical state of individuals who are memory impaired but are otherwise functioning well and do not meet clinical criteria for dementia.

The term "obesity" as used herein refers to a body mass index (BMI) which is greater than 30 kg/m$^2$.

The term "dementia" as used herein refers to a group of symptoms involving progressive impairment of brain function. American Geriatrics Society refers to dementia as a condition of declining mental abilities, especially memory. The person will have problems doing things he or she used to be able to do, like keep the check book, drive a car safely, or plan a meal. He or she will often have problems finding the right words and may become confused when given too many things to do at once. The person with dementia may also change in personality, becoming aggressive, paranoid, or depressed.

The term "schizophrenia" as used herein refers to a group of psychotic disorders characterized by disturbances in thought, perception, attention, affect, behavior, and communication that last longer than 6 months. It is a disease that makes it difficult for a person to tell the difference between real and unreal experiences, to think logically, to have normal emotional responses to others, and to behave normally in social situations.

The term "anxiety" as used herein refers to a feeling of apprehension or fear. Anxiety is often accompanied by physical symptoms, including twitching or trembling, muscle tension, headaches, sweating, dry mouth, difficulty swallowing and/or abdominal pain.

The term "narcolepsy" as used herein refers to a sleep disorder associated with uncontrollable sleepiness and frequent daytime sleeping.

The term "depression" as used herein refers to a disturbance of mood and is characterized by a loss of interest or pleasure in normal everyday activities. People who are depressed may feel "down in the dumps" for weeks, months, or even years at a time. Some of the following symptoms may be symptoms of depression: persistent sad, anxious, or "empty" mood; feelings of hopelessness, pessimism; feelings of guilt, worthlessness, helplessness; loss of interest or pleasure in hobbies and activities that were once enjoyed, including sex; decreased energy, fatigue, being "slowed down"; difficulty concentrating, remembering, making decisions; insomnia, early-morning awakening, or oversleeping; appetite and/or weight loss or overeating and weight gain; thoughts of death or suicide; suicide attempts; restlessness, irritability; persistent physical symptoms that do not respond to treatment, such as headaches, digestive disorders, and chronic pain.

The term "epilepsy" as used herein refers a brain disorder in which clusters of nerve cells, or neurons, in the brain sometimes signal abnormally. In epilepsy, the normal pattern of neuronal activity becomes disturbed, causing strange sensations, emotions, and behavior or sometimes convulsions, muscle spasms, and loss of consciousness. Epilepsy is a disorder with many possible causes. Anything that disturbs the normal pattern of neuron activity—from illness to brain damage to abnormal brain development—can lead to seizures. Epilepsy may develop because of an abnormality in brain wiring, an imbalance of nerve signaling chemicals called neurotransmitters, or some combination of these factors. Having a seizure does not necessarily mean that a person has epilepsy. Only when a person has had two or more seizures is he or she considered to have epilepsy.

The term "seizure" as used herein refers to a transient alteration of behaviour due to the disordered, synchronous, and rhythmic firing of populations of brain neurones.

The term "migraine" as used herein means a disorder characterised by recurrent attacks of headache that vary widely in intensity, frequency, and duration. The pain of a migraine headache is often described as an intense pulsing or throbbing pain in one area of the head. It is often accompanied by extreme sensitivity to light and sound, nausea, and vomiting. Some individuals can predict the onset of a migraine because it is preceded by an "aura," visual disturbances that appear as flashing lights, zig-zag lines or a temporary loss of vision. People with migraine tend to have recurring attacks triggered by a lack of food or sleep, exposure to light, or hormonal irregularities (only in women). Anxiety, stress, or relaxation after stress can also be triggers. For many years, scientists believed that migraines were linked to the dilation and constriction of blood vessels in the head. Investigators now believe that migraine is caused by inherited abnormalities in genes that control the activities of certain cell populations in the brain. The International Headache Society (IHS, 1988) classifies migraine with aura (classical migraine) and migraine without aura (common migraine) as the major types of migraine.

Activity in any of the above-mentioned indications can of course be determined by carrying out suitable clinical trials in a manner known to a person skilled in the relevant art for the particular indication and/or in the design of clinical trials in general.

For treating diseases, compounds of formula (I) or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula (I) or a pharmaceutically acceptable salt thereof in combination with a pharmaceutically acceptable diluent or carrier.

To prepare a pharmaceutical composition according to the invention, one or more of the compounds of formula (I) or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula (I) in compositions for oral administration is at least 0.5% by weight and can be up to 80% by weight with respect to the total weight of the composition.

For the preferred oral compositions, the daily dosage is in the range 3 to 3000 milligrams (mg) of compounds of formula (I).

In compositions for parenteral administration, the quantity of compound of formula (I) present is at least 0.5% by weight and can be up to 33% by weight with respect to the total weight of the composition. For the preferred parenteral compositions, the dosage unit is in the range 3 mg to 3000 mg of compounds of formula (I).

The daily dose can fall within a wide range of dosage units of compound of formula (I) and is generally in the range 3 to 3000 mg. However, it should be understood that the specific doses can be adapted to particular cases depending on the individual requirements, at the physician's discretion.

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

Unless specified otherwise in the examples, characterization of the compounds is performed according to the following methods:

NMR spectra are recorded on a BRUKER AC 250 Fourier Transform NMR Spectrometer fitted with an Aspect 3000 computer and a 5 mm $^1H/^{13}C$ dual probehead or BRUKER DRX 400 FT NMR fitted with a SG Indigo$^2$ computer and a 5 mm inverse geometry $^1H/^{13}C/^{15}N$ triple probehead. The compound is studied in dimethylsulfoxide-$d_6$ (DMSO-$d_6$) or chloroform-d (CDCl$_3$) solution at a probe temperature of 313 K or 300 K and at a concentration of 20 mg/ml. The instrument is locked on the deuterium signal of dimethylsulfoxide-$d_6$ (DMSO-$d_6$) or chloroform-d (CDCl$_3$). Chemical shifts are given in ppm downfield from TMS taken as internal standard.

HPLC analyses are performed using one of the following systems:

an Agilent 1100 series HPLC system mounted with an INERTSIL ODS 3 C18, DP 5 µm, 250×4.6 mm column. The gradient runs from 100% solvent A (acetonitrile, water, phosphoric acid (5/95/0.001, v/v/v)) to 100% solvent B (acetonitrile, water, phosphoric acid (95/5/0.001, v/v/v)) in 6 min with a hold at 100% B of 4 min. The flow rate is set at 2.5 ml/min. The chromatography is carried out at 35° C.

a HP 1090 series HPLC system mounted with a HPLC Waters Symetry C18, 250×4.6 mm column. The gradient runs from 100% solvent A (methanol, water, phosphoric acid (15/85/0.001M, v/v/M)) to 100% solvent B (methanol, water, phosphoric acid (85/15/0.001 M, v/v/M)) in 10 min with a hold at 100% B of 10 min. The flow rate is set at 1 ml/min. The chromatography is carried out at 40° C.

Mass spectrometric measurements in LC/MS mode are performed as follows:

HPLC Conditions

Analyses are performed using a WATERS Alliance HPLC system mounted with an INERTSIL ODS 3, DP 5 μm, 250× 4.6 mm column.

The gradient runs from 100% solvent A (acetonitrile, water, trifluoroacetic acid (10/90/0.1, v/v/v)) to 100% solvent B (acetonitrile, water, trifluoroacetic acid (90/10/0.1, v/v/v)) in 7 min with a hold at 100% B of 4 min. The flow rate is set at 2.5 ml/min and a split of 1/25 is used just before API source.

MS Conditions

Samples are dissolved in acetonitrile/water, 70/30, v/v at the concentration of about 250 μg/ml. API spectra (+ or −) are performed using a FINNIGAN LCQ ion trap mass spectrometer. APCI source operated at 450° C. and the capillary heater at 160° C. ESI source operated at 3.5 kV and the capillary heater at 210° C.

Mass spectrometric measurements in DIP/EI mode are performed as follows: samples are vaporized by heating the probe from 50° C. to 250° C. in 5 min. EI (Electron Impact) spectra are recorded using a FINNIGAN TSQ 700 tandem quadrupole mass spectrometer. The source temperature is set at 150° C.

Mass spectrometric measurements on a TSQ 700 tandem quadrupole mass spectrometer (Finnigan MAT) in GC/MS mode are performed with a gas chromatograph model 3400 (Varian) fitted with a split/splitless injector and a DB-5MS fused-silica column (15 m×0.25 mm I.D., 1 μm) from J&W Scientific. Helium (purity 99.999%) is used as carrier gas. The injector (CTC A200S autosampler) and the transfer line operate at 290 and 250° C., respectively. Sample (1 μl) is injected in splitless mode and the oven temperature is programmed as follows: 50° C. for 5 min., increasing to 280° C. (23° C./min) and holding for 10 min. The TSQ 700 spectrometer operates in electron impact (EI) or chemical ionization (CI/CH$_4$) mode (mass range 33-800, scan time 1.00 sec). The source temperature is set at 150° C.

Specific rotation is recorded on a Perkin-Elmer 341 polarimeter. The angle of rotation is recorded at 25° C. on 1% solutions in methanol, at 589 mm. For some molecules, the solvent is dichloromethane or dimethylsulfoxide, due to solubility problems.

Melting points are determined on a Büchi 535 or 545 Tottoli-type fusionometre, and are not corrected, or by the onset temperature on a Perkin Elmer DSC 7.

Preparative chromatographic separations are performed on silicagel 60 Merck, particle size 15-40 μm, reference 1.15111.9025, using Novasep axial compression columns (80 mm i.d.), flow rates between 70 and 150 ml/min. Amount of silicagel and solvent mixtures as described in individual procedures.

Preparative Chiral Chromatographic separations are performed on a DAICEL Chiralpak AD 20 μm, 100*500 mm column using an in-house build instrument with various mixtures of lower alcohols and C5 to C8 linear, branched or cyclic alkanes at +350 ml/min. Solvent mixtures as described in individual procedures.

Experiments requiring microwave irradiation were performed either on a CEM Discover apparatus (CEM corporation) or on a Biotage Initiator (Biotage AB) microwave oven using the flasks and stirrers sold by these companies.

EXAMPLES

Example 1

Synthesis of 1-[3-(4-{4-[(2-methylpyrrolidin-1-yl)methyl]-1,3-oxazol-2-yl}phenoxy)propyl]piperidine 30

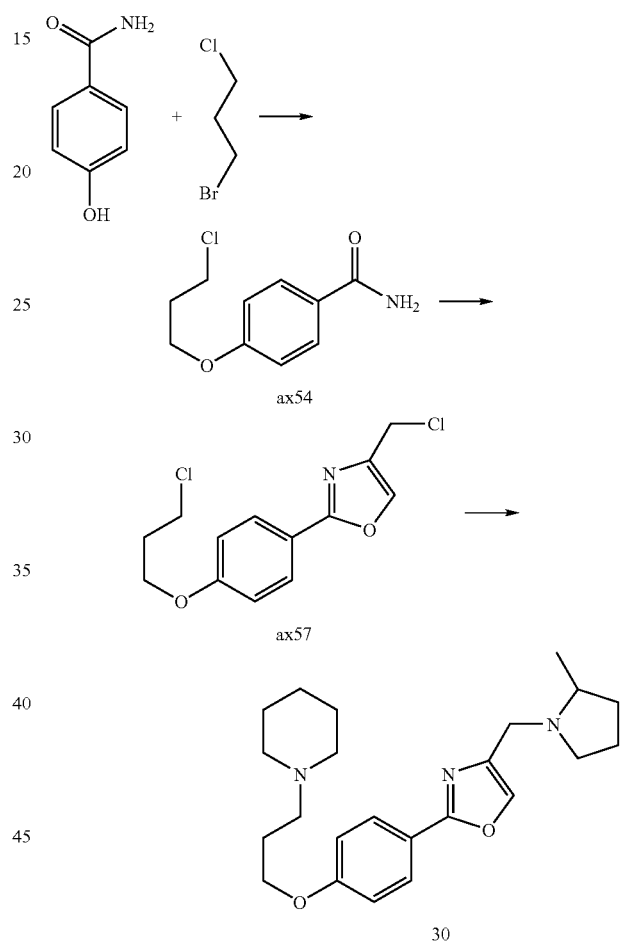

1.1 Synthesis of 4-(3-chloropropoxy)benzamide ax54

A mixture of 4-hydroxybenzamide (5 g, 36.5 mmol, 1 eq), potassium carbonate (10.08 g, 72.9 mmol, 2 eq), 3-chloro-1-bromopropane (4.7 ml, 47.4 mmol, 1.3 eq) in butanone is stirred at reflux for 48 h. The solvent is then removed under vacuum and the residue is triturated in hexane and filtered. The solid is taken up in ethyl acetate and washed with a saturated solution of sodium hydrogencarbonate. The organic layer is dried over magnesium sulfate and concentrated to give 4-(3-chloropropoxy)benzamide ax54 (6.8 g) as a white solid.

Yield: 87%.

LC-MS (MH$^+$): 214/216.

| | | |
|---|---|---|
| ax55 | 4-(2-chloroethoxy)benzamide | LC-MS (MH+): 199/201 |
| ax56 | 4-(4-chlorobutoxy)benzamide | LC-MS (MH+): 227/229 |
| ax69 | 3-(3-chloropropoxy)benzamide | LC-MS (MH+): 214/219 |

1.2 Synthesis of 4-(chloromethyl)-2-[4-(3-chloropropoxy)phenyl]-1,3-oxazole ax57

A mixture of 4-(3-chloropropoxy)benzamide ax54 (1.9 g, 8.9 mmol, 1 eq), 1,3-dichloro-propan-2-one (1.13 g, 8.9 mmol, 1 eq) in propionitrile (45 ml) is stirred at reflux for 48 h. The solvent is then removed under vacuum and filtered over silicagel with dichloromethane. The dichloromethane is evaporated under vacuum to give 4-(chloromethyl)-2-[4-(3-chloropropoxy)phenyl]-1,3-oxazole ax57 (2.1 g) as a white solid.

Yield: 83%.
LC-MS (MH+): 286/288/290.

The following compounds may be synthesized according to the same methano

| | | |
|---|---|---|
| ax58 | 2-[4-(2-chloroethoxy)phenyl]-4-(chloromethyl)-1,3-oxazole | LC-MS (MH+): 272/274/276 |
| ax59 | 2-[4-(4-chlorobutoxy)phenyl]-4-(chloromethyl)-1,3-oxazole | LC-MS (MH+): 300/302/304 |
| ax70 | 4-(chloromethyl)-2-[3-(3-chloropropoxy)phenyl]-1,3-oxazole | LC-MS (MH+): 286/288/290 |

1.3 Synthesis of 1-[3-(4-{4-[(2-methylpyrrolidin-1-yl)methyl]-1,3-oxazol-2-yl}phenoxy)propyl]piperidine 30

A mixture of 4-(chloromethyl)-2-[4-(3-chloropropoxy)phenyl]-1,3-oxazole ax57 (0.172 g, 0.6 mmol, 1 eq), sodium iodide (0.018 g, 0.12 mmol, 0.2 eq), potassium carbonate (0.373 g, 2.7 mmol, 4.5 eq) and 2-methylpyrrolidine in acetonitrile (5 ml) is stirred at room temperature for 72 h. Piperidine (0.05 g, 0.6 mmol, 1 eq) is then added and the mixture is stirred at 80° C. overnight. The volatiles are then removed under vacuum and the residue is purified by chromatography (dichloromethane/methanol/ammonia 96:3.6:0.4) to give 1-[3-(4-{4-[(2-methylpyrrolidin-1-yl)methyl]-1,3-oxazol-2-yl}phenoxy)propyl]piperidine 30 as a pale yellow oil.

Yield: 42%.
LC-MS (MH+): 384.

Compounds 29, 31, 32, 33, 34, 35, 36, 37, 38, 39, 40, 41, 42, 43, 44, 45, 54, 56, 57, 58, 59, 60, 62, 63, 64, 65, 66, 67, 68, 69, 70, 71, 84, 85, 86, 94, 118, 119, 120, 125, 129, 130, 138 and 146 of table I may be synthetized according to similar experimental conditions.

Example 2

Synthesis of 1-(3-{4-[4-methyl-5-(piperidin-1-ylmethyl)-1,3-oxazol-2-yl]phenoxy}propyl)piperidine 61

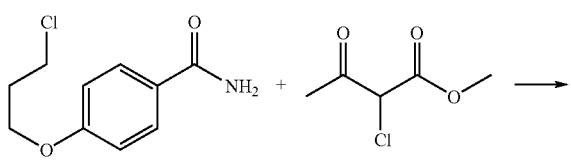

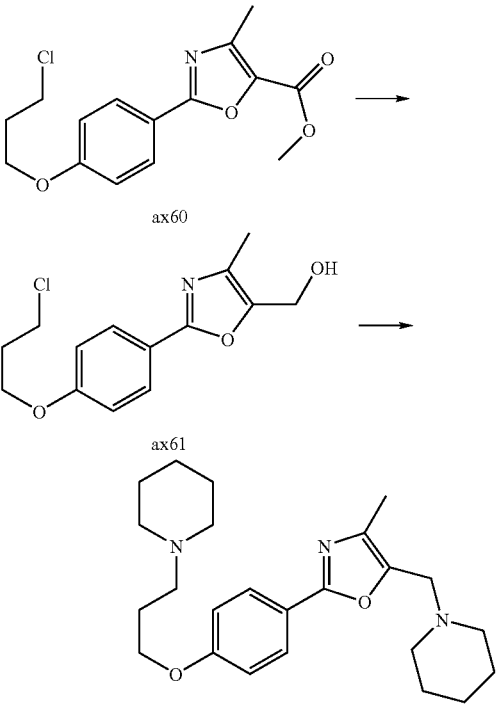

2.1 Synthesis of methyl 2-[4-(3-chloropropoxy)phenyl]-4-methyl-1,3-oxazole-5-carboxylate ax60

A solution of 4-(3-chloro-propoxy)-benzamide (0.5 g, 2.34 mmol, 1 eq) and methyl 2-chloro-3-oxobutanoate (0.7 ml, 5.62 mmol, 2.4 eq) in ethanol (5 ml) is heated at 110° C. in a sealed tube for 24 h. The mixture is concentrated, taken up in dichloromethane and washed with water. The organic phase is dried over magnesium sulfate and concentrated. The residue is purified by chromatography over silicagel (eluent: dichloromethane) to afford 0.7 g of methyl 2-[4-(3-chloropropoxy)phenyl]-4-methyl-1,3-oxazole-5-carboxylate ax60 as a pale yellow solid.

Yield: 96%.
LC-MS (MH+): 309/311.

2.2 Synthesis of {2-[4-(3-chloropropoxy)phenyl]-4-methyl-1,3-oxazol-5-yl}methanol ax61

A solution of methyl 2-[4-(3-chloropropoxy)phenyl]-4-methyl-1,3-oxazole-5-carboxylate ax60 (390 mg, 1.26 mmol, 1 eq) and methanol (165 µl, 4.08 mmol, 1.8 eq) in tetrahydrofuran (13 ml) is treated with lithium borohydride (49 mg, 2.27 mmol, 1.8 eq) and the mixture is stirred at 70° C. for 1 h. After cooling back to 0° C., the mixture is treated dropwise with 1 N aqueous hydrochloric acid (1 ml). The mixture is then made basic (pH 10) with 2 N aqueous sodium hydroxide and extracted with ethyl acetate. The organic phase is then dried over magnesium sulfate and concentrated to give 330 mg of {2-[4-(3-chloropropoxy)phenyl]-4-methyl-1,3-oxazol-5-yl}methanol ax61 as a yellow solid.

Yield: 93%.
LC-MS (MH+): 282/284.

2.3 Synthesis of 1-(3-{4-[4-methyl-5-(piperidin-1-ylmethyl)-1,3-oxazol-2-yl]phenoxy}propyl)piperidine 61

A solution of {2-[4-(3-chloropropoxy)phenyl]-4-methyl-1,3-oxazol-5-yl}methanol ax61 (330 mg, 1.21 mmol, 1 eq) and triethylamine (187 µl, 1.33 mmol, 1.1 eq) in dichloromethane (25 ml) is cooled to 0° C. (ice bath) and treated dropwise with methanesulfonyl chloride (103 µl, 1.33 mmol, 1.1 eq). The mixture is stirred 1 h at 0° C. and poured into 20 ml of a saturated aqueous solution of ammonium chloride and extracted with dichloromethane. The organic phases are dried over magnesium sulfate and concentrated. The oily residue is taken up in acetonitrile (25 ml) and treated with sodium iodide (18 mg, 0.12 mmol, 0.1 eq) and piperidine (360 µl, 3.64 mmol, 3 eq). The mixture is stirred at 22° C. for 1 h and then heated at 90° C. (oil bath) overnight. After cooling, the mixture is poured into 10 ml of 1 N aqueous hydrogen chloride and extracted with ether. The aqueous phase is then made basic (pH 10) by addition of 3 N aqueous sodium hydroxide, and extracted with ethyl acetate. The ethyl acetate solution is dried over magnesium sulfate and concentrated to yield 310 mg of an orange oil. This oil is purified by chromatography over silicagel (eluent: dichloromethane/methanol/ammonia 98:1.8:0.2) to afford 60 mg of 1-(3-{4-[4-methyl-5-(piperidin-1-ylmethyl)-1,3-oxazol-2-yl]phenoxy}propyl)piperidine 61 as a pale yellow oil.

Yield: 12%.
LC-MS (MH$^+$): 398.

Example 3

Synthesis of 2-{4-[3-(2-methylpyrrolidin-1-yl)propoxy]phenyl}-4-(2-pyrrolidin-1-ylethyl)-1,3-oxazole 55

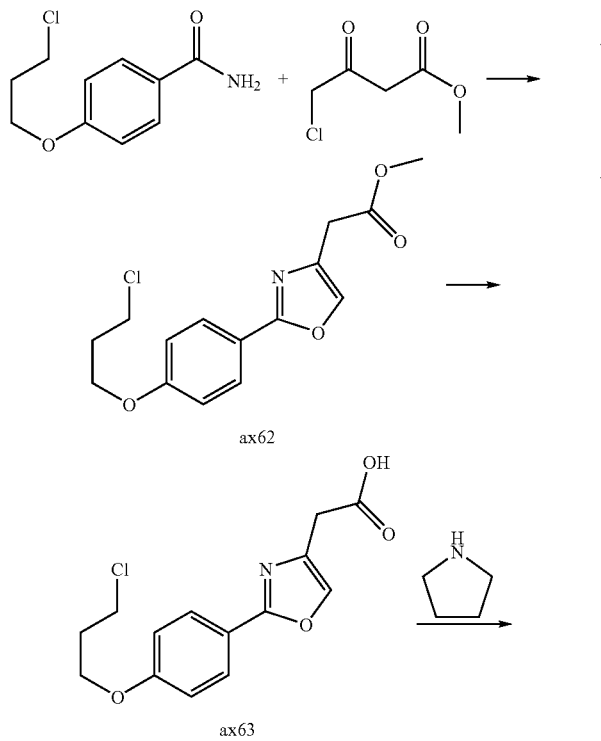

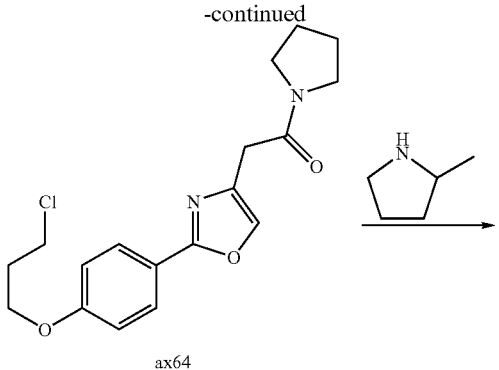

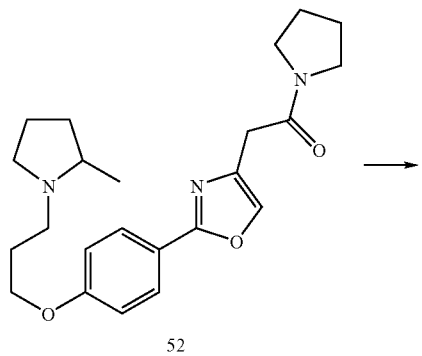

3.1 Synthesis of methyl {2-[4-(3-chloropropoxy)phenyl]-1,3-oxazol-4-yl}acetate ax62

Methyl 4-chloro-3-oxobutanoate (4.32 ml, 37.44 mmol, 2 eq) is added to a solution of 4-(3-chloropropoxy)benzamide (4 g, 18.72 mmol, 1 eq) in propionitrile (50 ml). The mixture is heated at reflux for 48 h. The mixture is then diluted with dichloromethane and filtered. The solvent is removed under vacuum and the residue is purified on silica gel (eluent: ethyl acetate) to give 2.8 g methyl {2-[4-(3-chloropropoxy)phenyl]-1,3-oxazol-4-yl}acetate ax62 as a brown oil.

Yield: 50%.
LC-MS (MH$^+$): 310/312.

3.2 Synthesis of {2-[4-(3-chloropropoxy)phenyl]-1,3-oxazol-4-yl}acetic acid ax63

A solution of lithium hydroxide hydrate (0.76 g, 18.11 mmol, 2 eq) in water (10 ml) is added to a solution of methyl {2-[4-(3-chloropropoxy)phenyl]-1,3-oxazol-4-yl}acetate ax62 (2.8 g, 9.06 mmol, 1 eq) in tetrahydrofuran (100 ml). The mixture is stirred at room temperature for 1 h. The mixture is then poured into water and extracted with diethyl ether (2×75 ml). The aqueous layer is acidified with 6 N aqueous hydrochloric acid and extracted with ethyl acetate. The organic layer is dried over magnesium sulfate and concentrated under vacuum to give 2.1 g of {2-[4-(3-chloropropoxy) phenyl]-1,3-oxazol-4-yl}acetic acid ax63 as a brown solid.

Yield: 81%.

LC-MS (MH$^+$): 296/298.

3.3 Synthesis of 2-[4-(3-chloropropoxy)phenyl]-4-(2-oxo-2-pyrrolidin-1-ylethyl)-1,3-oxazole ax64

To a solution of {2-[4-(3-chloropropoxy)phenyl]-1,3-oxazol-4-yl}acetic acid ax63 (0.5 g, 1.69 mmol, 1 eq) in dichloromethane (50 ml) is added 1-hydroxybenzotriazole (0.025 g, 0.19 mmol, 0.11 eq) and 1-(3-dimethylaminopropyl)-3-ethylcarbodiimide hydrochloride (0.357 g, 1.86 mmol, 1.1 eq). To that solution is added pyrrolidine (0.29 ml, 3.38 mmol, 2 eq) and the mixture is stirred at room temperature overnight. The mixture is poured into water and extracted with dichloromethane. The organic layer is dried over magnesium sulfate and the solvent is removed under vacuum to afford 0.51 g of 2-[4-(3-chloropropoxy)phenyl]-4-(2-oxo-2-pyrrolidin-1-yl-ethyl)-1,3-oxazole ax64 as a pale yellow oil.

Yield: 86%.

LC-MS (MH$^+$): 349/351.

The following compounds may be synthesized according to the same method:

| | | |
|---|---|---|
| i14 | 1-({2-[4-(3-chloropropoxy)phenyl]-1,3-oxazol-4-yl}acetyl)piperidine | LC-MS (MH$^+$): 363/365 |
| i15 | 2-{2-[4-(3-chloropropoxy)phenyl]-1,3-oxazol-4-yl}-N-(4-fluorophenyl)acetamide | LC-MS (MH$^+$): 365/367 |
| i16 | 4-({2-[4-(3-chloropropoxy)phenyl]-1,3-oxazol-4-yl}acetyl)morpholine | LC-MS (MH$^+$): 389/391 |
| i17 | 2-{2-[4-(3-chloropropoxy)phenyl]-1,3-oxazol-4-yl}-N-cyclopentylacetamide | LC-MS (MH$^+$): 363/365 |
| i18 | 2-{2-[4-(3-chloropropoxy)phenyl]-1,3-oxazol-4-yl}-N-(cyclopropylmethyl)-N-propylacetamide | LC-MS (MH$^+$): 391/393 |
| i19 | 1-({2-[4-(3-chloropropoxy)phenyl]-1,3-oxazol-4-yl}acetyl)azepane | LC-MS (MH$^+$): 377/379 |

3.4 Synthesis of 2-{4-[3-(2-methylpyrrolidin-1-yl) propoxy]phenyl}-4-(2-oxo-2-pyrrolidin-1-ylethyl)-1,3-oxazole 52

To a solution of 2-[4-(3-chloropropoxy)phenyl]-4-(2-oxo-2-pyrrolidin-1-ylethyl)-1,3-oxazole ax64 (0.51 g, 1.46 mmol, 1 eq) in acetonitrile (10 ml) is added sodium iodide (0.022 g, 0.15 mmol, 0.1 eq) and 2-methylpyrrolidine (0.25 ml, 2.92 mmol, 2 eq). The mixture is stirred at reflux overnight. The mixture is poured into dichloromethane and washed with water. The organic layer is dried over magnesium sulfate and the solvent is removed under vacuum. The crude product is purified by chromatography over silica gel (eluent: dichloromethane/methanol/ammonia 95:4.5:0.5) to give 0.29 g of 2-{4-[3-(2-methylpyrrolidin-1-yl)propoxy]phenyl}-4-(2-oxo-2-pyrrolidin-1-ylethyl)-1,3-oxazole 52 as a yellow oil.

Yield: 50%.

LC-MS (MH$^+$): 398.

Compounds 80, 81, 128, 132, 133, 134 and 135 of table I may be synthetized according to similar experimental conditions.

3.5 Synthesis of 2-{4-[3-(2-methylpyrrolidin-1-yl) propoxy]phenyl}-4-(2-pyrrolidin-1-ylethyl)-1,3-oxazole 55

To a solution of sodium borohydride (0.05 g, 1.21 mmol, 2.4 eq) in tetrahydrofuran (0.5 ml) is added a solution of 2-{4-[3-(2-methylpyrrolidin-1-yl)propoxy]phenyl}-4-(2-oxo-2-pyrrolidin-1-ylethyl)-1,3-oxazole 52 (0.2 g, 0.5 mmol, 1 eq) in tetrahydrofuran (2 ml). The mixture is cooled down to 0° C. (ice bath) and a solution of iodine (0.13 g, 0.5 mmol, 1 eq) in tetrahydrofuran (1 ml) is added dropwise. When the release of gas has stopped, the mixture is heated to reflux overnight. Methanol is added to the mixture at 0° C. until complete dissolution. The solvent is removed under vacuum to give a white solid. The solid is taken up into a 20% methanolic solution of potassium hydroxide and the mixture is heated at 60° C. for 10 h. The mixture is poured onto water and extracted with dichloromethane. The organic layer is dried over magnesium sulfate and the solvent is removed in vacuum. The crude product is purified by chromatography over silica gel (eluent: gradient of dichloromethane/methanol/ammonia) to give 0.03 g of 2-{4-[3-(2-methylpyrrolidin-1-yl)propoxy]phenyl}-4-(2-pyrrolidin-1-ylethyl)-1,3-oxazole 55 as an orange oil.

Yield: 16%.

LC-MS (MH$^+$): 384.

Compound 82 of table I may be synthetized according to similar experimental conditions.

Example 4

Synthesis of 2-methyl-1-[3-(4-{4-[(2-methylpyrrolidin-1-yl)methyl]-1,3-oxazol-2-yl}phenoxy)propyl] piperidine bis(trifluoroacetate) 47

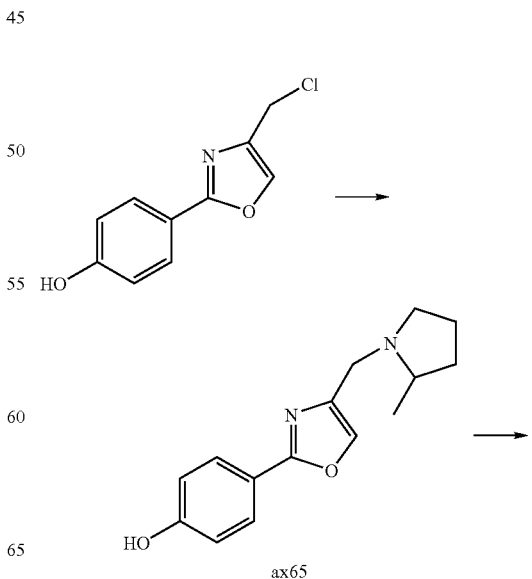

ax65

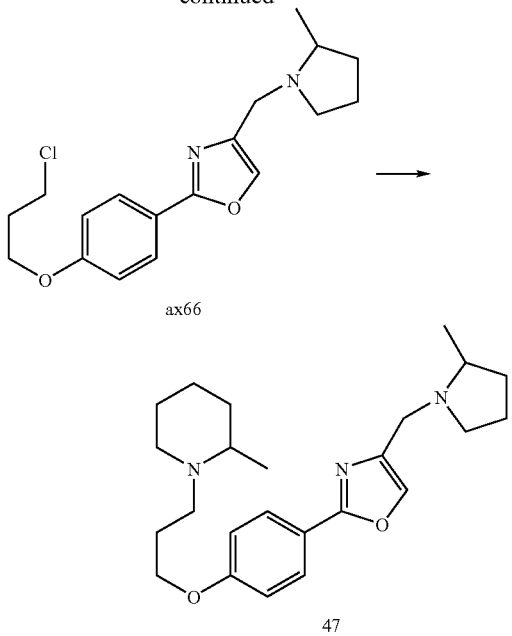

| ax67 | 2-[4-(2-chloroethoxy)phenyl]-4-[(2-methylpyrrolidin-1-yl)methyl]-1,3-oxazole | LC-MS (MH$^+$): 321/323 |
| --- | --- | --- |
| ax68 | 2-[4-(4-chlorobutoxy)phenyl]-4-[(2-methylpyrrolidin-1-yl)methyl]-1,3-oxazole | LC-MS (MH$^+$): 349/351 |

4.3 Synthesis of 2-methyl-1-[3-(4-{4-[(2-methylpyrrolidin-1-yl)methyl]-1,3-oxazol-2-yl}phenoxy)propyl]piperidine bis(trifluoroacetate) 47

A solution of 2-[4-(3-chloropropoxy)phenyl]-4-[(2-methylpyrrolidin-1-yl)methyl]-1,3-oxazole ax66 (0.05 mmol, 1 eq, 17 mg) in 150 µL of acetonitrile is added to a solution of sodium iodide (0.1 mmol, 2 eq, 15 mg) and 2-methylpiperidine (0.1 mmol, 2 eq, 10 mg) in 270 µl of acetonitrile. The mixture is then stirred at 85° C. overnight, filtered, washed with acetonitrile, and concentrated under reduced pressure. The residue is purified by preparative liquid chromatography (gradient: acetonitrile/water/trifluoroacetic acid 95:5:0.1 to 5:95:0.1) to provide 9 mg of 2-methyl-1-[3-(4-{4-[(2-methylpyrrolidin-1-yl)methyl]-1,3-oxazol-2-yl}phenoxy)propyl]piperidine bis(trifluoroacetate) 47.

LC-MS (MH$^+$): 398.

Compounds 46, 48, 49, 50 and 51 of table I may be synthetized according to the same method.

4.1 Synthesis of 4-{4-[(2-methylpyrrolidin-1-yl)methyl]-1,3-oxazol-2-yl}phenol ax65

4-{4-[(2-chloromethyl]-1,3-oxazol-2-yl}phenol (1.7 g, 8.1 mmol), prepared according to the method described in PCT patent application WO 03/097047, is reacted with 2-methylpyrrolidine (0.88 ml, 8.9 mmol) in the presence of potassium carbonate (2.24 g, 16.2 mmol) and sodium iodide (0.12 g, 0.81 mmol) in refluxing acetonitrile (50 ml). After 20 h, the solvent is evaporated, taken up in ethyl acetate and washed two times with an aqueous solution of sodium hydrogenocarbonate. The organic layer is dried over magnesium sulfate, filtered and concentrated under vacuum. Purification by chromatography on silicagel (eluent: dichloromethane/methanol/ammonia 94:5.4:0.6) affords 1.3 g of compound ax65.

Yield: 62%.

LC-MS (MH$^+$): 259.

4.2 Synthesis of 2-[4-(3-chloropropoxy)phenyl]-4-[(2-methylpyrrolidin-1-yl)methyl]-1,3-oxazole ax66

A mixture of 1-bromo-3-chloropropane (0.7 mmol, 2 eq, 11.5 mg), potassium carbonate (0.7 mmol, 2 eq, 98 mg) and 4-{4-[(2-methylpyrrolidin-1-yl)methyl]-1,3-oxazol-2-yl}phenol ax65 (0.35 mmol, 1 eq, 91.5 mg) in acetone (1.25 ml) is stirred at 56° C. overnight. The mixture is then filtered, washed with acetone (2×500 µl), and the solvent is removed under reduced pressure. The residue is dissolved in 3.5 ml of dichloromethane and washed twice with water (2×3.5 ml) and finally with brine (3.5 ml). The organic layer is dried over magnesium sulfate, filtered and the solvent is removed under reduced pressure. The crude product is used directly in the next step.

LC-MS (MH$^+$): 335/337.

The following compounds may be synthesized according to the same method:

Example 5

Synthesis of 4-(1-pyrrolidinylmethyl)-2-{4-[3-(1-pyrrolidinyl)propoxy]phenyl}-1,3-thiazole 73

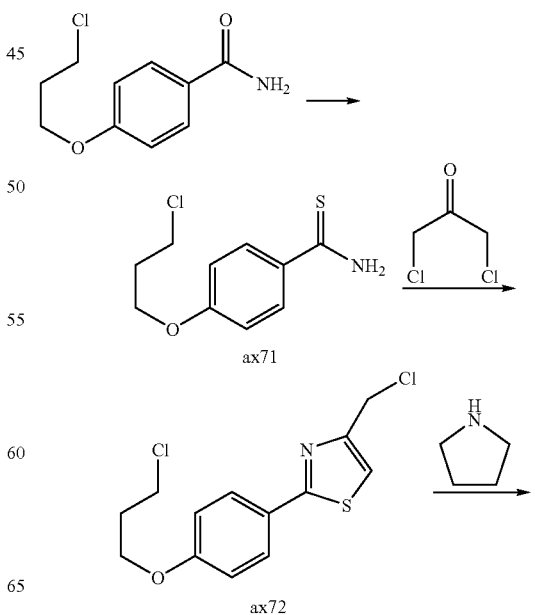

-continued

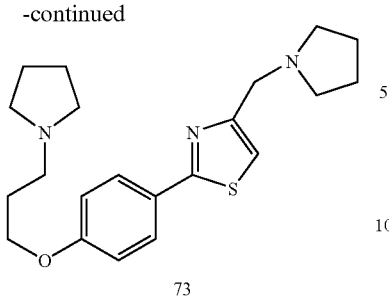

73

5.1 Synthesis of 4-(3-chloropropoxy)benzenecarbothioamide ax71

4-(3-Chloropropoxy)benzamide ax54 (1.0 g, 4.6 mmole, 1 eq) is dissolved in a 1:1 mixture of chloroform and toluene, 2,4-bis-(4-methoxyphenyl)-1,3-dithia-2,4-diphosphetane-2,4-disulfide (1.5 g, 3.7 mmole, 0.8 eq) is added. The reaction is stirred overnight at 85° C. Water is then added and the phases are separated. The organic layer is dried over magnesium sulfate and concentrated under reduce pressure. The crude material is purified by chromatography on silicagel (eluent: dichloromethane/methanol/ammonia 98:1.8:0.2) to provide 0.91 g of 4-(3-chloropropoxy)benzenecarbothioamide ax71 as a white solid.

Yield: 85%.
LC-MS (MH$^+$): 230/232.

5.2. Synthesis of 4-(chloromethyl)-2-[4-(3-chloropropoxy)phenyl]-1,3-thiazole ax72

4-(3-chloropropoxy)benzenecarbothioamide ax71 (0.9 g, 4 mmole, 1 eq) is dissolved in propionitrile (20 ml) and 1,3-dichloroacetone (0.6 g, 4.7 mmole, 1.17 eq) is added. The mixture is refluxed 1 h at 100° C. then concentrated to dryness. The crude material is taken up in dichloromethane, washed with water and dried over magnesium sulfate. The residue is triturated in diisopropylether and filtered off to give 1.1 g of 4-(chloromethyl)-2-[4-(3-chloropropoxy)phenyl]-1,3-thiazole ax72 as a white solid.

Yield: 91%.
LC-MS (MH$^+$): 302/304/306.

5.3. Synthesis of 4-(1-pyrrolidinylmethyl)-2-{4-[3-(1-pyrrolidinyl)propoxy]phenyl}-1,3-thiazole 73

A mixture of 4-(chloromethyl)-2-[4-(3-chloropropoxy)phenyl]-1,3-thiazole ax72 (250 mg, 0.83 mmole, 1 eq) and pyrrolidine (0.3 ml, 3.6 mmol, 4.4 eq) is dissolved in acetonitrile (10 ml). Potassium carbonate (0.5 g, 3.6 mmole, 4.4 eq) and sodium iodide (25 mg, 0.17 mmole, 0.2 eq) are added. The solution is heated at 90° C. in a sealed tube for 48 h. After cooling, the solution is taken up in dichloromethane, washed with water and dried over magnesium sulfate. The crude material is purified by chromatography on silicagel (gradient: dichloromethane/methanol/ammonia 95:4.5:0.5 to 90:9:1) to provide 0.31 g of 4-(1-pyrrolidinylmethyl)-2-{4-[3-(1-pyrrolidinyl)propoxy]phenyl}-1,3-thiazole 73 as a brown oil.

Yield: 13%.
LC-MS (MH$^+$): 372.

Compounds 72 and 74 of table I may be synthetized according to similar experimental conditions.

Compounds 75, 76, 77, 78 and 79 of table I may be synthetized from intermediate ax72 using similar experimental conditions than in example 1.3.

Example 6

Synthesis of 1-(3-{4-[5-methyl-4-(piperidin-1-ylmethyl)-1,3-oxazol-2-yl]phenoxy}propyl)piperidine 87

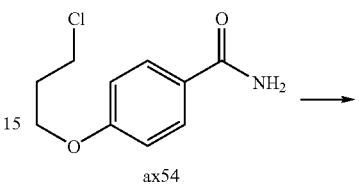

ax54

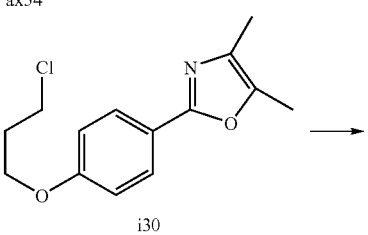

i30

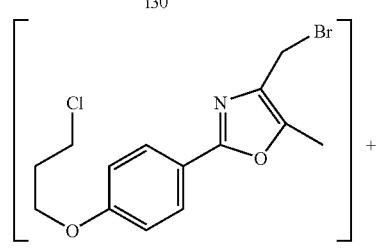

i31

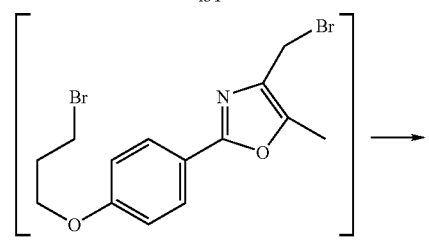

i32

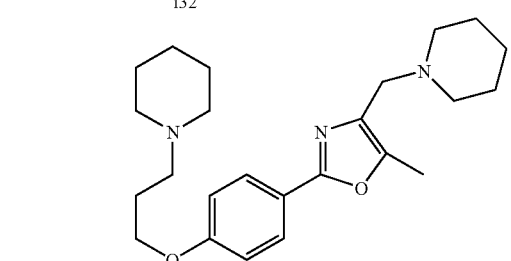

87

6.1 Synthesis of 2-[4-(3-chloropropoxy)phenyl]-4,5-dimethyl-1,3-oxazole i30

A suspension of 4-(3-chloropropoxy)benzamide ax54 (1.2 g, 5.62 mmol) and 3-bromobutan-2-one (1.02 g, 6.74 mmol) is heated in propionitrile (50 ml) at reflux for 10 days. The mixture is then concentrated and the resulting black mixture is filtered through a pad of silicagel, eluting first with dichloromethane (100 ml) and then with a 96:4 mixture of dichloromethane and dimethoxymethane to afford two fractions. The second fraction is concentrated, and the resulting yellow solid (0.67 g) is further purified by chromatography over silicagel (eluent: dichloromethane) to afford 330 mg of 2-[4-(3-chloropropoxy)phenyl]-4,5-dimethyl-oxazole i30 as a pale yellow solid.

Yield: 10%.

LC-MS (MH$^+$): 266/268.

6.2 Synthesis of 4-(bromomethyl)-2-[4-(3-chloropropoxy)phenyl]-5-methyl-1,3-oxazole i31 and 4-(bromomethyl)-2-[4-(3-bromopropoxy)phenyl]-5-methyl-1,3-oxazole i32

A solution of 2-[4-(3-chloropropoxy)phenyl]-4,5-dimethyl-oxazole i30 (0.33 g, 1.24 mmol) in acetonitrile (5 ml) is treated with N-bromosuccinimide (0.22 g, 1.24 mmol) and the mixture is stirred at 22° C. for 2 hours. The mixture is then poured into 20 ml of saturated sodium hydrogenocarbonate and extracted with dichloromethane (2×15 ml). The combined organic phases are dried over magnesium sulfate and concentrated to afford 390 mg of a pale yellow solid corresponding to a 2:1 mixture of 4-(bromomethyl)-2-[4-(3-chloropropoxy)phenyl]-5-methyl-1,3-oxazole i31 and 4-(bromomethyl)-2-[4-(3-bromopropoxy)phenyl]-5-methyl-1,3-oxazole i32 which is used directly in the next step.

Yield: 91%.

LC-MS (MH$^+$): 344/346/348 (i31) and 388/390/392 (i32).

6.3 Synthesis of 1-(3-{4-[5-methyl-4-(piperidin-1-ylmethyl)-1,3-oxazol-2-yl]phenoxy}propyl)piperidine 87

A solution of the above mixture (330 mg) and piperidine (379 µl, 3.83 mmol) in acetonitrile (10 ml) is treated with sodium iodide (14 mg, 0.10 mmol) and stirred at 22° C. for 1 hour, then heated at 90° C. for 20 hours. The mixture is then poured into 10 ml of 0.1 N hydrochloric acid and extracted with ether (10 ml). The aqueous phase is then treated with 2 M sodium hydroxide to reach pH 10 and extracted with dichloromethane (3×5 ml). The combined dichloromethane extracts are dried over magnesium sulfate and concentrated to afford an orange oil (300 mg), which is purified by chromatography over silicagel (eluent: dichloromethane/methanol/ammonia 96/3.6/0.4) to afford 1-(3-{4-[5-methyl-4-(piperidin-1-ylmethyl)-1,3-oxazol-2-yl]phenoxy}propyl)piperidine 87 (190 mg).

Yield: 49%.

LC-MS (MH$^+$): 398.

Example 7

Synthesis of 4-[(2-{4-[3-(2-methylpyrrolidin-1-yl)propoxy]phenyl}-1,3-oxazol-4-yl)carbonyl]morpholine 90

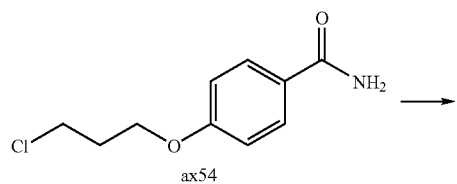
ax54

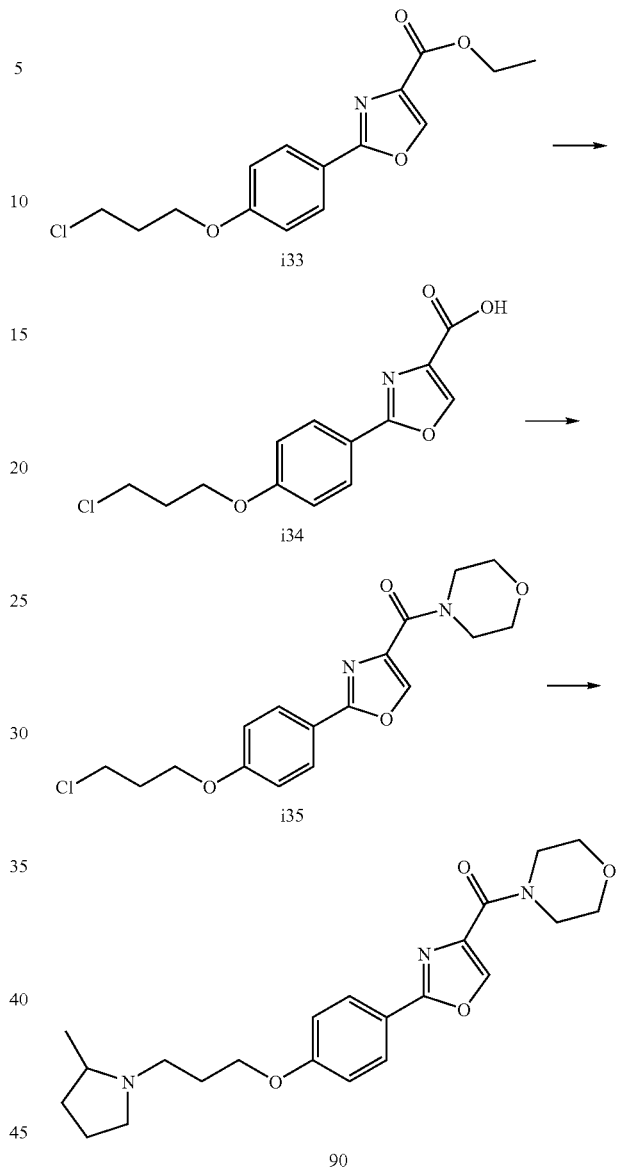

7.1 Synthesis of ethyl 2-[4-(3-chloropropoxy)phenyl]-1,3-oxazole-4-carboxylate i33

A mixture of 4-(3-chloropropoxy)benzamide ax54 (3.55 g, 16.6 mmol, 1 eq) and ethyl bromopyruvate (3.24 g, 16.6 mmol, 1 eq) in propionitrile (60 ml) is heated at reflux. After 24 h, the solvent is evaporated, and the residue is taken up in ethyl acetate and washed two times with an aqueous solution of sodium hydrogenocarbonate. The organic layer is dried over magnesium sulfate, filtered and concentrated under vacuum. Purification by chromatography over silicagel (eluent: dichloromethane/hexane 90:10) affords 2.12 g of ethyl 2-[4-(3-chloropropoxy)phenyl]-1,3-oxazole-4-carboxylate i33.

Yield: 41%.

LC-MS (MH$^+$): 310/312.

7.2 Synthesis of 2-[4-(3-chloropropoxy)phenyl]-1,3-oxazole-4-carboxylic acid i34

A 2 N aqueous solution of sodium hydroxide (10 ml, 20.3 mmol, 3 eq) is added dropwise to a solution of ethyl 2-[4-(3-chloropropoxy)phenyl]-1,3-oxazole-4-carboxylate i33 (2.1 g, 6.8 mmol, 1 eq) in ethanol (60 ml). The mixture is refluxed for 2 h 30 and the solvent is evaporated. The residue is taken up in water and acidified to pH 2 with a 2 N hydrochloric acid solution. The solid that precipitates is filtered off and washed with water to give 1.5 g of 2-[4-(3-chloropropoxy)phenyl]-1,3-oxazole-4-carboxylic acid i34.
Yield: 79%.
LC-MS (MH+): 282/284.

7.3 Synthesis of 4-({2-[4-(3-chloropropoxy)phenyl]-1,3-oxazol-4-yl}carbonyl)morpholine i35

A solution of 2-[4-(3-chloropropoxy)phenyl]-1,3-oxazole-4-carboxylic acid i34 (0.5 g, 1.57 mmol, 1 eq), morpholine (0.15 g, 1.73 mmol, 1.1 eq) and triethylamine (0.44 ml, 3.14 mmol, 2 eq) in dichloromethane (20 ml) is cooled to 0° C. N-(3-dimethylaminopropyl)-N'-ethylcarbodiimide hydrochloride (0.33 g, 1.73 mmol, 1.1 eq) and 1-hydroxybenzotriazole (0.04 g, 0.31 mmol, 0.2 eq) are added to the solution and the mixture is stirred 24 h at room temperature. The mixture is then washed with water and a saturated solution of aqueous ammonium chloride. The organic layer is dried over magnesium sulfate, filtered and concentrated under vacuum to give 0.54 g of 4-({2-[4-(3-chloropropoxy)phenyl]-1,3-oxazol-4-yl}carbonyl)morpholine i35.
Yield: 98%.
LC-MS (MH+): 351/353.

The following compounds may be synthesized according to the same method:

| | | |
|---|---|---|
| i36 | 1-({2-[4-(3-chloropropoxy)phenyl]-1,3-oxazol-4-yl}carbonyl)piperidine | LC-MS (MH+): 349:351 |
| i37 | 1-({2-[4-(3-chloropropoxy)phenyl]-1,3-oxazol-4-yl}carbonyl)-4-cyclopentylpiperazine | LC-MS (MH+): 418/420 |
| i38 | 2-[4-(3-chloropropoxy)phenyl]-N-(cyclopropylmethyl)-N-propyl-1,3-oxazole-4-carboxamide | LC-MS (MH+): 377/379 |
| i39 | 2-[4-(3-chloropropoxy)phenyl]-N-cyclopentyl-1,3-oxazole-4-carboxamide | LC-MS (MH+): 349/351 |
| i40 | 2-[4-(3-chloropropoxy)phenyl]-N-(4-fluorobenzyl)-1,3-oxazole-4-carboxamide | LC-MS (MH+): 389/391 |
| i41 | 2-[4-(3-chloropropoxy)phenyl]-4-(pyrrolidin-1-ylcarbonyl)-1,3-oxazole | LC-MS (MH+): 335/337 |
| i42 | 2-[4-(3-chloropropoxy)phenyl]-4-{[(2S)-2-(pyrrolidin-1-ylmethyl)pyrrolidin-1-yl]carbonyl}-1,3-oxazole | LC-MS (MH+): 418/420 |

7.4 Synthesis of 4-[(2-{4-[3-(2-methylpyrrolidin-1-yl)propoxy]phenyl}-1,3-oxazol-4-yl)carbonyl]morpholine 90

4-({2-[4-(3-chloropropoxy)phenyl]-1,3-oxazol-4-yl}carbonyl)morpholine i35 (0.26 g, 0.75 mmol, 1 eq) is reacted with 2-methylpyrrolidine (0.11 ml, 1.13 mmol, 1.5 eq) in the presence of potassium carbonate (0.2 g, 1.5 mmol, 2 eq) and a catalytic amount of sodium iodide in refluxing acetonitrile (15 ml) overnight. The solvent is then evaporated, and the residue taken up in ethyl acetate and washed two times with an aqueous solution of sodium hydrogenocarbonate. The organic layer is dried over magnesium sulfate, filtered and concentrated under vacuum. Purification by chromatography over silicagel (eluent: dichloromethane/methanol/ammonia 96:3.6:0.4) affords 0.11 g of 4-[(2-{4-[3-(2-methylpyrrolidin-1-yl)propoxy]phenyl}-1,3-oxazol-4-yl)carbonyl]morpholine 90.
Yield: 37%.
LC-MS (MH+): 400.

Compounds 91, 92, 93, 102, 103, 104, 107 and 131 of table (I) may be synthetized according to similar experimental conditions.

Example 8

Synthesis of N-(cyclopropylmethyl)-4-methyl-2-{4-[3-(2-methyl-1-pyrrolidinyl)propoxy]phenyl}-N-propyl-1,3-oxazole-5-carboxamide 97 and N-(cyclopropylmethyl)-N-[(4-methyl-2-{4-[3-(2-methylpyrrolidin-1-yl)propoxy]phenyl}-1,3-oxazol-5-yl)methyl]-N-propylamine 112

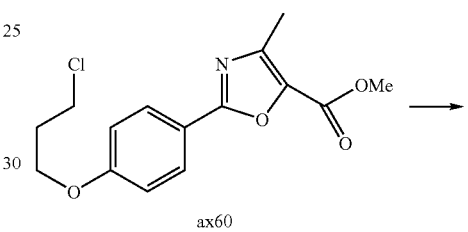

ax60

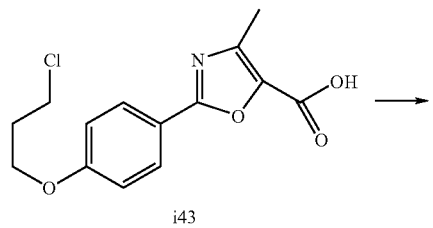

i43

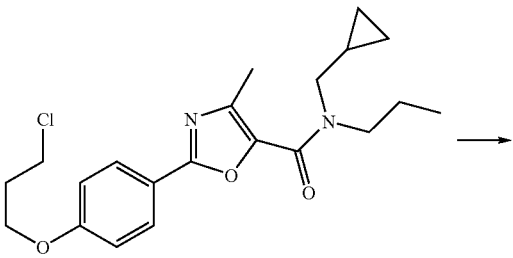

i44

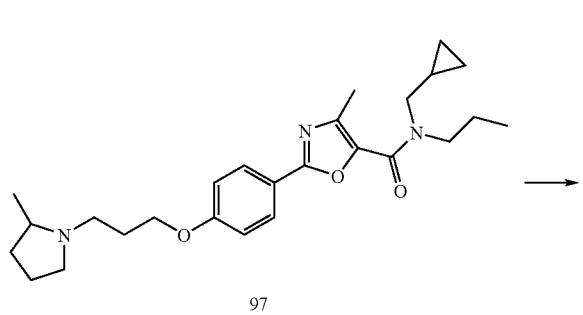

97

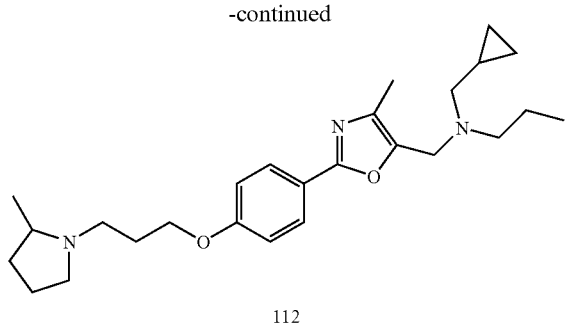

112

8.1 Synthesis of 2-[4-(3-chloropropoxy)phenyl]-4-methyl-1,3-oxazole-5-carboxylic acid i43

A suspension of methyl 2-[4-(3-chloropropoxy)phenyl]-4-methyl-1,3-oxazole-5-carboxylate ax60 (4.0 g, 12.9 mmol, 1 eq) in a 1:1 mixture of methanol and water (100 ml) is treated with a 1 M solution of sodium hydroxide (14 ml, 14 mmol, 1.1 eq). The mixture is stirred at 60° C. during 2 h, then the mixture is concentrated. The residue is taken up in water (20 ml) and a 1 M hydrochloric acid solution (14 ml, 14 mmol, 1.1 eq) is added. The resulting suspension is filtered and the filtrate is concentrated to give 3.4 g of 2-[4-(3-chloropropoxy)phenyl]-4-methyl-1,3-oxazole-5-carboxylic acid i43.

Yield: 88%.

LC-MS (MH+): 296/298.

8.2 Synthesis of 2-[4-(3-chloropropoxy)phenyl]-N-(cyclopropylmethyl)-4-methyl-N-propyl-1,3-oxazole-5-carboxamide i44

A mixture of 2-[4-(3-chloropropoxy)phenyl]-4-methyl-1,3-oxazole-5-carboxylic acid i43 (3.18 g, 10.75 mmol, 1 eq) and triethylamine (1.5 ml, 10.75 mmol, 1 eq) in chloroform (70 ml) is cooled to 0° C. Thionyl chloride (2.3 ml, 32 mmol, 3 eq) is then added dropwise. The mixture is refluxed for 2 h 30 and the solvent is evaporated. The residue is taken up in cold dichloromethane (20 ml, 0° C.) and treated with triethylamine (0.6 ml, 4.3 mmol, 2 eq) and N-(cyclopropylmethyl) propan-1-amine (0.29 g, 2.58 mmol, 1.2 eq). The mixture is stirred at room temperature overnight and then washed two times with a saturated solution of aqueous ammonium chloride. The organic layer is dried over magnesium sulfate, filtered and concentrated under vacuum to give 0.82 g of 2-[4-(3-chloropropoxy)phenyl]-N-(cyclopropylmethyl)-4-methyl-N-propyl-1,3-oxazole-5-carboxamide i44.

Yield: 97%.

LC-MS (MH+): 391/393.

The following compounds may be synthesized according to the same method:

| | | |
|---|---|---|
| i45 | 1-({2-[4-(3-chloropropoxy)phenyl]-4-methyl-1,3-oxazol-5-yl}carbonyl)piperidine | LC-MS (MH+): 363/365 |
| i46 | 1-({2-[4-(3-chloropropoxy)phenyl]-4-methyl-1,3-oxazol-5-yl}carbonyl)-4-cyclopentylpiperazine | LC-MS (MH+): 432/434 |
| i47 | N-benzyl-2-[4-(3-chloropropoxy)phenyl]-4-methyl-1,3-oxazole-5-carboxamide | LC-MS (MH+): 385/387 |
| i48 | 4-({2-[4-(3-chloropropoxy)phenyl]-4-methyl-1,3-oxazol-5-yl}carbonyl)morpholine | LC-MS (MH+): 365/367 |
| i49 | 2-[4-(3-chloropropoxy)phenyl]-N-cyclopentyl-4-methyl-1,3-oxazole-5-carboxamide | LC-MS (MH+): 363/365 |

8.3 Synthesis of N-(cyclopropylmethyl)-4-methyl-2-{4-[3-(2-methylpyrrolidin-1-yl)propoxy]phenyl}-N-propyl-1,3-oxazole-5-carboxamide 97

2-methylpyrrolidine (0.24 ml, 2.46 mmol, 1.2 eq) is added to a solution of 2-[4-(3-chloropropoxy)phenyl]-N-(cyclopropylmethyl)-4-methyl-N-propyl-1,3-oxazole-5-carboxamide i44 (0.8 g, 2 mmol, 1 eq), potassium carbonate (0.55 g, 4 mmol, 2 eq) and a catalytic quantity of sodium iodide in refluxing acetonitrile (25 ml). After stirring for 20 h at reflux, the solvent is evaporated and the residue is taken up in ethyl acetate and washed two times with an aqueous solution of sodium hydrogenocarbonate. The organic layer is dried over magnesium sulfate, filtered and concentrated under vacuum. Purification by chromatography over silicagel (eluent: dichloromethane/methanol/ammonia 96:3.6:0.4) affords 0.31 g of N-(cyclopropylmethyl)-4-methyl-2-{4-[3-(2-methylpyrrolidin-1-yl)propoxy]phenyl}-N-propyl-1,3-oxazole-5-carboxamide 97.

Yield: 35%.

LC-MS (MH+): 440.

Compounds 96, 98, 105, 106, 108, 109, and 110 of table (I) may be synthetized according to similar experimental conditions.

8.4 Synthesis of N-(cyclopropylmethyl)-N-[(4-methyl-2-{4-[3-(2-methyl pyrrolidin-1-yl)propoxy]phenyl}-1,3-oxazol-5-yl)methyl]-N-propylamine 112

A solution of N-(cyclopropylmethyl)-4-methyl-2-{4-[3-(2-methylpyrrolidin-1-yl)propoxy]phenyl}-N-propyl-1,3-oxazole-5-carboxamide 97 (0.25 g, 0.57 mmol, 1 eq) in tetrahydrofuran (15 ml) is treated with borane-tetrahydrofuran complex 1 M in tetrahydrofuran (2.2 ml, 2.2 mmol, 4 eq) and refluxed overnight. The solvent is then removed under reduced pressure and the residue is taken up in ethyl acetate and washed with a saturated solution of aqueous ammonium chloride. The organic layer is dried over magnesium sulfate, filtered and concentrated. The residue is then dissolved in tetrahydrofuran and a 2 N sodium hydroxide solution is added to reach pH 10. The mixture is refluxed for 40 h and a saturated solution of aqueous ammonium chloride is added and the solution extracted two times with ethyl acetate. The organic layers are dried over magnesium sulfate, filtered and concentrated under vacuum. Purification by chromatography over silicagel (eluent: dichloromethane/methanol/ammonia 96/3.6/0.4) gives 0.115 g of N-(cyclopropylmethyl)-N-[(4-methyl-2-{4-[3-(2-methylpyrrolidin-1-yl)propoxy]phenyl}-1,3-oxazol-5-yl)methyl]-N-propylamine 112.

Yield: 48%.

LC-MS (MH+): 426.

Compounds 111, 113, 116 and 143 of table I may be synthetized according to similar experimental conditions.

Example 9

Synthesis of 1-[2-(2-{4-[2-(2-methylpyrrolidin-1-yl)ethoxy]phenyl}-1,3-oxazol-4-yl)ethyl]piperidine 121

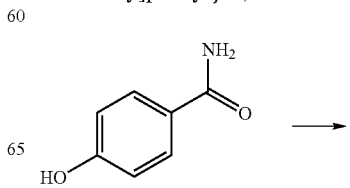

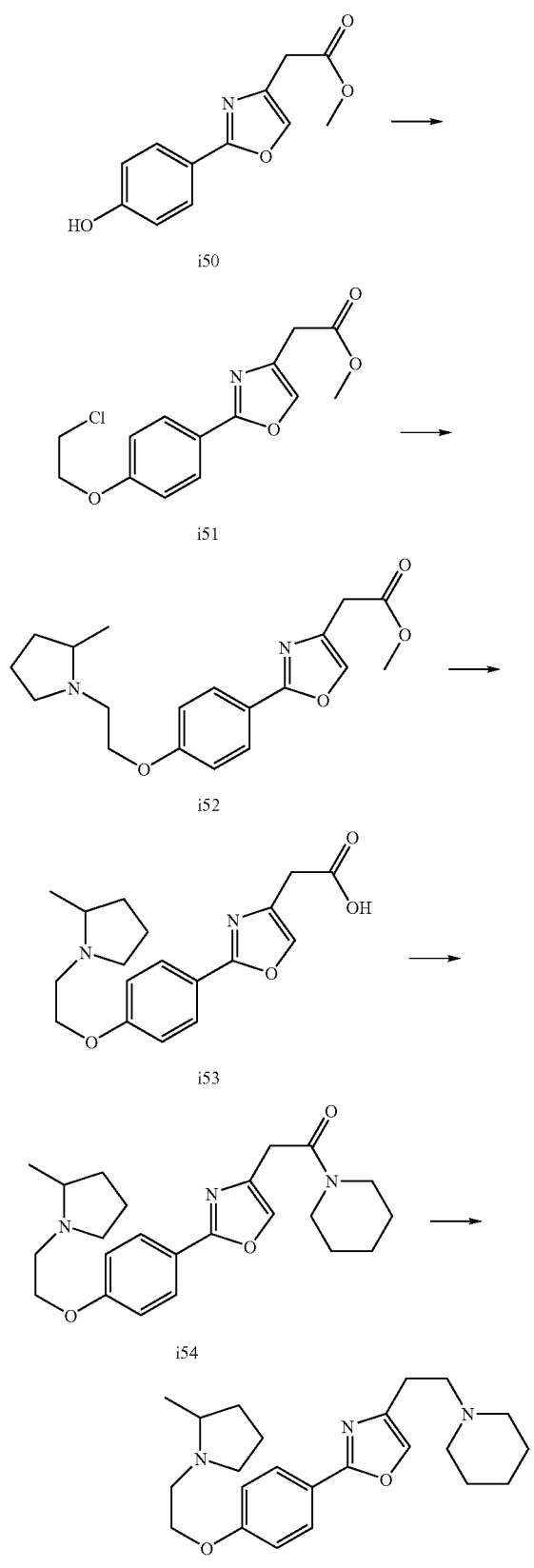

9.1 Synthesis of methyl[2-(4-hydroxyphenyl)-1,3-oxazol-4-yl]acetate i50

A solution of 4-hydroxybenzamide (10 g, 7.3 mmol, 1 eq) and methyl 4-chloro-3-oxobutanoate (15 g, 11 mmol, 5 eq) in propionitrile (300 ml) is stirred at reflux (98° C.) during 3 days. After concentration under reduced pressure, the residue is purified over silicagel (eluent: dichloromethane/methanol/ammonia 90:9:1) to yield 7 g of methyl[2-(4-hydroxyphenyl)-1,3-oxazol-4-yl]acetate i50.

Yield: 41%.
LC-MS (MH$^+$): 234.

9.2 Synthesis of methyl {2-[4-(2-chloroethoxy)phenyl]-1,3-oxazol-4-yl}acetate i51

A mixture of methyl[2-(4-hydroxyphenyl)-1,3-oxazol-4-yl]acetate 150 (1 g, 4.29 mmol, 1 eq), potassium carbonate (2.37 g, 17.16 mmol, 4 eq) and 1-bromo-2-chloroethane (1.54 g, 10.7 mmol, 2.5 eq) in acetone (50 ml) is stirred at reflux for 140 h. Potassium carbonate is then filtered off and the solvent is evaporated. The residue is taken up in ethyl acetate and washed two times with an aqueous solution of sodium hydrogenocarbonate. The organic layer is dried over magnesium sulfate, filtered and concentrated under vacuum to give 1.1 g of methyl {2-[4-(2-chloroethoxy)phenyl]-1,3-oxazol-4-yl}acetate i51.

Yield: 87%.
LC-MS (MH$^+$): 296/298.

9.3 Synthesis of methyl (2-{4-[2-(2-methylpyrrolidin-1-yl)ethoxy]phenyl}-1,3-oxazol-4-yl)acetate i52

Methyl {2-[4-(2-chloroethoxy)phenyl]-1,3-oxazol-4-yl}acetate 151 (0.55 g, 1.86 mmol, 1 eq) is reacted with 2-methylpyrrolidine (0.28 ml, 2.79 mmol, 1.5 eq) in the presence of potassium carbonate (0.77 g, 5.58 mmol, 3 eq) and a catalytic quantity of sodium iodide in refluxing acetonitrile (20 ml). After 45 h, the solvent is evaporated, the residue is then taken up in ethyl acetate and washed two times with an aqueous solution of sodium hydrogenocarbonate. The organic layer is dried over magnesium sulfate, filtered and concentrated under vacuum. Purification by chromatography over silicagel (eluent: dichloromethane/methanol/ammonia 97:2.7:0.3) affords 0.3 g of methyl (2-{4-[2-(2-methylpyrrolidin-1-yl)ethoxy]phenyl}-1,3-oxazol-4-yl)acetate i52.

Yield: 47%.
LC-MS (MH$^+$): 345.

9.4 Synthesis of (2-{4-[2-(2-methylpyrrolidin-1-yl)ethoxy]phenyl}-1,3-oxazol-4-yl)acetic acid i53

A 2 N aqueous sodium hydroxide solution (2.6 ml, 5.23 mmol, 6 eq) is added to a solution of methyl (2-{4-[2-(2-methylpyrrolidin-1-yl)ethoxy]phenyl}-1,3-oxazol-4-yl)acetate 152 (0.3 g, 0.87 mmol, 1 eq) in ethanol (15 ml). The mixture is stirred at reflux for 3 h and the solvent is then evaporated. The residue is taken up in water, acidified with 2 N hydrochloric acid and the solvent is evaporated under reduced pressure to give 0.8 g of (2-{4-[2-(2-methylpyrrolidin-1-yl)ethoxy]phenyl}-1,3-oxazol-4-yl)acetic acid i53 together with remaining sodium chloride. The compound is used in the next step without any other treatment.

LC-MS (MH$^+$): 331.

9.5 Synthesis of 1-[(2-{4-[2-(2-methylpyrrolidin-1-yl)ethoxy]phenyl}-1,3-oxazol-4-yl)acetyl]piperidine i54

A solution of (2-{4-[2-(2-methylpyrrolidin-1-yl)ethoxy]phenyl}-1,3-oxazol-4-yl)acetic acid i53 (0.29 g, 0.87 mmol, 1 eq), piperidine (0.18 ml, 1.75 mmol, 2 eq) and triethylamine (0.36 ml, 3.6 mmol, 3 eq) in dichloromethane (20 ml) is cooled to 0° C. N-(3-dimethylaminopropyl)-N'-ethylcarbodiimide hydrochloride (0.42 g, 2.17 mmol, 2.5 eq) and 1-hydroxybenzotriazole (0.12 g, 0.87 mmol, 1 eq) are then added. The mixture is stirred 24 h at room temperature, and washed two times with a saturated solution of aqueous ammonium chloride. The organic layer is dried over magnesium sulfate, filtered and concentrated under vacuum. Purification by chromatography over silicagel (eluent: dichloromethane/methanol/ammonia 97/2.7/03) affords 0.15 g of 1-[(2-{4-[2-(2-methylpyrrolidin-1-yl)ethoxy]phenyl}-1,3-oxazol-4-yl)acetyl]piperidine i54.

Yield: 44%.

LC-MS (MH$^+$): 398.

9.6 Synthesis of 1-[2-(2-{4-[2-(2-methylpyrrolidin-1-yl)ethoxy]phenyl}-1,3-oxazol-4-yl)ethyl]piperidine 121

A solution of 1-[(2-{4-[2-(2-methylpyrrolidin-1-yl)ethoxy]phenyl}-1,3-oxazol-4-yl)acetyl]piperidine i54 (0.13 g, 0.33 mmol, 1 eq) in tetrahydrofuran (5 ml) is treated with borane-tetrahydrofuran complex (1.0 M in tetrahydrofuran, 1.3 ml, 1.3 mmol, 4 eq) and the resulting mixture is refluxed overnight. A 2 N sodium hydroxide solution is added to reach pH 10 and the mixture is refluxed for 6 h. A saturated solution of aqueous ammonium chloride is added and the solution is extracted two times with ethyl acetate. The organic layers are dried over magnesium sulfate, filtered and concentrated under vacuum. Purification by chromatography over silicagel (eluent: dichloromethane/methanol/ammonia 96/3.6/0.4) gives 0.115 g of 1-[2-(2-{4-[2-(2-methylpyrrolidin-1-yl)ethoxy]phenyl}-1,3-oxazol-4-yl)ethyl]piperidine 121.

Yield: 23%.

LC-MS (MH$^+$): 384.

Example 10

Synthesis of 1-[(2-{4-[3-(2-methylpyrrolidin-1-yl)propoxy]phenyl}-1,3-oxazol-4-yl)methyl]piperidin-2-one 122

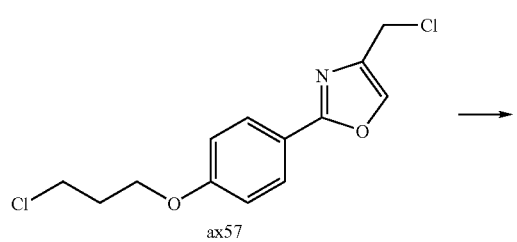

ax57

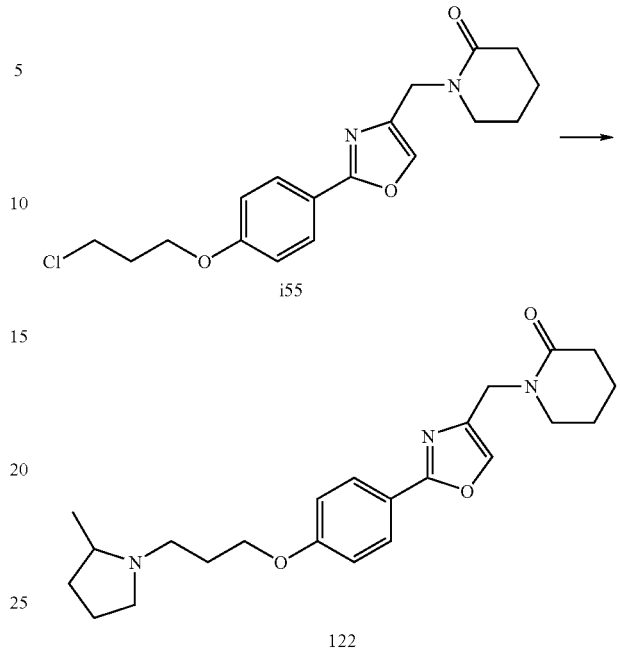

10.1 Synthesis of 1-({2-[4-(3-chloropropoxy)phenyl]-1,3-oxazol-4-yl}methyl)piperidin-2-one i55

A suspension of delta-valerolactam (0.14 g, 1.4 mmol, 1 eq) and sodium hydride (60% dispersion in mineral oil, 0.056 g, 1.4 mmol, 1 eq) in N,N-dimethylformamide (10 ml) is cooled to 0° C. and treated with 4-(chloromethyl)-2-[4-(3-chloropropoxy)phenyl]-1,3-oxazole ax57 (0.4 g, 1.4 mmol, 1 eq). The mixture is then stirred at room temperature. After 20 h, the solvent is evaporated, the residue is taken up in ethyl acetate and washed two times with an aqueous solution of sodium hydrogenocarbonate. The organic layer is dried over magnesium sulfate, filtered and concentrated under vacuum to give 0.58 g of 1-({2-[4-(3-chloropropoxy)phenyl]-1,3-oxazol-4-yl}methyl)piperidin-2-one i55 immediately engaged in the next step without any further purification.

LC-MS (MH$^+$): 349/351.

The following compounds may be synthesized according to the same method:

| | | |
|---|---|---|
| i56 | (5S)-1-({2-[4-(3-chloropropoxy)phenyl]-1,3-oxazol-4-yl}methyl)-5-(pyrrolidin-1-ylmethyl)pyrrolidin-2-one | LC-MS (MH$^+$): 418/420 |
| i58 | (5S)-1-({2-[4-(3-chloropropoxy)phenyl]-1,3-oxazol-4-yl}methyl)-5-(morpholin-4-ylmethyl)pyrrolidin-2-one | LC-MS (MH$^+$): 434/436 |
| i67 | 1-({2-[4-(3-chloropropoxy)phenyl]-1,3-oxazol-4-yl}methyl)pyrrolidin-2-one | LC-MS (MH$^+$): 335/337 |

10.2 Synthesis of 1-[(2-{4-[3-(2-methylpyrrolidin-1-yl)propoxy]phenyl}-1,3-oxazol-4-yl)methyl]piperidin-2-one 122

1-({2-[4-(3-chloropropoxy)phenyl]-1,3-oxazol-4-yl}methyl)piperidin-2-one i55 (0.564 g, 1.62 mmol, 1 eq) is reacted with 2-methylpyrrolidine (0.19 ml, 1.94 mmol, 1.2 eq) in the presence of potassium carbonate (0.45 g, 3.24 mmol, 2 eq) and a catalytic quantity of sodium iodide in refluxing acetonitrile (20 ml). After 45 h, the solvent is evaporated. The residue is then taken up in ethyl acetate and washed two times with an aqueous solution of sodium hydrogenocarbonate. The organic layer is dried over magnesium sulfate, filtered and concentrated under vacuum. Purification by chromatography over silicagel (eluent: dichloromethane/methanol/ammonia 95:4.5:0.5) affords 0.27 g of 1-[(2-{4-[3-(2-methylpyrrolidin-1-yl)propoxy]phenyl}-1,3-oxazol-4-yl)methyl]piperidin-2-one 122.

Yield: 41%.

LC-MS (MH+): 398.

Compounds 53, 123 and 137 of table I may be synthetized according to similar experimental conditions.

Example 11

Synthesis of 1-[(2-{3-chloro-4-[3-(2-methyl-1-pyrrolidinyl) propoxy]phenyl}-1,3-oxazol-4-yl)methyl]piperidine 124

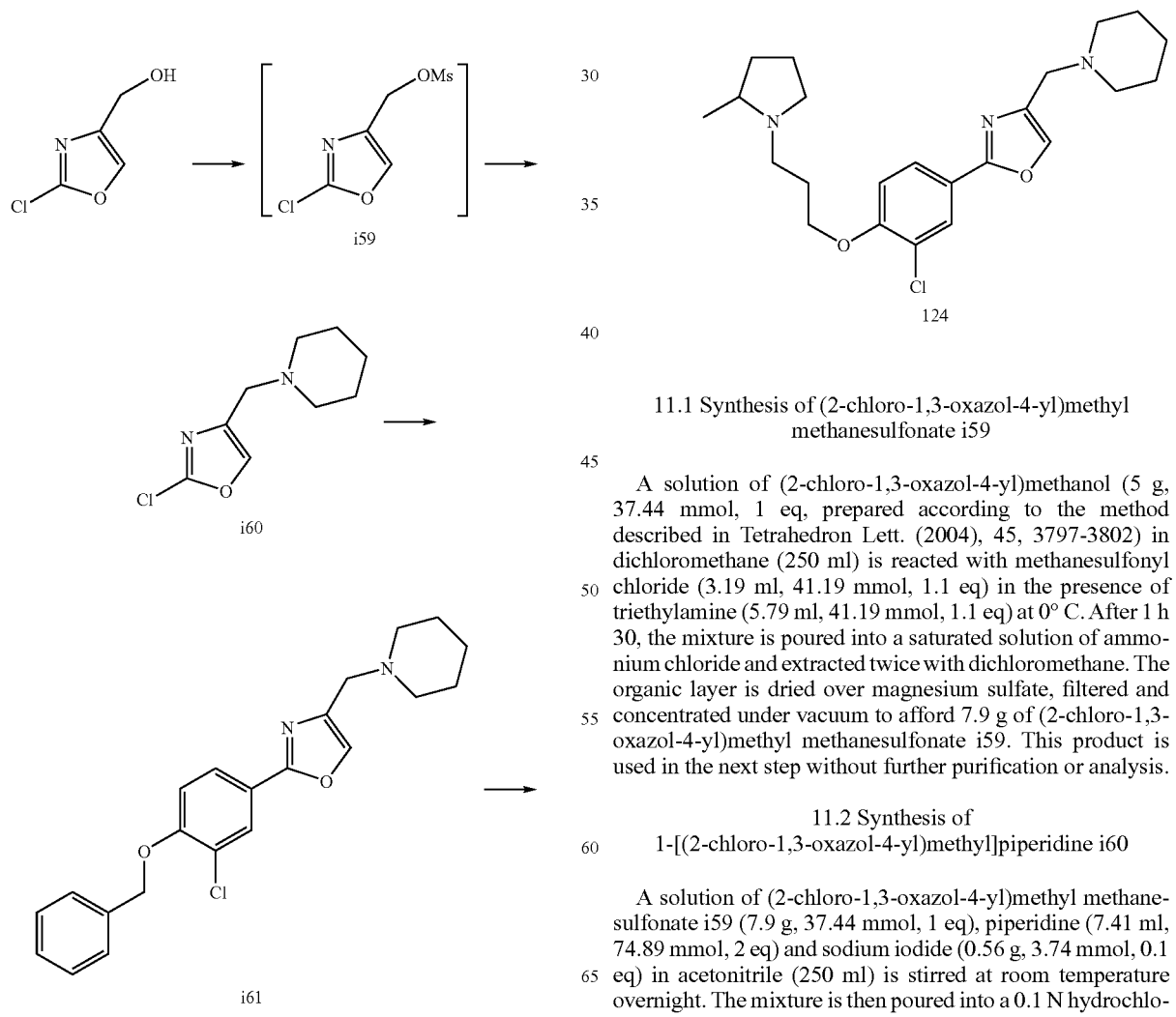

11.1 Synthesis of (2-chloro-1,3-oxazol-4-yl)methyl methanesulfonate i59

A solution of (2-chloro-1,3-oxazol-4-yl)methanol (5 g, 37.44 mmol, 1 eq, prepared according to the method described in Tetrahedron Lett. (2004), 45, 3797-3802) in dichloromethane (250 ml) is reacted with methanesulfonyl chloride (3.19 ml, 41.19 mmol, 1.1 eq) in the presence of triethylamine (5.79 ml, 41.19 mmol, 1.1 eq) at 0° C. After 1 h 30, the mixture is poured into a saturated solution of ammonium chloride and extracted twice with dichloromethane. The organic layer is dried over magnesium sulfate, filtered and concentrated under vacuum to afford 7.9 g of (2-chloro-1,3-oxazol-4-yl)methyl methanesulfonate i59. This product is used in the next step without further purification or analysis.

11.2 Synthesis of 1-[(2-chloro-1,3-oxazol-4-yl)methyl]piperidine i60

A solution of (2-chloro-1,3-oxazol-4-yl)methyl methanesulfonate i59 (7.9 g, 37.44 mmol, 1 eq), piperidine (7.41 ml, 74.89 mmol, 2 eq) and sodium iodide (0.56 g, 3.74 mmol, 0.1 eq) in acetonitrile (250 ml) is stirred at room temperature overnight. The mixture is then poured into a 0.1 N hydrochloric acid solution and extracted with diethyl ether. The organic layer is dried over magnesium sulfate, filtered and the solvent is removed under reduced pressure. Purification by chromatography over silicagel (eluent: dichloromethane/methanol/ammonia 98:1.8:0.2) affords 3 g of 1-[(2-chloro-1,3-oxazol-4-yl)methyl]piperidine i60.

Yield: 40%.
LC-MS (MH$^+$): 201/203.

11.3 Synthesis of 1-({2-[4-(benzyloxy-3-chlorophenyl]-1,3-oxazol-4-yl}methyl)piperidine i61

A solution of 1-[(2-chloro-1,3-oxazol-4-yl)methyl]piperidine i60 (0.8 g, 3.99 mmol, 1 eq) in toluene (60 ml) is treated with (3-chloro-4-benzyloxyphenyl)boronic acid (1.05 g, 3.99 mmol, 1 eq) and a solution of potassium carbonate (1.1 g, 7.97 mmol, 2 eq), in water (5 ml). The mixture is degassed under argon and tetrakis(triphenylphosphine)palladium (0) (0.18 g, 0.16 mmol, 0.04 eq) is added. The mixture is then stirred at 70° C. in a sealed tube. After 24 h, the mixture is poured onto dichloromethane and washed with a 2 M sodium hydroxide solution. The organic layer is dried over magnesium sulfate, filtered and the solvent is removed under reduced pressure. The residue is purified by chromatography over silicagel (eluent: dichloromethane/methanol/ammonia 97.5:2.5:0.25 to 92.5:7.5:0.75) to provide 500 mg of 1-({2-[4-(benzyloxy)-3-chlorophenyl]-1,3-oxazol-4-25 yl}methyl)piperidine i61.

Yield: 33%.
LC-MS (MH$^+$): 383/385.

The following compounds may be synthesized according to the same method:

| | | |
|---|---|---|
| i63 | 1-({2-[4-(benzyloxy)-3-fluorophenyl]-1,3-oxazol-4-yl}methyl)piperidine | LC-MS (MH$^+$): 367 |
| i64 | 2,6-dimethyl-4-[4-(piperidin-1-ylmethyl)-1,3-oxazol-2-yl]phenol | LC-MS (MH$^+$): 287 |
| i65 | 2-methoxy-4-[4-(piperidin-1-ylmethyl)-1,3-oxazol-2-yl]phenol | LC-MS (MH$^+$): 289 |

11.4 Synthesis of 2-chloro-4-[4-(piperidin-1-ylmethyl)-1,3-oxazol-2-yl]phenol i66 and 2-fluoro-4-(4-piperidin-1-ylmethyl-oxazol-2-yl)-phenol i68

To a solution of 1-({2-[4-(benzyloxy)-3-chlorophenyl]-1,3-oxazol-4-yl}methyl)piperidine i61 (0.3 g, 0.78 mmol, 1 eq) in dodecanethiol (5 ml) is added dropwise boron trifluoride diethyl etherate (1.59 ml, 12.54 mmol, 48 eq). The mixture is stirred at room temperature for 60 h. Diethyl ether is poured onto the mixture and the solid that precipitates is filtered off and recrystallized from diethyl ether to give 150 mg of 2-chloro-4-[4-(piperidin-1-ylmethyl)-1,3-oxazol-2-yl]phenol i66.

Yield: 66%
LC-MS (MH$^+$): 293/295.

2-fluoro-4-(4-piperidin-1-ylmethyl-oxazol-2-yl)-phenol i68 is synthesized according to the following method: a solution of 1-({2-[4-(benzyloxy)-3-fluorophenyl]-1,3-oxazol-4-yl}methyl)piperidine i63 (0.34 g, 0.94 mmol, 1 eq) in ethanol is placed under hydrogen atmosphere (20 psi) at 30° C. for 6 hours. The mixture is filtered over cellite and concentrated under vacuo to give 0.22 g of 2-fluoro-4-(4-piperidin-1-ylmethyl-oxazol-2-yl)-phenol i68 as a brown solid. This crude product is used in the next step without any purification.

Yield: 65%.
$^1$H NMR (DMSO) δ: 1.49 (m, 5H), 2.38 (s, 4H), 3.36 (s, 2H), 7.07 (m, 1H), 7.62 (s, 2H), 7.95 (s, 1H).

11.5 Synthesis of 1-({2-[3-chloro-4-(3-chloropropoxy)phenyl]-1,3-oxazol-4-yl}methyl)piperidine i71

A suspension of 2-chloro-4-[4-(piperidin-1-ylmethyl)-1,3-oxazol-2-yl]phenol i66 (0.13 g, 0.44 mmol, 1 eq), 1-bromo-3-chloropropane (57 μl, 0.58 mmol, 1.3 eq) and potassium carbonate (0.12 g, 0.89 mmol, 2 eq) is stirred at 50° C. overnight. The carbonate is then filtered off and the resulting solution is concentrated under reduced pressure to give 0.12 g of crude 1-({2-[3-chloro-4-(3-chloropropoxy)phenyl]-1,3-oxazol-4-yl}methyl)piperidine i71 as an oil, which is directly used in the next step.

Yield: 74%.
$^1$H NMR (CDCl$_3$) δ: 1.45 (d, 5.02 Hz, 3H), 1.61 (m, 7H), 2.32 (m, 3H), 2.48 (s Hz, 6H), 3.48 (s Hz, 3H), 3.81 (t, 6.15 Hz, 3H), 4.24 (t, 5.78 Hz, 3H), 6.99 (d, 8.79 Hz, 1H), 7.54 (s Hz, 1H), 7.90 (dd, 8.79, 1.88 Hz, 1H), 8.08 (d, 1.76 Hz, 1H).

The following compounds may be synthesized according to the same method:

| | | |
|---|---|---|
| i72 | 1-({2-[4-(3-chloropropoxy)-3,5-dimethylphenyl]-1,3-oxazol-4-yl}methyl)piperidine | LC-MS (MH$^+$): 363/365 |
| i73 | 1-({2-[4-(3-chloropropoxy)-3-fluorophenyl]-1,3-oxazol-4-yl}methyl)piperidine | LC-MS (MH$^+$): 353/355 |
| i75 | 1-({2-[4-(3-chloropropoxy)-3-methoxyphenyl]-1,3-oxazol-4-yl}methyl)piperidine | LC-MS (MH$^+$): 365/367 |

11.6 Synthesis of 1-[(2-{3-chloro-4-[3-(2-methylpyrrolidin-1-yl)propoxy]phenyl}-1,3-oxazol-4-yl)methyl]piperidine 124

A solution of 1-({2-[3-chloro-4-(3-chloropropoxy)phenyl]-1,3-oxazol-4-yl}methyl)piperidine i71 (0.12 g, 0.32 mmol, 1 eq) and 2-methylpyrrolidine (63 Pl, 0.65 mmol, 2 eq) in acetonitrile (10 ml) is treated with sodium iodide (5 mg, 0.03 mmol, 0.1 eq) and stirred at room temperature overnight. The mixture is then washed with water, dried over magnesium sulfate, and concentrated to give the crude product. Purification by chromatography over silicagel (eluent: dichloromethane/methanol/ammonia 90:10:0.1) gives 75 mg of 1-[(2-{3-chloro-4-[3-(2-methylpyrrolidin-1-yl)propoxy]phenyl}-1,3-oxazol-4-yl)methyl]piperidine 124 as an orange oil.

Yield: 56%.
LC-MS (MH$^+$): 418/420.

Compounds 89, 95 and 114 of table I may be synthetized according to similar experimental conditions.

Example 12

Synthesis of 1-[(2-{2-fluoro-4-[3-(2-methylpyrrolidin-1-yl)propoxy]phenyl}-1,3-oxazol-4-yl)methyl]piperidine dimethanesulfonate 145

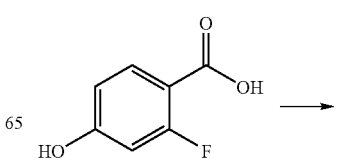

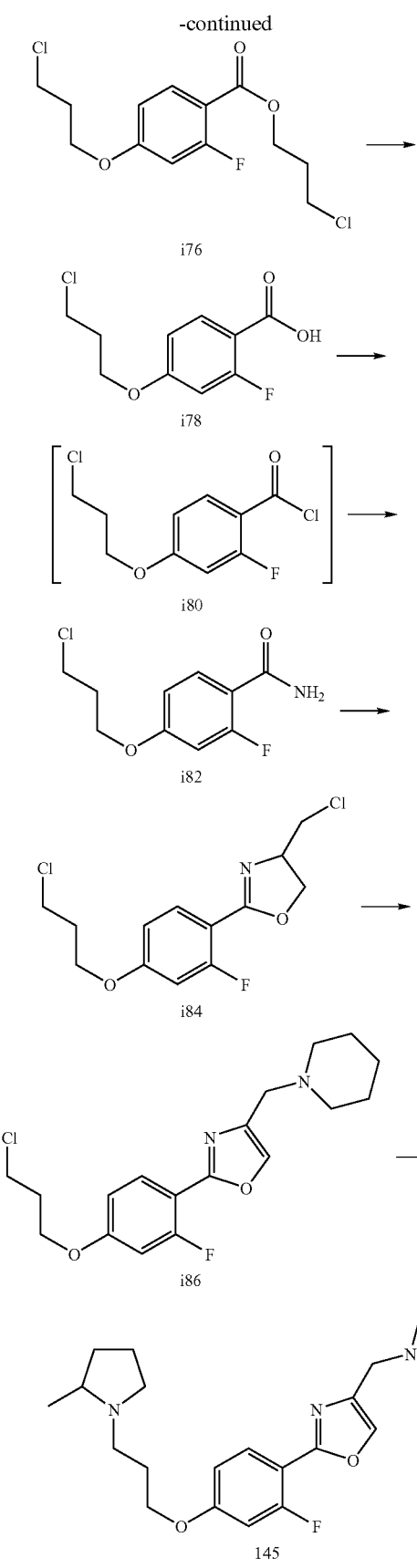

12.1 Synthesis of 3-chloropropyl 4-(3-chloropropoxy)-2-fluorobenzoate i76

2-fluoro-4-hydroxybenzoic acid (1 g, 6.41 mmol, 1 eq) is reacted with bromochloropropane (0.82 ml, 8.33 mmol, 1.3 eq) in the presence of potassium carbonate (1.77 g, 12.81 mmol, 2 eq) in methyl ethyl ketone (18 ml) at 80° C. overnight, filtered, washed with acetone and concentrated under vacuum to afford 2 g of 3-chloropropyl 4-(3-chloropropoxy)-2-fluorobenzoate i76.

Yield: 100%.
LC-MS (MH$^+$): 309/311/313.

| | | |
|---|---|---|
| i77 | 3-chloropropyl 4-(3-chloropropoxy)-2-methylbenzoate | LC-MS (MH$^+$): 305/307/309 |
| i111 | 3-chloropropyl 4-(3-chloropropoxy)-3,5-difluorobenzoate | LC-MS (MH$^+$): 326/328/330 |

12.2 Synthesis of 4-(3-chloropropoxy)-2-fluorobenzoic acid i78

A mixture of 3-chloropropyl 4-(3-chloropropoxy)-2-fluorobenzoate i76 (2 g, 6.47 mmol, 1 eq) and 1 M sodium hydroxide (6.47 ml, 6.47 mmol, 1 eq) in methanol (25 ml) is stirred at room temperature overnight. The mixture is concentrated under vacuum, taken up in water and extracted with diethyl ether. The aqueous phase is acidified with a 1 N hydrochloric acid solution to reach pH 2, and the resulting suspension is filtered and the solid dried to give 0.68 g of 4-(3-chloropropoxy)-2-fluorobenzoic acid i78.

Yield: 45%.
LC-MS (MH$^+$): 233/235.

The following compounds may be synthesized according to the same method:

| | | |
|---|---|---|
| i79 | 4-(3-chloropropoxy)-2-methylbenzoic acid | LC-MS (MH$^+$): 229/231. |
| i112 | 4-(3-chloropropoxy)-3,5-difluorobenzoic acid | LC-MS (MH$^-$): 249/251 |

12.3 Synthesis of 4-(3-chloropropoxy)-2-fluorobenzoyl chloride i80

4-(3-chloropropoxy)-2-fluorobenzoic acid i78 (0.68 g, 2.92 mmol, 1 eq) is refluxed in thionyl chloride (4.27 ml, 57.46 mmol, 20 eq) for 3 hours. The mixture is then concentrated under reduced pressure to give 0.73 g of crude 4-(3-chloropropoxy)-2-fluorobenzoyl chloride i80, which is used in the next step without purification.

4-(3-chloropropoxy)-2-methylbenzoyl chloride i81 and 4-(3-chloropropoxy)-3,5-difluorobenzoyl chloride i113 may be synthesized according to the same method.

12.4 Synthesis of 4-(3-chloropropoxy)-2-fluorobenzamide i82

4-(3-chloropropoxy)-2-fluorobenzoyl chloride i80 (0.73 g, 2.91 mmol, 1 eq) is treated with aqueous ammonia (35 ml) and the resulting mixture is vigorously stirred at room temperature overnight. The mixture is then filtered to give 0.41 g of 4-(3-chloropropoxy)-2-fluorobenzamide i82 as a white solid.

Yield: 61%.
LC-MS (MH+): 232/234.
The following compounds may be synthesized according to the same method:

| i83 | 4-(3-chloropropoxy)-2-methylbenzamide | LC-MS (MH+): 228/230 |
|---|---|---|
| i114 | 4-(3-chloropropoxy)-3,5-difluorobenzamide | LC-MS (MH+): 250/252 |

12.5 Synthesis of 4-(chloromethyl)-2-[4-(3-chloropropoxy)-2-fluorophenyl]-1,3-oxazole i84

A mixture of 4-(3-chloropropoxy)-2-fluorobenzamide i82 (0.41 g, 1.75 mmol, 1 eq) and 1,3-dichloroacetone (0.49 g, 3.85 mmol, 2.2 eq) in propionitrile (9 ml) is stirred at 100° C. for 60 h. The mixture is then concentrated under vacuum, taken up in dichloromethane, and washed with water. The organic phase is dried over magnesium sulfate and concentrated under reduced pressure. The residue is purified by chromatography over silicagel (eluent: dichloromethane) to afford 0.23 g of 4-(chloromethyl)-2-[4-(3-chloropropoxy)-2-fluorophenyl]-1,3-oxazole i84.
Yield: 44%.
LC-MS (MH+): 304/306/308.

| i85 | 4-(chloromethyl)-2-[4-(3-chloropropoxy)-2-methylphenyl]-1,3-oxazole | LC-MS (MH+): 300/302/304 |
|---|---|---|
| i115 | 4-(chloromethyl)-2-[4-(3-chloropropoxy)-3,5-difluorophenyl]-1,3-oxazole | LC-MS (MH+): 322/324/326 |

12.6 Synthesis of 1-({2-[4-(3-chloropropoxy)-2-fluorophenyl]-1,3-oxazol-4-yl}methyl)piperidine i86

A solution of 4-(chloromethyl)-2-[4-(3-chloropropoxy)-2-fluorophenyl]-1,3-oxazole i84 (0.23 g, 0.75 mmol, 1 eq) in acetonitrile (10 ml) is treated with piperidine (0.14 ml, 1.5 mmol, 2 eq). The mixture is stirred at room temperature for 24 h and concentrated under vacuum. The residue is taken up in dichloromethane and washed with water. The organic layer is dried over magnesium sulfate and concentrated under reduced pressure to give 0.20 g of 1-({2-[4-(3-chloropropoxy)-2-fluorophenyl]-1,3-oxazol-4-yl}methyl)piperidine i86.
Yield: 74%.
LC-MS (MH+): 353/355.

| i87 | 1-({2-[4-(3-chloropropoxy)-2-methylphenyl]-1,3-oxazol-4-yl}methyl)piperidine | LC-MS (MH+): 349/351 |
|---|---|---|
| i116 | 1-({2-[4-(3-chloropropoxy)-3,5-difluorophenyl]-1,3-oxazol-4-yl}methyl)piperidine | LC-MS (MH+): 371/373 |

12.7 Synthesis of 1-[(2-{2-fluoro-4-[3-(2-methylpyrrolidin-1-yl)propoxy]phenyl}-1,3-oxazol-4-yl)methyl]piperidine dimethanesulfonate 145

A solution of 1-({2-[4-(3-chloropropoxy)-2-fluorophenyl]-1,3-oxazol-4-yl}methyl)piperidine i86 (0.195 g, 0.55 mmol, 1 eq) and 2-methylpyrrolidine (0.107 ml, 1.11 mmol, 2 eq) in acetonitrile (25 ml) is treated with sodium iodide (8 mg, 0.06 mmol, 0.1 eq) and stirred at 90° C. overnight. The mixture is then poured into dichloromethane, and washed with water. The organic layer is dried over magnesium sulfate and concentrated. The residue is purified by chromatography over silicagel (eluent: dichloromethane/methanol/ammonia 90:10:0.1) to give 0.10 g of an oil. This oil is taken up in diethyl ether and an excess of methanesulfonic acid (1 M solution in diethyl ether) is added. The resulting suspension is filtered and the solid is washed several times with diethyl ether to remove the excess of methanesulfonic acid. The solid is dried to give 0.10 g of 1-[(2-{2-fluoro-4-[3-(2-methylpyrrolidin-1-yl)propoxy]phenyl}-1,3-oxazol-4-yl)methyl]piperidine dimethanesulfonate 145.
Yield: 30%.
LC-MS (MH+): 402.

Compounds 148 and 155 of table I may be synthetized according to similar experimental conditions.

Example 13

Synthesis of 2-{4-[3-(2-methylpyrrolidin-1-yl)propoxy]phenyl}-1,3-thiazole 83

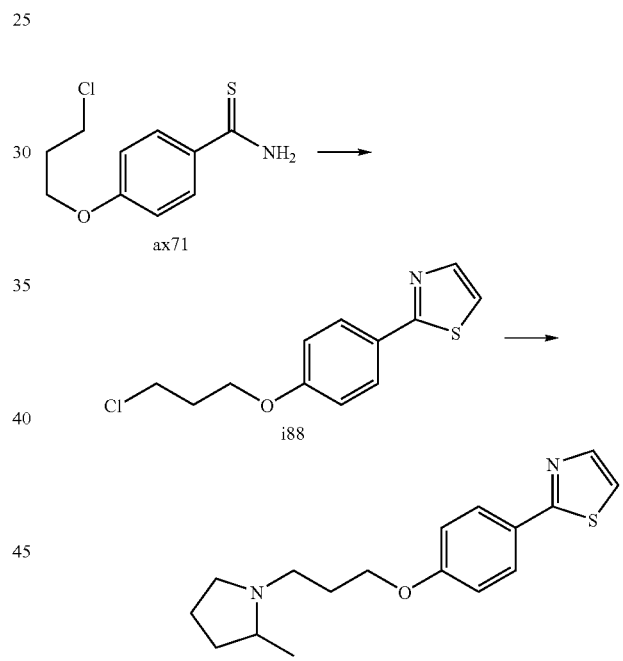

13.1 Synthesis of 2-[4-(3-chloropropoxy)phenyl]-1,3-thiazole i88

A solution of 4-(3-chloropropoxy)benzenecarbothioamide ax71 (0.3 g, 1 eq, 1.31 mmol) in ethyl alcohol (5 ml) is treated with 1,3-dichloro-1-ethoxy-propane (0.4 ml, 2.7 eq, 3.6 mmol) and the mixture is stirred at 110° C. during 4 h. The mixture is then poured into dichloromethane (10 ml) and is washed with water. The organic phase is dried over magnesium sulfate and concentrated. Purification by chromatography over silicagel (eluent: dichloromethane) affords 120 mg of 2-[4-(3-chloropropoxy)phenyl]-1,3-thiazole i88.
Yield: 36%.
LC-MS (MH+): 254/256.

13.2 Synthesis of 2-{4-[3-(2-methylpyrrolidin-1-yl)propoxy]phenyl}-1,3-thiazole 83

A solution of 2-[4-(3-chloropropoxy)phenyl]-1,3-thiazole i88 (120 mg, 1 eq, 0.47 mmol) in acetonitrile (1 ml) is added to a solution of sodium iodide (10 mg, 0.1 eq, 0.07 mmol) and 2-methylpyrrolidine (0.1 ml, 2 eq, 0.9 mmol) in acetonitrile (1 ml). The mixture is stirred at 85° C. overnight, filtered, washed with acetonitrile, and concentrated under reduced pressure. Purification of the residue by chromatography over silicagel (eluent: dichloromethane/methanol/ammonia 96/4/0.4) affords 40 mg of 2-{4-[3-(2-methylpyrrolidin-1-yl)propoxy]phenyl}-1,3-thiazole 83.

Yield: 27%.
LC-MS (MH+): 303.

Example 14

Synthesis of 1-[(5-bromo-2-{4-[3-(2-methylpyrrolidin-1-yl)propoxy]phenyl}-1,3-oxazol-4-yl)methyl]piperidine 117

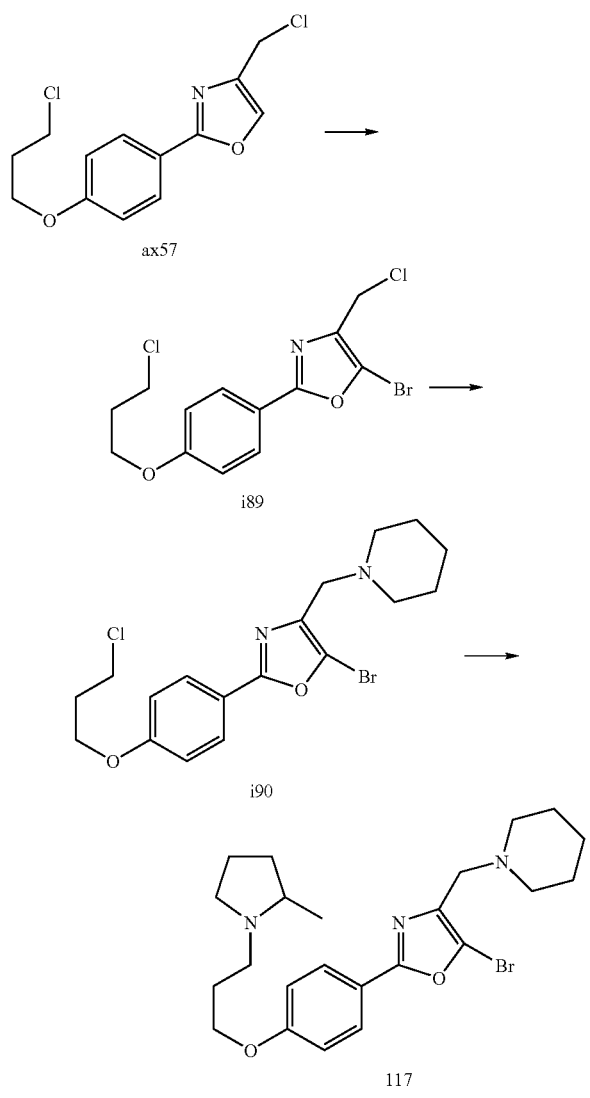

14.1 Synthesis of 5-bromo-2-[4-(3-chloropropoxy)-phenyl]-4-chloromethyl-oxazole i89

A solution of 4-(chloromethyl)-2-[4-(3-chloropropoxy)phenyl]-1,3-oxazole ax57 (0.5 g, 1.75 mmol, 1 eq) and N-bromosuccinimide (0.31 g, 1.75 mmol, 1 eq) in acetonitrile (16 ml) is stirred at 22° C. for 30 minutes. A heavy white precipitate forms during the reaction. The suspension is then filtered, the solid is washed with the minimum amount acetonitrile, collected and dried under vacuum at 40° C. to yield 290 mg of the title compound. The acetonitrile solution is concentrated to half its original volume to yield an additional 110 mg of 5-bromo-2-[4-(3-chloropropoxy)-phenyl]-4-chloromethyl-oxazole i89.

Yield: 63%.
LC-MS (MH+): 364.

14.2 Synthesis of 1-[(5-bromo-2-[4-(3-chloropropoxy)phenyl]-1,3-oxazol-4-yl)methyl]piperidine i90

A solution of 5-bromo-2-[4-(3-chloropropoxy)-phenyl]-4-chloromethyl-oxazole i89 (0.41 g, 1.12 mmol, 1 eq) and piperidine (222 µl, 2.25 mmol, 2 eq) in dichloromethane (3 ml) and acetonitrile (20 ml) is stirred at 22° C. for 6 h. The mixture is then poured into 20 ml of 0.1 N hydrochloric acid and extracted with dichloromethane (10 ml). The aqueous phase is then treated with 2 M sodium hydroxide to reach pH 10 and is extracted again with dichloromethane (3×10 ml). The three last extracts are combined, dried over magnesium sulfate and concentrated to yield 450 mg of a colourless oil, which is purified by chromatography over silicagel (eluent: dichloromethane/methanol/ammonia 97:2.7:0.3) to afford 390 mg of 1-[(5-bromo-2-[4-(3-chloropropoxy)phenyl]-1,3-oxazol-4-yl)methyl]piperidine i90.

Yield: 84%.
LC-MS (MH+): 413/415/417.

14.3 Synthesis of 1-[(5-bromo-2-{4-[3-(2-methylpyrrolidin-1-yl)propoxy]phenyl}-1,3-oxazol-4-yl)methyl]piperidine 117

A solution of 1-[(5-bromo-2-[4-(3-chloropropoxy)phenyl]-1,3-oxazol-4-yl)methyl]piperidine i90 (0.39 g, 0.94 mmol, 1 eq) and 2-metlhylpyrrolidine (192 µl, 1.89 mmol, 2 eq) in acetonitrile (6 ml) is treated with sodium iodide (14 mg, 0.09 mmol, 0.1 eq) and stirred for 24 h at 90° C. 2-Methylpyrrolidine (100 µl, 1 mmol) is then added and the mixture is stirred for a further 24 h at 90° C. The mixture is then poured into 0.1 N hydrochloric acid (10 ml) and extracted with diethyl ether (10 ml). The aqueous phase is then treated with 1 N sodium hydroxide to reach pH 10 and extracted with dichloromethane (3×10 ml). The combined dichloromethane extracts are then dried over magnesium sulfate and concentrated to yield 370 mg of an orange oil which is purified by chromatography over silicagel (eluent: dichloromethane/methanol/ammonia 96:3.6:0.4) to yield 86 mg of 1-[(5-bromo-2-{4-[3-(2-methylpyrrolidin-1-yl)propoxy]phenyl}-1,3-oxazol-4-yl)methyl]piperidine 117.

Yield: 20%.
LC-MS (MH+): 462/464.

Example 15

Synthesis of methyl 2-{3-bromo-4-[3-(2-methyl-1-pyrrolidinyl)propoxy]phenyl}-4-methyl-1,3-thiazole-5-carboxylate 126

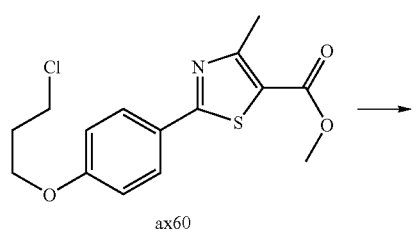

ax60

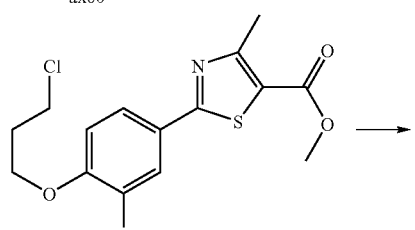

i91

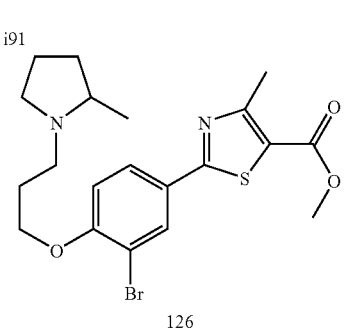

126

15.1 Synthesis of methyl 2-[3-bromo-4-(3-chloropropoxy)phenyl]-4-methyl-1,3-thiazole-5-carboxylate i91

A solution of methyl 2-[4-(3-chloropropoxy)phenyl]-4-methyl-1,3-thiazole-5-carboxylate ax60 (2 g, 6.15 mmol, 1 eq) in acetonitrile (50 ml) is treated with a solution of N-bromosuccinimide (1.8 g, 10 mmol, 1.5 eq) in acetonitrile (10 ml) and the resulting solution is stirred 2 h at room temperature and 2 h at 60° C. After cooling, the mixture is concentrated to dryness. The residue is taken up with ethyl acetate, washed with water, dried over magnesium sulfate and concentrated under reduced pressure. Purification of the residue over silicagel (eluent: dichloromethane/benzine) affords 0.6 g of methyl 2-[3-bromo-4-(3-chloropropoxy)phenyl]-4-methyl-1,3-thiazole-5-carboxylate i91.

Yield: 24%.
LC-MS (MH+): 404/406/408.

15.2 Synthesis of methyl 2-{3-bromo-4-[3-(2-methyl-1-pyrrolidinyl)propoxy]phenyl}-4-methyl-1,3-thiazole-5-carboxylate 126

A suspension of methyl 2-[3-bromo-4-(3-chloropropoxy)phenyl]-4-methyl-1,3-thiazole-5-carboxylate i91 (0.5 g, 1.24 mmol, 1 eq), 2-methylpyrrolidine (0.3 ml, 3.0 mmol, 2.5 eq), potassium carbonate (0.68 g, 5 mmol, 4 eq) and sodium iodide (20 µg, 0.12 mmol, 0.1 eq) in acetonitrile (10 ml) is stirred overnight at 90° C. The resulting mixture is taken up with dichloromethane, washed with water, dried over magnesium sulfate and concentrated under reduced pressure. The crude product is triturated in diethyl ether to afford 50 mg of methyl 2-{3-bromo-4-[3-(2-methyl-1-pyrrolidinyl)propoxy]phenyl}-4-methyl-1,3-thiazole-5-carboxylate 126.

Yield: 8%.
LC-MS (MH+): 453/455.

Compound 100 of table I may be synthetized according to similar experimental conditions.

Example 16

Synthesis of methyl-4-[(benzylamino)methyl]-2-{4-[3-(2-methyl-1-pyrrolidinyl)propoxy]phenyl}-1,3-oxazole-5-carboxylate 99

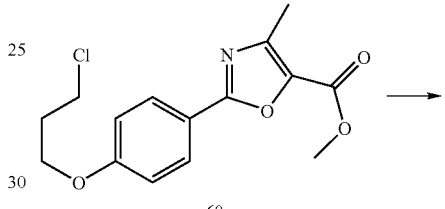

ax60

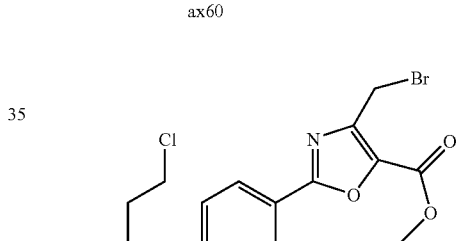

i92

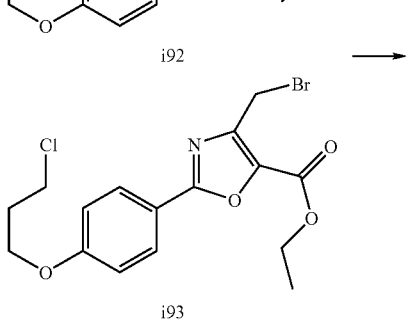

i93

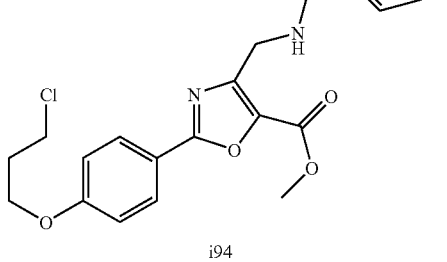

i94

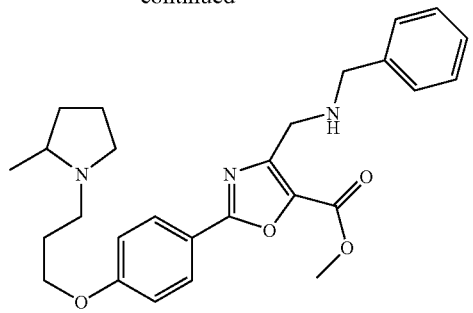

99

16.1 Synthesis of a 1:1 Mixture of methyl 4-(bromomethyl)-2-[4-(3-chloropropoxy)phenyl]-1,3-oxazole-5-carboxylate i92 and methyl 4-(bromomethyl)-2-[4-(3-chloropropoxy)phenyl]-1,3-oxazole-5-carboxylate i93

A solution of methyl 2-[4-(3-chloropropoxy)phenyl]-4-methyl-1,3-oxazole-5-carboxylate ax60 (1.6 g, 1 eq, 5.2 mmol) in acetonitrile (50 ml) is treated with N-bromosuccinimide (1.7 g, 1.7 eq, 9.6 mmol). The mixture is stirred at room temperature during 6 h. The solution is then poured into diethyl ether (200 ml) and is washed with water and with diluted sodium bicarbonate. The organic layer is dried over magnesium sulfate and concentrated under reduced pressure. Purification over silicagel (eluent: ethyl acetate/benzine) gives 0.6 g of a 1:1 mixture of methyl 4-(bromomethyl)-2-[4-(3-chloropropoxy)phenyl]-1,3-oxazole-5-carboxylate i92 and ethyl 4-(bromomethyl)-2-[4-(3-chloropropoxy)phenyl]-1,3-oxazole-5-carboxylate i93.

Yield: 32%.
i92: LC-MS (MH$^+$): 388/390/392.
i93: LC-MS (MH$^+$): 402/404/406.

16.2 Synthesis of methyl 4-[(benzylamino)methyl]-2-[4-(3-chloropropoxy)phenyl]-1,3-oxazole-5-carboxylate i94

A solution of the 1:1 mixture of i92 and i93 (0.35 g, 0.9 mmol, 1 eq) in acetonitrile (10 ml) is added dropwise to a suspension of benzyl amine (0.1 ml, 0.9 mmol, 1 eq) and potassium carbonate (0.3 g, 2.26 mmol, 2.5 eq) in acetonitrile (10 ml). The resulting mixture is stirred overnight. It is then diluted by diethyl ether, and washed by water and brine. The organic layer is dried over magnesium sulfate, concentrated under reduced pressure and purified over silicagel (eluent: dichloromethane/methanol/ammonia 95/5/0.5) to yield 110 mg of methyl 4-[(benzylamino)methyl]-2-[4-(3-chloropropoxy)phenyl]-1,3-oxazole-5-carboxylate i94.

Yield: 29%.
LC-MS (MH$^+$): 415/417.

16.3 Synthesis of methyl 4-[(benzylamino)methyl]-2-{4-[3-(2-methyl-1-pyrrolidinyl) propoxy]phenyl}-1,3-oxazole-5-carboxylate 99

A suspension of methyl 4-[(benzylamino)methyl]-2-[4-(3-chloropropoxy)phenyl]-1,3-oxazole-5-carboxylate i94 (0.11 g, 0.27 mmol, 1 eq), 2-methylpyrrolidine (30 µl, 0.32 mmol, 1.2 eq) and potassium carbonate (0.15 g, 1.06 mmol, 4 eq) in acetonitrile (5 ml) is stirred at 110° C. overnight. The mixture is then poured into ethyl acetate (50 ml) and washed with water. The organic layer is dried over magnesium sulfate and concentrated under reduced pressure. Two successive purifications over silicagel (eluent: dichloromethane, methanol, ammonia 90/10/1) and one purification by preparative liquid chromatography (gradient: acetonitrile/water/trifluoroacetic acid 95:5:01 to 5:95:01) yield 6 mg of methyl 4-[(benzylamino)methyl]-2-{4-[3-(2-methyl-1-pyrrolidinyl)propoxy]phenyl}-1,3-oxazole-5-carboxylate 99.

Yield: 5%.
LC-MS (MH$^+$): 464.

Example 17

Synthesis of 2-{4-[3-(2-methyl-1-pyrrolidinyl)propoxy]phenyl}-4-(piperidin-1-ylmethyl)-1,3-oxazole-5-carboxylic acid 101

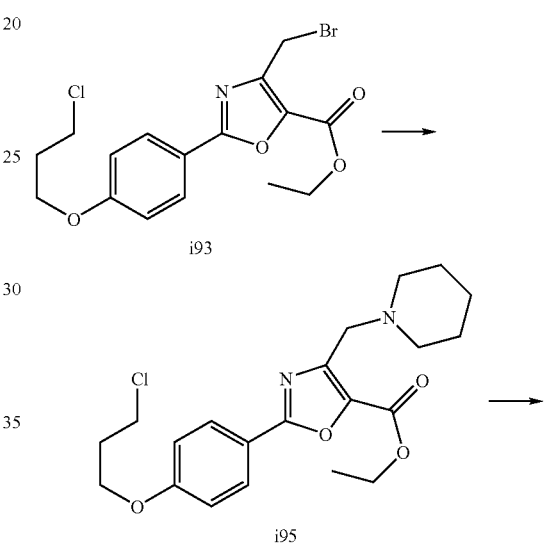

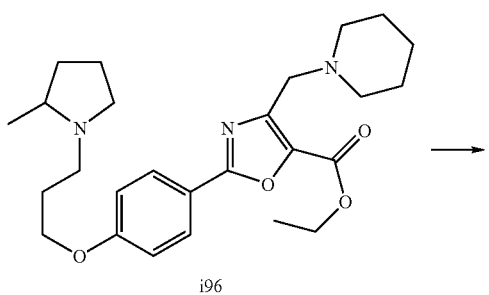

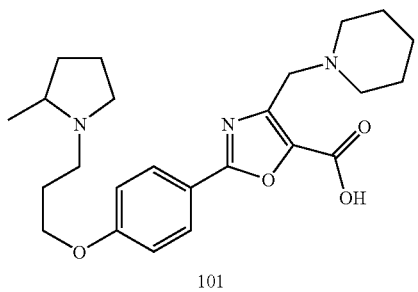

101

17.1 Synthesis of ethyl 2-[4-(3-chloropropoxy)phenyl]-4-(piperidin-1-ylmethyl)-1,3-oxazole-5-carboxylate i95

A suspension of piperidine (90 µl, 0.86 mmol, 1.1 eq) and potassium carbonate (0.43 g, 3 mmol, 4 eq) in acetonitrile (5 ml) is treated dropwise with a solution of ethyl 4-(bromomethyl)-2-[4-(3-chloropropoxy)phenyl]-1,3-oxazole-5-carboxylate i93 (0.30 g, 0.77 mmol, 1 eq) in acetonitrile (2 ml) and is stirred at room temperature overnight. Diethyl ether is then added and the solution is washed with water, dried over magnesium sulfate and concentrated under reduced pressure to give 210 mg of crude ethyl 2-[4-(3-chloropropoxy)phenyl]-4-(piperidin-1-ylmethyl)-1,3-oxazole-5-carboxylate i95, used as such in the next step.

Yield: 69%.
LC-MS (MH$^+$): 407/409.

17.2 Synthesis of ethyl 2-{4-[3-(2-methylpyrrolidin-1-yl)propoxy]phenyl}-4-(piperidin-1-ylmethyl)-1,3-oxazole-5-carboxylate i96

A solution of ethyl 2-[4-(3-chloropropoxy)phenyl]-4-(piperidin-1-ylmethyl)-1,3-oxazole-5-carboxylate i95 (0.22 g, 0.56 mmol, 1 eq) in acetonitrile (10 ml) is treated with potassium carbonate (0.31 g, 2.24 mmol, 4 eq) and 2-methylpyrrolidine (60 µl, 0.67 mmol, 1.2 eq) and the resulting mixture is stirred at 110° C. overnight. Ethyl acetate is then added and the organic layer is washed with water, dried over magnesium sulfate and concentrated under reduced pressure. Purification over silicagel (eluent: dichloromethane/methanol/ammonia) affords 90 mg of ethyl 2-{4-[3-(2-methylpyrrolidin-1-yl)propoxy]phenyl}-4-(piperidin-1-ylmethyl)-1,3-oxazole-5-carboxylate i96.

Yield: 36%.
LC-MS (MH$^+$): 456.

17.3 Synthesis of 2-{4-[3-(2-methyl-1-pyrrolidinyl)propoxy]phenyl}-4-(piperidinyl-1-methyl)-1,3-oxazole-5-carboxylic acid 101

A solution of ethyl 2-{4-[3-(2-methylpyrrolidin-1-yl)propoxy]phenyl}-4-(piperidin-1-ylmethyl)-1,3-oxazole-5-carboxylate i96 (0.1 g, 0.22 mmol, 1 eq) in methanol (5 ml) is treated with 1 M sodium hydroxide (2 ml, 2 mmol, 10 eq) and the mixture is heated at 40° C. during 1 h. Methanol is then evaporated under reduced pressure and 1 M hydrochloric acid (2 ml) is added. The solution is concentrated under reduced pressure. Purification by preparative liquid chromatography (gradient: acetonitrile/water/trifluoroacetic acid 95:5:01 to 5:95:01) provides, after lyophilisation, 45 mg of 2-{4-[3-(2-methyl-1-pyrrolidinyl)propoxy]phenyl}-4-(piperidinyl-1-methyl)-1,3-oxazole-5-carboxylic acid 101.

Yield: 50%.
LC-MS (MH$^+$): 428.

Example 18

Synthesis of 4-[(4-methyl-2-{6-[3-(2-methylpyrrolidin-1-yl)propoxy]pyridin-3-yl}-1,3-thiazol-5-yl)carbonyl]morpholine 147

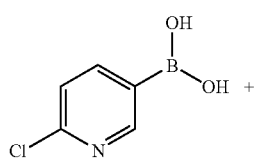

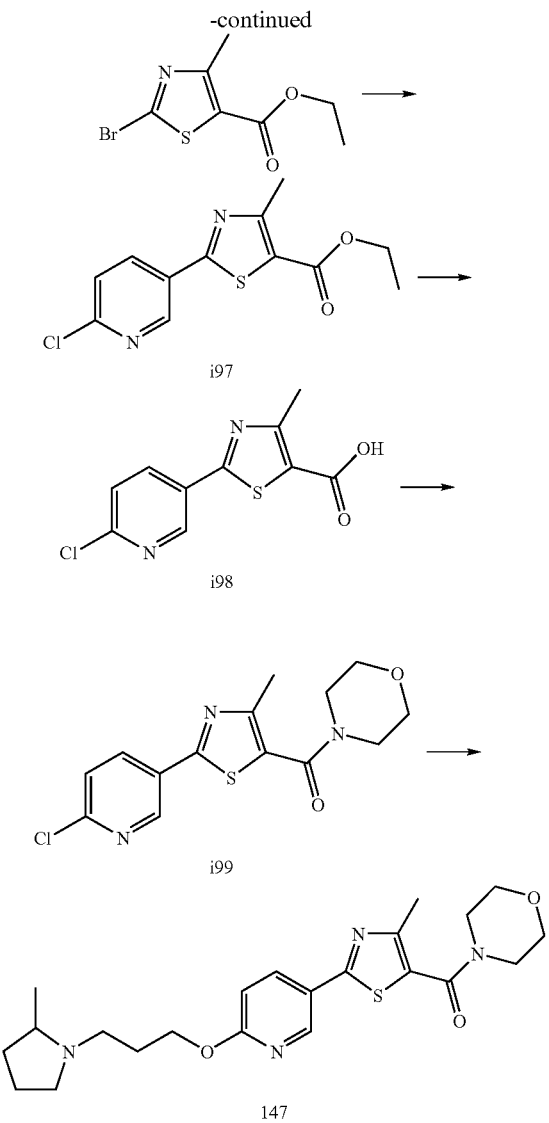

18.1 Synthesis of ethyl 2-(6-chloropyridin-3-yl)-4-methyl-1,3-thiazole-5-carboxylate i97

Ethyl 2-bromo-4-methyl-1,3-thiazole-5-carboxylate (1 g, 1.3 eq, 4 mmol) is added to a mixture of 2-chloro-5-pyridine boronic acid (0.48 g, 1 eq, 3.07 mmol), tetrakis(triphenylphosphine)palladium (0.18 g, 0.05 eq, 0.15 mmol) and an aqueous solution of 2 M potassium carbonate (3 ml, 2 eq, 6.14 mmol) in toluene/ethanol (18 ml, 2:1 v/v). The mixture is refluxed overnight and the solvent is evaporated, then taken up in ethyl acetate, and washed two times with an aqueous solution of sodium hydrogenocarbonate. The organic layer is dried over magnesium sulfate, filtered and concentrated under vacuum. Purification by chromatography over silicagel (eluent: dichloromethane 100%) affords 0.6 g of ethyl 2-(6-chloropyridin-3-yl)-4-methyl-1,3-thiazole-5-carboxylate i97.

Yield: 69%.
LC-MS (MH$^+$): 283/285.

18.2 Synthesis of 2-(6-chloropyridin-3-yl)-4-methyl-1,3-thiazole-5-carboxylic acid i98

A mixture of ethyl 2-(6-chloropyridin-3-yl)-4-methyl-1,3-thiazole-5-carboxylate i97 (0.55 g, 1 eq, 1.94 mmol) and lithium hydroxide monohydrate (0.16 g, 2 eq, 3.89 mmol) in tetrahydrofurane/water (28 ml 1:0.1, v/v) is stirred at room temperature for 1 h 30. The mixture is diluted with water and extracted with ethyl acetate. The aqueous layer is then acidified to pH 2 with 2 N hydrochloric acid. The precipitate that forms is filtered and washed with water to give 0.48 g of 2-(6-chloropyridin-3-yl)-4-methyl-1,3-thiazole-5-carboxylic acid i98.

Yield: 98%.

LC-MS (MH$^+$): 253/255.

18.3 Synthesis of 4-{[2-(6-chloropyridin-3-yl)-4-methyl-1,3-thiazol-5-yl]carbonyl}morpholine i99

A mixture of ethyl 2-(6-chloropyridin-3-yl)-4-methyl-1,3-thiazole-5-carboxylate i98 (0.47 g, 1 eq, 1.84 mmol), morpholine (0.19 g, 1.2 eq, 2.21 mmol) and triethylamine (0.5 ml, 2 eq, 3.68 mmol) in dichloromethane (15 ml) is cooled to 0° C. N-(3-dimethylaminopropyl)-N'-ethylcarbodiimide hydrochloride (0.39 g, 1.1 eq, 2.02 mmol) and 1-hydroxybenzotriazole (0.05 g, 0.2 eq, 0.37 mmol) are then added to the solution and the mixture is stirred 24 h at room temperature. The mixture is then washed with water and a saturated solution of aqueous ammonium chloride. The organic layer is dried over magnesium sulfate, filtered and concentrated under vacuum to give 0.53 g of 4-{[2-(6-chloropyridin-3-yl)-4-methyl-1,3-thiazol-5-yl]carbonyl}morpholine i99.

Yield: 90%.

LC-MS (MH$^+$): 324/326.

18.4 Synthesis of 4-[(4-methyl-2-{6-[3-(2-methylpyrrolidin-1-yl)propoxy]pyridin-3-yl}-1,3-thiazol-5-yl)carbonyl]morpholine 147

Sodium hydride 60% in oil (0.11 g, 2.2 eq, 2.82 mmol) is added to a mixture of 3-(2-methyl-1-pyrrolidinyl)-1-propanol (0.31 g, 2.2 eq, 2.18 mmol) in dimethylformamide (15 ml) cooled to 0° C. The mixture is stirred at 22° C. for 20 min, and cooled again to 0° C. 4-{[2-(6-chloropyridin-3-yl)-4-methyl-1,3-thiazol-5-yl]carbonyl}morpholine i99 (0.415 g, 1 eq, 1.28 mmol) is then added to the solution and the mixture is stirred 48 h at room temperature. The solvent is evaporated, and the residue is taken up in ethyl acetate and washed two times with an aqueous solution of sodium hydrogenocarbonate. The organic layer is dried over magnesium sulfate, filtered and concentrated under vacuum. Purification by chromatography over silicagel (eluent: dichloromethane/methanol/ammonia 97/2.7/0.3) affords 0.047 g of 4-[(4-methyl-2-{6-[3-(2-methylpyrrolidin-1-yl)propoxy]pyridin-3-yl}-1,3-thiazol-5-yl)carbonyl]morpholine 147.

Yield: 8%.

LC-MS (MH$^+$): 431.

Example 19

Synthesis of 2-methyl-N-[(2-{4-[3-(2-methylpyrrolidin-1-yl)propoxy]phenyl}-1,3-oxazol-4-yl)methyl]-2H-tetraazol-5-amine 139

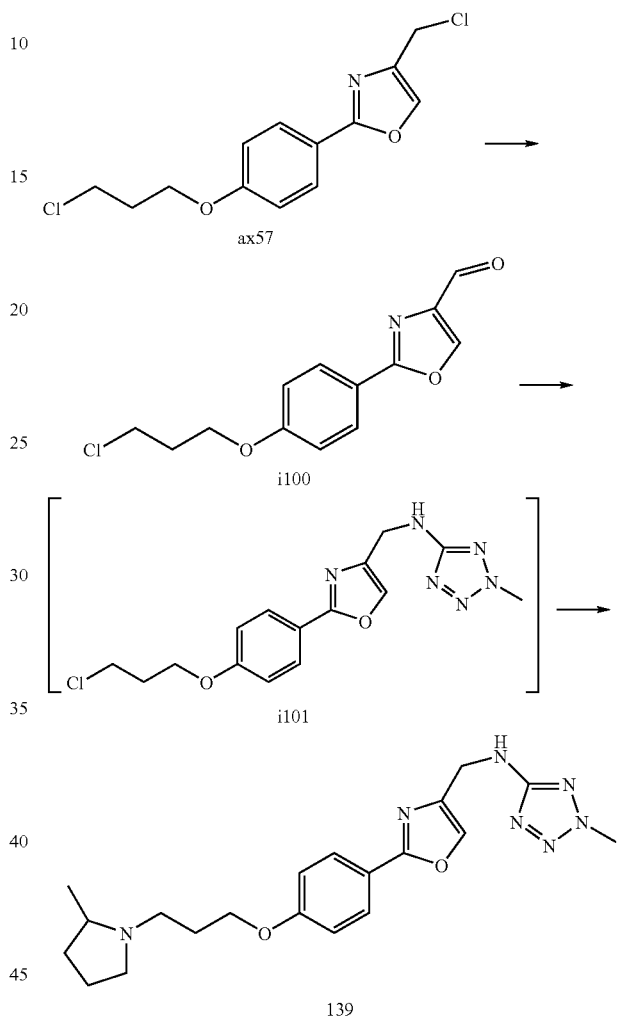

19.1 Synthesis of 2-[4-(3-chloro-propoxy)-phenyl]-oxazole-4-carbaldehyde i100

A cold (−20° C.) solution of anhydrous trimethylamine N-oxide (2.10 g, 27.96 mmol) in a dry mixture of dichloromethane and dimethylsulfoxide (20 ml, 1/3 v/v) is treated with a solution of 4-chloromethyl-2-[4-(3-chloro-propoxy)-phenyl]-oxazole ax57 (2.00 g, 6.99 mmol) in the same mixture of solvents (20 ml). The mixture is then allowed to warm up to 20° C. and is stirred at that temperature for 24 h. The dark mixture is then poured into water (50 ml) and extracted with dichloromethane. The organic phases are concentrated and the resulting DMSO solution is treated with ether and water. The heterogeneous mixture is further extracted with ether (2×20 ml). The organic phases are then dried over magnesium sulfate and concentrated to afford 760 mg of 2-[4-(3-chloro-propoxy)-phenyl]-oxazole-4-carbaldehyde i100.

Yield: 41%

LC-MS (MH$^+$): 266/268.

19.2 Synthesis of 2-methyl-N-[(2-{4-[3-(2-methylpyrrolidin-1-yl)propoxy]phenyl}-1,3-oxazol-4-yl)methyl]-2H-tetraazol-5-amine 139

A mixture of 2-[4-(3-chloro-propoxy)-phenyl]-oxazole-4-carbaldehyde i100 (0.042 mmol), 2-methyl-2H-tetrazol-5-ylamine (4.16 mg, 0.042 mmol, 1 eq) and cyanoborohydride supported on polystyrene (26 mg, 0.1 mmol, 2.5 eq) is suspended in tetrahydrofuran (300 µl) containing 10% acetic acid and is stirred at 65° C. overnight. The polystyrene beads are then filtered off and the resulting solution is concentrated to dryness under a stream of nitrogen and taken up in dichloromethane (2 ml). The solution is washed with 1 M potassium hydrogenosulfate (1 ml) and concentrated under reduced pressure. The residue N-({2-[4-(3-chloropropoxy)phenyl]-1,3-oxazol-4-yl}methyl)-2-methyl-2H-tetrazol-5-amine i101 is then treated with a solution of 2-methylpyrrolidine (4 mg, 1 eq) in acetonitrile (300 µl). Sodium carbonate (14 mg, 0.1 mmol, 2 eq) and sodium iodide (15 mg, 0.1 mmol, 2 eq) are added and the suspension is stirred overnight at 80° C. Water (1 ml) is then added and the mixture is extracted with dichloromethane (2×1 ml). The organic phases are concentrated and purified by preparative liquid chromatography (gradient: acetonitrile/water/hydrogen carbonate) to afford 2-methyl-N-[(2-{4-[3-(2-methylpyrrolidin-1-yl)propoxy]phenyl}-1,3-oxazol-4-yl)methyl]-2H-tetraazol-5-amine 139.

LC-MS (MH$^+$): 398.

Compounds 115, 140, 141 and 142 of table I may be synthetized according to similar experimental conditions.

Example 20

Synthesis of 1-(3-{4-[4-methyl-5-(2-oxo-2-piperidin-1-ylethyl)-1,3-thiazol-2-yl]phenoxy}propyl)piperidine 127 and 1-(3-{4-[4-methyl-5-(2-piperidin-1-ylethyl)-1,3-thiazol-2-yl]phenoxy}propyl)piperidine 136

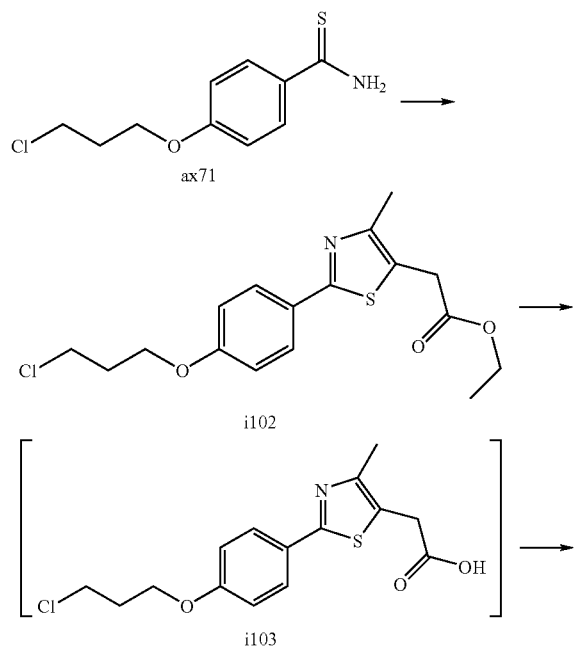

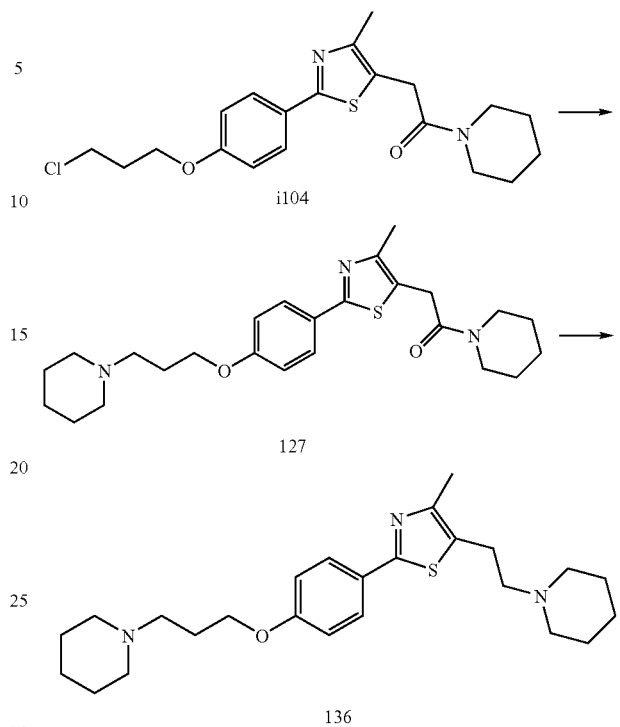

20.1 Synthesis of ethyl{2-[4-(3-chloropropoxy)phenyl]-4-methyl-1,3-thiazol-5-yl}acetate i102

A mixture of ethyl 3-bromo-4-oxopentanoate (2 g, 8.98 mmol, 1 eq), and 4-(3-chloropropoxy)benzenecarbothioamide ax71 (2.06 g, 8.97 mmol, 1 eq) in dimethylformamide (4 ml) is stirred at 100° C. for 2 h. The reaction mixture is then added to ethyl acetate (200 ml) and the precipitate filtered off. The organic layer is washed with water (4×100 ml), brine, dried over magnesium sulfate and filtered. The solvent is removed under reduced pressure. Purification by chromatography over silicagel (eluent: benzine/ethyl acetate 95:5 to 85:15) affords 1.3 g of ethyl {2-[4-(3-chloropropoxy)phenyl]-4-methyl-1,3-thiazol-5-yl}acetate i102.

Yield: 40%.

LC-MS (MH$^+$): 354/356.

20.2 Synthesis of {2-[4-(3-chloropropoxy)phenyl]-4-methyl-1,3-thiazol-5-yl}acetic acid i103

A mixture of ethyl {2-[4-(3-chloropropoxy)phenyl]-4-methyl-1,3-thiazol-5-yl}acetate i102 (0.5 g, 1.41 mmol, 1 eq) and sodium hydroxide (0.2 g, 5 mmol, 3.5 eq) in ethanol (15 ml) is stirred at 60° C. for 1 h 30. A 1 N hydrochloric acid solution (6 ml) is added and ethanol is removed under vacuum. The residue is dissolved in ethyl acetate (200 ml). The organic layer is washed with water (2×50 ml), brine, dried over magnesium sulfate, filtered and concentrated to yield 0.5 g of {2-[4-(3-chloropropoxy)phenyl]-4-methyl-1,3-thiazol-5-yl}acetic acid i103 as a white solid. This solid is used as such in the next step.

20.3 Synthesis of 1-({2-[4-(3-chloropropoxy)phenyl]-4-methyl-1,3-thiazol-5-yl}acetyl)piperidine i104

A solution of {2-[4-(3-chloropropoxy)phenyl]-4-methyl-1,3-thiazol-5-yl}acetic acid i103 (0.5 g, 1.41 mmol, 1 eq), triethylamine (0.2 ml, 1.41 mmol, 1 eq), and piperidine (0.15 ml, 1.45 mmol, 1.03 eq) in dichloromethane (30 ml) is cooled (ice bath) and treated with 1-hydroxybenzotriazole (38 mg, 0.28 mmol, 0.2 eq) and N-(3-dimethylaminopropyl)-N'-ethylcarbodiimide (0.271 g, 1.41 mmol, 1 eq). The mixture is stirred at room temperature overnight, then diluted with 70 ml of dichloromethane. The organic layer is washed with water (2×50 ml), brine, dried over magnesium sulfate and filtered. The solvent is removed under reduced pressure to obtain an orange solid. The solid is triturated in acetonitrile, filtered and rinsed with cold diethyl ether to give 0.18 g of 1-({2-[4-(3-chloropropoxy)phenyl]-4-methyl-1,3-thiazol-5-yl}acetyl)piperidine i104 as a yellow solid.

Yield: 39%.

$^{1}$H NMR (CDCl$_{3}$) δ (ppm): 1.56 (m, 5H), 1.64 (m, 2H), 2.25 (t, 6.05 Hz, 2H), 2.41 (s Hz, 3H), 3.47 (m, 2H), 3.60 (m, 2H), 3.75 (td, 6.23, 1.33 Hz, 2H), 3.80 (s, 2H), 4.15 (m, 2H), 6.92 (d, 8.7 Hz 2H), 7.82 (d, 8.7 Hz, 2H).

20.4 Synthesis of 1-(3-{4-[4-methyl-5-(2-oxo-2-piperidin-1-ylethyl)-1,3-thiazol-2-yl]phenoxy}propyl)piperidine 127

A suspension of 1-({2-[4-(3-chloropropoxy)phenyl]-4-methyl-1,3-thiazol-5-yl}acetyl)piperidine i104 (0.18 g, 0.51 mmol, 1 eq), potassium carbonate (0.14 g, 1.02 mmol, 2 eq) and sodium iodide (16 mg, 0.03 mmol, 0.2 eq) in acetonitrile (3 ml) is stirred at 80° C. for 20 minutes before addition of piperidine (0.15 ml, 0.51 mmol, 1.03 eq). The mixture is then stirred at reflux overnight, concentrated under vacuum and the residue is taken up in ethyl acetate (50 ml). The organic layer is washed with water (3×25 ml), brine, dried over magnesium sulfate and filtered. The solvent is removed under reduced pressure to obtain an orange solid. Purification by chromatography over silicagel (eluent: dichloromethane/methanol/ammonia 90:10:1) affords 150 mg of 1-(3-{4-[4-methyl-5-(2-oxo-2-piperidin-1-ylethyl)-1,3-thiazol-2-yl]phenoxy}propyl)piperidine 127.

Yield: 67%.

LC-MS (MH$^{+}$): 442.

20.5 Synthesis of 1-(3-{4-[4-methyl-5-(2-piperidin-1-ylethyl)-1,3-thiazol-2-yl]phenoxy}propyl)piperidine 136

A suspension of lithium aluminium hydride (0.14 g, 3.68 mmol, 5.2 eq) in tetrahydrofuran (10 ml) at −78° C. is treated with 1-(3-{4-[4-methyl-5-(2-oxo-2-piperidin-1-ylethyl)-1,3-thiazol-2-yl]phenoxy}propyl)piperidine 127 (0.31 g, 0.7 mmol, 1 eq). The mixture is allowed to warm up and stirred at room temperature overnight. Sodium sulfate decahydrate (3.68 g) is then added and the mixture is stirred for a further 3 h. The mixture is filtered on magnesium sulfate and concentrated. Two purifications by chromatography over silicagel (eluent: dichloromethane/methanol/ammonia 90:10:1), afford 55 mg of 1-(3-{4-[4-methyl-5-(2-piperidin-1-ylethyl)-1,3-thiazol-2-yl]phenoxy}propyl)piperidine 136.

Yield: 16%.

LC-MS (MH$^{+}$): 428.

Example 21

Synthesis of (4-methyl-2-{4-[3-(2-methyl-pyrrolidin-1-yl)-propoxy]-phenyl}-thiazol-5-yl)-morpholin-4-yl-methanone 152

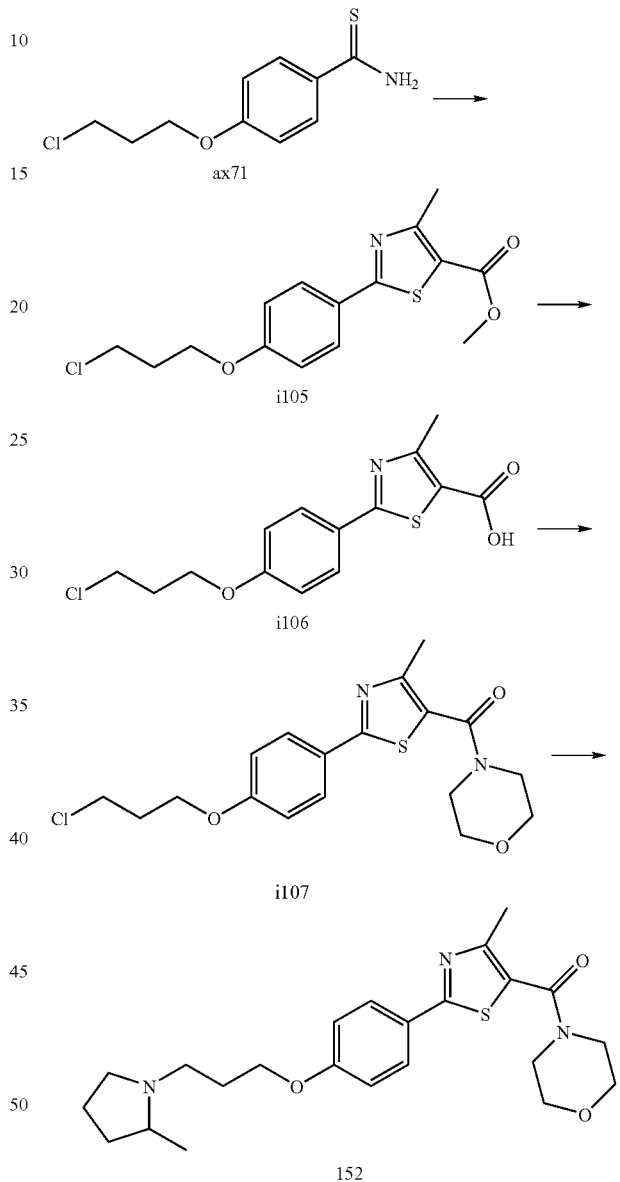

21.1 Synthesis of methyl 2-[4-(3-chloropropoxy)phenyl]-4-methyl-1,3-thiazole-5-carboxylate i105

A mixture of 4-(3-chloropropoxy)benzenecarbothioamide ax71 (34.67 mmol, 1 eq, 7.96 g), and 2-chloroacetoacetic acid methyl ester (34.67 mmol, 1 eq, 5.2 g) in methanol is stirred at 70° C. for 2 hours. The reaction mixture is then poured into a sealed tube and stirred at 100° C. for 3 hours. The mixture is taken up in dichloromethane and washed with water then dried over magnesium sulfate. The solvent is removed under reduced pressure to give 11.8 g of methyl 2-[4-(3-chloropropoxy)phenyl]-4-methyl-1,3-thiazole-5-carboxylate i105. The product is used as such in the next step.

Yield: 100%.

LC-MS (MH+): 325/327.

21.2 Synthesis of 2-[4-(3-chloropropoxy)phenyl]-4-methyl-1,3-thiazole-5-carboxylic acid i106

A mixture of 2-[4-(3-chloropropoxy)phenyl]-4-methyl-1,3-thiazole-5-carboxylate i105 (14.1 mmol, 1 eq, 4.6 g) and 2 M sodium hydroxide (28.2 mmol, 2 eq, 14.1 ml) in methanol (100 ml) is stirred at 70° C. overnight. The mixture is concentrated to dryness and taken up in a minimum of water. The aqueous phase is acidified by 1 N hydrogen chloride to reach pH 2 and poured into ice to afford precipitation of a white solid. The solid is filtered and dried under reduced pressure to give 3.9 g of 2-[4-(3-chloropropoxy)phenyl]-4-methyl-1,3-thiazole-5-carboxylic acid i106 as a white solid. This solid is used as such in the next step.

Yield: 89%.

LC-MS (MH+): 312/314.

21.3 Synthesis of 4-({2-[4-(3-chloropropoxy)phenyl]-4-methyl-1,3-thiazol-5-yl}carbonyl)morpholine i107

To a solution of 2-[4-(3-chloropropoxy)phenyl]-4-methyl-1,3-thiazole-5-carboxylic acid i106 (1.6 mmol, 1 eq, 0.5 g), triethylamine (3.2 mmol, 2 eq, 0.45 ml) in dichloromethane (20 ml) is added 1-hydroxybenzotriazole (0.32 mmol, 0.2 eq, 43 mg), N-(3-dimethylaminopropyl)-N'-ethylcarbodiimide (1.76 mmol, 1.1 eq, 0.33 g) and morpholine (1.92 mmol, 1.2 eq, 0.17 g). The mixture is stirred at room temperature overnight. The organic layer is washed with water and with a saturated aqueous solution of ammonium chloride, then dried over magnesium sulfate and filtered. The solvent is removed under reduced pressure. The crude product is purified by flash chromatography over silicagel (eluent: dichloromethane/ethanol 99:1 to 95:5) to afford 380 mg of 4-({2-[4-(3-chloropropoxy)phenyl]-4-methyl-1,3-thiazol-5-yl}carbonyl)morpholine i107.

Yield: 63%.

LC-MS (MH+): 381/383.

1-({2-[4-(3-chloropropoxy)phenyl]-4-methyl-1,3-thiazol-5-yl}carbonyl)-4,4-difluoropiperidine i108 may be synthesized according to the same method.

LC-MS (MH+): 415/417.

21.4 Synthesis of 4-[(4-methyl-2-{4-[3-(2-methylpyrrolidin-1-yl)propoxy]phenyl}-1,3-thiazol-5-yl)carbonyl]morpholine 152

To a solution of 4-({2-[4-(3-chloropropoxy)phenyl]-4-methyl-1,3-thiazol-5-yl}carbonyl)morpholine i107 (1.0 mmol, 1 eq, 0.38 g) in acetonitrile (10 ml), is added potassium carbonate (1.99 mmol, 2 eq, 0.27 g) and approximately 0.01 g of sodium iodide. The mixture is stirred at 80° C. for 30 minutes in a sealed tube before addition of 2-methylpyrrolidine (1.2 mmol, 1.2 eq, 0.12 ml). The mixture is then stirred at 80° C. overnight. The mixture is taken up in ethyl acetate and washed with a saturated solution of sodium bicarbonate, then dried over magnesium sulfate. The solvent is removed under reduced pressure and purified by chromatography over silica gel (eluent: dichloromethane/methanol/ammonia 96:3.6:0.4) to give 0.132 g of 4-[(4-methyl-2-{4-[3-(2-methylpyrrolidin-1-yl)propoxy]phenyl}-1,3-thiazol-5-yl)carbonyl]morpholine 152 as a yellow oil.

Yield: 31%.

LC-MS (MH+): 430.

Compounds 149, 150, 151, 153 and 154 of table I may be synthetized according to similar experimental conditions.

Example 22

Synthesis of 1-(3-{2-fluoro-4-[4-(piperidin-1-ylmethyl)-1,3-oxazol-2-yl]phenoxy}propyl)piperidine 88

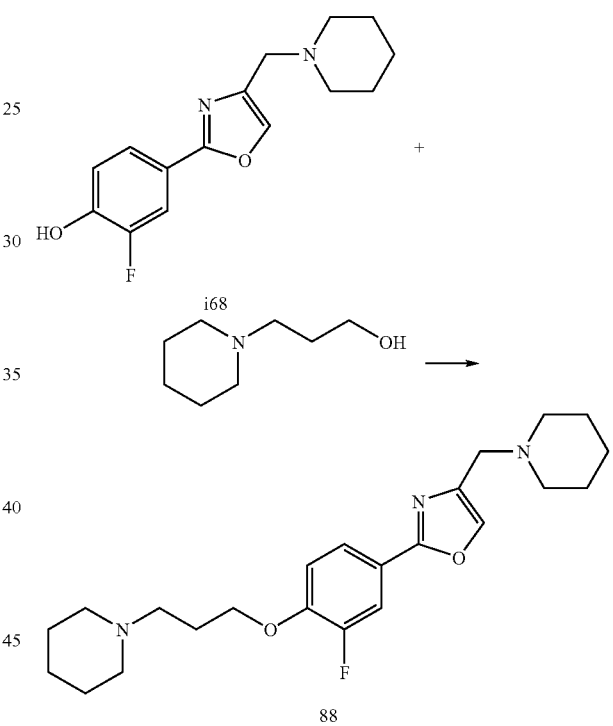

To a solution of triphenylphosphine (0.81 g, 3.08 mmol, 1 eq) in dry tetrahydrofuran at 0° C. is added dropwise diisopropylazodicarboxylate (0.61 ml, 3.08 mmol, 1 eq). A solution of 2-fluoro-4-[4-(1-piperidinylmethyl)-1,3-oxazol-2-yl]phenol i68 (0.85 g, 3.08 mmol, 1 eq) and 3-(1-piperidinyl)-1-propanol (0.44 g, 3.08 mmol, 1 eq) in tetrahydrofuran is added dropwise to the mixture at 0° C. After 2 days, the mixture is poured onto 0.5 N hydrochloric acid and extracted with diethyl ether. The aqueous phase is basified with 1 N sodium hydroxide to pH 9 and extracted with ethyl acetate. The organic layer is dried on magnesium sulfate and concentrated under reduced pressure. The crude product is purified by chromatography over silica gel to afford 0.25 g of 1-(3-{2-fluoro-4-[4-(piperidin-1-ylmethyl)-1,3-oxazol-2-yl]phenoxy}propyl)piperidine 88 as a yellow oil.

Yield: 20%.

LC-MS (MH+): 371.

Example 23

Synthesis of 1-[(4-methyl-2-{4-[3-(2-methyl-1-pyrrolidinyl)propoxy]phenyl}-1,3-thiazol-5-yl)methyl]-2-pyrrolidinone trifluoroacetate 156

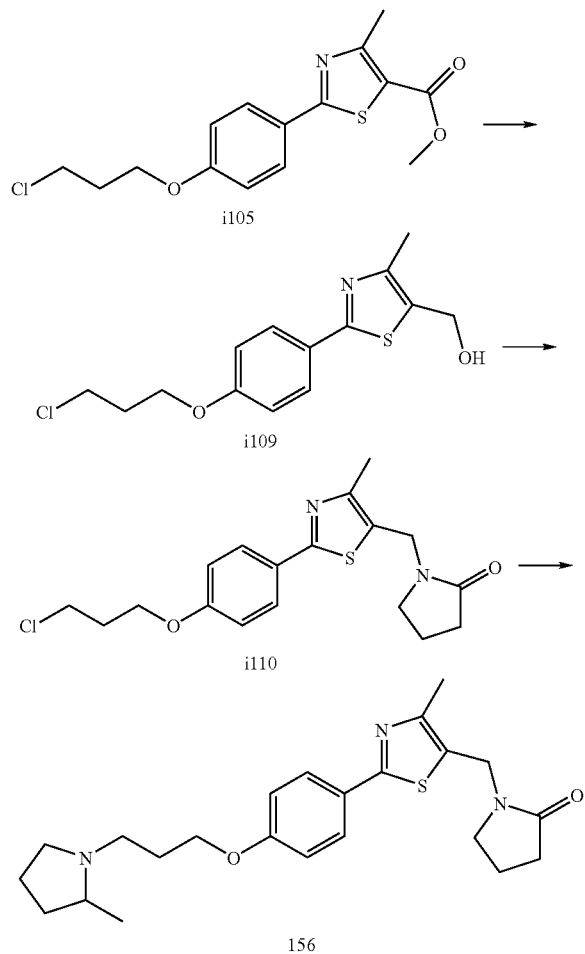

23.1 Synthesis of {2-[4-(3-chloropropoxy)phenyl]-4-methyl-1,3-thiazol-5-yl}methanol i109

To a solution of methyl 2-[4-(3-chloropropoxy)phenyl]-4-methyl-1,3-thiazole-5-carboxylate i105 (6.13 mmol, 1 eq, 2 g) in tetrahydrofuran (60 ml) is added methanol (19.6 mmol, 3.2 eq, 0.8 ml) and lithium borohydride (13.49 mmol, 2.2 eq, 0.29 g). The mixture is stirred at 75° C. overnight. 1 N aqueous hydrogen chloride (2 ml) is added and the mixture is then stirred at room temperature for 1 hour. Then, a 2 M aqueous sodium hydroxide solution is added to reach pH 12 and the mixture is stirred for 6 hours, then extracted twice with ethyl acetate. The organic layer is dried over magnesium sulfate and the solvent is removed under reduced pressure to give 1.65 g of {2-[4-(3-chloropropoxy)phenyl]-4-methyl-1,3-thiazol-5-yl}methanol i109 as a white solid.

Yield: 91%.

LC-MS (MH$^+$): 298.

23.2 Synthesis of 1-({2-[4-(3-chloropropoxy)phenyl]-4-methyl-1,3-thiazol-5-yl}methyl)pyrrolidin-2-one i110

In a flask fitted with a magnetic stirrer and a reflux condenser, {2-[4-(3-chloropropoxy)phenyl]-4-methyl-1,3-thiazol-5-yl}methanol i109 (0.67 mmol, 1 eq, 0.2 g), pyrrolidinone (0.8 mmol, 1.2 eq, 0.069 g) and p-toluenesulfonic acid (0.067 mmol, 0.1 eq, 0.013 g) are dissolved in toluene (5 ml) and the mixture is brought to reflux overnight. After this time, the mixture is concentrated, taken up in ethyl acetate and washed with a saturated solution of sodium bicarbonate. The organic layer is dried over magnesium sulfate and concentrated to dryness to give 0.295 g of 1-({2-[4-(3-chloropropoxy)phenyl]-4-methyl-1,3-thiazol-5-yl}methyl)pyrrolidin-2-one i110. This crude product is used in the next step without further purification.

Yield: 100%.

LC-MS (MH$^+$): 365.

23.3 Synthesis of 1-[(4-methyl-2-{4-[3-(2-methyl-1-pyrrolidinyl)propoxy]phenyl}-1,3-thiazol-5-yl)methyl]-2-pyrrolidinone trifluoroacetate 156

To a solution of 1-({2-[4-(3-chloropropoxy)phenyl]-4-methyl-1,3-thiazol-5-yl}methyl)pyrrolidin-2-one i110 (1.0 mmol, 1 eq, 0.36 g) in acetonitrile (10 ml) is added potassium carbonate (1.99 mmol, 2 eq, 0.27 g) and approximatively 0.01 g of sodium iodide. The mixture is stirred at 80° C. for 30 minutes in a sealed tube before addition of 2-methylpyrrolidine (1.2 mmol, 1.2 eq, 0.12 ml). The mixture is then stirred at 80° C. overnight. The mixture is taken up in ethyl acetate and washed with a saturated solution of sodium bicarbonate, then dried over magnesium sulfate. The solvent is removed under reduced pressure and purified by chromatography over silicagel (eluent: dichloromethane/methanol/ammonia 96:3.6:0.4) then by preparative liquid chromatography (gradient: acetonitrile/water/trifluoroacetic acid 95:5:0.1 to 5:95:0.1) to give 0.132 g of 1-[(4-methyl-2-{4-[3-(2-methyl-1-pyrrolidinyl)propoxy]phenyl}-1,3-thiazol-5-yl)methyl]-2-pyrrolidinone trifluoroacetate 156.

Yield: 15.5%.

LC-MS (MH$^+$): 414.

Example 24

Synthesis of 4-({(2S)-1-[(2-{4-[3-(2-methylpyrrolidin-1-yl)propoxy]phenyl}-1,3-oxazol-4-yl)methyl]pyrrolidin-2-yl}methyl)morpholine 144

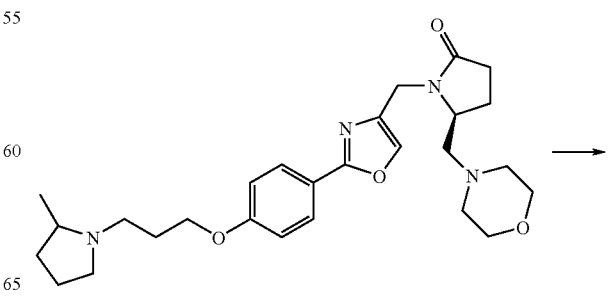

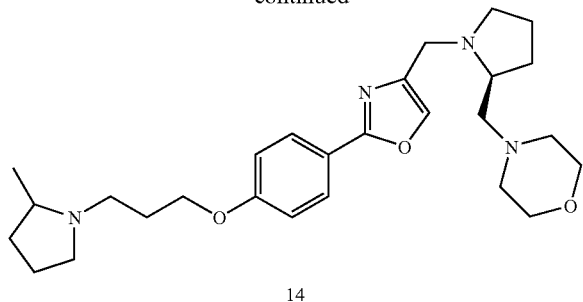

14

(5S)-1-[(2-{4-[3-(2-methylpyrrolidin-1-yl)propoxy]phenyl}-1,3-oxazol-4-yl)methyl]-5-(morpholin-4-ylmethyl)pyrrolidin-2-one 137 (0.21 g, 1 eq, 0.43 mmol) is dissolved in tetrahydrofuran (5 ml), then the mixture is cooled to 0° C. and lithium aluminium hydride (0.03 g, 2 eq, 0.87 mmol) is added. The mixture is stirred 1 h at 0° C. and then overnight at room temperature. Water (0.05 ml), a solution of sodium hydroxide 2N (0.05 ml) and again water (0.15 ml) are added. Then, the mixture is filtered through celite and concentrated under vacuum. Purification by chromatography on silicagel (eluent: dichloromethane/methanol/ammonia 951510.5) affords 0.058 g of 4-({(2S)-1-[(2-{4-[3-(2-methylpyrrolidin-1-yl)propoxy]phenyl}-1,3-oxazol-4-yl)methyl]pyrrolidin-2-yl}methyl)morpholine 144.

Yield: 29%
LC-MS (MH+): 469

Table I gives characteristics of some compounds of general formula (I). Said table indicates the stereochemical information in the columns headed "configuration": the second one indicates whether a compound has no stereogenic center (achiral), is a pure enantiomer (pure), a racemate (rac) or is a mixture of two stereoisomers, possibly in unequal proportions (mixture); the first one contains the stereochemical assignment for the recognized center, following the IUPAC numbering used in the "IUPAC name" column. A number alone indicates the existence of both configurations at that center. A number followed by 'R' or 'S' indicates the known absolute configuration at that center. Table 1 indicates also the type and stochiometry of salt, which was synthesized (if not the free base), the IUPAC name of the compound, the ion peak observed in mass spectrometry, the $^1$H NMR description and the optical rotation in the case of enantiomerically pure compounds.

TABLE I

| n° | Salt | Configuration | | IUPAC Name | MH+ (M+) |
|---|---|---|---|---|---|
| 29 | | | achiral | 1-(3-{4-[4-(piperidin-1-ylmethyl)-1,3-oxazol-2-yl]phenoxy}propyl)piperidine | 384 |
| 30 | | 2 | rac | 1-[3-(4-{4-[(2-methylpyrrolidin-1-yl)methyl]-1,3-oxazol-2-yl}phenoxy)propyl]piperidine | 384 |
| 31 | | | achiral | 1-(3-{4-[4-(pyrrolidin-1-ylmethyl)-1,3-oxazol-2-yl]phenoxy}propyl)piperidine | 370 |
| 32 | | | achiral | 1-({2-[4-(3-piperidin-1-ylpropoxy)phenyl]-1,3-oxazol-4-yl}methyl)azepane | 398 |
| 33 | | | achiral | 4-methyl-1-({2-[4-(3-piperidin-1-ylpropoxy)phenyl]-1,3-oxazol-4-yl}methyl)piperidine | 398 |
| 34 | | 2 | rac | 2-methyl-1-({2-[4-(3-piperidin-1-ylpropoxy)phenyl]-1,3-oxazol-4-yl}methyl)piperidine | 398 |
| 35 | | 3, 5 | mixture | 3,5-dimethyl-1-({2-[4-(3-piperidin-1-ylpropoxy)phenyl]-1,3-oxazol-4-yl}methyl)piperidine | 412 |
| 36 | | | achiral | N-hexyl-N-methyl-N-({2-[4-(3-piperidin-1-ylpropoxy)phenyl]-1,3-oxazol-4-yl}methyl)amine | 414 |
| 37 | | | achiral | N-benzyl-N-methyl-N-({2-[4-(3-piperidin-1-ylpropoxy)phenyl]-1,3-oxazol-4-yl}methyl)amine | 420 |
| 38 | | | achiral | 4-(pyrrolidin-1-ylmethyl)-2-[4-(3-pyrrolidin-1-ylpropoxy)phenyl]-1,3-oxazole | 356 |
| 39 | | | achiral | N-[(2-{4-[3-(4-isopropylpiperazin-1-yl)propoxy]phenyl}-1,3-oxazol-4-yl)methyl]-N-methylhexan-1-amine | 457 |
| 40 | Bis(trifluoroacetate) | 1 | rac | N-(2-methoxy-1-methylethyl)-N-({2-[4-(3-piperidin-1-ylpropoxy)phenyl]-1,3-oxazol-4-yl}methyl)amine | 388 |
| 41 | Bis(trifluoroacetate) | 2 | rac | 2-[(2-{4-[3-(2-methylpyrrolidin-1-yl)propoxy]phenyl}-1,3-oxazol-4-yl)methyl]-2-azaspiro[5.5]undecane | 452 |
| 42 | Bis(trifluoroacetate) | 7, 8 | mixture | 7,8-dimethyl-1-({2-[4-(3-piperidin-1-ylpropoxy)phenyl]- | 452 |

TABLE I-continued

| | | | | | |
|---|---|---|---|---|---|
| 43 | | 2, 2 | mixture | 1,3-oxazol-4-yl}methyl)-1-azaspiro[4.4]nonane<br>4-[(2-methylpyrrolidin-1-yl)methyl]-2-{4-[3-(2-methylpyrrolidin-1-yl)propoxy]phenyl}-1,3-oxazole | 384 |
| 44 | | | achiral | 1-isopropyl-4-(3-{4-[4-(pyrrolidin-1-ylmethyl)-1,3-oxazol-2-yl]phenoxy}propyl)piperazine | 413 |
| 45 | | 2 | rac | 1-isopropyl-4-[3-(4-{4-[(2-methylpiperidin-1-yl)methyl]-1,3-oxazol-2-yl}phenoxy)propyl]piperazine | 441 |
| 46 | Bis(trifluoro-acetate) | 2 | rac | 4-methyl-1-[3-(4-{4-[(2-methylpyrrolidin-1-yl)methyl]-1,3-oxazol-2-yl}phenoxy)propyl]piperidine | 398 |
| 47 | Bis(trifluoro-acetate) | 2, 2 | mixture | 2-methyl-1-[3-(4-{4-[(2-methylpyrrolidin-1-yl)methyl]-1,3-oxazol-2-yl}phenoxy)propyl]piperidine | 398 |
| 48 | Bis(trifluoro-acetate) | 2, 2 | mixture | 4-[(2-methylpyrrolidin-1-yl)methyl]-2-(4-{3-[2-(pyrrolidin-1-ylmethyl)pyrrolidin-1-yl]propoxy}phenyl)-1,3-oxazole | 453 |
| 49 | Bis(trifluoro-acetate) | 2 | rac | 1-cyclopentyl-4-[3-(4-{4-[(2-methylpyrrolidin-1-yl)methyl]-1,3-oxazol-2-yl}phenoxy)propyl]piperazine | 453 |
| 50 | Bis(trifluoro-acetate) | 3, 2 | mixture | N,N-dimethyl-1-[4-(4-{4-[(2-methylpyrrolidin-1-yl)methyl]-1,3-oxazol-2-yl}phenoxy)butyl]pyrrolidin-3-amine | 427 |
| 51 | Bis(trifluoro-acetate) | 2 | rac | 1-[2-(4-{4-[(2-methylpyrrolidin-1-yl)methyl]-1,3-oxazol-2-yl}phenoxy)ethyl]-4-(2-pyrrolidin-1-ylethyl)piperazine | 468 |
| 52 | | 2 | rac | 2-{4-[3-(2-methylpyrrolidin-1-yl)propoxy]phenyl}-4-(2-oxo-2-pyrrolidin-1-ylethyl)-1,3-oxazole | 398 |
| 53 | | 2 | rac | 1-[(2-{4-[3-(2-methylpyrrolidin-1-yl)propoxy]phenyl}-1,3-oxazol-4-yl)methyl]pyrrolidin-2-one | 384 |
| 54 | | 2 | rac | N-[(2-{4-[3-(2-methylpyrrolidin-1-yl)propoxy]phenyl}-1,3-oxazol-4-yl)methyl]-N-phenylamine | 392 |
| 55 | | 2 | rac | 2-{4-[3-(2-methylpyrrolidin-1-yl)propoxy]phenyl}-4-(2-pyrrolidin-1-ylethyl)-1,3-oxazole | 384 |
| 56 | | 2 | rac | 4-[(2-methyl-1H-imidazol-1-yl)methyl]-2-{4-[3-(2-methylpyrrolidin-1-yl)propoxy]phenyl}-1,3-oxazole | 381 |
| 57 | | 2 | rac | 1-[(2-{4-[3-(2-methylpyrrolidin-1-yl)propoxy]phenyl}-1,3-oxazol-4-yl)methyl]-1H-1,2,4-triazole | 368 |
| 58 | | | achiral | 4-(pyrrolidin-1-ylmethyl)-2-[3-(3-pyrrolidin-1-ylpropoxy)phenyl]-1,3-oxazole | 356 |
| 59 | | 2 | rac | 1-[(2-{4-[3-(2-methylpyrrolidin-1-yl)propoxy]phenyl}-1,3-oxazol-4-yl)methyl]piperidine | 384 |
| 60 | | 2 | rac | 1-[3-(4-{4-[(2-methylpyrrolidin-1-yl)methyl]-1,3-oxazol-2-yl}phenoxy)propyl]azepane | 397 |
| 61 | | | achiral | 1-(3-{4-[4-methyl-5-(piperidin-1-ylmethyl)-1,3-oxazol-2-yl]phenoxy}propyl)piperidine | 398 |
| 62 | dimaleate | 2, 2R | mixture | (2R)-4-methyl-2-{[(2-{4-[3-(2-methylpyrrolidin-1- | 416 |

TABLE I-continued

| | | | | | |
|---|---|---|---|---|---|
| 63 | dimaleate | 2 | rac | yl)propoxy]phenyl}-1,3-oxazol-4-yl)methyl]amino}pentan-1-ol N-[(2-{4-[3-(2-methylpyrrolidin-1-yl)propoxy]phenyl}-1,3-oxazol-4-yl)methyl]cyclopentanamine | 384 |
| 64 | fumarate | 2 | rac | 1-[4-(4-{4-[(2-methylpyrrolidin-1-yl)methyl]-1,3-oxazol-2-yl}phenoxy)butyl]azepane | 412 |
| 65 | di-(+)-tartrate, 0.6 EtOH | 2 | rac | 1-[2-(4-{4-[(2-methylpyrrolidin-1-yl)methyl]-1,3-oxazol-2-yl}phenoxy)ethyl]azepane | 412 |
| 66 | bis(trifluoro-acetate) | 2, 1 | mixture | N-(1,3-dimethylbutyl)-N-[(2-{4-[3-(2-methylpyrrolidin-1-yl)propoxy]phenyl}-1,3-oxazol-4-yl)methyl]amine | 400 |
| 67 | difumarate | 2 | rac | N-(cyclopropylmethyl)-N-[(2-{4-[3-(2-methylpyrrolidin-1-yl)propoxy]phenyl}-1,3-oxazol-4-yl)methyl]-N-propylamine | 412 |
| 68 | difumarate | 2, 6, 2, 6 | mixture | 1-[3-(4-{4-[(2,6-dimethylpiperidin-1-yl)methyl]-1,3-oxazol-2-yl}phenoxy)propyl]-2,6-dimethylpiperidine | 440 |
| 69 | difumarate | | achiral | 1-({2-[4-(2-piperidin-1-ylethoxy)phenyl]-1,3-oxazol-4-yl}methyl)piperidine | 370 |
| 70 | di-(+)-tartrate | 2 | rac | 1-[(2-{4-[2-(2-methylpyrrolidin-1-yl)ethoxy]phenyl}-1,3-oxazol-4-yl)methyl]piperidine | 370 |
| 71 | (bis)trifluoro-acetate | 2, 2 | mixture | 2-methyl-1-[4-(4-{4-[(2-methylpyrrolidin-1-yl)methyl]-1,3-oxazol-2-yl}phenoxy)butyl]piperidine | 412 |
| 72 | | | achiral | 1-(3-{4-[4-(piperidin-1-ylmethyl)-1,3-thiazol-2-yl]phenoxy}propyl)piperidine | 400 |
| 73 | | | achiral | 4-(pyrrolidin-1-ylmethyl)-2-[4-(3-pyrrolidin-1-ylpropoxy)phenyl]-1,3-thiazole | 372 |
| 74 | | 7, 8, 2 | mixture | 7,8-dimethyl-1-[(2-{4-[3-(2-methylpyrrolidin-1-yl)propoxy]phenyl}-1,3-thiazol-4-yl)methyl]-1-azaspiro[4.4]nonane | 468 |
| 75 | | 2 | rac | N-(2-furylmethyl)-N-methyl-N-[(2-{4-[3-(2-methylpyrrolidin-1-yl)propoxy]phenyl}-1,3-thiazol-4-yl)methyl]amine | 426 |
| 76 | | 1, 2 | mixture | N-(sec-butyl)-N-[(2-{4-[3-(2-methylpyrrolidin-1-yl)propoxy]phenyl}-1,3-thiazol-4-yl)methyl]-N-propylamine | 430 |
| 77 | (bis)trifluoro-acetate | | achiral | 1-(3-{4-[4-(pyrrolidin-1-ylmethyl)-1,3-thiazol-2-yl]phenoxy}propyl)piperidine | 386 |
| 78 | (bis)trifluoro-acetate | | achiral | 1-({2-[4-(3-piperidin-1-ylpropoxy)phenyl]-1,3-thiazol-4-yl}methyl)azepane | 414 |
| 79 | dihydrochloride | 2 | rac | 1-[(2-{4-[3-(2-methylpyrrolidin-1-yl)propoxy]phenyl}-1,3-thiazol-4-yl)methyl]piperidine | 400 |
| 80 | | 2 | rac | 1-[(2-{4-[3-(2-methylpyrrolidin-1-yl)propoxy]phenyl}-1,3-oxazol-4-yl)acetyl]piperidine | 412 |
| 81 | | | achiral | 1-(3-{4-[4-(2-oxo-2-piperidin-1-ylethyl)-1,3-oxazol-2-yl]phenoxy}propyl)piperidine | 412 |
| 82 | | 2 | rac | 1-[2-(2-{4-[3-(2-methylpyrrolidin-1-yl)propoxy]phenyl}-1,3-oxazol-4-yl)ethyl]piperidine | 398 |
| 83 | | 2 | rac | 2-{4-[3-(2-methylpyrrolidin-1-yl)propoxy]phenyl}-1,3-thiazole | 303 |
| 84 | Bis(trifluoro acetate) | 2 | rac | 4-benzyl-1-[(2-{4-[3-(2-methylpyrrolidin-1-yl)propoxy]phenyl}-1,3-oxazol-4-yl)methyl]piperidine | 474 |

TABLE I-continued

| | | | | | |
|---|---|---|---|---|---|
| 85 | tris(trifluoro acetate) | 2 | rac | 1-cyclopentyl-4-[(2-{4-[3-(2-methylpyrrolidin-1-yl)propoxy]phenyl}-1,3-oxazol-4-yl)methyl]piperazine | 453 |
| 86 | | 2S | pure | 1-{[2-(4-{3-[(2S)-2-(pyrrolidin-1-ylmethyl)pyrrolidin-1-yl]propoxy}phenyl)-1,3-oxazol-4-yl]methyl}piperidine | 453 |
| 87 | | | achiral | 1-(3-{4-[5-methyl-4-(piperidin-1-ylmethyl)-1,3-oxazol-2-yl]phenoxy}propyl)piperidine | 398 |
| 88 | | | achiral | 1-(3-{2-fluoro-4-[4-(piperidin-1-ylmethyl)-1,3-oxazol-2-yl]phenoxy}propyl)piperidine | 402 |
| 89 | | | achiral | 1-(3-{2,6-dimethyl-4-[4-(piperidin-1-ylmethyl)-1,3-oxazol-2-yl]phenoxy}propyl)piperidine | 412 |
| 90 | | 2 | rac | 4-[(2-{4-[3-(2-methylpyrrolidin-1-yl)propoxy]phenyl}-1,3-oxazol-4-yl)carbonyl]morpholine | 400 |
| 91 | | | achiral | 1-cyclopentyl-4-({2-[4-(3-piperidin-1-ylpropoxy)phenyl]-1,3-oxazol-4-yl}carbonyl)piperazine | 467 |
| 92 | | 2 | rac | 1-[(2-{4-[3-(2-methylpyrrolidin-1-yl)propoxy]phenyl}-1,3-oxazol-4-yl)carbonyl]piperidine | 398 |
| 93 | | 2 | rac | 1-cyclopentyl-4-[(2-{4-[3-(2-methylpyrrolidin-1-yl)propoxy]phenyl}-1,3-oxazol-4-yl)carbonyl]piperazine | 467 |
| 94 | | 2, 2S | mixture | 4-[(2-methylpyrrolidin-1-yl)methyl]-2-(4-{3-[(2S)-2-(pyrrolidin-1-ylmethyl)pyrrolidin-1-yl]propoxy}phenyl)-1,3-oxazole | 453 |
| 95 | | 2 | rac | 1-[(2-{3-fluoro-4-[3-(2-methylpyrrolidin-1-yl)propoxy]phenyl}-1,3-oxazol-4-yl)methyl]piperidine | 402 |
| 96 | | 2 | rac | 1-[(4-methyl-2-{4-[3-(2-methylpyrrolidin-1-yl)propoxy]phenyl}-1,3-oxazol-5-yl)carbonyl]piperidine | 412 |
| 97 | | 2 | rac | N-(cyclopropylmethyl)-4-methyl-2-{4-[3-(2-methylpyrrolidin-1-yl)propoxy]phenyl}-N-propyl-1,3-oxazole-5-carboxamide | 440 |
| 98 | | 2 | rac | N-cyclopentyl-4-methyl-2-{4-[3-(2-methylpyrrolidin-1-yl)propoxy]phenyl}-1,3-oxazole-5-carboxamide | 412 |
| 99 | | 2 | rac | methyl 4-[(benzylamino)methyl]-2-{4-[3-(2-methylpyrrolidin-1-yl)propoxy]phenyl}-1,3-oxazole-5-carboxylate | 464 |
| 100 | | 2 | rac | methyl 4-methyl-2-{4-[3-(2-methylpyrrolidin-1-yl)propoxy]phenyl}-1,3-thiazole-5-carboxylate | 375 |
| 101 | | 2 | rac | 2-{4-[3-(2-methylpyrrolidin-1-yl)propoxy]phenyl}-4-(piperidin-1-ylmethyl)-1,3-oxazole-5-carboxylic acid | 428 |
| 102 | | 2 | rac | N-(cyclopropylmethyl)-2-{4-[3-(2-methylpyrrolidin-1-yl)propoxy]phenyl}-N-propyl-1,3-oxazole-4-carboxamide | 426 |
| 103 | | 2 | rac | N-cyclopentyl-2-{4-[3-(2-methylpyrrolidin-1-yl)propoxy]phenyl}-1,3-oxazole-4-carboxamide | 398 |
| 104 | | 2 | rac | N-(4-fluorobenzyl)-2-{4-[3-(2-methylpyrrolidin-1- | 438 |

TABLE I-continued

| | | | | |
|---|---|---|---|---|
| 105 | | 2 | rac | N-benzyl-4-methyl-2-{4-[3-(2-methylpyrrolidin-1-yl)propoxy]phenyl}-1,3-oxazole-5-carboxamide | 432 |
| 106 | | 2 | rac | 1-cyclopentyl-4-[(4-methyl-2-{4-[3-(2-methylpyrrolidin-1-yl)propoxy]phenyl}-1,3-oxazol-5-yl)carbonyl]piperazine | 481 |
| 107 | | 2 | rac | 2-{4-[3-(2-methylpyrrolidin-1-yl)propoxy]phenyl}-4-(pyrrolidin-1-ylcarbonyl)-1,3-oxazole | 384 |
| 108 | | 2 | rac | 4-[(4-methyl-2-{4-[3-(2-methylpyrrolidin-1-yl)propoxy]phenyl}-1,3-oxazol-5-yl)carbonyl]morpholine | 414 |
| 109 | | 2R | pure | 4-{[4-methyl-2-(4-{3-[(2R)-2-methylpyrrolidin-1-yl]propoxy}phenyl)-1,3-oxazol-5-yl]carbonyl}morpholine | 414 |
| 110 | | 2S | pure | 4-{[4-methyl-2-(4-{3-[(2S)-2-methylpyrrolidin-1-yl]propoxy}phenyl)-1,3-oxazol-5-yl]carbonyl}morpholine | 414 |
| 111 | | 2 | rac | 1-cyclopentyl-4-[(4-methyl-2-{4-[3-(2-methylpyrrolidin-1-yl)propoxy]phenyl}-1,3-oxazol-5-yl)methyl]piperazine | 467 |
| 112 | | 2 | rac | N-(cyclopropylmethyl)-N-[(4-methyl-2-{4-[3-(2-methylpyrrolidin-1-yl)propoxy]phenyl}-1,3-oxazol-5-yl)methyl]-N-propylamine | 426 |
| 113 | | 2 | rac | N-benzyl-N-[(4-methyl-2-{4-[3-(2-methylpyrrolidin-1-yl)propoxy]phenyl}-1,3-oxazol-5-yl)methyl]amine | 420 |
| 114 | | 2 | rac | 1-[(2-{3-methoxy-4-[3-(2-methylpyrrolidin-1-yl)propoxy]phenyl}-1,3-oxazol-4-yl)methyl]piperidine | 414 |
| 115 | | 2 | rac | N-(4-chlorobenzyl)-N-[(2-{4-[3-(2-methylpyrrolidin-1-yl)propoxy]phenyl}-1,3-oxazol-4-yl)methyl]amine bis(trifluoroacetate) | 440 |
| 116 | | 2 | rac | N-[(4-methyl-2-{4-[3-(2-methylpyrrolidin-1-yl)propoxy]phenyl}-1,3-oxazol-5-yl)methyl]cyclopentanamine | 398 |
| 117 | | 2 | rac | 1-[(5-bromo-2-{4-[3-(2-methylpyrrolidin-1-yl)propoxy]phenyl}-1,3-oxazol-4-yl)methyl]piperidine | 462/464 |
| 118 | difumarate | 2R | pure | 1-{[2-(4-{3-[(2R)-2-methylpyrrolidin-1-yl]propoxy}phenyl)-1,3-oxazol-4-yl]methyl}piperidine | 384 |
| 119 | difumarate | 2S | pure | 1-{[2-(4-{3-[(2S)-2-methylpyrrolidin-1-yl]propoxy}phenyl)-1,3-oxazol-4-yl]Methyl}piperidine | 384 |
| 120 | | 2 | rac | 4-[(2-{4-[3-(2-methylpyrrolidin-1-yl)propoxy]phenyl}-1,3-oxazol-4-yl)methyl]morpholine | 386 |
| 121 | | 2 | rac | 1-[2-(2-{4-[2-(2-methylpyrrolidin-1-yl)ethoxy]phenyl}-1,3-oxazol-4-yl)ethyl]piperidine | 384 |
| 122 | | 2 | rac | 1-[(2-{4-[3-(2-methylpyrrolidin-1-yl)propoxy]phenyl}-1,3-oxazol-4-yl)methyl]piperidin-2-one | 398 |
| 123 | | 2, 5S | mixture | (5S)-1-[(2-{4-[3-(2-methylpyrrolidin-1-yl)propoxy]phenyl}-1,3-oxazol-4-yl)methyl]-5-(pyrrolidin-1- | 467 |

TABLE I-continued

| | | | | | |
|---|---|---|---|---|---|
| 124 | | 2 | rac | ylmethyl)pyrrolidin-2-one 1-[(2-{3-chloro-4-[3-(2-methylpyrrolidin-1-yl)propoxy]phenyl}-1,3-oxazol-4-yl)methyl]piperidine | 418/420 |
| 125 | 1.7 fumarate | 2 | rac | 1-[(2-{4-[3-(2-isobutylpyrrolidin-1-yl)propoxy]phenyl}-1,3-oxazol-4-yl)methyl]piperidine | 426 |
| 126 | | 2 | rac | methyl 2-{3-bromo-4-[3-(2-methylpyrrolidin-1-yl)propoxy]phenyl}-4-methyl-1,3-thiazole-5-carboxylate | 453/455 |
| 127 | | | achiral | 1-(3-{4-[4-methyl-5-(2-oxo-2-piperidin-1-ylethyl)-1,3-thiazol-2-yl]phenoxy}propyl)piperidine | 442 |
| 128 | | 2 | rac | N-(4-fluorophenyl)-2-(2-{4-[3-(2-methylpyrrolidin-1-yl)propoxy]phenyl}-1,3-oxazol-4-yl)acetamide | 438 |
| 129 | 1.7 fumarate | 2 | rac | 1-[(2-{4-[3-(2-ethylpyrrolidin-1-yl)propoxy]phenyl}-1,3-oxazol-4-yl)methyl]piperidine | 388 |
| 130 | | 8aS, 4aR, 2 | mixture | (4aR,8aS)-2-[(2-{4-[3-(2-methylpyrrolidin-1-yl)propoxy]phenyl}-1,3-oxazol-4-yl)methyl]decahydroisoquinoline | 438 |
| 131 | | 2, 2S | mixture | 2-{4-[3-(2-methylpyrrolidin-1-yl)propoxy]phenyl}-4-{[(2S)-2-(pyrrolidin-1-ylmethyl)pyrrolidin-1-yl]carbonyl}-1,3-oxazole | 467 |
| 132 | | 2 | rac | 4-[(2-{4-[3-(2-methylpyrrolidin-1-yl)propoxy]phenyl}-1,3-oxazol-4-yl)acetyl]morpholine | 414 |
| 133 | | 2 | rac | N-cyclopentyl-2-(2-{4-[3-(2-methylpyrrolidin-1-yl)propoxy]phenyl}-1,3-oxazol-4-yl)acetamide | 412 |
| 134 | | 2 | rac | N-(cyclopropylmethyl)-2-(2-{4-[3-(2-methylpyrrolidin-1-yl)propoxy]phenyl}-1,3-oxazol-4-yl)-N-propylacetamide | 440 |
| 135 | | 2 | rac | 1-[(2-{4-[3-(2-methylpyrrolidin-1-yl)propoxy]phenyl}-1,3-oxazol-4-yl)acetyl]azepane | 426 |
| 136 | | | achiral | 1-(3-{4-[4-methyl-5-(2-piperidin-1-ylethyl)-1,3-thiazol-2-yl]phenoxy}propyl)piperidine | 428 |
| 137 | | 2, 5S | mixture | (5S)-1-[(2-{4-[3-(2-methylpyrrolidin-1-yl)propoxy]phenyl}-1,3-oxazol-4-yl)methyl]-5-(morpholin-4-ylmethyl)pyrrolidin-2-one | 483 |
| 138 | | 4aS, 8aR | pure | (4aS,8aR)-2-(3-{4-[4-(piperidin-1-ylmethyl)-1,3-oxazol-2-yl]phenoxy}propyl)decahydroisoquinoline | 438 |
| 139 | | 2 | rac | 2-methyl-N-[(2-{4-[3-(2-methylpyrrolidin-1-yl)propoxy]phenyl}-1,3-oxazol-4-yl)methyl]-2H-tetraazol-5-amine | 398 |
| 140 | | 2 | rac | N-(3-methoxyphenyl)-N-[(2-{4-[3-(2-methylpyrrolidin-1-yl)propoxy]phenyl}-1,3-oxazol-4-yl)methyl]amine | 422 |
| 141 | | 2 | rac | N-(4-fluorophenyl)-N-[(2-{4-[3-(2-methylpyrrolidin-1-yl)propoxy]phenyl}-1,3-oxazol-4-yl)methyl]amine | 410 |
| 142 | | 2 | rac | N-[(2-{4-[3-(2-methylpyrrolidin-1-yl)propoxy]phenyl}-1,3-oxazol-4-yl)methyl]pyridin-3-amine | 393 |
| 143 | | 2 | rac | 4-[(4-methyl-2-{4-[3-(2-methylpyrrolidin-1-yl)propoxy]phenyl}-1,3-oxazol-5-yl)methyl]morpholine | 400 |

TABLE I-continued

| | | | | |
|---|---|---|---|---|
| 144 | | 2, 2S | mixture | 4-({(2S)-1-[(2-{4-[3-(2-methylpyrrolidin-1-yl)propoxy]phenyl}-1,3-oxazol-4-yl)methyl]pyrrolidin-2-yl}methyl)morpholine | 469 |
| 145 | | 2 | rac | 1-[(2-{2-fluoro-4-[3-(2-methylpyrrolidin-1-yl)propoxy]phenyl}-1,3-oxazol-4-yl)methyl]piperidine dimethanesulfonate | 402 |
| 146 | | 2 | rac | 4,4-difluoro-1-[(2-{4-[3-(2-methylpyrrolidin-1-yl)propoxy]phenyl}-1,3-oxazol-4-yl)methyl]piperidine | 420 |
| 147 | | 2 | rac | 4-[(4-methyl-2-{6-[3-(2-methylpyrrolidin-1-yl)propoxy]pyridin-3-yl}-1,3-thiazol-5-yl)carbonyl]morpholine | 431 |
| 148 | | 2 | rac | 1-[(2-{3,5-difluoro-4-[3-(2-methylpyrrolidin-1-yl)propoxy]phenyl}-1,3-oxazol-4-yl)methyl]piperidine | 420 |
| 149 | | 2 | rac | 4,4-difluoro-1-[(4-methyl-2-{4-[3-(2-methylpyrrolidin-1-yl)propoxy]phenyl}-1,3-thiazol-5-yl)carbonyl]piperidine | 464 |
| 150 | | 2S | pure | 4,4-difluoro-1-{[4-methyl-2-(4-{3-[(2S)-2-methylpyrrolidin-1-yl]propoxy}phenyl)-1,3-thiazol-5-yl]carbonyl}piperidine | 464 |
| 151 | | 2R | pure | 4,4-difluoro-1-{[4-methyl-2-(4-{3-[(2R)-2-methylpyrrolidin-1-yl]propoxy}phenyl)-1,3-thiazol-5-yl]carbonyl}piperidine | 464 |
| 152 | | 2 | rac | 4-[(4-methyl-2-{4-[3-(2-methylpyrrolidin-1-yl)propoxy]phenyl}-1,3-thiazol-5-yl)carbonyl]morpholine | 430 |
| 153 | | 2R | pure | 4-{[4-methyl-2-(4-{3-[(2R)-2-methylpyrrolidin-1-yl]propoxy}phenyl)-1,3-thiazol-5-yl]carbonyl}morpholine | 430 |
| 154 | | 2S | pure | 4-{[4-methyl-2-(4-{3-[(2S)-2-methylpyrrolidin-1-yl]propoxy}phenyl)-1,3-thiazol-5-yl]carbonyl}morpholine | 430 |
| 155 | | 2 | rac | 1-[(2-{2-methyl-4-[3-(2-methylpyrrolidin-1-yl)propoxy]phenyl}-1,3-oxazol-4-yl)methyl]piperidine | 398 |
| 156 | trifluoro acetate | 2 | rac | 1-[(4-methyl-2-{4-[3-(2-methylpyrrolidin-1-yl)propoxy]phenyl}-1,3-thiazol-5-yl)methyl]pyrrolidin-2-one | 414 |

| n° | ¹H NMR (solvent) δH (ppm) | Alpha$_D$ |
|---|---|---|
| 29 | (DMSO): 1.53 (m, 12H), 2.05 (m, 2H), 2.54 (s, 4H), 2.83 (m, 6H), 3.53 (s, 2H), 4.10 (t, 6.03 Hz, 2H), 6.56 (s, 2H), 7.07 (d, 8.54 Hz, 2H), 7.89 (d, 8.54 Hz, 2H), 8.00 (s, 1H) | |
| 30 | (CDCl$_3$): 1.18 (d, 6.29 Hz, 3H), 1.72 (m, 10H), 2.30 (d, 9.05 Hz, 1H), 2.45 (m, 7H), 3.14 (d, 1.76 Hz, 1H), 3.31 (d, 13.83 Hz, 1H), 3.94 (d, 13.83 Hz, 1H), 4.05 (t, 6.41 Hz, 2H), 5.30 (s, 2H), 6.94 (d, 9.05 Hz, 2H), 7.52 (s, 1H), 7.96 (d, 8.80 Hz, 2H) | |
| 31 | (CDCl$_3$): 1.71 (m, 12H), 2.01 (m, 2H), 2.49 (m, 10H), 3.63 (m, 2H), 4.06 (m, 2H), 6.94 (dd, 3.02 and 1.51 Hz, 2H), 7.53 (m, 1H), 7.97 (m, 2H) | |
| 32 | (CDCl$_3$): 1.45 (m, 2H), 1.63 (m, 10H), 1.99 (m, 2H), 2.45 (m, 6H), 2.74 (m, 4H), 3.67 (s, 2H), 4.06 (t, 6.41 Hz, 2H), 5.30 (s, 2H), 6.94 (d, 8.80 Hz, 2H), 7.52 (s, 1H), 7.95 (d, 9.05 Hz, 2H) | |
| 33 | (CDCl$_3$): 0.84 (d, 6.29 Hz, 6H), 1.60 (m, 9H), 1.99 (m, 2H), 2.45 (m, 6H), 2.92 (m, 2H), 3.49 (m, 3H), 4.06 (t, 6.41 Hz, 2H), 6.95 (d, 8.80 Hz, 2H), 7.52 (s, 1H), 7.96 (d, 8.80 Hz, 2H) | |

TABLE I-continued 34 (CDCl$_3$): 1.20 (d, 6.29 Hz, 3H), 1.45 (d, 5.28 Hz, 2H), 1.63 (m, 9H), 1.99 (m, 2H), 2.37 (m, 8H), 2.93 (d, 11.32 Hz, 1H), 3.61 (d, 14.59 Hz, 1H), 3.83 (dd, 14.59, 0.75 Hz, 1H), 4.06 (t, 6.41 Hz, 2H), 6.95 (d, 9.05 Hz, 2H), 7.51 (s, 1H), 7.95 (d, 8.80 Hz, 2H)

35 (CDCl$_3$): 0.84 (d, 6.29 Hz, 6H), 1.60 (m, 11H), 1.99 (m, 2H), 2.45 (m, 6H), 2.92 (m, 2H), 3.49 (m, 3H), 4.06 (t, 6.41 Hz, 2H), 6.95 (d, 8.80 Hz, 2H), 7.52 (s, 1H), 7.96 (d, 8.80 Hz, 2H)

36 (CDCl$_3$): 0.88 (m, 3H), 1.29 (s, 6H), 1.53 (m, 8H), 2.00 (m, 2H), 2.30 (s, 3H), 2.42 (m, 8H), 3.52 (s, 2H), 4.06 (s, 2H), 6.94 (d, 9.05 Hz, 2H), 7.52 (s, 1H), 7.96 (d, 8.80 Hz, 2H)

37 (CDCl$_3$): 1.59 (dd, 6.79, 6.79, 2.01, 1.13 Hz, 4H), 2.02 (m, 2H), 2.30 (m, 3H), 2.48 (m, 6H), 3.55 (m, 5H), 4.05 (m, 2H), 5.31 (m, 3H), 6.95 (m, 2H), 7.35 (m, 4H), 7.54 (m, 1H), 7.94 (m, 2H)

38 (CDCl$_3$): 1.83 (m, 8H), 2.05 (m, 2H), 2.58 (m, 10H), 3.64 (m, 2H), 4.08 (m, 2H), 6.95 (m, 2H), 7.55 (m, 1H), 7.98 (m, 2H)

39 (CDCl$_3$): 0.88 (m, 3H), 1.06 (d, 6.57 Hz, 6H), 1.29 (s, 6H), 1.52 (m, 2H), 2.01 (m, 4H), 2.29 (s, 3H), 2.42 (m, 2H), 2.60 (m, 10H), 3.51 (s, 2H), 4.06 (t, 6.31 Hz, 2H), 6.94 (d, 8.34 Hz, 2H), 7.52 (s, 1H), 7.96 (d, 8.34 Hz, 2H)

40 (DMSO): 1.14 (d, 6.28 Hz, 3H), 1.61 (dd, 4.27 and 2.01 Hz, 5H), 2.04 (m, 2H), 3.09 (m, 2H), 3.20 (s, 3H), 4.02 (m, 4H), 7.81 (d, 8.54 Hz, 2H), 8.12 (s, 1H) (some signals obscured by solvent)

41 (DMSO): 1.15, 1.27 (d, 2H), 1.44, 1.63, 2.09, 3.04, 3.57, 4.07 (m, 2H), 4.20 (m, 2H) 7.86 (d, 2H), 8.22 (s, 1H)

42 (DMSO): 0.77 (m, 4H), 0.84 (d, 6.03 Hz, 3H), 1.62 (m, 16H), 1.98 (m, 3H), 2.36 (s, 1H), 3.03 (d, 7.28 Hz, 3H), 3.94 (t, 5.90 Hz, 3H), 6.92 (d, 8.78 Hz, 2H), 7.75 (d, 8.79 Hz, 2H), 8.09 (s, 1H) (some signals obscured by solvent)

43 (CDCl$_3$): 1.15 (m, 7H), 1.95 (m, 14H), 3.11 (m, 4H), 4.02 (m, 3H), 6.94 (m, 2H), 7.53 (m, 1H), 7.96 (m, 2H)

44 (CDCl$_3$): 1.06 (d, 6.29 Hz, 6H), 1.81 (t, 3.27 Hz, 4H), 2.00 (m, 3H), 2.57 (m, 14H), 3.62 (s, 2H), 4.06 (t, 6.41 Hz, 2H), 6.94 (d, 8.80 Hz, 2H), 7.54 (s, 1H), 7.97 (d, 8.80 Hz, 2H)

45 (CDCl$_3$): 1.06 (d, 6.31 Hz, 6H), 1.23 (m, 7H), 1.62 (m, 3H), 1.86 (s, 2H), 1.99 (m, 2H), 2.28 (m, 2H), 2.53 (m, 8H), 2.92 (d, 11.37 Hz, 1H), 3.59 (d, 14.65 Hz, 1H), 3.83 (m, 1H), 4.05 (m, 2H), 6.94 (d, 9.09 Hz, 2H), 7.51 (s, 1H), 7.95 (d, 9.09 Hz, 2H)

46 (DMSO): 0.89 (d, 6.53 Hz, 3H), 1.34 (d, 6.28 Hz, 3H), 1.78 (m, 4H), 2.12 (m, 2H), 2.89 (m, 2H), 4.09 (t, 5.90 Hz, 2H), 7.91 (d, 8.79 Hz, 2H), 8.29 (s, 1H) (some signals obscured by solvent)

47 (DMSO): 1.26 (d, 6.03 Hz, 4H), 1.34 (d, 6.28 Hz, 3H), 1.56 (dd, 5.27 and 2.26 Hz, 6H), 1.85 (m, 5H), 2.12 (m, 4H), 4.11 (m, 3H), 4.21 (s, 1H), 4.42 (s, 1H), 7.08 (d, 8.80 Hz, 2H), 7.91 (d, 8.79 Hz, 2H), 8.29 (s, 1H) (some signals obscured by solvent)

48 (DMSO): 1.33 (d, 6.03 Hz, 3H), 1.95 (m, 16H), 4.08 (s, 3H), 4.19 (d, 3.77 Hz, 2H), 4.41 (s, 2H), 7.89 (d, 8.29 Hz, 2H), 8.28 (s, 1H) (some signals obscured by solvent)

49 (DMSO): 1.27 (d, 4.52 Hz, 3H), 1.51 (m, 8H), 1.88 (s, 7H), 2.09 (s, 1H), 2.72 (d, 3.01 Hz, 3H), 3.99 (s, 3H), 4.13 (s, 2H), 4.37 (d, 13.56 Hz, 2H), 6.99 (d, 7.30 Hz, 2H), 7.82 (d, 7.28 Hz, 2H), 8.21 (s, 1H) (some signals obscured by solvent)

50 (DMSO): 1.31 (d, 6.31 Hz, 3H), 1.72 (d, 1.26 Hz, 5H), 2.69 (d, 1.01 Hz, 7H), 4.01 (s, 3H), 4.40 (d, 0.76 Hz, 1H), 7.04 (d, 8.59 Hz, 2H), 7.87 (d, 8.59 Hz, 2H), 8.26 (s, 1H) (some signals obscured by solvent)

51 (DMSO): 1.31 (d, 4.50 Hz, 3H), 1.55 (m, 1H), 1.88 (m, 6H), 2.16 (m, 1H), 2.64 (m, 4H), 4.18 (d 13.49 Hz, 2H), 4.36 (s, 2H), 4.42 (d, 13.56 Hz, 2H), 7.91 (d, 7.28 Hz, 2H), 8.28 (s, 1H) (some signals obscured by solvent)

52 (CDCl$_3$): 1.16 (d, 6.06 Hz, 3H), 1.50 (m, 1H), 1.88 (m, 5H), 1.98 (m, 3H), 2.07 (m, 2H), 2.34 (m, 4H), 3.04 (m, 1H), 3.26 (m, 1H), 3.52 (t, 6.95 Hz, 2H),

TABLE I-continued

| | |
|---|---|
| | 3.58 (t, 6.82 Hz, 2H), 3.65 (s, 2H), 4.09 (m, 2H), 6.94 (d, 8.84 Hz, 2H), 7.72 (s, 1H), 7.93 (d, 8.84 Hz, 2H) |
| 53 | (CDCl$_3$): 1.10 (d, 6.04 Hz, 3H), 1.86 (m, 12H), 2.41 (t, 8.17 Hz, 2H), 2.98 (m, 1H), 3.19 (m, 1H), 3.54 (m, 1H), 4.08 (d, 2.26 Hz, 2H), 4.42 (s, 2H), 6.96 (d, 8.80 Hz, 2H), 7.57 (s, 1H), 7.93 (d, 8.80 Hz, 2H) |
| 54 | (CDCl$_3$): 1.08 (d, 6.29 Hz, 3H), 1.41 (m, 1H), 1.80 (m, 3H), 1.99 (m, 2H), 2.11 (q, 8.87 Hz, 1H), 2.20 (m, 1H), 2.29 (m, 1H), 2.97 (dt, 12.07, 7.99 Hz, 1H), 3.17 (m, 1H), 4.05 (m, 2H), 4.28 (m, 3H), 6.70 (m, 3H), 6.95 (m, 2H), 7.17 (m, 2H), 7.53 (s, 1H), 7.94 (d, 9.05 Hz, 2H) |
| 55 | (CDCl$_3$): 1.09 (d, 6.04 Hz, 3H), 1.26 (s, 1H), 1.41 (d, 2.26 Hz, 1H), 1.80 (t, 3.40 Hz, 5H), 1.96 (m, 3H), 2.11 (m, 1H), 2.20 (s, 1H), 2.30 (m, 1H), 2.58 (s, 4H), 2.81 (s, 4H), 2.98 (d, 12.07 Hz, 1H), 3.18 (m, 1H), 4.08 (d, 2.77 Hz, 2H), 6.95 (d, 9.05 Hz, 2H), 7.43 (s, 1H), 7.93 (d, 8.80 Hz, 2H) |
| 56 | (CDCl$_3$): 1.09 (d, 6.29 Hz, 3H), 1.44 (m, 1H), 1.99 (m, 8H), 2.46 (s, 3H), 2.97 (m, 1H), 3.17 (dd, 8.55, 2.52 Hz, 1H), 4.08 (d, 2.01 Hz, 2H), 4.99 (d, 1.01 Hz, 2H), 6.96 (m, 4H), 7.36 (s, 1H), 7.92 (d, 8.80 Hz, 2H) |
| 57 | (CDCl$_3$): 1.55 (m, 3H), 2.18 (m, 7H), 2.93 (m, 1H), 3.04 (m, 1H), 3.24 (m, 1H), 3.56 (m, 1H), 4.19 (m, 12H), 6.94 (d, 7.32 Hz, 2H), 7.73 (s, 1H), 7.95 (d, 7.07 Hz, 2H), 8.07 (d, 1.52 Hz, 1H), 8.50 (d, 0.76 Hz, 1H) |
| 58 | (DMSO): 1.70 (s, 8H), 1.92 (m, 2H), 2.54 (m, 10H), 3.55 (s, 2H), 4.10 (t, 6.31 Hz, 2H), 7.08 (dd, 8.08, 2.02 Hz, 1H), 7.44 (d, 8.34 Hz, 2H), 7.53 (m, 1H), 8.03 (s, 1H) (some signals obscured by solvent) |
| 59 | (CDCl$_3$): 1.09 (d, 6.04 Hz, 3H), 1.43 (m, 3H), 2.05 (m, 16H), 2.98 (m, 1H), 3.18 (d, 2.52 Hz, 1H), 3.48 (s, 2H), 4.07 (m, 2H), 6.95 (d, 8.80 Hz, 2H), 7.52 (s, 1H), 7.96 (d, 9.05 Hz, 2H) |
| 60 | (DMSO): 1.10 (d, 6.06 Hz, 3H), 1.33 (m, 1H), 1.57 (m, 11H), 1.87 (m, 3H), 2.23 (q, 8.84 Hz, 1H), 2.41 (m, 1H), 2.59 (m, 6H), 2.97 (m, 1H), 3.25 (d, 14.14 Hz, 1H), 3.83 (d, 14.40 Hz, 1H), 4.08 (t, 6.44 Hz, 2H), 7.06 (d, 8.84 Hz, 2H), 7.88 (d, 8.84 Hz, 2H), 7.95 (s, 1H) |
| 61 | (CDCl$_3$): 1.42 (m, 4H), 1.59 (m, 8H), 1.98 (m, 2H), 2.20 (s, 3H), 2.45 (m, 10H), 3.56 (s, 2H), 4.04 (t, 6.31 Hz, 2H), 6.93 (d, 8.84 Hz, 2H), 7.94 (d, 8.84 Hz, 2H) |
| 62 | (DMSO): 0.88 (dd, 13.89, 6.44 Hz, 6H), 1.47 (m, 7H), 2.07 (m, 5H), 3.44 (m, 6H), 4.17 (m, 4H), 6.02 (s, 4H), 7.13 (d, 8.84 Hz, 2H), 7.94 (d, 8.59 Hz, 2H), 8.25 (s, 1H) |
| 63 | (DMSO): 1.19 (d, 6.04 Hz, 3H), 1.47 (m, 7H), 1.93 (m, 7H), 2.94 (m, 2H), 3.97 (m, 7H), 5.99 (s, 4H), 6.96 (d, 8.80 Hz, 2H), 7.80 (d, 8.80 Hz, 2H), 7.99 (s, 1H) |
| 64 | (DMSO): 1.1 (d, 3H), 1.3 (m, 1H) 1.60 (m, 12H), 1.9 (m, 1H), 2.3 (q, 1H), 2.56 (m, 1H), 2.85 (s, 2H), 3.0 (s, 5H), 3.35 (d, 1H), 3.82 (d, 1H), 4.1 (s, 2H), 6.5 (s, 3H), 7.1 (d, 2H), 7.85 (d, 2H), 8.1 (s, 1H) |
| 65 | (DMSO): 1.06 (t, 7.03 Hz, 2H), 1.21 (d, 3.77 Hz, 3H), 1.45 (s, 1H), 1.58 (s, 5H), 1.70 (s, 6H), 2.00 (m, 1H), 2.66 (s, 1H), 2.88 (s, 1H), 3.01 (s), 3.20 (s, 3H), 3.44 (q, 7.03 Hz, 2H), 3.66 (m, 2H), 4.14 (s, 8H), 4.26 (d, 4.02 Hz, 2H), 7.12 (d, 8.54 Hz, 2H), 7.92 (d, 8.54 Hz, 2H), 8.11 (d, 2.51 Hz, 1H) |
| 66 | (DMSO): 0.86 (m, 6H), 1.24 (m, 9H), 1.48 (m, 2H), 1.67 (m, 1H), 1.78 (s, 2H), 2.02 (s, 3H), 2.58 (m, 1H), 2.83 (d, 5.27 Hz, 1H), 3.11 (m, 2H), 3.34 (d, 1.76 Hz, 1H), 3.98 (s, 2H), 4.12 (d, 3.77 Hz, 2H), 6.53 (m, 4H), 7.09 (m, 2H), 7.90 (m, 2H), 8.12 (s, 1H) |
| 67 | (DMSO): −0.17 (s, 1H), −0.01 (d, 4.28 Hz, 2H), 0.31 (m, 2H), 0.69 (t, 7.42 Hz, 3H), 1.07 (d, 6.29 Hz, 3H), 1.36 (m, 3H), 1.68 (m, 2H), 1.92 (m, 3H), 2.41 (m, 2H), 2.64 (m, 2H), 2.93 (m, 1H), 3.08 (m, 1H), 3.29 (m, 1H), 3.60 (s, 2H), 3.95 (m, 2H), 6.40 (s, 5H), 6.91 (d, 8.80 Hz, 2H), 7.72 (d, 8.55 Hz, 2H), 7.84 (s, 1H) (some signals obscured by solvent) |
| 68 | (CDCl$_3$): 1.04 (d, 6.04 Hz, 3H), 1.24 (d, 5.53 Hz, 12H), 1.60 (m, 8H), 2.02 (m, 2H), 2.61 (m, 2H), |

TABLE I-continued

|   |   |
|---|---|
|   | 3.14 (m, 3H), 3.97 (s, 2H), 4.14 (s, 2H), 6.55 (s, 2H), 7.09 (d, 8.80 Hz, 2H), 7.90 (d, 8.55 Hz, 2H), 8.11 (s, 1H) |
| 69 | (CDCl$_3$): 1.41 (m, 2H), 1.95 (m, 11H), 2.82 (m, 4H), 3.50 (m, 2H), 3.71 (dd, 32.08 and 11.87 Hz, 4H), 4.19 (s, 2H), 4.46 (m, 2H), 6.96 (d, 8.84 Hz, 2H), 7.87 (s, 1H), 7.95 (d, 8.84 Hz, 2H) |
| 70 | (DMSO): 1.06 (s, 1H), 1.21 (d, 6.28 Hz, 3H), 1.44 (m, 3H), 1.59 (m, 4H), 1.81 (m, 2H), 2.06 (m, 1H), 2.72 (m, 4H), 2.98 (m, 2H), 3.42 (m, 2H), 3.69 (s, 2H), 4.13 (s, 3H), 4.28 (t, 5.27 Hz, 2H), 7.12 (d, 8.79 Hz, 2H), 7.92 (d, 8.54 Hz, 2H), 8.08 (s, 1H) |
| 71 | (DMSO): 1.24 (d, 3.77 Hz, 3H), 1.33 (d, 3.85 Hz, 3H), 1.60 (m, 8H), 4.05 (s, 3H), 4.19 (d, 9.82 Hz, 2H), 4.42 (d, 10.02 Hz, 2H), 7.06 (d, 8.49 Hz, 2H), 7.89 (d, 8.51 Hz, 2H), 8.28 (s, 1H) (some signals obscured by solvent) |
| 72 | (DMSO): 1.17 (d, 4.28 Hz, 4H), 1.42 (d, 5.28 Hz, 13H), 1.82 (m, 2H), 3.50 (s, 3H), 3.95 (m, 2H), 6.93 (d, 8.80 Hz, 2H), 7.27 (s, 1H), 7.74 (d, 8.55 Hz, 2H) (some signals obscured by solvent) |
| 73 | (DMSO): 1.51 (d, 4.02 Hz, 9H), 1.72 (t, 6.79 Hz, 2H), 2.33 (m, 12H), 3.54 (s, 2H), 3.89 (s, 2H), 6.84 (d, 8.55 Hz, 2H), 7.18 (s, 1H), 7.65 (d, 8.55 Hz, 2H) |
| 74 | (CDCl$_3$): 1.05 (m, 6H), 1.31 (d, 6.79 Hz, 1H), 1.55 (d, 6.54 Hz, 5H), 2.12 (m, 13H), 2.99 (m, 2H), 3.23 (m, 2H), 3.57 (m, 2H), 4.12 (m, 4H), 6.92 (d, 8.80 Hz, 2H), 7.70 (s, 1H), 7.83 (d, 8.55 Hz, 2H) |
| 75 | (CDCl$_3$): 1.55 (d, 6.54 Hz, 2H), 2.27 (m, 4H), 2.96 (m, 2H), 2.96 (d, 10.31 Hz, 2H), 3.05 (d, 0.75 Hz, 1H), 3.25 (m, 1H), 3.58 (dd, 1.76, 1.13 Hz, 1H), 4.13 (m, 3H), 4.45 (s, 2H), 6.49 (dd, 3.27 and 2.01 Hz, 1H), 6.76 (d, 3.27 Hz, 1H), 6.93 (d, 8.80 Hz, 2H), 7.55 (m, 2H), 7.87 (d, 8.80 Hz, 2H) (some signals obscured by solvent) |
| 76 | (CDCl$_3$): 0.97 (m, 6H), 1.40 (d, 6.54 Hz, 3H), 1.55 (d, 6.54 Hz, 3H), 2.12 (m, 10H), 3.25 (m, 14H), 4.11 (m, 3H), 4.45 (m, 2H), 6.93 (d, 8.55 Hz, 2H), 7.71 (s, 1H), 7.85 (d, 8.80 Hz, 2H) |
| 77 | (CDCl$_3$): 1.43 (m, 1H), 2.02 (m, 9H), 2.31 (m, 2H), 2.68 (m, 2H), 3.24 (m, 4H), 3.74 (m, 4H), 4.11 (t, 5.41 Hz, 2H), 4.43 (s, 2H), 5.13 (m, 4H), 6.91 (d, 8.80 Hz, 2H), 7.51 (s, 1H), 7.84 (d, 8.55 Hz, 2H) |
| 78 | (CDCl$_3$): 1.44 (m, 1H), 1.83 (m, 13H), 2.31 (m, 2H), 2.69 (m, 2H), 3.22 (m, 4H), 3.69 (m, 3H), 4.11 (t, 5.53 Hz, 2H), 4.42 (s, 2H), 6.92 (d, 8.80 Hz, 2H), 7.53 (s, 1H), 7.85 (d, 8.80 Hz, 2H) |
| 79 | (DMSO): 1.42 (d, 6.53 Hz, 3H), 1.67 (m, 2H), 1.80 (s, 4H), 1.94 (m, 2H), 2.22 (m, 3H), 2.95 (m, 2H), 3.06 (m, 2H), 3.60 (m, 1H), 4.17 (t, 5.40 Hz, 2H), 4.39 (d, 4.52 Hz, 2H), 7.10 (d, 8.79 Hz, 2H), 7.91 (d, 8.79 Hz, 2H), 7.98 (s, 1H) (some signals obscured by solvent) |
| 80 | (CDCl$_3$): 1.10 (s, 3H), 1.86 (m, 18H), 2.98 (m, 1H), 3.18 (s, 1H), 3.57 (d, 19.09 Hz, 4H), 3.71 (s, 2H), 4.08 (s, 2H), 6.95 (d, 7.03 Hz, 2H), 7.65 (s, 1H), 7.93 (d, 7.28 Hz, 2H) |
| 81 | (CDCl$_3$): 1.45 (m, 1H), 1.63 (m, 2H), 1.93 (m, 5H), 2.30 (dd, 10.31, 5.53 Hz, 2H), 2.71 (m, 2H), 3.26 (m, 2H), 3.59 (m, 4H), 3.73 (d, 11.57 Hz, 2H), 3.83 (s, 2H), 4.11 (t, 5.53 Hz, 2H), 6.94 (d, 8.80 Hz, 2H), 7.05 (s, 4H), 7.72 (s, 1H), 7.95 (d, 8.80 Hz, 2H) |
| 82 | (CDCl$_3$): 0.86 (m, 3H), 1.09 (d, 6.04 Hz, 4H), 1.26 (s, 5H), 1.43 (m, 4H), 1.69 (m, 8H), 2.09 (m, 7H), 2.47 (s, 3H), 2.66 (m, 2H), 2.78 (m, 2H), 2.98 (m, 1H), 3.18 (m, 1H), 4.07 (m, 2H), 6.95 (d, 8.80 Hz, 2H), 7.44 (s, 1H), 7.93 (d, 8.80 Hz, 2H) |
| 83 | (DMSO): 0.99 (d, 5.78 Hz, 3H), 1.28 (m, 1H), 2.05 (m, 6H), 2.91 (m, 1H), 3.08 (m, 1H), 3.33 (s, 2H), 4.08 (t, 6.15 Hz, 2H), 7.04 (d, 8.54 Hz, 2H), 7.68 (d, 0.50 Hz, 1H), 7.87 (m, 3H) |
| 84 | (CD$_3$CN): 1.34 (d, 6.54 Hz, 3H), 1.46 (d, 12.83 Hz, 2H), 1.71 (m, 4H), 1.95 (m, 2H), 2.15 (m, 4H), 2.82 (s, 2H), 2.97 (m, 1H), 3.28 (m, 2H), 3.46 (m, 3H), 3.70 (m, 1H), 4.06 (m, 4H), 6.97 (d, 8.80 Hz, 2H), 7.11 (m, 3H), 7.23 (m, 2H), 7.86 (m, 3H) |
| 85 | (CD$_3$CN): 1.34 (d, 6.54 Hz, 3H), 1.52 (s, 2H), 1.65 (m, 5H), 1.86 (m, 2H), 2.15 (m, 3H), 3.02 (m, 2H), 4.07 (m, 3H), 4.18 (s, 2H), 6.98 (d, 8.55 Hz, 2H), |

TABLE I-continued

| | | |
|---|---|---|
| | 7.87 (d, 8.55 Hz, 2H), 7.91 (s, 1H) (some signals obscured by solvent) | |
| 86 | (DMSO): 1.37 (m, 2H), 1.49 (m, 5H), 1.62 (m, 6H), 1.85 (m, 3H), 2.26 (m, 2H), 2.40 (m, 10H), 3.03 (m, 2H), 4.08 (m, 2H), 7.05 (d, 8.80 Hz, 2H), 7.87 (d, 8.80 Hz, 2H), 7.94 (s, 1H) (some signals obscured by solvent) | −52.65 |
| 87 | (CDCl$_3$): 1.43 (m, 4H), 1.59 (m, 8H), 1.98 (m, 3H), 2.35 (s, 3H), 2.45 (m, 9H), 3.39 (s, 2H), 4.05 (t, 6.41 Hz, 2H), 6.92 (d, 8.80 Hz, 2H), 7.93 (d, 8.80 Hz, 2H) | |
| 88 | (CDCl$_3$): 1.44 (m, 4H), 1.60 (m, 8H), 1.72 (s, 3H), 2.02 (m, 2H), 2.45 (m, 10H), 3.48 (s, 2H), 4.14 (t, 6.41 Hz, 2H), 7.02 (m, 1H), 7.53 (s, 1H), 7.75 (m, 2H) | |
| 89 | (CDCl$_3$): 1.45 (m, 4H), 1.62 (m, 14H), 2.01 (m, 2H), 2.30 (m, 6H), 2.46 (m, 7H), 2.55 (m, 2H), 3.49 (s, 2H), 3.83 (t, 6.40 Hz, 2H), 7.53 (s, 1H), 7.70 (s, 2H) | |
| 90 | (CDCl$_3$): 1.10 (d, 6.04 Hz, 3H), 1.43 (m, 1H), 2.01 (m, 8H), 2.99 (m, 1H), 3.19 (m, 1H), 3.78 (s, 5H), 4.09 (m, 2H), 4.26 (m, 2H), 6.98 (d, 8.80 Hz, 2H), 7.95 (d, 8.80 Hz, 2H), 8.18 (s, 1H) | |
| 91 | (CDCl$_3$): 1.44 (m, 4H), 1.58 (m, 6H), 1.71 (m, 2H), 1.87 (m, 2H), 2.00 (m, 2H), 2.50 (m, 11H), 3.79 (d, 0.50 Hz, 2H), 4.07 (t, 6.41 Hz, 2H), 4.22 (s, 2H), 6.97 (d, 8.80 Hz, 2H), 7.95 (d, 9.05 Hz, 2H), 8.14 (s, 1H) | |
| 92 | (CDCl$_3$): 1.10 (d, 6.03 Hz, 3H), 1.44 (m, 1H), 2.00 (m, 15H), 2.99 (m, 1H), 3.19 (m, 1H), 3.87 (m, 4H), 4.09 (m, 2H), 6.97 (d, 8.79 Hz, 2H), 7.96 (d, 8.79 Hz, 2H), 8.09 (s, 1H) | |
| 93 | (CDCl$_3$): 1.09 (d, 6.03 Hz, 3H), 1.86 (m, 19H), 2.56 (m, 5H), 2.99 (dt, 12.06 and 7.97 Hz, 1H), 3.18 (dt, 8.54 and 2.51 Hz, 1H), 3.80 (s, 2H), 4.09 (m, 2H), 4.23 (s, 2H), 6.97 (d, 8.79 Hz, 2H), 7.96 (d, 9.04 Hz, 2H), 8.14 (s, 1H) | |
| 94 | (DMSO): 1.09 (d, 6.03 Hz, 3H), 1.60 (m, 9H), 1.87 (m, 4H), 2.21 (m, 4H), 3.03 (m, 3H), 3.82 (d, 14.07 Hz, 1H), 4.08 (m, 2H), 7.05 (d, 8.79 Hz, 2H), 7.87 (d, 8.79 Hz, 2H), 7.94 (s, 1H) (some signals obscured by solvent) | |
| 95 | (CDCl$_3$): 1.08 (d, 6.04 Hz, 3H), 1.43 (m, 3H), 1.61 (m, 4H), 1.99 (m, 9H), 2.49 (m, 4H), 2.98 (s, 1H), 3.48 (s, 2H), 4.15 (m, 2H), 7.01 (m, 1H), 7.53 (s, 1H), 7.77 (s, 2H) | |
| 96 | (CDCl$_3$): 1.09 (d, 6.03 Hz, 3H), 1.43 (m, 1H), 1.74 (m, 9H), 2.11 (m, 6H), 2.43 (s, 3H), 2.98 (m, 1H), 3.17 (d, 2.26 Hz, 1H), 3.68 (m, 4H), 4.09 (m, 2H), 6.97 (d, 9.04 Hz, 2H), 7.95 (d, 8.79 Hz, 2H) | |
| 97 | (CDCl$_3$): 0.29 (s, 2H), 0.59 (d, 6.53 Hz, 2H), 0.96 (t, 7.41 Hz, 3H), 1.09 (d, 6.03 Hz, 3H), 1.74 (m, 5H), 2.14 (m, 6H), 2.48 (s, 3H), 2.98 (dt, 12.06 and 8.04 Hz, 1H), 3.17 (m, 1H), 3.42 (d, 6.78 Hz, 2H), 3.56 (t, 7.28 Hz, 2H), 4.09 (m, 2H), 6.98 (d, 8.79 Hz, 2H), 7.95 (d, 8.79 Hz, 2H) | |
| 98 | (CDCl$_3$): 1.02 (d, 6.04 Hz, 3H), 1.19 (s, 0H), 1.36 (m, 1H), 1.46 (m, 2H), 1.64 (m, 6H), 1.90 (m, 3H), 2.03 (m, 3H), 2.16 (m, 1H), 2.24 (m, 1H), 2.48 (s, 3H), 2.92 (m, 1H), 3.11 (m, 1H), 4.03 (m, 2H), 4.31 (h, 7.07 Hz, 1H), 6.06 (d, 7.55 Hz, 1H), 6.91 (d, 9.05 Hz, 2H), 7.90 (d, 9.05 Hz, 2H) | |
| 99 | (CDCl$_3$): 1.28 (d, 6.53 Hz, 1H), 1.55 (d, 6.28 Hz, 3H), 2.25 (m, 3H), 2.39 (m, 1H), 2.96 (m, 2H), 3.20 (m, 1H), 3.88 (s, 3H), 4.07 (m, 3H), 4.24 (s, 2H), 4.35 (s, 2H), 6.91 (d, 7.53 Hz, 2H), 7.36 (d, 2.26 Hz, 3H), 7.44 (m, 2H), 8.01 (m, 2H) | |
| 100 | (CDCl$_3$): 1.09 (d, 6.03 Hz, 3H), 1.43 (m, 1H), 1.74 (m, 2H), 1.97 (m, 3H), 2.12 (d, 8.79 Hz, 1H), 2.25 (m, 2H), 2.76 (s, 3H), 2.98 (d, 11.80 Hz, 1H), 3.18 (d, 2.51 Hz, 1H), 3.88 (s, 3H), 4.09 (m, 2H), 6.95 (d, 8.79 Hz, 2H), 7.89 (d, 8.79 Hz, 2H) | |
| 101 | (DMSO): 1.04 (d, 6.03 Hz, 3H), 1.34 (s, 1H), 1.54 (m, 3H), 1.69 (m, 6H), 1.92 (m, 3H), 2.27 (m, 2H), 3.00 (m, 6H), 4.13 (m, 4H), 7.09 (m, 2H), 7.91 (m, 2H) | |
| 102 | (CDCl$_3$): 0.32 (m, 2H), 0.55 (m, 2H), 0.95 (s, 3H), 1.11 (d, 6.03 Hz, 4H), 1.44 (m, 1H), 1.76 (m, 4H), 1.94 (m, 1H), 2.03 (m, 2H), 2.15 (q, 8.85 Hz, 1H), 2.24 (m, 1H), 2.34 (m, 1H), 3.00 (dt, 11.80 and 8.04 Hz, | |

TABLE I-continued

| | | |
|---|---|---|
| | 1H), 3.20 (m, 1H), 3.48 (m, 2H), 3.85 (m, 2H), 4.09 (m, 2H), 6.98 (d, 8.79 Hz, 2H), 7.95 (d, 8.54 Hz, 2H), 8.14 (s, 1H) | |
| 103 | (CDCl$_3$): 1.10 (d, 6.03 Hz, 2H), 1.44 (m, 1H), 1.56 (m, 1H), 1.72 (m, 4H), 2.03 (m, 5H), 2.23 (m, 1H), 2.32 (m, 1H), 2.99 (m, 1H), 3.19 (t, 8.41 Hz, 1H), 4.10 (t, 6.03 Hz, 1H), 4.39 (m, 1H), 6.98 (d, 8.04 Hz, 2H), 7.96 (d, 8.04 Hz, 1H), 8.16 (s, 1H) (some signals obscured by solvent) | |
| 104 | (CDCl$_3$): 1.09 (d, 6.03 Hz, 3H), 1.43 (m, 1H), 1.74 (m, 2H), 1.96 (m, 4H), 2.12 (q, 8.79 Hz, 1H), 2.22 (m, 1H), 2.30 (m, 1H), 2.98 (m, 1H), 3.17 (m, 1H), 4.09 (m, 2H), 4.60 (d, 6.03 Hz, 2H), 6.96 (m, 2H), 7.03 (m, 2H), 7.34 (m, 3H), 7.93 (m, 2H), 8.21 (m, 1H) | |
| 105 | (CDCl$_3$): 1.01 (d, 6.04 Hz, 3H), 1.34 (m, 1H), 1.66 (m, 3H), 1.88 (m, 3H), 2.04 (q, 8.93 Hz, 1H), 2.13 (m, 1H), 2.22 (m, 1H), 2.51 (s, 3H), 2.89 (m, 1H), 3.09 (td, 8.55 and 2.52 Hz, 1H), 4.01 (m, 2H), 4.57 (d, 5.79 Hz, 2H), 6.47 (t, 5.41 Hz, 1H), 6.88 (d, 8.80 Hz, 2H), 7.26 (m, 2H), 7.31 (m, 4H), 7.87 (d, 8.80 Hz, 2H) | |
| 106 | (CDCl$_3$): 1.09 (d, 6.04 Hz, 3H), 1.43 (m, 3H), 1.75 (m, 9H), 2.01 (m, 2H), 2.14 (m, 1H), 2.26 (m, 2H), 2.45 (s, 3H), 2.57 (m, 5H), 2.99 (m, 1H), 3.18 (d, 2.52 Hz, 1H), 3.79 (d, 4.02 Hz, 4H), 4.09 (m, 2H), 6.98 (d, 8.80 Hz, 2H), 7.94 (d, 8.80 Hz, 2H) | |
| 107 | (CDCl$_3$): 1.10 (d, 6.03 Hz, 3H), 1.45 (m, 1H), 1.75 (m, 3H), 1.98 (m, 7H), 2.22 (m, 3H), 3.00 (m, 1H), 3.20 (m, 1H), 3.66 (t, 6.78 Hz, 2H), 4.07 (m, 4H), 6.97 (d, 9.04 Hz, 2H), 7.97 (d, 8.79 Hz, 2H), 8.18 (s, 1H) | |
| 108 | (CDCl$_3$): 1.10 (d, 6.03 Hz, 3H), 1.43 (m, 1H), 1.83 (m, 3H), 2.03 (m, 2H), 2.15 (m, 1H), 2.28 (m, 2H), 2.47 (s, 3H), 2.99 (m, 1H), 3.19 (td, 8.79 and 2.57 Hz, 1H), 3.78 (m, 8H), 4.10 (m, 2H), 6.98 (d, 8.79 Hz, 2H), 7.94 (d, 8.79 Hz, 2H) | |
| 109 | (CDCl$_3$): 1.09 (m, 3H), 1.42 (m, 1H), 1.81 (m, 4H), 2.01 (m, 2H), 2.11 (m, 1H), 2.22 (d, 6.05 Hz, 1H), 2.30 (m, 1H), 2.47 (d, 1.28 Hz, 3H), 2.98 (m, 1H), 3.18 (t, 8.43 Hz, 1H), 3.70 (m, 8H), 4.09 (t, 6.23 Hz, 2H), 6.98 (m, 2H), 7.93 (m, 2H) | −45.65 |
| 110 | (CDCl$_3$): 1.09 (d, 6.05 Hz, 3H), 1.42 (m, 1H), 1.74 (m, 2H), 1.96 (m, 3H), 2.12 (q, 8.79 Hz, 1H), 2.21 (m, 1H), 2.29 (m, 1H), 2.47 (s Hz, 3H), 2.98 (dt, 11.91, 8.06 Hz, 1H), 3.18 (m, 1H), 3.79 (s Hz, 8H), 4.09 (m, 2H), 6.98 (d, 8.79 Hz, 2H), 7.93 (d, 8.98 Hz, 2H) | +47.03 |
| 111 | (CDCl$_3$): 1.10 (d, 6.03 Hz, 3H), 1.45 (m, 5H), 1.81 (m, 8H), 2.03 (m, 2H), 2.19 (m, 5H), 2.33 (m, 1H), 2.59 (m, 8H), 2.99 (m, 1H), 3.19 (d, 1.76 Hz, 1H), 3.62 (s, 2H), 4.07 (m, 2H), 6.93 (d, 8.79 Hz, 2H), 7.93 (d, 8.79 Hz, 2H) | |
| 112 | (CDCl$_3$): −0.01 (d, 5.02 Hz, 2H), 0.38 (m, 2H), 0.75 (t, 7.41 Hz, 4H), 0.95 (d, 6.03 Hz, 3H), 1.30 (m, 1H), 1.39 (m, 2H), 1.60 (m, 2H), 1.82 (m, 4H), 1.98 (q, 8.85 Hz, 1H), 2.07 (m, 4H), 2.17 (d, 7.03 Hz, 1H), 2.26 (d, 6.53 Hz, 2H), 2.36 (m, 2H), 2.84 (m, 1H), 3.04 (td, 8.54, 2.45 Hz, 1H), 3.64 (s, 2H), 3.93 (m, 2H), 6.80 (d, 8.79 Hz, 2H), 7.77 (d, 8.79 Hz, 2H) | |
| 113 | (CDCl$_3$): 1.09 (d, 6.03 Hz, 3H), 1.43 (m, 1H), 1.75 (m, 4H), 1.97 (m, 3H), 2.17 (m, 5H), 2.30 (m, 1H), 2.98 (m, 1H), 3.18 (m, 1H), 3.82 (d, 3.77 Hz, 4H), 4.08 (m, 2H), 6.95 (d, 8.79 Hz, 2H), 7.34 (d, 4.27 Hz, 4H), 7.93 (d, 8.79 Hz, 2H) | |
| 114 | (CDCl$_3$): 1.09 (d, 6.03 Hz, 3H), 1.44 (m, 3H), 1.96 (m, 12H), 2.48 (s, 4H), 2.98 (m, 1H), 3.17 (td, 8.54, 2.70 Hz, 1H), 3.48 (s, 2H), 3.94 (s, 3H), 4.14 (m, 2H), 6.94 (d, 8.29 Hz, 1H), 7.53 (s, 1H), 7.58 (m, 2H) | |
| 115 | | |
| 116 | (CDCl$_3$): 1.65 (dd, 6.03 and 1.00 Hz, 3H), 1.95 (m, 3H), 2.10 (m, 2H), 2.41 (m, 11H), 2.68 (d, 8.79 Hz, 1H), 2.78 (m, 4H), 2.86 (m, 1H), 3.54 (m, 1H), 3.70 (m, 2H), 4.36 (s, 2H), 4.64 (m, 2H), 7.49 (m, 2H), 8.48 (m, 2H) | |
| 117 | (CDCl$_3$): 1.71 (d, 6.03 Hz, 3H), 2.06 (m, 3H), 2.22 (m, 4H), 2.37 (m, 3H), 2.57 (m, 4H), 2.74 (q, 8.79 Hz, 1H), 2.87 (m, 2H), 3.10 (s, 4H), 3.60 (m, 1H), 3.80 (m, 1H), 4.03 (s, 2H), 4.69 (m, 2H), 7.55 (d, | |

TABLE I-continued

| | | |
|---|---|---|
| | 8.79 Hz, 2H), 8.55 (d, 8.79 Hz, 2H) | |
| 118 | (DMSO): 1.23 (d, 6.53 Hz, 3H), 1.40 (d, 4.52 Hz, 2H), 1.54 (m, 5H), 1.85 (m, 2H), 2.08 (m, 3H), 2.77 (m, 2H), 3.07 (m, 1H), 3.23 (m, 1H), 3.45 (m, 1H), 4.12 (t, 6.03 Hz, 2H), 7.08 (d, 8.79 Hz, 2H), 7.90 (d, 8.79 Hz, 2H), 8.01 (s, 1H) (some signals obscured by solvent) | −20.99 |
| 119 | (DMSO): 1.21 (d, 6.28 Hz, 3H), 1.40 (d, 4.77 Hz, 2H), 1.54 (m, 5H), 1.82 (m, 2H), 2.06 (m, 3H), 2.71 (m, 2H), 2.99 (d, 7.03 Hz, 1H), 3.20 (dd, 8.29 and 4.40 Hz, 1H), 3.41 (dd, 5.78 and 4.27 Hz, 1H), 3.52 (s, 2H), 4.12 (t, 6.15 Hz, 2H), 6.56 (s, 3H), 7.08 (d, 8.79 Hz, 2H), 7.89 (d, 8.54 Hz, 2H), 8.00 (s, 1H) | +20.79 |
| 120 | (CDCl$_3$): 1.15 (d, 6.03 Hz, 3H), 1.51 (m, 1H), 1.79 (m, 2H), 1.96 (m, 1H), 2.07 (m, 2H), 2.28 (m, 2H), 2.44 (d, 6.03 Hz, 1H), 2.56 (m, 4H), 3.04 (m, 1H), 3.26 (m, 1H), 3.51 (s, 2H), 3.75 (m, 4H), 4.09 (m, 2H), 6.95 (d, 8.79 Hz, 2H), 7.54 (s, 1H), 7.97 (d, 8.79 Hz, 2H) | |
| 121 | (CDCl$_3$): 1.14 (d, 6.03 Hz, 3H), 1.46 (m, 3H), 1.62 (m, 4H), 1.77 (m, 2H), 1.93 (m, 1H), 2.29 (q, 8.85 Hz, 2H), 2.49 (m, 6H), 2.68 (m, 2H), 2.80 (m, 2H), 3.23 (m, 2H), 4.15 (m, 2H), 6.95 (d, 8.79 Hz, 2H), 7.44 (s, 1H), 7.93 (d, 8.54 Hz, 2H) | |
| 122 | (DMSO): 1.12 (d, 6.28 Hz, 3H), 1.47 (m, 1H), 1.77 (m, 6H), 1.95 (m, 1H), 2.05 (m, 2H), 2.22 (m, 3H), 2.39 (m, 3H), 3.01 (dt, 12.06, 8.04 Hz, 1H), 3.22 (td, 8.79 and 2.70 Hz, 1H), 3.49 (m, 2H), 4.08 (td, 6.28 and 2.89 Hz, 2H), 4.51 (s, 2H), 6.95 (m, 2H), 7.59 (s, 1H), 7.93 (m, 2H) | |
| 123 | (CDCl$_3$): 1.16 (d, 6.03 Hz, 3H), 1.50 (m, 1H), 1.77 (m, 5H), 1.90 (m, 3H), 2.20 (m, 7H), 2.51 (m, 7H), 2.83 (dd, 12.31 and 5.53 Hz, 1H), 3.04 (m, 1H), 3.26 (m, 1H), 3.86 (m, 1H), 4.09 (m, 2H), 4.27 (d, 15.32 Hz, 1H), 4.83 (d, 15.32 Hz, 1H), 6.95 (m, 2H), 7.54 (s, 1H), 7.93 (m, 2H) | |
| 124 | (CDCl$_3$): 1.09 (d, 6.28 Hz, 3H), 1.43 (m, 3H), 1.61 (m, 4H), 1.81 (m, 5H), 2.09 (m, 3H), 2.29 (m, 2H), 2.48 (s, 4H), 3.04 (dt, 12.06 and 7.97 Hz, 1H), 3.19 (m, 1H), 3.48 (s, 2H), 4.16 (t, 6.15 Hz, 2H), 6.98 (d, 8.79 Hz, 1H), 7.53 (s, 1H), 7.88 (dd, 8.54, 2.01 Hz, 1H), 8.07 (d, 2.01 Hz, 1H) | |
| 125 | (DMSO): 0.88 (dd, 16.85, 5.86 Hz, 6H), 1.39 (m, 3H), 1.54 (m, 7H), 1.83 (m, 2H), 2.05 (m, 3H), 2.68 (m, 2H), 3.19 (d, 0.55 Hz, 1H), 3.41 (m, 1H), 3.52 (s, 2H), 4.12 (t, 5.77 Hz, 2H), 6.56 (s, 4H), 7.07 (d, 8.79 Hz, 2H), 7.89 (d, 8.79 Hz, 2H), 8.00 (s, 1H) | |
| 126 | (DMSO): 1.35 (d, 6.28 Hz, 3H), 1.63 (dd, 12.56, 8.29 Hz, 1H), 1.96 (m, 2H), 2.20 (m, 3H), 2.67 (s, 3H), 3.07 (d, 8.04 Hz, 2H), 3.41 (m, 2H), 3.57 (d, 0.75 Hz, 1H), 4.25 (t, 5.53 Hz, 2H), 7.25 (d, 8.79 Hz, 1H), 7.96 (d, 8.29 Hz, 1H), 8.17 (d, 1.26 Hz, 1H) | |
| 127 | (CDCl$_3$): 1.45 (m, 2H), 1.58 (m, 12H), 1.98 (m, 2H), 2.41 (m, 6H), 2.46 (d, 7.69 Hz, 2H), 3.46 (m, 2H), 3.59 (m, 2H), 3.80 (s, 2H), 4.04 (t, 6.41 Hz, 2H), 6.91 (m, 2H), 7.81 (m, 2H) | |
| 128 | (CDCl$_3$): 1.09 (d, 6.05 Hz, 3H), 1.42 (m, 1H), 1.74 (m, 3H), 1.97 (m, 3H), 2.12 (q, 8.79 Hz, 1H), 2.26 (m, 2H), 2.99 (m, 1H), 3.18 (m, 1H), 3.67 (s, 2H), 4.11 (t, 6.32 Hz, 2H), 4.11 (m), 7.00 (m, 4H), 7.49 (m, 2H), 7.58 (s, 1H), 7.98 (d, 8.61 Hz, 2H), 9.13 (s, 1H) | |
| 129 | (DMSO): 0.88 (t, 7.42 Hz, 3H), 1.41 (m, 3H), 1.56 (m, 5H), 1.80 (m, 3H), 2.05 (m, 3H), 2.58 (d, 0.37 Hz, 4H), 2.77 (m, 4H), 3.22 (m, 1H), 3.57 (s, 2H), 4.12 (t, 6.14 Hz, 2H), 6.56 (s, 4H), 7.07 (d, 8.79 Hz, 2H), 7.89 (d, 8.61 Hz, 2H), 8.02 (s, 1H) | |
| 130 | (CDCl$_3$): 0.93 (m, 3H), 1.09 (d, 5.86 Hz, 3H), 1.50 (m, 13H), 2.02 (m, 6H), 2.21 (m, 1H), 2.30 (m, 1H), 2.85 (m, 1H), 3.00 (m, 2H), 3.18 (m, 1H), 3.49 (s, 2H), 4.07 (m, 2H), 6.95 (d, 8.61 Hz, 2H), 7.52 (s, 1H), 7.96 (d, 8.61 Hz, 2H) | |
| 131 | (CDCl$_3$): 1.09 (d, 6.03 Hz, 3H), 1.43 (m, 1H), 1.75 (m, 6H), 2.11 (m, 12H), 2.57 (m, 6H), 2.79 (m, 1H), 2.99 (m, 1H), 3.18 (m, 1H), 3.69 (s, 1H), 3.99 (m, 1H), 4.09 (t, 6.03 Hz, 2H), 5.30 (s, 1H), 6.97 (d, 8.79 Hz, 2H), 7.96 (d, 8.54 Hz, 2H), 8.19 (d, 17.58 Hz, 1H) | |

TABLE I-continued 132 (CDCl₃): 1.09 (d, 6.03 Hz, 3H), 1.43 (m, 1H), 1.74 (m, 2H), 1.96 (m, 4H), 2.12 (q, 8.79 Hz, 1H), 2.25 (m, 2H), 2.98 (m, 1H), 3.18 (td, 8.54 and 2.76 Hz, 1H), 3.69 (m, 10H), 4.08 (m, 2H), 6.95 (d, 8.79 Hz, 2H), 7.64 (s, 1H), 7.91 (d, 8.79 Hz, 2H)

133 (CDCl₃): 1.09 (d, 6.03 Hz, 3H), 1.42 (m, 3H), 1.81 (m, 12H), 2.12 (q, 8.79 Hz, 1H), 2.21 (m, 1H), 2.30 (m, 1H), 2.98 (m, 1H), 3.18 (m, 1H), 3.49 (s, 2H), 4.09 (m, 2H), 4.21 (m, 1H), 6.86 (d, 4.77 Hz, 1H), 6.98 (d, 8.79 Hz, 2H), 7.53 (s, 1H), 7.93 (m, 2H)

134 (CDCl₃): 0.26 (t, 5.15 Hz, 2H), 0.55 (m, 2H), 0.92 (m, 3H), 1.09 (d, 6.03 Hz, 3H), 1.43 (m, 1H), 1.69 (m, 4H), 1.96 (m, 4H), 2.13 (m, 1H), 2.26 (m, 2H), 2.98 (m, 1H), 3.18 (m, 1H), 3.30 (m, 2H), 3.41 (q, 7.72 Hz, 2H), 3.73 (d, 4.02 Hz, 2H), 4.08 (m, 2H), 6.95 (d, 8.54 Hz, 2H), 7.69 (d, 5.27 Hz, 1H), 7.93 (dd, 8.79 and 2.76 Hz, 2H)

135 (CDCl₃): 1.09 (d, 6.03 Hz, 3H), 1.42 (m, 1H), 1.58 (d, 2.76 Hz, 4H), 1.73 (m, 6H), 1.95 (m, 4H), 2.12 (q, 8.79 Hz, 1H), 2.25 (m, 2H), 2.98 (dt, 11.80 and 8.04 Hz, 1H), 3.18 (td, 8.54 and 2.45 Hz, 1H), 3.57 (m, 4H), 3.72 (s, 2H), 4.08 (m, 2H), 6.95 (d, 8.79 Hz, 2H), 7.70 (s, 1H), 7.93 (d, 8.79 Hz, 2H)

136 (CDCl₃): 1.47 (d, 5.02 Hz, 5H), 1.63 (m, 10H), 2.04 (d, 7.28 Hz, 1H), 2.48 (m, 14H), 2.92 (t, 7.66 Hz, 2H), 4.05 (t, 6.28 Hz, 2H), 6.90 (d, 8.79 Hz, 2H), 7.79 (d, 8.79 Hz, 2H)

137 (CDCl₃): 1.16 (d, 5.86 Hz, 3H), 1.51 (m, 1H), 1.79 (m, 3H), 1.97 (m, 1H), 2.11 (m, 3H), 2.41 (m, 10H), 2.69 (dd, 12.82 and 6.60 Hz, 1H), 3.05 (m, 1H), 3.26 (s, 1H), 3.70 (t, 4.58 Hz, 4H), 3.95 (m, 1H), 4.09 (m, 2H), 4.38 (d, 15.39 Hz, 1H), 4.85 (d, 15.21 Hz, 1H), 6.95 (d, 8.79 Hz, 2H), 7.55 (s, 1H), 7.91 (d, 8.98 Hz, 2H)

138 (CDCl₃): 0.95 (m, 3H), 1.48 (m, 16H), 1.98 (m, 3H), 2.48 (d, 7.28 Hz, 6H), 2.80 (dd, 10.80, 1.76 Hz, 1H), 2.96 (d, 11.05 Hz, 1H), 3.48 (s, 2H), 4.05 (t, 6.40 Hz, 2H), 6.94 (d, 8.79 Hz, 2H), 7.52 (s, 1H), 7.96 (d, 8.79 Hz, 2H)

139 (DMSO): 1.35 (d, 6.53 Hz, 3H), 1.61 (m, 1H), 2.06 (m, 4H), 3.13 (dd, 10.30 and 8.16 Hz, 1H), 3.63 (dd, 11.80 and 5.78 Hz, 1H), 4.14 (m, 3H), 4.30 (d, 5.53 Hz, 2H), 7.09 (d, 8.79 Hz, 2H), 7.90 (m, 2H) (some signals obscured by solvent)

140 (CDCl₃): 1.35 (d, 6.53 Hz, 3H), 1.61 (m, 1H), 2.07 (m, 6H), 3.12 (m, 3H), 3.65 (m, 4H), 4.15 (m, 4H), 6.14 (dd, 8.04 and 1.76 Hz, 1H), 6.25 (d, 8.29 Hz, 2H), 6.97 (t, 8.04 Hz, 1H), 7.09 (d, 8.79 Hz, 2H), 7.91 (d, 8.79 Hz, 2H), 7.96 (s, 1H), 9.34 (m, 1H)

141 (CDCl₃): 1.35 (d, 6.53 Hz, 3H), 1.61 (m, 1H), 2.06 (m, 6H), 2.54 (s, 2H), 3.12 (m, 2H), 4.14 (m, 4H), 6.65 (dd, 9.04 and 4.65 Hz, 2H), 6.90 (m, 2H), 7.09 (d, 8.79 Hz, 2H), 7.91 (d, 8.79 Hz, 2H), 7.96 (s, 1H)

142

143 (CDCl₃): 1.09 (d, 6.05 Hz, 3H), 1.43 (m, 1H), 1.86 (m, 6H), 2.12 (q, 8.79 Hz, 1H), 2.21 (s, 4H), 2.30 (m, 1H), 2.52 (m, 4H), 2.98 (m, 1H), 3.18 (m, 1H), 3.58 (s, 2H), 3.73 (m, 4H), 4.07 (m, 2H), 6.94 (d, 8.98 Hz, 2H), 7.94 (d, 8.98 Hz, 2H)

144 (CDCl₃): 1.09 (d, 6.03 Hz, 3H), 1.43 (m, 1H), 1.70 (m, 5H), 1.97 (m, 5H), 2.13 (m, 1H), 2.23 (m, 1H), 2.35 (m, 3H), 2.48 (m, 4H), 2.57 (dd, 12.56 and 5.15 Hz, 1H), 2.75 (m, 1H), 2.98 (m, 1H), 3.16 (m, 2H), 3.51 (d, 14.07 Hz, 1H), 3.70 (m, 3H), 4.08 (m, 3H), 6.95 (d, 9.04 Hz, 2H), 7.52 (s, 1H), 7.95 (d, 8.79 Hz, 2H)

145 (DMSO): 1.36 (d, 6.53 Hz, 3H), 1.64 (m, 4H), 1.83 (m, 2H), 1.96 (m, 2H), 2.17 (m, 3H), 2.34 (s, 8H), 3.04 (m, 4H), 3.64 (m, 2H), 4.18 (m, 2H), 4.31 (d, 4.52 Hz, 2H), 7.00 (dd, 8.79 and 2.26 Hz, 1H), 7.09 (m, 1H), 7.96 (t, 8.79 Hz, 1H), 8.39 (s, 1H), 9.22 (m, 1H), 9.61 (m, 1H) (some signals obscured by solvent)

146 (CDCl₃): 1.09 (d, 5.86 Hz, 3H), 1.43 (m, 1H), 1.74 (m, 3H), 2.02 (m, 9H), 2.26 (m, 2H), 2.65 (t, 5.04 Hz, 4H), 2.98 (m, 1H), 3.18 (m, 1H), 3.55 (s, 2H), 4.08 (m, 2H), 6.95 (d, 8.98 Hz, 2H), 7.53 (s, 1H), 7.97 (d, 8.79 Hz, 2H)

TABLE I-continued

| | | |
|---|---|---|
| 147 | (CDCl$_3$): 1.10 (d, 6.03 Hz, 3H), 1.42 (m, 1H), 1.85 (m, 5H), 2.16 (m, 2H), 2.30 (m, 1H), 2.49 (s, 3H), 2.98 (m, 1H), 3.19 (d, 2.01 Hz, 1H), 3.70 (m, 8H), 4.41 (t, 6.40 Hz, 2H), 6.80 (d, 8.79 Hz, 1H), 8.09 (dd, 8.79, 2.26 Hz, 1H), 8.66 (d, 2.26 Hz, 1H) | |
| 148 | (CDCl$_3$): 1.09 (d, 6.03 Hz, 3H), 1.43 (m, 3H), 1.69 (m, 6H), 1.94 (m, 3H), 2.10 (q, 8.85 Hz, 1H), 2.25 (m, 2H), 2.47 (s, 4H), 3.02 (m, 1H), 3.15 (m, 1H), 3.47 (s, 2H), 4.27 (t, 6.15 Hz, 2H), 7.58 (m, 3H) | |
| 149 | (CDCl$_3$): 1.09 (d, 6.03 Hz, 3H), 1.43 (m, 1H), 1.91 (m, 10H), 2.21 (m, 1H), 2.30 (m, 1H), 2.48 (s, 3H), 2.98 (dt, 11.80, 8.04 Hz, 1H), 3.18 (td, 8.54, 2.76 Hz, 1H), 3.77 (t, 5.02 Hz, 4H), 4.08 (m, 2H), 6.95 (d, 8.79 Hz, 2H), 7.83 (d, 8.79 Hz, 2H) | |
| 150 | (CDCl$_3$): 1.09 (d, 6.05 Hz, 3H), 1.42 (m, 1H), 1.74 (m, 2H), 1.91 (m, 1H), 2.07 (m, 7H), 2.20 (m, 1H), 2.29 (m, 1H), 2.48 (s Hz, 3H), 2.98 (m, 1H), 3.18 (td, 8.61, 2.56 Hz, 1H), 3.77 (s Hz, 4H), 4.08 (m, 2H), 6.95 (d, 8.79 Hz, 2H), 7.83 (d, 8.79 Hz, 2H) | +41.98 |
| 151 | (CDCl$_3$): 1.09 (d, 6.05 Hz, 3H), 1.42 (m, 1H), 1.74 (m, 2H), 2.01 (m, 8H), 2.21 (m, 1H), 2.29 (m, 1H), 2.48 (s Hz, 3H), 2.99 (m, 1H), 3.18 (td, 8.61, 2.52 Hz, 1H), 3.77 (s Hz, 4H), 4.08 (m, 2H), 6.95 (d, 8.79 Hz, 2H), 7.83 (d, 8.79 Hz, 2H) | −40.65 |
| 152 | (CDCl$_3$): 1.10 (d, 6.03 Hz, 3H), 1.45 (m, 1H), 1.87 (m, 5H), 2.15 (q, 8.79 Hz, 1H), 2.24 (m, 1H), 2.34 (m, 1H), 2.48 (s, 3H), 3.00 (m, 1H), 3.20 (m, 1H), 3.70 (m, 8H), 4.08 (m, 2H), 6.94 (d, 8.79 Hz, 2H), 7.83 (d, 8.79 Hz, 2H) | |
| 153 | (CDCl$_3$): 1.09 (dd, 6.05, 0.92 Hz, 3H), 1.43 (m, 1H), 1.74 (m, 2H), 1.96 (m, 3H), 2.12 (q, 8.79 Hz, 1H), 2.21 (m, 1H), 2.30 (m, 1H), 2.48 (s, 3H), 2.98 (m, 1H), 3.18 (m, 1H), 3.70 (m, 8H), 4.08 (m, 2H), 6.94 (dd, 8.43, 1.01 Hz, 2H), 7.83 (dd, 8.43, 1.01 Hz, 2H) | −38.05 |
| 154 | (CDCl$_3$): 1.10 (d, 6.05 Hz, 3H), 1.44 (m, 1H), 1.75 (m, 2H), 1.97 (m, 3H), 2.13 (q, 8.84 Hz, 1H), 2.22 (m, 1H), 2.31 (m, 1H), 2.48 (s, 3H), 2.99 (m, 1H), 3.19 (m, 1H), 3.70 (m, 8H), 4.08 (m, 2H), 6.95 (dd, 8.43, 1.01 Hz, 2H), 7.83 (dd, 8.43, 1.01 Hz, 2H) | +39.08 |
| 155 | (CDCl$_3$): 1.09 (d, 6.03 Hz, 3H), 1.44 (m, 3H), 1.64 (m, 6H), 1.96 (m, 3H), 2.12 (d, 9.04 Hz, 1H), 2.25 (m, 2H), 2.52 (s, 4H), 2.63 (s, 3H), 2.97 (m, 1H), 3.18 (td, 8.79, 2.57 Hz, 1H), 3.52 (s, 2H), 4.06 (m, 2H), 6.79 (m, 2H), 7.55 (s, 1H), 7.89 (d, 9.29 Hz, 1H) | |
| 156 | (CDCl$_3$): 1.55 (d, 6.53 Hz, 3H), 2.01 (m, 4H), 2.25 (m, 3H), 2.43 (m, 6H), 2.90 (m, 1H), 3.03 (m, 1H), 3.21 (m, 1H), 3.37 (t, 7.16 Hz, 2H), 3.54 (td, 11.55, 4.58 Hz, 1H), 4.07 (m, 5H), 4.59 (s Hz, 2H), 6.90 (d, 8.79 Hz, 2H), 7.82 (d, 8.79 Hz, 2H) | |

Example 25

Affinity for the Histamine H$_3$-Receptor; Inverse Agonism, Antagonism and Agonism Activity: [$^{35}$S]GTPγS-Binding Assay Human Histamine H$_3$-Receptor Material and Methods Reagents Reagents and reference compounds were of analytical grade and obtained from various commercial sources. [$^3$H]-N-α-methylhistamine (80-85 Ci/mmol) and [$^{35}$S]-GTPγS (1250 Ci/mmol) were purchased from Perkin Elmer (Belgium). Cell culture reagents were purchased from Cambrex (Belgium).

Test and reference compounds were dissolved in 100% DMSO to give a 1 mM stock solution. Final DMSO concentration in the assay did not exceed 1%.

A CHO cell line expressing the human H$_3$ histamine receptor (sequence as published by Lovenberg et al. in Mol. Pharmacol. 1999, 55, 1101-1107) was purchased from Euroscreen S.A. (Belgium).

Cell Culture

Cells were grown in HAM-F 12 culture media containing 10% fetal bovine serum, 100 IU/ml penicillin, 100 μg/ml streptomycin, 1% sodium pyruvate and 400 μg/ml of gentamycin. Cells were maintained at 37° C. in a humidified atmosphere composed of 95% air and 5% CO$_2$.

Membrane Preparation

Confluent cells were detached by 10 min incubation at 37° C. in PBS/EDTA 0.02%. The cell suspension was centrifuged at 1,500×g for 10 min at 4° C. The pellet was homogenized in a 15 mM Tris-HCl buffer (pH 7.5) containing 2 mM MgCl$_2$, 0.3 mM EDTA, 1 mM EGTA (buffer A). The crude homogenate was frozen in liquid nitrogen and thawed. DNAse (1 μl/ml) was then added and the homogenate was further incubated for 10 min at 25° C. before being centrifuged at 40,000×g for 25 min at 4° C. The pellet was resuspended in buffer A and washed once more under the same conditions. The final membrane pellet was resuspended, at a protein concentration of 1-3 mg/ml, in a 7.5 mM Tris-HCl buffer (pH 7.5) enriched with 12.5 mM MgCl$_2$, 0.3 mM EDTA, 1 mM EGTA and 250 mM sucrose and stored in liquid nitrogen until used.

Binding Assays

[$^3$H]-N-α-methylhistamine binding assay

Affinity of compounds for human H$_3$ histamine receptors was measured by competition with [$^3$H]-N-α-methylhistamine. This binding assay was performed essentially as described by Lovenberg et al. (Mol. Pharmacol. 1999, 55, 1101-1107) and Tedford et al. (J. Pharmacol. Exper. Ther. 1999, 289, 1160-1168) with minor modifications. Briefly, membranes (20-40 μg proteins) expressing human H$_3$ histamine receptors were incubated at 25° C. in 0.5 ml of a 50 mM Tris-HCl buffer (pH 7.4) containing 2 mM MgCl$_2$, 0.2 nM [$^3$H]-N-α-methylhistamine and increasing concentrations of drugs. The non specific binding (NSB) was defined as the residual binding observed in the presence of 10 μM thioperamide or histamine. Membrane-bound and free radioligand were separated by rapid filtration through glass fiber filters presoaked in 0.1% PEI. Samples and filters were rinsed by at least 6 ml of ice-cold 50 mM Tris-HCl buffer (pH 7.4). The entire filtration procedure did not exceed 10 seconds per sample. Radioactivity trapped onto the filters was counted by liquid scintillation in a β-counter.

[$^{35}$S]-GTPγS Binding Assay

Stimulation (agonist) or inhibition (inverse agonist) of [$^{35}$S]-GTPγS binding to membrane expressing human H$_3$ histamine receptors was measured as described by Lorenzen et al. (Mol. Pharmacol. 1993, 44, 115-123) with a few modifications. Briefly, membranes (10-20 μg proteins) expressing human H$_3$ histamine receptors were incubated at 25° C. in 0.2 ml of a 50 mM Tris-HCl buffer (pH 7.4) containing 3 mM MgCl$_2$, 50 mM NaCl, 1 μM GDP, 2 μg saponin and increasing concentrations of drugs. After 15 min preincubation, 0.2 nM of [$^{35}$S]-GTPγS were added to the samples. The non specific binding (NSB) was defined as the residual binding observed in the presence of 100 μM Gpp(NH)$_p$. Membrane-bound and free radioligand were separated by rapid filtration through glass fiber filters. Samples and filters were rinsed by at least 6 ml of ice-cold 50 mM Tris-HCl buffer (pH 7.4). The entire filtration procedure did not exceed 10 seconds per sample. Radioactivity trapped onto the filters was counted by liquid scintillation in a β-counter.

Data Analysis

Determination of pIC$_{50}$/pKi/pEC$_{50}$/pEC$_{50}$INV

Analysis

Raw data are analyzed by non-linear regression using XLfit™ (IDBS, United Kingdom) according to the following generic equation $$B=MIN+[(MAX-MIN)/(1+(((10^X)/(10^{-pX50}))^{nH}))]$$

where:

B is the radioligand bound in the presence of the unlabelled compound (dpm),

MIN is the minimal binding observed (dpm)

MAX is maximal binding observed (dpm),

X is the concentration of unlabelled compound (log M), pX$_{50}$ (−log M) is the concentration of unlabelled compound causing 50% of its maximal effect (inhibition or stimulation of radioligand binding). It stands for pIC$_{50}$ when determining the affinity of a compound for the receptor in binding studies with [$^3$H]-N-α-methylhistamine, for pEC$_{50}$ for compounds stimulating the binding of [$^{35}$S]-GTPγS (agonists) and for pEC$_{50}$INV for compounds inhibiting the binding of [$^{35}$S]-GTPγS (inverse agonists).

n$_H$ is the Hill coefficient.

pKi is obtained by applying the following equation (Cheng and Prusoff, 1973, Biochem. Pharmacol., 22: 3099-3108):

$$pKi=pIC_{50}+\log(1+L/Kd)$$

where:

pKi is the unlabelled compound equilibrium dissociation constant (−log M),

L is the radioligand concentration (nM),

Kd is the radioligand equilibrium dissociation constant (nM).

Compounds of formula (I) according to the invention showed pIC$_{50}$ values ranging from 6.5 to 10 for the histamine H$_3$ receptor.

Some compounds of formula (I) according to the present invention show pIC$_{50}$ values greater than or equal to 6.9.

Some compounds of formula (I) according to the present invention show pIC$_{50}$ values greater than or equal to 7.5.

Some compounds of formula (I) according to the present invention show pIC$_{50}$ values greater than or equal to 8.2.

Compounds of formula (I) according to the invention showed pEC$_{50}$INV values typically ranging from 6.5 to 10 for the histamine H$_3$ receptor.

Example 26

Antagonism Activity: Paced Isolated Guinea Pig Myenteric Plexus—Electric-Field Stimulation Assay Material and Methods Reagents Stock solutions ($10^{-2}$ M) of compounds to be tested and further dilutions were freshly prepared in DMSO (WNR, Leuven, Belgium). All other reagents (R(−)-α-methylhistamine, mepyramine, ranitidine, propranolol, yohimbine and components of the Krebs' solution) were of analytical grade and obtained from conventional commercial sources.

Animals

Four week-old male Dunkin-Hartley guinea pigs (200-300 g) were supplied by Charles River (Sultfeld, Germany). All animals were ordered and used under protocol "orgisol-GP" approved by the UCB Pharma ethical committee. Animals were housed in the UCB animal facility in groups of 12, in stainless steel cages (75×50×30 cm) and allowed to acclimatise for a minimum of one week before inclusion in the study. Room temperature was maintained between 20 and 24° C. with 40 to 70% relative humidity. A light and dark cycle of 12 h was applied. Animals had free access to food and water.

Organ Preparation

The method was adapted from that described by Menkveld et al. in Eur. J. Pharmacol. 1990, 186, 343-347. Longitudinal myenteric plexus was prepared from the isolated guinea pig ileum. Tissues were mounted in 20-ml organ baths containing modified Krebs' solution with $10^{-7}$ M mepyramine, $10^{-5}$ M ranitidine, $10^{-5}$ M propranolol and $10^{-6}$ M yohimbine. The bathing solution was maintained at 37° C. and gassed with 95% O$_2$-5% CO$_2$. Tissues were allowed to equilibrate for a 60-min period under a resting tension of 0.5 g and an electrical field stimulation (pulses of 5-20 V, 1 ms and 0.1 Hz was applied during the whole experiment). Such a stimulation induces stable and reproductive twitch contractions. Isometric contractions were measured by force-displacement transducers coupled to an amplifier connected to a computer system (EMKA Technologies) capable of controlling (i) automatic data acquisition, (ii) bath washout by automatic fluid circulation through electrovalves at predetermined times or signal stability and (iii) automatic dilution/injection of drug in the bath at predetermined times or signal stability.

Protocol

After a 60 min-stabilisation period, tissues were stimulated twice with $10^{-6}$ M R(−)-α-methylhistamine at 30-min interval. After a 60-min incubation period in the presence of solvent or antagonist test compound, a cumulative concentration-response to R(−)-α-methylhistamine was elicited ($10^{-10}$ à $10^{-4}$ M). Only one concentration of antagonist was tested on each tissue.

Data Analysis

An appropriate estimate of interactions between agonist and antagonist can be made by studying the family of curves observed in the absence or presence of increasing antagonist concentrations. The value of each relevant parameter of each concentration-response curve ($pD_2$ and $E_{max}$) was calculated by an iterative computer software (XLfit, IDBS, Guildford, UK) fitting the experimental data to the four parameter logistic equation. Antagonistic activity of the test substance was estimated by the calculation of $pD'_2$ and/or $pA_2$ values according to the methods described by Van Rossum et al. in Arch. Int. Pharmacodyn. Ther. 1963, 143, 299 and/or by Arunlakshana & Schild in Br. J. Pharmacol 1959, 14, 48

Results are expressed as the mean±SD. The number of observations is indicated as n. Compounds of formula (I) according to the invention showed $pA_2$ values typically greater than or equal to 6.5 for the histamine $H_3$ receptor.

The invention claimed is:

1. A compound of formula (I), geometrical isomers, enantiomers, diastereoisomers, pharmaceutically acceptable salts and mixtures thereof,

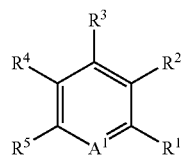
(I)

wherein
$A^1$ is CH;
$R^1$ is hydrogen or halogen;
$R^2$ is

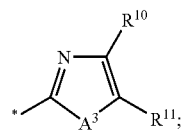
(II')

$A^3$ is O or S;
$R^3$ is hydrogen, halogen, $C_{1-4}$ alkyl or $C_{1-4}$alkoxy;
$R^4$ is hydrogen, halogen, $C_{1-4}$ alkyl, $C_{1-4}$alkoxy or —O—$(CH_2)_n$—$NR^{12a}R^{12b}$;
$R^5$ is hydrogen or —O—$(CH_2)_m$—$NR^{13a}R^{13b}$;

$R^{10}$ is hydrogen, $C_{1-8}$ alkyl or —$(CH_2)_w$—(C=O)$_t$—$NR^{15}R^{16}$;

$R^{11}$ is hydrogen, $C_{1-8}$ alkyl, ester, carboxylic acid, halogen, or —$(CH_2)_r$—(C=O)$_z$—$NR^{17}R^{18}$;

$R^{12a}$ and $R^{12b}$ are linked together to form a $C_{3-6}$ alkylene, each methylene of the alkylene being optionally substituted by one or two $C_{1-4}$ alkyl;

$R^{13a}$ and $R^{13b}$ are linked together to form a $C_{3-6}$ alkylene, each methylene of the alkylene being optionally substituted by one or two $C_{1-4}$ alkyl, an amino group or a $C_{1-6}$ alkyl amino, one methylene being optionally replaced by a nitrogen atom, said nitrogen atom being optionally substituted by a $C_{1-8}$ alkyl, $C_{3-6}$ cycloalkyl or $C_{1-6}$ alkyl amino; or one methylene of the alkylene being linked with a second methylene of the alkylene to form a $C_{3-6}$ alkylene;

$R^{15}$ is hydrogen or $C_{1-4}$ alkyl;

$R^{16}$ is aryl or $C_{1-8}$ alkyl;

or $R^{15}$ and $R^{16}$ are linked together to form a $C_{3-6}$ alkylene, each methylene of the alkylene being optionally substituted by one or two $C_{1-4}$ alkyl or by one or two halogen; or one methylene of the alkylene being optionally substituted by an alkylamine or by an $C_{1-6}$ alkyl aryl; one methylene of the alkylene being optionally replaced by a nitrogen atom or an oxygen atom, said nitrogen atom being optionally substituted by a $C_{3-6}$ cycloalkyl; or one methylene of the alkylene being optionally replaced by a $C_{3-8}$ cycloalkyl or a carbonyl; or $R^{15}$ and $R^{16}$ are linked together to form with N an unsaturated 5- or 6-membered heteroaryl optionally substituted by a $C_{1-4}$ alkyl;

$R^{17}$ is hydrogen or a $C_{1-8}$ alkyl;

$R^{18}$ is $C_{1-8}$ alkyl, $C_{1-6}$ alkyl aryl or $C_{1-6}$ alkyl cycloalkyl;

or $R^{17}$ and $R^{18}$ are linked together to form a $C_{3-6}$ alkylene, each methylene of the alkylene being optionally substituted by one or two $C_{1-4}$ alkyl or by one or two halogen, one methylene of the alkylene being optionally replaced by a carbonyl, a nitrogen atom or an oxygen atom, said nitrogen atom being optionally substituted by a $C_{1-8}$ alkyl or $C_{3-6}$ cycloalkyl;

n and m are independently an integer comprised between 2 and 8;

w and r are independently an integer comprised between 0 and 4;

t and z are independently an integer equal to 0 or 1;

with the proviso that $R^4$ is —O—$(CH_2)_n$—$NR^{12a}R^{12b}$, when $R^5$ is hydrogen and that $R^5$ is —O—$(CH_2)_m$—$NR^{13a}R^{13b}$, when $R^4$ is hydrogen, halogen, $C_{1-4}$ alkyl or $C_{1-4}$ alkoxy;

with the proviso that when $R^{11}$ is an ester or a carboxylic acid, $R^4$ is hydrogen, $C_{1-4}$ alkyl or $C_{1-4}$ alkoxy;

with the proviso that at least one of w and t is different from 0; and with the proviso that at least one of r and z is different from 0.

2. A compound according to claim 1 wherein $R^3$ is hydrogen, halogen or $C_{1-4}$ alkyl.

3. A compound according to claim 1, geometrical isomers, enantiomers, diastereoisomers, pharmaceutically acceptable salts and mixtures thereof,

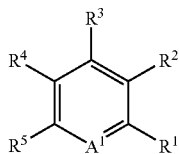

(I)

wherein
A¹ is CH;
R¹ is hydrogen;
R² is

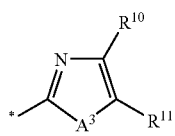

(II')

A³ is O or S;
R³ is hydrogen, fluorine or methyl;
R⁴ is hydrogen, chlorine, bromine, fluorine, methyl, methoxy or —O—$(CH_2)_n$—$NR^{12a}R^{12b}$;
R⁵ is hydrogen or —O—$(CH_2)_m$—$NR^{13a}R^{13b}$;
R¹⁰ is hydrogen, methyl or —$(CH_2)_w$—(C=O)$_t$—$NR^{15}R^{16}$;
R¹¹ is hydrogen, methyl, COOCH₃, COOH, bromine or —$(CH_2)_r$—(C=O)$_z$—$NR^{17}R^{18}$;
—$NR^{12a}R^{12b}$ is 1-pyrrolidinyl;
—$NR^{13a}R^{13b}$ is selected from the group consisting of 1-piperidinyl, 1-pyrrolidinyl, 2-methylpyrrolidin-1-yl, (2S)-2-methylpyrrolidin-1-yl, (2R)-2-methylpyrrolidin-1-yl, 4-isopropylpiperazin-1-yl, 4-methylpiperidin-1-yl, 2-methylpiperidin-1-yl, 2-(pyrrolidin-1-ylmethyl)pyrrolidin-1-yl, 4-cyclopentylpiperazin-1-yl, 3-(dimethylamino)pyrrolidin-1-yl, 4-(2-pyrrolidin-1-ylethyl)piperazin-1-yl, 1-azepanyl, 2,6-dimethylpiperidin-1-yl, (2S)-2-(pyrrolidin-1-ylmethyl)pyrrolidin-1-yl, 2-isobutylpyrrolidin-1-yl, 2-ethylpyrrolidinyl and (4aR,8aS) octahydroisoquinolin-2(1H)-yl.
—$NR^{15}R^{16}$ is selected from the group consisting of 1-piperidinyl, 2-methylpyrrolidin-1-yl, 1-pyrrolidinyl, 1-azepanyl, 4-methylpiperidin-1-yl, 2-methylpiperidin-1-yl, (3,5-dimethyl)piperidin-1-yl, hexyl(methyl) amino, benzyl(methyl)amino, (2-methoxy-1-methylethyl)amino, 2-azaspiro[5.5]undec-2-yl, 7,8-dimethyl-1azaspiro[4.4] non-1-yl, 2-oxopyrrolidin-1-yl, anilino, 2-methyl-1H-imidazol-1-yl, 1H-1,2,4-triazol-1-yl, [1-(hydroxymethyl)-3-methylbutyl]amino, cyclopentylamino, (1,3-dimethylbutyl)amino, (cyclopropylmethyl)(propyl)amino, 2,6-dimethylpiperidin-1yl, (2-furylmethyl)(methyl)amino, sec-butyl(propyl) amino, 4-benzylpiperidin-1-yl, 4-cyclopentylpiperazin-1-yl, 4-morpholinyl, (4-fluorobenzyl)amino, (4-chlorobenzyl)amino, 2-oxo-piperidin-1-yl, (5S)-2-oxo-(5-pyrrolidin-1-ylmethyl)pyrrolidin-1-yl, (4-fluorophenyl)amino, (4aR,8aS)-octahydroisoquinoline-2(1H)-yl, (2S)-2-(pyrrolidin-1-ylmethyl)pyrrolidin-1-yl, (2-methyl-2H-tetrazol-5-yl)amino, (3-methoxyphenyl)amino, (pyridin-3-yl)amino, (2S)-2-(morpholin-4-ylmethyl)pyrrolidin-1-yl, (2S)-2-(morpholin-4-ylmethyl)-5-oxopyrrolidin-1-yl, benzylamino and 4,4-difluoropiperidin-1-yl.

—$NR^{17}R^{18}$ is 1-piperidinyl, 2-oxopyrrolidin-1-yl, (cyclopropylmethyl)(propyl)amino, cyclopentylamino, benzylamino, (4-cyclopentyl)piperazine-1-yl, 4-morpholinyl or (4,4-difluoro)piperidin-1-yl.

n is equal to 3;
m is an integer comprised between 2 and 4;
w is an integer equal to 0, 1 or 2;
z is an integer equal to 0 or 1;
r is an integer equal to 0, 1 or 2;
t is an integer equal to 0 or 1;
with the proviso that R⁴ is —O—$(CH_2)_n$—$NR^{12a}R^{12b}$ when R⁵ is hydrogen and that R⁵ is —O—(CH₂), $NR^{13a}R^{13b}$ when R⁴ is hydrogen, chlorine, bromine, fluorine, methyl, or methoxy;
with the proviso that when R¹¹ is COOCH₃ or COOH, R⁴ is hydrogen, bromine, fluorine, methyl, or methoxy; and
with the proviso that when R¹⁰ is —(CH₂)—(C=O)$_t$—$NR^{15}R^{16}$, R¹¹ is hydrogen, methyl, COOCH₃, COOH or bromine; and
with the proviso that at least one of w and t is different from 0; and
with the proviso that at least one of r and z is different from 0.

4. A compound according to claim 1 wherein R⁴ is hydrogen or fluorine.

5. A compound according to claim 1 wherein R¹⁰ is methyl.

6. A compound according to claim 1 wherein R¹¹ is hydrogen or —$(CH_2)_r$—(C=O)$_z$—$NR^{17}R^{18}$.

7. A compound according to claim 1 wherein A³ is O.

8. A compound according to claim 1 wherein A³ is S.

9. A compound according to claim 1 wherein t is equal to 0.

10. A compound according to claim 1 wherein r is equal to 0.

11. A compound according to claim 1 wherein z is to 1.

12. A compound according to claim 1 formula (Ii) geometrical isomers, enantiomers, diastereoisomers, pharmaceutically acceptable salts and mixtures thereof,

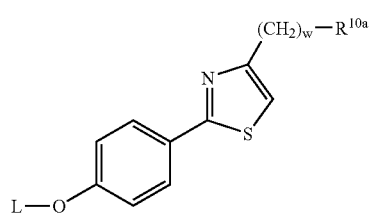

(Ii)

wherein
L is $C_{1-6}$-alkyl amino;
w is an integer comprised between 1 and 4; and
$R^{10a}$ is an amino group.

13. A compound according to claim 1 of formula (Ij) geometrical isomers, enantiomers, diastereoisomers, pharmaceutically acceptable salts and mixtures thereof,

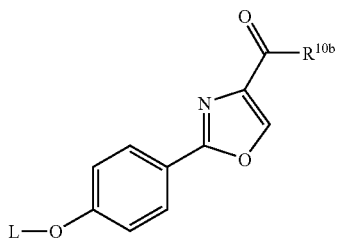

wherein
L is $C_{1-6}$-alkyl amino; and
$R^{10b}$ is an amino group.

14. A compound according to claim 1 of formula (Ik) geometrical isomers, enantiomers, diastereoisomers, pharmaceutically acceptable salts and mixtures thereof,

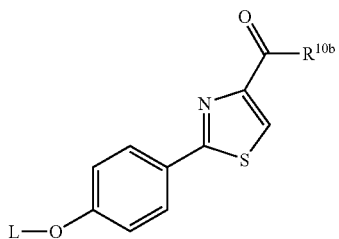

wherein
L is $C_{1-6}$-alkyl amino; and
$R^{10b}$ is an amino group.

15. A compound according to claim 1 of formula (Il), geometrical isomers, enantiomers, diastereoisomers, pharmaceutically acceptable salts and mixtures thereof,

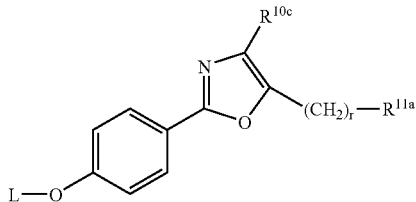

wherein
L is $C_{1-6}$-alkyl amino;
r is an integer comprised between 1 and 4;
$R^{10c}$ is a $C_{1-6}$ alkyl; and
$R^{11a}$ is an amino group.

16. A compound according to claim 1 of formula (Im) geometrical isomers, enantiomers, diastereoisomers, pharmaceutically acceptable salts and mixtures thereof,

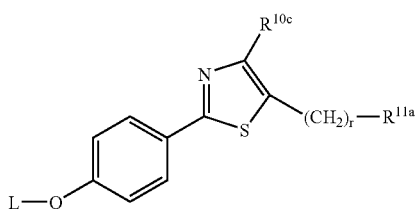

wherein
L is $C_{1-6}$-alkyl amino;
r is an integer comprised between 1 and 4;
$R^{10c}$ is a $C_{1-6}$ alkyl; and
$R^{11a}$ is an amino group.

17. A compound according to claim 1 of formula (In) geometrical isomers, enantiomers, diastereoisomers, pharmaceutically acceptable salts and mixtures thereof,

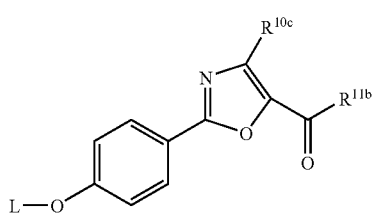

wherein
L is $C_{1-6}$-alkyl amino;
$R^{10c}$ is a $C_{1-6}$ alkyl; and
$R^{11b}$ is an amino group.

18. A compound according to claim 1 of formula (Io), geometrical isomers, enantiomers, diastereoisomers, pharmaceutically acceptable salts and mixtures thereof,

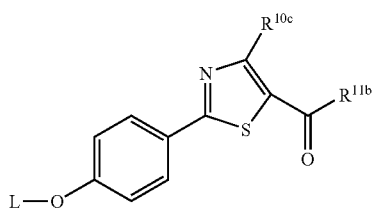

wherein
L is $C_{1-6}$-alkyl amino;
$R^{10c}$ is a $C_{1-6}$alkyl; and
$R^{11b}$ is an amino group.

19. A compound according to claim 12 wherein L is $(CH_2)_m-NR^{13a}R^{13b}$.

20. A compound according to claim 1 wherein $-NR^{13a}R^{13b}$ is selected from the group consisting of 1-piperidinyl, 2-methylpyrrolidin-1-yl, (2S)-2-methylpyrrolidin-1-yl, (2R)-2-methylpyrrolidin-1-yl, 4-methylpiperidin-1-yl, 2-methylpiperidin-1-yl, 2-(pyrrolidin-1-ylmethyl)pyrrolidin-1-yl, (2S)-2-(pyrrolidin-1-ylmethyl)pyrrolidin-1-yl, 2-isobutylpyrrolidin-1-yl, 2-ethylpyrrolidin-1-yl, (4aR,8aS)-octahydroisoquinolin-2(1H)-yl, 1-azepanyl, or 2,6-dimethylpiperidin-1-yl.

21. A compound according to claim 1 wherein $-NR^{13a}R^{13b}$ is 2-methylpyrrolidin-1-yl.

22. A compound of formula (I) according to claim 1 wherein $-NR^{15}R^{16}$ is selected from the group consisting of -piperidinyl, 2-methylpyrrolidin-1-yl, 1-pyrrolidinyl, 1-azepanyl, 2-methylpiperidin-1-yl, (3,5-dimethyl)piperidin-1-yl, hexyl(methyl)amino, benzyl(methyl)amino, 2-azaspiro[5.5]undec-2-yl, 7,8-dimethyl-1 azaspiro[4.4]non-1-yl, 2-oxopyrrolidin-1-yl, anilino, 2-methyl-1H-imidazol-1-yl, 1H-1,2,4-triazol-1-yl, [1-(hydroxymethyl)-3-methylbutyl]amino, cyclopentylamino, (1,3-dimethylbutyl)amino, (cyclopropylmethyl)(propyl)amino, 2,6-dimethylpiperidin-1-yl, (2-furylmethyl)(methyl)amino, sec-butyl(propyl)amin, 4-benzylpiperidin-1-yl, 4-cyclopentylpiperazin-1-yl, 4-morpholinyl, (4-fluorobenzyl)amino, (4-chlorobenzyl)amino, 2-oxopiperidin-1-yl, (5S)-2-oxo-5-pyrrolidin-1-yl, (4-fluorophenyl)amino, (4aR,8aS)-octahydroisoquinolin-2(1H)-yl, (2S)-2-(pyrrolidin-1-ylmethyl)pyrrolidin-1-yl, (3-methoxyphenyl)amino, (pyridin-3-yl)amino, benzylamino and 4,4-difluoropiperidin-1-yl.

23. A compound of formula (I) according to claim 1 wherein —$NR^{15}R^{16}$ is 1-piperidinyl, 1-pyrrolidinyl, 2-methylpyrrolidin-1-yl, 7,8-dimethyl-1azaspiro[4.4]non-1-yl, 1H-1,2,4-triazol-1-yl, [1-(hydroxymethyl)-3-methylbutyl]amino, 2,6-dimethylpiperidin-1-yl, benzylamino, sec-butyl(propyl)amino, (4aR,8aS)-octahydroisoquinolin-2(1H)-yl and (2S)-2-(pyrrolidin-1-ylmethyl)pyrrolidin-1-yl.

24. A compound of formula (I) according to claim 1 wherein —$NR^{15}R^{16}$ is 1-piperidinyl.

25. A compound of formula (I) according to claim 1 wherein —$NR^{17}R^{18}$ is 4-morpholinyl or 4,4-difluoropiperidin-1-yl.

26. A compound according to claim 1 wherein m is equal to 3.

27. A compound according to claim 1 wherein w is equal to 1.

28. A compound of formula (I) according to claim 1 selected from the group consisting of
- 1-(3-{4-[4-(piperidin-1-ylmethyl)-1,3-oxazol-2-yl]phenoxy}propyl)piperidine;
- 1-[3-(4-{4-[(2-methylpyrrolidin-1-yl)methyl]-1,3-oxazol-2-yl}phenoxy)propyl]piperidine;
- 1-(3-{4-[4-(pyrrolidin-1-ylmethyl)-1,3-oxazol-2-yl]phenoxy}propyl)piperidine;
- 1-({2-[4-(3-piperidin-1-ylpropoxy)phenyl]-1,3-oxazol-4-yl}methyl)azepane;
- 4-methyl-1-({2-[4-(3-piperidin-1-ylpropoxy)phenyl]-1,3-oxazol-4-yl}methyl)piperidine;
- 2-methyl-1-({2-[4-(3-piperidin-1-ylpropoxy)phenyl]-1,3-oxazol-4-yl}methyl)piperidine;
- 3,5-dimethyl-1-({2-[4-(3-piperidin-1-ylpropoxy)phenyl]-1,3-oxazol-4-yl}methyl)piperidine;
- N-hexyl-N-methyl-N-({2-[4-(3-piperidin-1-ylpropoxy)phenyl]-1,3-oxazol-4-yl}methyl)amine;
- N-benzyl-N-methyl-N-({2-[4-(3-piperidin-1-ylpropoxy)phenyl]-1,3-oxazol-4-yl}methyl)amine;
- 4-(pyrrolidin-1-ylmethyl)-2-[4-(3-pyrrolidin-1-ylpropoxy)phenyl]-1,3-oxazole;
- N-[(2-{4-[3-(4-isopropylpiperazin-1-yl)propoxy]phenyl-1,3-oxazol-4-yl)methyl]-N-methylhexan-1-amine;
- N-(2-methoxy-1-methylethyl)-N-({2-[4-(3-piperidin-1-ylpropoxy)phenyl]-1,3-oxazol-4-yl}methyl)amine;
- 2-[(2-{4-[3-(2-methylpyrrolidin-1-yl)propoxy]phenyl}-1,3-oxazol-4-yl)methyl]-2-azaspiro[5.5]undecane;
- 7,8-dimethyl-1-({2-[4-(3-piperidin-1-ylpropoxy)phenyl]-1,3-oxazol-4-yl}methyl)-1-azaspiro[4.4]nonane;
- 4-[(2-methylpyrrolidin-1-yl)methyl]-2-{4-[3-(2-methylpyrrolidin-1-yl)propoxy]phenyl}-1,3-oxazole;
- 1-isopropyl-4-(3-{4-[4-(pyrrolidin-1-ylmethyl)-1,3-oxazol-2-yl]phenoxy 1 propyl)piperazine;
- 1-isopropyl-4-[3-(4-{4-[(2-methylpiperidin-1-yl)methyl]-1,3-oxazol-2-yl}phenoxy)propyl]piperazine;
- 4-methyl-1-[3-(4-{4-[(2-methylpyrrolidin-1-yl)methyl]-1,3-oxazol-2-yl}phenoxy)propyl]piperidine;
- 2-methyl-1-[3-(4-{4-[(2-methylpyrrolidin-1-yl)methyl]-1,3-oxazol-2-yl}phenoxy)propyl]piperidine;
- 4-[(2-methylpyrrolidin-1-yl)methyl]-2-(4-{3-[2-(pyrrolidin-1-ylmethyl)pyrrolidin-1-yl]propoxy}phenyl)-1,3-oxazole;
- 1-cyclopentyl-4-[3-(4-{4-[(2-methylpyrrolidin-1-yl)methyl]-1,3-oxazol-2-yl}phenoxy)propyl]piperazine;
- N,N-dimethyl-1-[4-(4-{4-[(2-methylpyrrolidin-1-yl)methyl]-1,3-oxazol-2-yl}phenoxy)butyl]pyrrolidin-3-amine;
- 1-[2-(4-{4-[(2-methylpyrrolidin-1-yl)methyl]-1,3-oxazol-2-yl}phenoxy)ethyl]-4-(2-pyrrolidin-1-ylethyl)piperazine;
- 2-{4-[3-(2-methylpyrrolidin-1-yl)propoxy]phenyl}-4-(2-oxo-2-pyrrolidin-1-ylethyl)-1,3-oxazole;
- 1-[(2-{4-[3-(2-methylpyrrolidin-1-yl)propoxy]phenyl}-1,3-oxazol-4-yl)methyl]pyrrolidin-2-one;
- N-[(2-{4-[3-(2-methylpyrrolidin-1-yl)propoxy]phenyl}-1,3-oxazol-4-yl)methyl]-N-phenylamine;
- 2-{4-[3-(2-methylpyrrolidin-1-yl)propoxy]phenyl}-4-(2-pyrrolidin-1-ylethyl)-1,3-oxazole;
- 4-[(2-methyl-1H-imidazol-1-yl)methyl]-2-{4-[3-(2-methylpyrrolidin-1-yl)propoxy]phenyl}-1,3-oxazole;
- 1-[(2-{4-[3-(2-methylpyrrolidin-1-yl)propoxy]phenyl}-1,3-oxazol-4-yl)methyl]-1H-1,2,4-triazole;
- 4-(pyrrolidin-1-ylmethyl)-2-[3-(3-pyrrolidin-1-ylpropoxy)phenyl]-1,3-oxazole;
- 1-[(2-{4-[3-(2-methylpyrrolidin-1-yl)propoxy]phenyl}-1,3-oxazol-4-yl)methyl]piperidine;
- 1-[3-(4-{4-[(2-methylpyrrolidin-1-yl)methyl]-1,3-oxazol-2-yl}phenoxy)propyl]azepane;
- 1-(3-{4-[4-methyl-5-(piperidin-1-ylmethyl)-1,3-oxazol-2-yl]phenoxy}propyl)piperidine;
- (2R)-4-methyl-2-[(2-{4-[3-(2-methylpyrrolidin-1-yl)propoxy]phenyl}-1,3-oxazol-4-yl)methyl]amino}pentan-1-ol;
- N-[(2-{4-[3-(2-methylpyrrolidin-1-yl)propoxy]phenyl}-1,3-oxazol-4-yl)methyl]cyclopentanamine;
- 1-[4-(4-{4-[(2-methylpyrrolidin-1-yl)methyl]-1,3-oxazol-2-yl}phenoxy)butyl]azepane;
- 1-[2-(4-{4-[(2-methylpyrrolidin-1-yl)methyl]-1,3-oxazol-2-yl}phenoxy)ethyl]azepane;
- N-(1,3-dimethylbutyl)-N-[(2-{4-[3-(2-methylpyrrolidin-1-yl)propoxy]phenyl}-1,3-oxazol-4-yl)methyl]amine;
- N-(cyclopropylmethyl)-N-[(2-{4-[3-(2-methylpyrrolidin-1-yl)propoxy]phenyl}-1,3-oxazol-4-yl)methyl]-N-propylamine;
- 1-[3-(4-{4-[(2,6-dimethylpiperidin-1-yl)methyl]-1,3-oxazol-2-yl}phenoxy)propyl]-2,6-dimethylpiperidine;
- 1-({2-[4-(2-piperidin-1-ylethoxy)phenyl]-1,3-oxazol-4-yl}methyl)piperidine;
- 1-[(2-{4-[2-(2-methylpyrrolidin-1-yl)ethoxy]phenyl}-1,3-oxazol-4-yl)methyl]piperidine;
- 2-methyl-1-[4-(4-{4-[(2-methylpyrrolidin-1-yl)methyl]-1,3-oxazol-2-yl}phenoxy)butyl]piperidine;
- 1-(3-{4-[4-(piperidin-1-ylmethyl)-1,3-thiazol-2-yl}phenoxy]propyl)piperidine;
- 4-(pyrrolidin-1-ylmethyl)-2-[4-(3-pyrrolidin-1-ylpropoxy)phenyl]-1,3-thiazole;
- 7,8-dimethyl-1-[(2-{4-[3-(2-methylpyrrolidin-1-yl)propoxy]phenyl}-1,3-thiazol-4-yl)methyl]-1-azaspiro[4.4]nonane;
- N-(2-furylmethyl)-N-methyl-N-[(2-{4-[3-(2-methylpyrrolidin-1-yl)propoxy]phenyl}-1,3-thiazol-4-yl)methyl]amine;
- N-(sec-butyl)-N-[(2-{4-[3-(2-methylpyrrolidin-1-yl)propoxy]phenyl}-1,3-thiazol-4-yl)methyl]-N-propylamine;
- 1-(3-{4-[4-(pyrrolidin-1-ylmethyl)-1,3-thiazol-2-yl]phenoxy}propyl)piperidine;
- 1-({2-[4-(3-piperidin-1-ylpropoxy)phenyl]-1,3-thiazol-4-yl}methyl)azepane;

1-[(2-{4-[3-(2-methylpyrrolidin-1-yl)propoxy]phenyl}-1,3-thiazol-4-yl)methyl]piperidine;
1-[(2-{4-[3-(2-methylpyrrolidin-1-yl)propoxy]phenyl}-1,3-oxazol-4-yl)acetyl]piperidine;
1-(3-{4-[4-(2-oxo-2-piperidin-1-ylethyl)-1,3-oxazol-2-yl]phenoxy}propyl)piperidine;
1-[2-(2-{4-[3-(2-methylpyrrolidin-1-yl)propoxy]phenyl}-1,3-oxazol-4-yl)ethyl]piperidine;
2-{4-[3-(2-methylpyrrolidin-1-yl)propoxy]phenyl}-1,3-thiazole;
4-benzyl-1-[(2-{4-[3-(2-methylpyrrolidin-1-yl)propoxy]phenyl}-1,3-oxazol-4-yl)methyl]piperidine;
1-cyclopentyl-4-[(2-{4-[3-(2-methylpyrrolidin-1-yl)propoxy]phenyl}-1,3-oxazol-4-yl)methyl]piperazine;
1-{[2-(4-{3-[(2S)-2-(pyrrolidin-1-ylmethyl)pyrrolidin-1-yl]propoxy}phenyl)-1,3-oxazol-4-yl]methyl}piperidine;
1-(3-{4-[5-methyl-4-(piperidin-1-ylmethyl)-1,3-oxazol-2-yl]phenoxy}propyl)piperidine;
1-(3-{2-fluoro-4-[4-(piperidin-1-ylmethyl)-1,3-oxazol-2-yl]phenoxy}propyl)piperidine;
1-(3-{2,6-dimethyl-4-[4-(piperidin-1-ylmethyl)-1,3-oxazol-2-yl]phenoxy}propyl)piperidine;
4-[(2-{4-[3-(2-methylpyrrolidin-1-yl)propoxy]phenyl}-1,3-oxazol-4-yl)carbonyl]morpholine;
1-cyclopentyl-4-({2-[4-(3-piperidin-1-ylpropoxy)phenyl]-1,3-oxazol-4-yl}carbonyl)piperazine;
1-[(2-{4-[3-(2-methylpyrrolidin-1-yl)propoxy]phenyl}-1,3-oxazol-4-yl)carbonyl]piperidine;
1-cyclopentyl-4-[(2-{4-[3-(2-methylpyrrolidin-1-yl)propoxy]phenyl}-1,3-oxazol-4-yl)carbonyl]piperazine;
4-[(2-methylpyrrolidin-1-yl)methyl]-2-(4-{3-[(2S)-2-(pyrrolidin-1-ylmethyl)pyrrolidin-1-yl]propoxy}phenyl)-1,3-oxazole;
1-[(2-{3-fluoro-4-[3-(2-methylpyrrolidin-1-yl)propoxy]phenyl}-1,3-oxazol-4-yl)methyl]piperidine;
1-[(4-methyl-2-{4-[3-(2-methylpyrrolidin-1-yl)propoxy]phenyl}-1,3-oxazol-5-yl)carbonyl]piperidine;
N-(cyclopropylmethyl)-4-methyl-2-{4-[3-(2-methylpyrrolidin-1-yl)propoxy]phenyl}-N-propyl-1,3-oxazole-5-carboxamide;
N-cyclopentyl-4-methyl-2-{4-[3-(2-methylpyrrolidin-1-yl)propoxy]phenyl}-1,3-oxazole-5-carboxamide;
methyl 4-[(benzylamino)methyl]-2-{4-[3-(2-methylpyrrolidin-1-yl)propoxy]phenyl}-1,3-oxazole-5-carboxylate;
methyl 4-methyl-2-{4-[3-(2-methylpyrrolidin-1-yl)propoxy]phenyl}-1,3-thiazole-5-carboxylate;
2-{4-[3-(2-methylpyrrolidin-1-yl)propoxy]phenyl}-4-(piperidin-1-ylmethyl)-1,3-oxazole-5-carboxylic acid;
N-(cyclopropylmethyl)-2-{4-[3-(2-methylpyrrolidin-1-yl)propoxy]phenyl}-N-propyl-1,3-oxazole-4-carboxamide;
N-cyclopentyl-2-{4-[3-(2-methylpyrrolidin-1-yl)propoxy]phenyl}-1,3-oxazole-4-carboxamide;
N-(4-fluorobenzyl)-2-{4-[3-(2-methylpyrrolidin-1-yl)propoxy]phenyl}-1,3-oxazole-4-carboxamide;
N-benzyl-4-methyl-2-{4-[3-(2-methylpyrrolidin-1-yl)propoxy]phenyl}-1,3-oxazole-5-carboxamide;
1-cyclopentyl-4-[(4-methyl-2-{4-[3-(2-methylpyrrolidin-1-yl)propoxy]phenyl}-1,3-oxazol-5-yl)carbonyl]piperazine;
2-{4-[3-(2-methylpyrrolidin-1-yl)propoxy]phenyl}-4-(pyrrolidin-1-ylcarbonyl)-1,3-oxazole;
4-[(4-methyl-2-{4-[3-(2-methylpyrrolidin-1-yl)propoxy]phenyl}-1,3-oxazol-5-yl)carbonyl]morpholine;
4-{[4-methyl-2-(4-{3-[(2R)-2-methylpyrrolidin-1-yl]propoxy}phenyl)-1,3-oxazol-5-yl]carbonyl}morpholine;
4-{[4-methyl-2-(4-{3-[(2S)-2-methylpyrrolidin-1-yl]propoxy}phenyl)-1,3-oxazol-5-yl]carbonyl}morpholine;
1-cyclopentyl-4-[(4-methyl-2-{4-[3-(2-methylpyrrolidin-1-yl)propoxy]phenyl}-1,3-oxazol-5-yl)methyl]piperazine;
N-(cyclopropylmethyl)-N-[(4-methyl-2-{4-[3-(2-methylpyrrolidin-1-yl)propoxy]phenyl}-1,3-oxazol-5-yl)methyl]-N-propylamine;
N-benzyl-N-[(4-methyl-2-{4-[3-(2-methylpyrrolidin-1-yl)propoxy]phenyl}-1,3-oxazol-5-yl)methyl]amine;
1-[(2-[3-methoxy-4-[3-(2-methylpyrrolidin-1-yl)propoxy]phenyl-1,3-oxazol-4-yl)methyl]piperidine;
N-(4-chlorobenzyl)-N-[(2-{4-[3-(2-methylpyrrolidin-1-yl)propoxy]phenyl}-1,3-oxazol-4-yl)methyl]amine;
N-[(4-methyl-2-{4-[3-(2-methylpyrrolidin-1-yl)propoxy]phenyl-1,3-oxazol-5-yl)methyl]cyclopentanamine;
1-[(5-bromo-2-{4-[3-(2-methylpyrrolidin-1-yl)propoxy]phenyl}-1,3-oxazol-4-yl)methyl]piperidine;
1-{[2-(4-{3-[(2R)-2-methylpyrrolidin-1-yl]propoxy}phenyl)-1,3-oxazol-4-yl]methyl}piperidine;
1-[2-(4-{3-[(2S)-2-methylpyrrolidin-1-yl]propoxy}phenyl)-1,3-oxazol-4-yl]methyl}piperidine;
4-[(2-{4-[3-(2-methylpyrrolidin-1-yl)propoxy]phenyl}-1,3-oxazol-4-yl)methyl]morpholine;
1-[2-(2-4-[2-(2-methylpyrrolidin-1-yl)ethoxy]phenyl}-1,3-oxazol-4-yl)ethyl]piperidine;
1-[(2-{4-[3-(2-methylpyrrolidin-1-yl)propoxy]phenyl}-1,3-oxazol-4-yl)methyl]piperidin-2-one;
(5S)-1-[(2-{4-[3-(2-methylpyrrolidin-1-yl)propoxy]phenyl}-1,3-oxazol-4-yl)methyl]-5-(pyrrolidin-1-ylmethyl)pyrrolidin-2-one;
1 [(2-{3-chloro-4-[3-(2-methylpyrrolidin-1-yl)propoxy]phenyl}-1,3-oxazol-4-yl)methyl]piperidine;
1-[(2-{4-[3-(2-isobutylpyrrolidin-1-yl)propoxy]phenyl}-1,3-oxazol-4-yemethyl]piperidine;
methyl 2-{3-bromo-4-[3-(2-methylpyrrolidin-1-yl)propoxy]phenyl}-4-methyl-1,3-thiazole-5-carboxylate;
1-(3-{4-[4-methyl-5-(2-oxo-2-piperidin-1-ylethyl)-1,3-thiazol-2-yl]phenoxy}propyl)piperidine;
N-(4-fluorophenyl)-2-(2-{4-[3-(2-methylpyrrolidin-1-yl)propoxy]phenyl}-1,3-oxazol-4-yl)acetamide;
1-[(2-{4-[3-(2-ethylpyrrolidin-1-yl)propoxy]phenyl}-1,3-oxazol-4-yl)methyl]piperidine;
(4aR,8aS)-2-[(2-{4-[3-(2-methylpyrrolidin-1-yl)propoxy]phenyl}-1,3-oxazol-4-yl)methyl]decahydroisoquinoline;
2-{4-[3-(2-methylpyrrolidin-1-yl)propoxy]phenyl}-4-{[(2S)-2-(pyrrolidin-1-ylmethyl)pyrrolidin-1-yl]carbonyl}-1,3-oxazole;
4-[(2-{4-[3-(2-methylpyrrolidin-1-yl)propoxy]phenyl}-1,3-oxazol-4-yl)acetyl]morpholine;
N-cyclopentyl-2-(2-{4-[3-(2-methylpyrrolidin-1-yl)propoxy]phenyl}-1,3-oxazol-4-yl)acetamide;
N-(cyclopropylmethyl)-2-(2-{4-[3-(2-methylpyrrolidin-1-yl)propoxy]phenyl}-1,3-oxazol-4-yl)-N-propylacetamide;
1-[(2-{4-[3-(2-methylpyrrolidin-1-yl)propoxy]phenyl}-1,3-oxazol-4-yl)acetyl]azepane;
1-(3-{4-[4-methyl-5-(2-piperidin-1-ylethyl)-1,3-thiazol-2-yl]phenoxy}propyl)piperidine;
(5S)-1-[(2-{4-[3-(2-methylpyrrolidin-1-yl)propoxy]phenyl}-1,3-oxazol-4-yl)methyl]-5-(morpholin-4-ylmethyl)pyrrolidin-2-one;

(4aS,8aR)-2-(3-{4-[4-(piperidin-1-ylmethyl)-1,3-oxazol-2-yl]phenoxy}propyl)decahydroisoquinoline;

2-methyl-N-[(2-{4-[3-(2-methylpyrrolidin-1-yl)propoxy]phenyl}-1,3-oxazol-4-yl)methyl]-2H-tetraazol-5-amine;

N-(3-methoxyphenyl)-N-[(2-{4-[3-(2-methylpyrrolidin-1-yl)propoxy]phenyl}-1,3-oxazol-4-yl)methyl]amine;

N-(4-fluorophenyl)-N-[(2-{4-[3-(2-methylpyrrolidin-1-yl)propoxy]phenyl}-1,3-oxazol-4-yl)methyl]amine;

N-[(2-{4-[3-(2-methylpyrrolidin-1-yl)propoxy]phenyl}-1,3-oxazol-4-yl)methyl]pyridin-3-amine;

4-[(4-methyl-2-{4-[3-(2-methylpyrrolidin-1-yl)propoxy]phenyl}-1,3-oxazol-5-yl)methyl]morpholine;

4-({(2S)-1-[(2-{4-[3-(2-methylpyrrolidin-1-yl)propoxy]phenyl}-1,3-oxazol-4-yl)methyl]pyrrolidin-2-yl}methyl)morpholine;

1-[(2-{2-fluoro-4-[3-(2-methylpyrrolidin-1-yl)propoxy]phenyl}-1,3-oxazol-4-yl)methyl]piperidine;

4,4-difluoro-1-[(2-4-[3-(2-methylpyrrolidin-1-yl)propoxy]phenyl}-1,3-oxazol-4-yl)methyl]piperidine;

4-[(4-methyl-2-6-[3-(2-methylpyrrolidin-1-yl)propoxy]pyridin-3-yl}-1,3-thiazol-5-yl)carbonyl]morpholine;

1-[(2-3,5-difluoro-4-[3-(2-methylpyrrolidin-1-yl)propoxy]phenyl}-1,3-oxazol-4-yl)methyl]piperidine;

4,4-difluoro-1-[(4-methyl-2-{4-[3-(2-methylpyrrolidin-1-yl)propoxy]phenyl}-1,3-thiazol-5-yl)carbonyl]piperidine;

4,4-difluoro-1-{[4-methyl-2-(4-{3-[(2R)-2-methylpyrrolidin-1-yl]propoxy}phenyl)-1,3-thiazol-5-yl]carbonyl}piperidine;

4,4-difluoro-1-{[4-methyl-2-(4-{3-[(2S)-2-methylpyrrolidin-1-yl]propoxy}phenyl)-1,3-thiazol-5-yl]carbonyl}piperidine;

4-[(4-methyl-2-{4-[3-(2-methylpyrrolidin-1-yl)propoxy]phenyl}-1,3-thiazol-5-yl)carbonyl]morpholine;

4-{[4-methyl-2-(4-{3-[(2R)-2-methylpyrrolidin-1-yl]propoxy}phenyl)-1,3-thiazol-5-yl]carbonyl}morpholine;

4-{[4-methyl-2-(4-{3-[(2S)-2-methylpyrrolidin-1-yl]propoxy}phenyl)-1,3-thiazol-5-yl]carbonyl}morpholine;

1-[(2-{2-methyl-4-[3-(2-methylpyrrolidin-1-yl)propoxy]phenyl}-1,3-oxazol-4-yl)methyl]piperidine; and 1-[(4-methyl-2-{4-[3-(2-methylpyrrolidin-1-yl)propoxy]phenyl}-1,3-thiazol-5-yl)methyl]pyrrolidin-2-one.

29. A pharmaceutical composition comprising an effective amount of a compound according to claim 1, or a pharmaceutically acceptable salt thereof in combination with a pharmaceutically acceptable diluent or carrier.

30. A method for treating mild-cognitive impairment, Alzheimer's disease, learning and memory disorders, attention-deficit hyperactivity disorder, Parkinson's disease, schizophrenia, dementia, depression, epilepsy, seizures, convulsions, sleep/wake disorders, cognitive dysfunctions, narcolepsy, hypersomnia, obesity, stress, inflammation and pain, comprising administering to a patient in need of such treatment a therapeutically effective amount of the compound according to claim 1.

31. A compound according to claim 1 of formula (Ih) geometrical isomers, enantiomers, diastereoisomers, pharmaceutically acceptable salts and mixtures thereof,

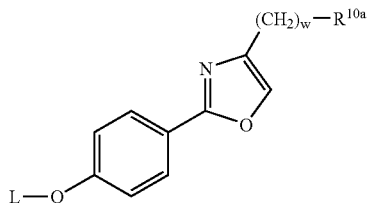

(Ih)

wherein

L is $C_{1-6}$-alkyl amino;

w is an integer comprised between 1 and 4; and $R^{10a}$ is an amino group.

* * * * *